US008192960B2

(12) United States Patent
Peters et al.

(10) Patent No.: US 8,192,960 B2
(45) Date of Patent: Jun. 5, 2012

(54) ONE COMPONENT AND TWO COMPONENT DNA POL III REPLICASES AND USES THEREOF

(75) Inventors: Lars-Erik Peters, Lafayette, CO (US); Anna Ettinger, Thornton, CO (US)

(73) Assignee: Qiagen North American Holdings, Valencia, CA (US)

( * ) Notice: Subject to any disclaimer, the term of this patent is extended or adjusted under 35 U.S.C. 154(b) by 192 days.

(21) Appl. No.: 11/101,977

(22) Filed: Apr. 7, 2005

(65) Prior Publication Data

US 2006/0211003 A1 Sep. 21, 2006

Related U.S. Application Data

(60) Provisional application No. 60/560,793, filed on Apr. 7, 2004, provisional application No. 60/641,183, filed on Jan. 3, 2005.

(51) Int. Cl.
*C12P 19/34* (2006.01)
*C12N 9/12* (2006.01)

(52) U.S. Cl. ........................ 435/91.1; 435/91.2; 435/194

(58) Field of Classification Search ........................ None
See application file for complete search history.

(56) References Cited

U.S. PATENT DOCUMENTS

| | | | |
|---|---|---|---|
| 5,583,026 | A | 12/1996 | O'Donnell |
| 5,668,004 | A | 9/1997 | O'Donnell |
| 6,221,642 | B1 | 4/2001 | O'Donnell |
| 6,238,905 | B1 | 5/2001 | McHenry et al. |
| 6,555,349 | B1 | 4/2003 | O'Donnell |
| 6,677,146 | B1 | 1/2004 | Janjic et al. |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
H. Guo et al., "Protein Tolerance to Random Amino Acid Change", PNAS 101(25): 9205-9210, Jun. 2004.*
Albà, M.M., et al., "Replicative DNA polymerases," *Gen. Biol.* 2(1):3002.1-3002.4 (Jan. 2001).
Anon., *TempliPhi: DNA amplification methods,* Amersham Biosciences Corp.: Piscataway, NJ (2002) (publ'd online at http://www.amershambiosciences.com).
Baker, T., et al., "Polymerases and the replisome: Machines within the machines," *Cell* 92(3):295-305 (Feb. 1998).
Bao, Q., et al., (Direct Submission), NCBI Accession No. Q8RA32 (GI 24418364), Jun. 15, 2002.
Barnes, M., et al., "DNA polymerases of low-GC gram-positive eubacteria: identification of the replication-specific enzyme encoded by dnaE," *J. Bacteriol.* 184(14):3834-3838 (Jul. 2002).
Barnes, M., et al., "Localization of the exonucleases and polymerase domains of *Bacillus subtilis* DNA polymerase III," *Gene* 111(1):43-49 (Feb. 1992).
Boshoff, H., et al., "DnaE2 polymerase contributes to in vivo survival and the emergence of drug resistance in *Mycobacterium tuberculosis,*" *Cell* 113(2):183-193 (Apr. 2003).
Bruck, I., et al., "Analysis of a multicomponent thermostable DNA polymerase III replicase from an extreme thermophile," *J. Biol. Chem.* 277(19):17334-17348 (May 2002) (first publ'd online Feb. 21, 2002).
Bruck, I., et al., "The DNA replication machine of a gram-positive organism," *J. Biol. Chem.* 275(37):28971-28983 (Sep. 2000).
Bullard, J., et al., "DNA polymerase III holoenzyme from *Thermus thermophilus* identification, expression, purification of components, and use to reconstitute a processive replicase," *J. Biol. Chem.* 277(16):13401-13408 (Apr. 2002) (first e-pub'd Jan. 31, 2002).
Cramer, P., "Common structural features of nucleic acid polymerases," *BioEssays* 24:724-729 (2002).
Dean, F., et al., "Rapid amplification of plasmid and phage DNA using Phi29 DNA polymerase and multiply-primed rolling circle amplification," *Genome Res.* 11(6):1095-1099 (Jun. 2001).
DeRose, E., et al., "Model for the catalytic domain of the proofreading ε-subunit of *Escherichia coli* DNA polymerase III based on NMR structural data," *Biochemistry* 41(1):94-110 (Jan. 2002) (first publ'd online Dec. 4, 2001).
DiFrancesco, R., et al., "The interaction of DNA polymerase III and the product of the *Escherichia coli* mutator gene, *mutD,*" *J. Biol. Chem.* 259(9):5567-5573 (May 1984).
Evans, S., et al., "Improving dideoxynucleotide-triphosphate utilization by the hyper-thermophilic DNA polymerase from the archaeon *Pyrococcus furiosus,*" *Nucleic Acids Res.* 28(5):1059-1066 (Mar. 2000).
Fay, P., et al., "Size classes of products synthesized processively by DNA polymerase III and DNA polymerase III holoenzyme of *Escherichia coli,*" *J. Biol. Chem.* 256(2):976-983 (Jan. 1981).
Flett, F., et al., "A 'gram negative-type' DNA polymerase III is essential for replication of the linear chromosome of *Streptomyces coelicolor* A3(2)," *Mol. Microbiol.* 31(3):949-958 (Feb. 1999).
Foster, K., et al., "DNA polymerase III of *Enterococcus faecalis*: expression and characterization of recombinant enzymes encoded by the polC and dnaE genes," *Protein Expr. Purif.* 27(1):90-97 (Jan. 2003).
Hafner, G.J., et al., "Isothermal amplification and multimerization of DNA by *Bst* DNA polymerase," *BioTechniques* 30(4):852-867 (Apr. 2001).
Huang, Y., et al., "The hyperthermophilic bacterium *Thermotoga maritime* has two different classes of family C DNA polymerases: evolutionary implications," *Nucleic Acids Res.* 26(23):5300-5309 (Dec. 1998).
Inoue, R., et al., "Genetic identification of two distinct DNA polymerases, DnaE and PolC, that are essential for chromosomal DNA replication in *Staphylococcus aureus,*" *Mol. Genet. Genomics* 266(4):565-571 (Dec. 2001) (first publ'd online Aug. 16, 2001).
Jeruzalmi, D., et al., "Mechanism of processivity clamp opening by the δ subunit wrench of the clamp loader complex of *E. coli* DNA polymerase III," *Cell* 106(4):417-428 (Aug. 2001).
Kim, S., et al. "Coupling of a replicative polymerase and helicase: A τ-DnaB interaction mediates rapid replication fork movement," *Cell* 84(4):643-650 (Feb. 1996).

(Continued)

*Primary Examiner* — Richard Hutson
(74) *Attorney, Agent, or Firm* — Arnold & Porter LLP; Todd Lorene

(57) ABSTRACT

The invention provides one-component and two-component DNA polymerases, as well as kits comprising the same, and methods of using the same for nucleic amplification and nucleic acid sequencing.

21 Claims, 41 Drawing Sheets

OTHER PUBLICATIONS

Kim, S., et al., "τ protects β in the leading-strand polymerase complex at the replication fork," *J. Biol. Chem.* 271(8):4315-4318; (Feb. 1996).

Kornberg, A., *1982 Supplement to DNA Replication*, pp. 122-125, W.H. Freeman & Co.: San Francisco, CA (1982).

Le Chatelier, E., et al., "Involvement of DnaE, the second replicative DNA polymerase from *Bacillus subtilis* in DNA mutagenesis," *J. Biol. Chem.* 279(3):1757-1767 (Jan. 2004) (first e-publ'd Oct. 30, 2003).

Liu, X., et al., "Split *dnaE* genes encoding multiple novel inteins in *Trichodesmium erythraeum*," *J. Biol. Chem.* 278(29):26315-26318 (Jul. 2003) (first publ. online May 24, 2003).

López de Saro, F., et al., "Competitive processivity-clamp usage by DNA polymerases during DNA replication and repair," *EMBO J.* 22(23):6408-6418 (2003).

López de Saro, F., et al., "Interaction of the β sliding clamp with MutS, ligase, and DNA polymerase I," *Proc. Natl. Acad. Sci. USA* 98(15):8376-8380 (Jul. 2001).

Maki, H., at al., "DNA Polymerase III holoenzyme of *Escherichia coli*. IV. The holoenzyme is an asymmetric dimer with twin active," *J. Biol. Chem.* 263(14):6570-6578 (May 1988).

Maki, H., et al., "The polymerase subunit of DNA polymerase III of *Escherichia coli*. I. Amplification of the *dnaE* gene product and polymerase activity of the α subunit," *J. Biol. Chem.* 260(24):12987-12992 (Oct. 1985).

Maki, S., et al., "DNA polymerase III holoenzyme of *Escherichia coli*. II. A novel complex including the γ subunit essential for processive synthesis," *J. Biol. Chem.* 263(14):6555-6560 (May 1988).

Maki, S., et al., "DNA polymerase III holoenzyme of *Escherichia coli*. I. Purification and distinctive functions of subunits τ and γ, the *dnaZX* gene products," *J. Biol. Chem.* 263(14):6547-6554 (May 1988).

Maki, S., et al., "DNA polymerase III holoenzyme of *Escherichia coli*. III. Distinctive processive polymerases reconstituted from purified subunits," *J. Biol. Chem.* 263(14):6561-6569 (May 1988).

McHenry, C., et al., "DNA polymerase III holoenzyme of *Escherichia coli*. Purification and resolution into subunits," *J. Biol. Chem.* 252(18):6478-6484 (Sep. 1977).

McHenry, C., et al., "DNA polymerase III holoenzyme. Components, structure, and mechanism of a true replicative complex," *J. Biol. Chem.* 266(29):19127-19130 (Oct. 1991).

Mok, M., et al., "The *Escherichia coli* preprimosome and DNA B helicase can form replication forks that move at the same rate," *J. Biol. Chem.* 262(34):16644-16654 (Dec. 1987).

O'Donnell, M., et al., "Complete replication of templates by *Escherichia coli* DNA polymerase III holoenzyme," *J. Biol. Chem.* 260(23):12884-12889 (Oct. 1985).

O'Donnell, M., et al., "Dynamics of DNA polymerase III holoenzyme of *Escherichia coli* in replication of a multiprimed template," *J. Biol. Chem.* 260(23)12875-12883 (Oct. 1985).

Pacitti, D., et al., "Characterization and overexpression of the gene encoding *Staphylococcus aureus* DNA polymerase III," *Gene* 165(1):51-56 (Nov. 1995).

Scheuerman, R., et al., "A separate editing exonuclease for DNA replication: the ε subunit of *Escherichia coli* DNA polymerase III holoenzyme," *Proc. Natl. Acad. Sci. USA* 81(24):7747-7751 (Dec. 1984).

Steitz, T., "DNA polymerases: Structural diversity and common mechanisms," *J. Biol. Chem.* 274(25):17395-17398 (Jun. 1999).

Studwell, P., "Processive replication is contingent on the exonuclease subunit of DNA polymerase III holoenzyme," *J. Biol. Chem.* 265(2):1171-1178 (Jan. 1990).

Studwell-Vaughan, P., et al., "DNA polymerase III accessory proteins v. θ encoded by *holE*," *J. Biol. Chem.* 268(16):11785-11791 (Jun. 1993).

Tsuchihashi, Z., et al., "Translational frameshifting generates the γ subunit of DNA polymerase III holoenzyme," *Proc. Natl. Acad. Sci. USA* 87(7):2516-2520 (Apr. 1990).

Voisey, J., et al., "Interrogation of multimeric DNA amplification products by competitive primer extension using *Bst* DNA polymerase (large fragment)," *BioTechniques* 31(5):1122-1129 (Nov. 2001).

Yurieva, O., et al., "*Thermus thermophilis* dnaX homolog encoding γ- and τ-like proteins of the chromosomal replicase," *J. Biol Chem.* 272(43):27131-27139 (Oct. 1997).

\* cited by examiner

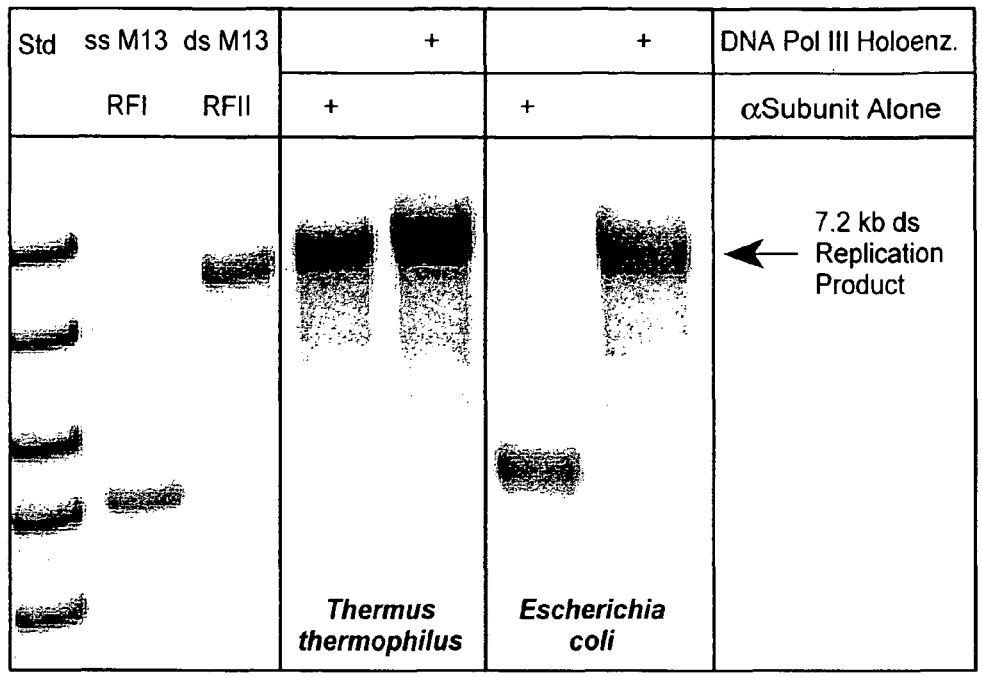
FIG. 1
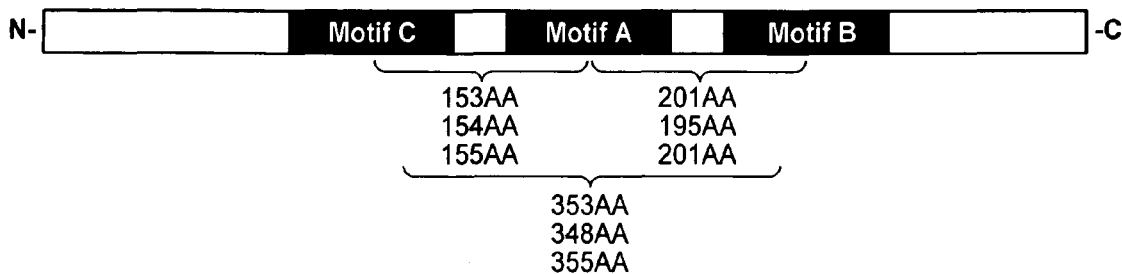
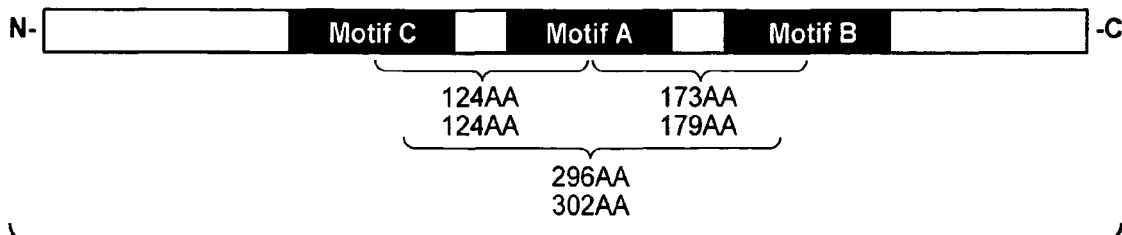
FIG. 4

**Low Primer Extension Rates of *Thermotoga maritima* DNA Pol III Alpha-Subunit (DnaE)**
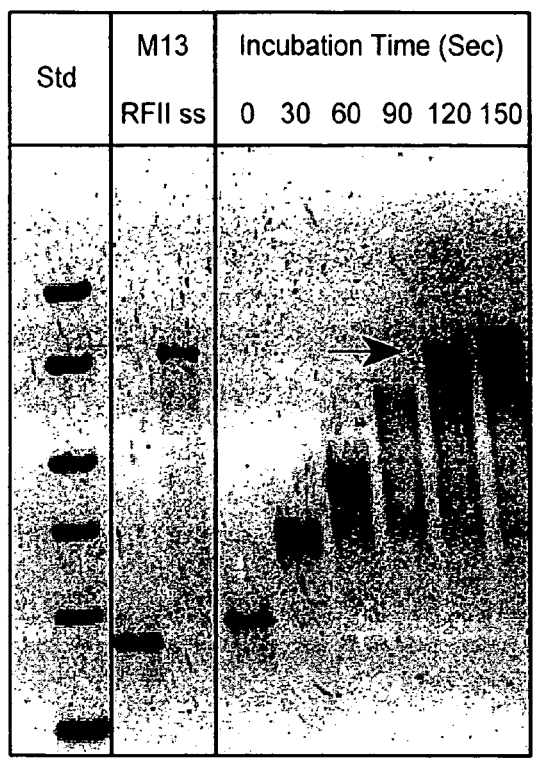
2 ug Tma DnaE
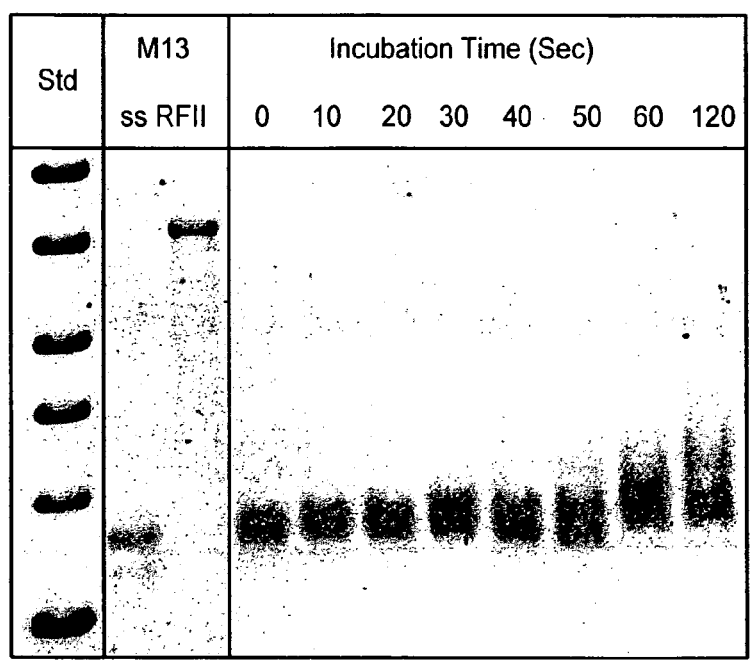
100 ng Tma DnaE
FIG. 2

PCR with a Single Component (Alpha Alone) and Two Component (Alpha/Beta; 1:2) Pol III Replicase from Aquifex Aeolicus and Thermus Thermophilus
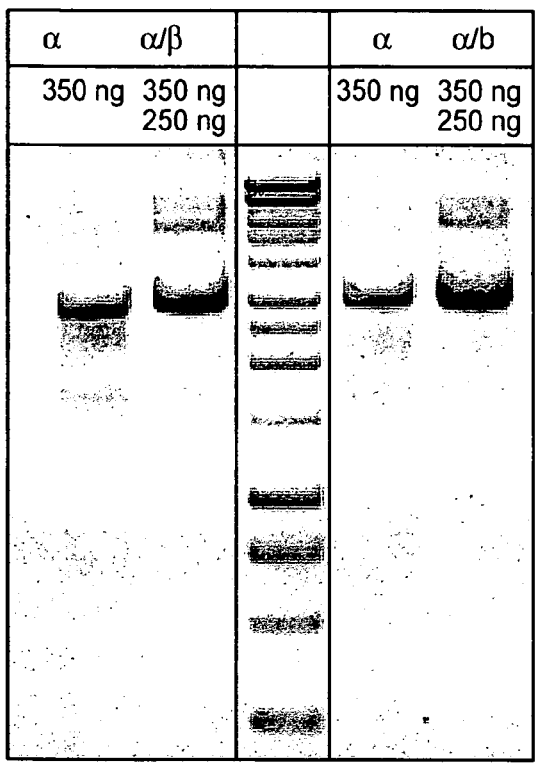
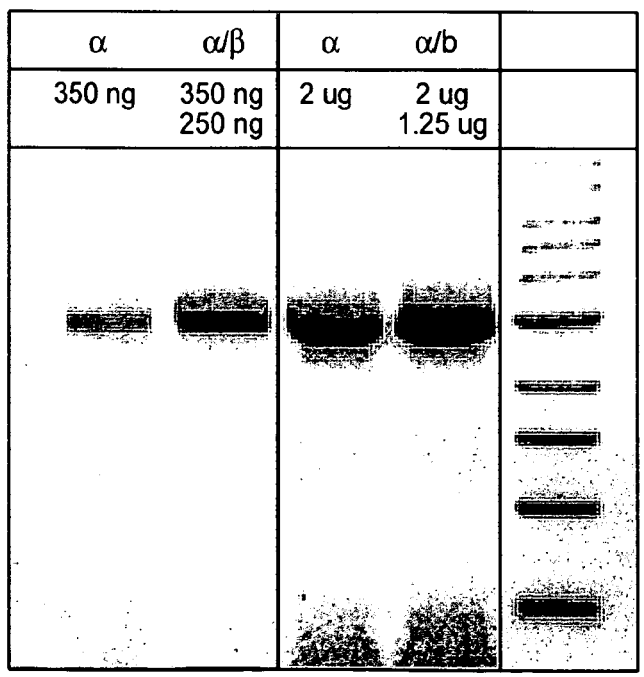
FIG. 3

```
                                          1                    10                   20                   30                   40                                     57
                                          |                    |                    |                    |                    |                                      |
Tth Pol III alpha US6238905          (1)   -------------------------MGRKERFAHLHQHTQFSLRLHTEHSLDGAAKLESDLLKWVKETEP--E
A. aeolicus Pol III alpha            (1)   --------------------------MSKDFVHLHLHTQFSLLDGAIKLEMKKAKEYGYK--------
P. aeroginosa Pol III alpha          (1)   --------------------------MTMSFVHLRLHTEHSLNDGLVRMKPLAKAMAGLGMP-------
E. coli Pol III alpha                (1)   ----------------------MSEPRFVHLRVHSDSMQDGLAKTAPLMKKAAALGMP----------
Deinococcus Pol III alpha            (1)   MTVSDAPTPHIHLPDGSCCOPKIKFAHLHQHTQXSLDGAAKLEKWAKEVPPEGQ--------------
Taq Pol III alpha                    (1)   --------------------------MGSKLKFAHLHQHTQRSLDGAAKIQDLLRKUWKETEP--E
Corrected Tth Pol III Alpha subunits AA Sequence (1) -------MGRKERFAHLHQHTQFSLLDGAAKLESDLLKWVKETEP--E
Consensus                            (1)                              LRFAHLHQHTQFSLLDGAAKL DLLKWVKE TP
                                                                                                                    Section 1
```

Section 8

```
                                            (400) 400       410       420       430       440       450    458
Tth Pol III alpha US6238905                 (337) ------------------------------------------LLGKLRPHGDGEALAEALAQVEREAWE
A. aeolicus Pol III alpha                   (334) --------------------------------------------------------------------
P. aeroginosa Pol III alpha                 (319) --------------------------------------------------------------------
E. coli Pol III alpha                       (318) --------------------------------------------------------------------
Deinococcus Pol III alpha                   (394) FLGSEWEARGKEAGEKYTPYPALEKMEQDGESGTLPAVAHADCRAARRQDSDTSIEL
Taq Pol III alpha                           (337) ------------------------------------------LLGTLRPHGDERALAEALARVEREAWE
Corrected Tth Pol III Alpha subunits AA Sequence (337) ------------------------------------------LLGKLRPHGDGEALAEALAQVEREAWE
Consenus                                    (400)                                            G  LP HG      A          E
```

Section 9

```
                                            (457) 457       470       480       490       500       513
Tth Pol III alpha US6238905                 (364) RLMKSLPPLAGVKEWTHEAHFHRALVELSVIERMGFPGYFLIVQDYINWAERNGVSV
A. aeolicus Pol III alpha                   (334) ---------------KEYWERLEVELEWINAMGFAGYFLIVQDIINWALKKNDIPV
P. aeroginosa Pol III alpha                 (319) -----R----QVYVDRLNELDIIQMGFPGYFLIVMDNIKWAKNMGWPV
E. coli Pol III alpha                       (318) -----R----INQMGFPGYFLIVMEHIUSKDMGWSV
Deinococcus Pol III alpha                   (451) -PEVDERLETELQINNNGFRDYFLIVADYINWAKDHDIWSV
Taq Pol III alpha                           (337) DPDTDDEETTRSHHRYALKILRRREAHLHRALVELSVIERMGFPGYFLIVQDMINWAHGHGWSV
Corrected Tth Pol III Alpha subunits AA Sequence (364) ELRKRLPPLEGVREWTEAHFHRALVELSMIERMGFPGYFLIVQDMINWAERNGVSV
Consenus                                    (457)                  A   I      RA YELSVI RMGFPGYFLIVQDYINWAK NGVSV
```

Section 10

```
                                            (514) 514       520       530       540       550       560       570
Tth Pol III alpha US6238905                 (421) GPGRGSAAGSLVAYAYGITNWDPLERFGLLFERFLNPERWSMPDIDTDFSDRERDRVI
A. aeolicus Pol III alpha                   (374) GPGRGSMAGSLVAYAYGITNWDPLKFGLLFERFLNPERWSMPDIDTDFCQDNRERVI
P. aeroginosa Pol III alpha                 (360) GPGRGSCMGSLVAYYLKITDDPLKHGFLFERFLNPERWSMPDFDMDFCMEGRDRVI
E. coli Pol III alpha                       (359) GPGRGSIAGSLVAYKITDDPLARGLLFERFLNPERWSMPDFDMDFCMEKRDQVI
Deinococcus Pol III alpha                   (508) GPGRGSIAGSLVAYATRITNWDPLGFGLLFERFLNPERDRTSMPDFDIDFNDARRTEVI
Taq Pol III alpha                           (421) GPGRGSMAGSLVAYAVGITNWDPLRFGLLFERFLNPERWSMPDIDTDFSDRERDRVI
Corrected Tth Pol III Alpha subunits AA Sequence (421) GPGRGSMAGSLVAYAYGITNWDPLERFGLLFERFLNPERWSMPDIDTDFSDRERDRVI
Consenus                                    (514) GPGRGSAAGSLVAYAVGITNIDPLRFGLLFERFLNPERVSMPDIDVDF D RDRVI
```

| FIG. 9a |
| FIG. 9b |
| FIG. 9c |
| FIG. 9d |
| FIG. 9e |
| FIG. 9f |
| FIG. 9g |
| FIG. 9h |
| FIG. 9i |

Alpha contig sequence

```
1    AACGATTCGG TCCCGGGTCT AGACCATGGG ATACCTAGGA GGTAATAAAT AATGAAAATC TACCTGGTTG GTGGTGCTGT TCGGATGCA TTGAGGAGGA
     TTGCTAAGCC AGGGCCCAGA TCTGGTACCC TATGGATCCT CCATTATTTA TTACTTTTAG ATGGACCAAC CACCACGACA AGCGCTACGT AACTCCTCCT
                    Met Gly Arg Lys Leu Arg Phe Ala His Leu His Gln His Thr Gln Phe Ser Leu Leu Asp Gly Ala Ala Lys Leu Ser Asp Leu Leu Lys Trp

101  TCGATTAATG GGCCGCAAAC TCCGCTTCGC CCACCTCCAC CAGCACACCC AGTTCTCCCT CCTGGACGGG GCGGCGAAGC TTTCCGACCT CCTCAAGTGG
     AGCTAATTAC CCGGCGTTTG AGGCGAAGCG GGTGGAGGTG GTCGTGTGGG TCAAGAGGGA GGACCTGCCC CGCCGCTTCG AAAGGCTGGA GGAGTTCACC
                 Val Lys Glu Thr Thr Pro Glu Asp Pro Ala Leu Ala Met Thr Asp His Gly Asn Leu Phe Gly Ala Val Glu Phe Tyr Lys Lys Ala Thr

201  GTCAAGGAGA CGACCCCCGA GGACCCCGCC TTGGCCATGA CCGACCACGG CAACCTCTTC GGGGCCGTGG AGTTCTACAA GAAGGCCACC GAAATGGGCA
     CAGTTCCTCT GCTGGGGGCT CCTGGGGCCG AACCGGTACT GGCTGGTGCC GTTGGAGAAG CCCCGGCACC TCAAGATGTT CTTCCGGTGG CTTTACCCGT
                 Ile Lys Pro Ile Leu Gly Tyr Glu Ala Ala Tyr Val Ala Ala Glu Ser Arg Phe Asp Arg Lys Arg Gly Leu Asp Gly Tyr Phe His Leu Thr Leu

301  TCAAGCCCAT CCTGGGCTAC GAGGCCGCTTAC GAGGCCGCCT GGGGGCGGA AAGCCCGCTTT GACCGCAAGC GGGGAAAGGG CCTAGACGGG GGCTACTTTC ACCTCACCCT
     AGTTCGGGTA GGACCCGATG CTCCGGCGATG ACCGGCGGCCCT TCGGGCGAAA CTGGCGTTCG CCCCTTTCCC GGATCTGCCC CCGATGAAAG TGGAGTGGGA
                 Glu Met Gly Ile
```

FIG. 9a

Alpha contig sequence

```
    Leu Leu Ala Lys Asp Phe Thr Gly Tyr Gln Asn Leu Val Arg Leu Ala Ser Arg Ala Tyr Leu Gly Gly Phe Tyr Glu Lys Pro Arg Ile Asp Arg Glu Ile
401 CCTCGCCAAG GACTTCACGG GGTACCAGAA CCTGGTGCGC CTGGCTAGCC GGGCTTACCT GGAGGGGTTT TACGAAAAGC CCCGGATTGA CCGGGAGATC
    GGAGCGGTTC CTGAAGTGCC CCATGGTCTT GGACCACGCG GACCGCTCGG CCCGAATGGA CCTCCCCAAA ATGCTTTTCG GGGCCTAACT GGCCCTCTAG

Leu Arg Glu His Ala Glu Gly Leu Ile Ala Leu Ser Gly Cys Leu Gly Ala Glu Ile Pro Gln Phe Ile Leu Gln Asp Arg Leu Asp Leu Ala Glu Ala Arg
501 CTCCGGGAGC ACGCCGAGGG CCTCATCGCC CTCTCGGGGT GCCTCGGGGC GGAGATCCCC CAGTTCATCC TCCAGGACCG TCTGGACCTG GCCGAGGCCC
    GACGCCCTCG TGCGGCTCCC GGAGTAGCGG GAGAGCCCCA CGGAGCCCCG CCTCTAGGGG GTCAAGTAGG AGGTCCTGGC AGACCTGGAC CGGCTCCGGG

Arg Leu Asn Glu Val Leu Ser Ile Phe Lys Asp Arg Phe Ile Glu Ile His Gly Leu Pro Glu Gln Lys Lys Val Asn Glu Val Leu Lys Glu
601 GGCTCAACGA GTACCTCTCC ATCTTCAAGG ACCGCTTCTT CATTGAGATC CAGGAACCACG GCCTCCCCGA GCAGAAAAAG GTCAACGAGG TCCTCAAGGA
    CCGAGTTGCT CATGGAGAGG TAGAAGTTCC TGGCGAAGAA GTAACTCTAG GTCTTGGTGC CGGAGGGGCT CGTCTTTTTC CAGTTGCTCC AGGAGTTCCT

Glu Phe Ala Arg Lys Tyr Gly Leu Gly Met Val Ala Thr Asn Asp Gly His Tyr Val Arg Lys Glu Asp Ala Arg Ala His Glu Val Leu Ala Ile Gln
701 GTTCGCCCGA AAGTACGGCC TGGGGATGGT GGCCACCAAC GACGGCCATT ACGTGAGGAA GGAGGACGCC CGGGCCCACG AGGTCCTCCT CGCCATCCAG
    CAAGCGGGCT TTCATGCCGG ACCCCTACCA CCGGTGGTTG CTGCCGGTAA TGCACTCCTT CCTCCTGCGG GCCCGGGTGC TCCAGGAGGA GCGGTAGGTC

Ser Lys Ser Thr Leu Asp Asp Pro Gly Arg Trp Arg Phe Pro Cys Asp Glu Phe Tyr Val Lys Thr Pro Gly Met Arg Ala Met Phe Pro Glu Glu Glu
801 TCCAAGAGCA CCCTGGACGA CCCCGGGCGC TGGCGCTTCC CCTGCGACGA GTTCTACGTG AAGACCCCCG AGGAGATGCG GGCCATGTTC CCCGAGGAGG
    AGGTTCTCGT GGGACCTGCT GGGGCCCGCG ACCGCGAAGG GGACGCTGCT CAAGATGCAC TTCTGGGGGC TCCTCTACGC CCGGTACAAG GGGCTCCTCC
```

FIG. 9b

Alpha contig sequence

```
                Glu Trp Gly Asp Glu Pro Phe Asp Asn Thr Val Glu Ile Ala Arg Met Cys Asn Val Glu Leu Pro Ile Gly Asp Lys Met Val Tyr Arg Ile Pro Arg Phe
         901    AGTGGGGGGA CGAGCCCTTT GACAACACCG TGGAGATCGC CCGCATGTGC AACGTGGAGC TGCCCATCGG GGACAAGATG GTCTACCGCA TCCCCCGCTT
                TCACCCCCCT GCTCGGGAAA CTGTTGTGCC ACCTCTAGCG GGCGTACACG TTGCACCTCG ACGGGTAGCC CCTGTTCTAC CAGATGGCGT AGGGGGCGAA

Phe Pro Leu Pro Ala Arg Arg Thr Glu Ala Gln Tyr Leu Met Glu Leu Thr Phe Lys Gly Leu Leu Arg Arg Tyr Pro Asp Arg Ile Thr Glu Gly Phe Tyr
        1001    CCCCCTCCCC GCCCGTCGGA CCGAGGCCCA GTACCTCATG GAGCTCACCT TTAAGGGGCT CCTCCGCCGC TACCCGGACC GGATCACCGA GGGCTTCTAC
                GGGGGAGGGG CGGGCAGCCT GGCTCCGGGT CATGGAGTAC CTCGAGTGGA AATTCCCCGA GGAGGCGGCG ATGGGCCTGG CCTAGTGGCT CCCGAAGATG

Arg Glu Val Phe Arg Leu Leu Gly Lys Leu Pro Pro His Gly Asp Gly Ala Leu Ala Ala Glu Ala Leu Ala Gln Val Glu Arg Glu Ala Trp Glu Arg Leu
        1101    CGGGAGGAGTCT TCCGCCTTTT GGGGAAGCTT CCCCCCCACG GGGACGGGGA GGCCCTGGCC GAGGCCTTGG CCCAGGTGGA GCGGGAGGCT TGGGAGAGGC
                GCCCCTCCAGA AGGCGGAAAA CCCCTTCGAA GGGGGGGTGC CCCTGCCCCT CCGGGACCGG CTCCGGAACC GGTCCACCT CGCCCTCCGA ACCCTCTCCG

Leu Met Lys Ser Leu Pro Pro Leu Ala Gly Val Lys Glu Trp Thr Ala Glu Ala Ile Phe His Arg Ala Leu Tyr Glu Leu Ser Val Ile Glu Arg Met Gly
        1201    TCATGAAGAG CCTCCCCCCC TTGGCCGGGG TCAAGGAGTG GACGGCGGAG GCCATTTTCC ACCGGGCCCT TTACGAGCTT TCCGTGATAG AGGCATGGG
                AGTACTTCTC GGAGGGGGGG AACCGGCCCC AGTTCCTCAC CTGCCGCCTC CGGTAAAAGG TGGCCCGGGA AATGCTCGAA AGGCACTATC TCGGGTACCC
```

FIG. 9c

Alpha contig sequence

```
      GlyPhe Pro Gly Tyr Phe Leu Ile Val Gln Asp Tyr Ile Asp Pro Leu Arg Phe Gly Leu Leu Phe Glu Arg Phe Leu Asn Pro Gly Arg Val Ser Met Pro Asp Ile Asp
1301  GTTCCCGGGC TACTTCCTCA TCGTCCAAGGA CTACATCAAC TGGGCCCGGA GAAACGGGCGT CTCCGTGGGG CCCGGCAGGG GGAGCGCCGC CGGGAGCCTG
      CAAAGGGCCG ATGAAGGAGT AGCAGGTCCT GATGTAGTTG ACCCGGGCCT CTTTGCCGCA GAGGCACCCC GGGCCGTCCC CCTCGCGGCG GCCCTCGGAC

Val Ala Tyr Ala Val Gly Ile Thr Asn Ile Asp Pro Leu Arg Asp Arg Glu Arg Asp Arg Glu Arg Tyr Gly Glu Arg Lys Glu Asp Val Ala Gln Ile Gly Thr Leu Gly Ser Leu
1401  GTGGCCTACG CCGTGGGGAT CACCAACATT GACCCCCTGC GCTTCGGCCT CCTCTTTGAG CGCTTCCTGA ACCCCGAGAG GGTCTCCATG CCCGACATTG
      CACCGGATGC GGCACCCCTA GTGGTTGTAA CTGGGGGACG CGAAGCCGGA GGAGAAACTC GCGAAGGACT TGGGGCTCTC CCAGAGGTAC GGGCTGTAAC

Asp Thr Asp Phe Ser Asp Arg Glu Arg Asp Arg Glu Arg Asp Arg Glu Arg Tyr Gly Glu Arg Tyr Gly Glu Arg Asp Asn Gly Val Ala Gln Ile Gly Ile Arg His Pro Trp Lys Pro
1501  ACACGGACTT CTCCGACCGG GAGCGGGACC GGGTGATCCA GTACGTGCCG GAACGCTACG GCGAGGACAA GGTGGCCCAG ATCGGCACCC TGGGAAGCCT
      TGTGCCTGAA GAGGCTGGCC CTCGCCCTGG CCCACTAGGT CATGCACGGC CTTGCGATGC CGCTCCTGTT CCACCGGGTC TAGCCGTGGG ACCCTTCGGA

Leu Ala Ser Lys Ala Ala Leu Lys Asp Val Ala Arg Ala Tyr Gly Ile Pro His Lys Lys Ala Glu Glu Leu Ala Lys Leu Ile Pro Val Gln Phe Gly Lys
1601  CGGCTCCAAG GCCGCCCTCA AGGACGTGGC CCGGGCTCTAC GGCATCCCCC ACAAGAAGGC GGAGGAATTG GCCAAGCTCA TCCCGGTGCA GTTCGGGAAG
      GCGGAGGTTC CGGCGGGAGT TCCTGCACCG GGCCCAGATG CCGTAGGGGG GGTAGGGGGG TGTTCTTCCG CCTCCTTAAC CGGTTCGAGT AGGGCCACGT CAAGCCCTTC

Pro Lys Pro Leu Gln Glu Ala Ile Gln Val Val Pro Gly Leu Arg Ala Ala Glu Met Glu Lys Asp Pro Lys Val Arg Glu Val Leu Gly Val Ala Met Arg Leu
1701  CCCAAGCCCC TGCAGGAGGC CATCCAGGTG GTGCCGGAGC TTAGGGCGGA GATGGAGAAG GACCCCAAGG TGCGGGAGGT CCTCGAGGTG GCCATGCGCC
      GGGTTCGGGG ACGTCCTCCG GTAGGTCCAC CACGGCCTCG AATCCCGCCT CTACCCTTTC CTGGGGTTCC ACGCGCCTCCA GGAGCTCCAC CGGTACGCGG
```

*FIG. 9d*

Alpha contig sequence

```
       Leu Glu Gly Leu Asn Arg His Ala Ser Val His Ala Ala Ala Glu Pro Leu Thr Asp Leu Val Pro Leu Met Arg Asp Gln Glu Gly
1801   TGGAGGGCCT GAACCCGGTC GCCTCCGTCC ACGCCGCCAC GCGCCGGAGC CCCTCACGGA CCTCGTCCCC CTCATGCGGG ACCAGGAAGG
       ACCTCCCGGA CTTGGGCCAG CGGAGGCAGG TGCGGCGGTG CGCGGCCTCG GGGAGTGCCT GGAGCAGGGG GAGTACGCCC TGGTCCTTCC

Gly Arg Pro Val Thr Gln Tyr Asp Met Gly Ala Val Glu Ala Leu Gly Leu Leu Lys Met Asp Phe Leu Gly Leu Arg Thr Leu Arg Thr Phe Leu Asp Glu Val
1901   GCGGCCCGTC ACCCAGTACG ACATGGGGGC GGTGGAGGCC TTGGGCCTTT TGAAGATGGA CTTTTTGGGC CTCCGCACCC TCACCTTCCT GGACGAGGTC
       CGCCGGGCAG TGGGTCATGC TGTACCCCCG CCACCTCCGG AACCCGGAAA ACTTCTACCT GAAAAACCCG GAGGCGTGGG AGTGGAAGGA CCTGCTCCAG

Lys Arg Ile Val Lys Ala Ser Gln Gly Val Glu Leu Asp Tyr Asp Ala Leu Pro Leu Asp Pro Lys Thr Phe Ala Leu Leu Ser Arg Gly Glu Thr Lys
2001   AAGGGCATCG TCAAGGCGTC CCAGGGGGTG GAGCTGGACT ACGATGCCCT CCCCCTGGAC GACCCCAAGA CCTTCGCCCT CCTCTCCCGG GGGGAGACCA
       TTCCCGTAGC AGTTCCGCAG GGTCCCCCAC CTCGACCTGA TGCTACGGGA CTGGGGTTCT GGAAGCGGGA GGAGAGGGCC CCCCTCTGGT

Arg Gly Met Glu His Leu Glu Ser Gly Gly Met Thr Ala Thr Leu Arg Thr Tyr Ile Arg Arg His His Gly Leu Glu Pro Val Ser Tyr Ser Glu Phe Pro His Ala Glu Lys Tyr Leu Lys
2101   AGGGGGTCTT CCAGCTGGAG TCGGGGGGGA TGACCGCCAC GCTCCGCGGC CTCAAGCCGC GGGCGCTTTGA GGACCTGATC GCCATCCTCT CCCTCTACCG
       TCCCCCAGAA GGTCGACCTC AGCCCCCCCT ACTGGCGGTG CGAGGCGCCG GAGTTCGGCG CCGGCGAAACT CCTGGACTAG CGGTAGGAGA GGGAGATGGC

Arg Pro Gly Pro Met Glu His Ile Pro Thr Tyr Ile Arg Arg His His Gly Leu Glu Pro Val Ser Tyr Ser Glu Phe Pro His Ala Glu Lys Tyr Leu Lys
2201   CCCCGGGGCCC ATGGAGCACA TCCCCACCTA CATCCGCCGC CACCACGGGC TGGAGCCCGT GAGCTACAGC GAGTTTCCCC ACGCCGAGAA GTACCTAAAG
       GGGGCCCCGGG TACCTCGTGT AGGGGTGGAT GTAGGCGGCG GTGGTGCCCG ACCTCGGGCA CTCGATGTCG CTCAAAGGGG TGCGGCTCTT CATGGATTTC
```

FIG. 9e

Alpha contig sequence

```
     Pro Ile Leu Asp Glu Thr Tyr Gly Ile Pro Val Tyr Gln Glu Gln Ile Met Gln Ile Ala Ser Ala Val Ala Gly Tyr Ser Leu Gly Glu Ala Asp Leu Leu
2301 CCCATCCTGG ACGAGACCTA CGGCATCCCC GTCTACCAAG AGCAGATCAT GCAGATCGCC TCGGCCGTGG CGGGTACTC CCTGGGCGAG GCGGACCTCC
     GGGTAGGACC TGCTCTGGAT GCCGTAGGGG CAGATGGTCC CGTCTAGTA GCCCGGCACC GCCCCGCTC CGGGATGAG GGACCCGCTC CGCCTGGAGG

Leu Arg Arg Ala Met Gly Lys Lys Lys Leu Glu Glu Met Gln Lys His Arg Glu Arg Phe Val Gln Gly Ala Lys Glu Glu Arg Gly Val Pro Glu Glu Ala
2401 TCAGGGGGGC CATGGGGAAG AAGAAGCTGG AGGAGATGCA GAAGCACCGG GAGCGCTTCG TCCAGGGGGC CAAGGAAGG GGGTGCCCG AGGAGGAGGC
     AGTCCCGCCCG GTACCCCTTC TTCTTCGACC TCCTCTACGT CTTCGTGGCC CTCGCGAAGC AGGTCCCCCG GTTCCTTTCC CCCACGGGC TCCTCCTCCG

Ala Asn Arg Leu Phe Asp Met Leu Glu Ala Phe Ala Asn Tyr Gly Phe Asn Lys Ser His Ala Ala Ala Tyr Ser Leu Leu Ser Tyr Gln Thr Ala Tyr Val
2501 CAACCGGCTC TTTGACATGC TGGAGGCCTT CGCCAACTAC GGCTTCAACA AATCTCATGC AGCGGCCTAC AGCCTCCTCT CCTACCAGAC CGCCTACGTG
     GTTGGCCGAG AAACTGTACG ACCTCCGGAA GCGGTTGATG CCGAAGTTGT TTAGAGTACG TCGCCGGATG TCGGAGGAGA GGATGGTCTG GCGGATGCAC

Lys Ala His Tyr Pro Val Glu Phe Met Ala Ala Leu Ser Val Glu Arg His Asp Ser Asp Lys Val Ala Glu Tyr Ile Arg Asp Ala Arg Ala Met Gly
2601 AAGGCCCACT ACCCCGTGGA GTTCATGGCC GCCCTCTCT CCGTGGAGCG GCACGACTCC GACAAGGTGG CCGAGTACAT CCGGGACGCC CGGGCCATGG
     TTCCGGGTGA TGGGGCACCT CAAGTACCGG CGGGAGAGA GGCACCTCGC CGTGCTGAGG CTGTTCCACC GGCTCATGTA GGCCCTGCGG GCCCGGTACC
```

FIG. 9f

Alpha contig sequence

```
      Gly Ile Glu Val Leu Pro Pro Asp Val Asn Arg Ser Gly Phe Asp Phe Leu Val Gln Gly Arg Gln Ile Leu Phe Gly Leu Ser Ala Val Lys Asn Val Gly
2701  GCATAGAGGT CCTTCCCCCG GACGTCAACC GCTCCGGGTT GTCCAGGGCC GGCAGATCCT CTTCGGCCTC TCCGCGGGTGA AAAACGTGGG
      CGTATCTCCA GGAAGGGGGC CTGCAGTTGG CGAGGCCCAA ACTGAAAGAC CAGGTCCCGG CCGTCTAGGA GAAGCCGGAG AGGCGCCACT TTTTGCACCC

Gly Glu Ala Ala Ala Ile Leu Arg Glu Arg Arg Gly Gly Pro Tyr Arg Ser Leu Gly Asp Phe Leu Lys Arg Leu Asp Lys Val Leu Asn
2801  CGAGGCGGCG GCGGAGGCCA TTCTCCCGGA GCGGAGGCGG GGCGGCCCCT ACCGGAGCCT CGGGGACTTC CTCAAGCGGC TGGACGAGAA GGTGCTCAAC
      GCTCCGCCGC CGCCTCCGGT AAGAGGGCCT CGCCTCCGCC CCGCCGGGGA TGGCCTCGGA GCCCCTGAAG GAGTTCGCCG ACCTGCTCTT CCACGAGTTG

Lys Arg Thr Leu Glu Ser Leu Ile Lys Ala Gly Phe Gly Glu Arg Ala Arg Leu Leu Ala Ser Leu Gly Leu Leu Arg Trp Ala Ala
2901  AAGCGGACCC TGGAGTCCCT CATCAAGGCG GGTGCCCTGG ACGGCTTCGG GGAAAGGGCG CGGCTCCTCG CCTCCCTGGA GGGGCTCCTC AGGTGGGCGG
      TTCGCCTGGG ACCTCAGGGA GTAGTTCCGG CCACGGGACC TGCCGAAGCC CCTTTTCCCGC GCCGAGGAGC GGAGGGACCT CCCCGAGGAG TCCACCCGCC

Ala Glu Thr Arg Glu Lys Ala Arg Ser Gly Met Met Gly Leu Phe Ser Glu Val Glu Glu Pro Pro Leu Ala Glu Ala Ala Pro Leu Asp Glu Ile Thr Arg
3001  CCGAGACTCG GGAGAAGGCC CGCTCGGGCA TGATGGGCCT CTTCAGCGAA GTGGAGGAGC CGCCTTTGGC CGAGGCCGCC CCCCTGGACG AGATCACCCG
      GGCTCTGAGC CCTCTTCCGG GCGAGCCCGT ACTACCCGGA GAAGTCGCTT CACCTCCTCG GCGGAAACCG GCTCCGGCGG GGGGACCTGC TCTAGTGGGC
```

FIG. 9g

Alpha contig sequence

```
+3  Arg Leu Arg Tyr Glu Lys Glu Ala Leu Gly  Ile Tyr Val Ser Gly His Pro  Ile Leu Arg Tyr Pro Gly  Leu Arg Glu Thr  Ala Thr Cys Thr Leu Glu Glu
+2
+1
3101  GCTCCGCTAC GAAAAGGAGG CCCTGGGGAT TTATGTTTCC GGCCATCCCA TCTTGGGGTA TCCCGGGCTC CGGGAGACGG CCACCTGCAC CCTGGAGGAG
      CGAGGCGATG CTTTTCCTCC GGGACCCCTA AATACAAAGG CCGGTAGGGT AGAACGCCAT AGGGCCCGAG GCCCTCTGCC GGTGGACGTG GGACCTCCTC
-3
-2

+3  Leu Pro His Leu Ala Arg Asp Leu Pro Pro Arg Ser Arg Val Leu Leu Ala Gly Met Val Glu Glu Val Val Arg Lys Pro Thr Lys Ser Gly Gly Met Met
+2
+1
3201  CTTCCCCACC TGGCCCGGGA CCTGCCGCCC CGGTCTAGGG TCCTCCTCGC CGGCATGGTG GAGGAGGTGG TGCGCAAGCC CACGAAAAGC GGCGGGATGA
      GAAGGGGTGG ACCGGGCCCT GGACGGCGGG GCCAGATCCC AGGAGGAGCG GCCGTACCAC CTCCTCCACC ACGCGTTCGG GTGCTTTTCG CCGCCCTACT
-3
-2

+3  Met Ala Arg Phe Val Leu Ser Asp Glu Thr Gly Ala Leu Glu Ala Val Ala Phe Gly Arg Ala Tyr Asp Gln Val Ser Pro Arg Leu Lys Glu Asp Thr Pro
+2
+1
3301  TGGCCCGGCTT CGTCCTCTCC GACGAGACGG GGGCGCTTGA GGGCGGTGGC TTCGGCCGGG CCTACGACCA GGTCTCCCCG AGGCTCAAGG AGGACACCCC
      ACCGGGCCGAA GCAGGAGAGG CTGCTCTGCC CCCGCGAACT CCCGCCACCG AAGCCGGCCC GGATGCTGGT CCAGAGGGGC TCCGAGTTCC TCCTGTGGGG
-3
-2

+3  Pro Val Leu Val Leu Ala Glu Val Leu Glu Arg Glu Glu Gly Val Arg Gly Val Leu Ala Gln Ala Val Trp Thr Tyr Glu Glu Leu Glu Gln Val Pro Arg Ala
+2
+1
3401  CGTGCTCGTC CTCGCCGAGG TGGAGCGGGA GGAGGGGGGC GTGCGGGGTGC TGGCCCAGGC CGTTTGGACC TACGAGGAGC TGGAGCAGGT CCCCCGGGCC
      GCACGAGCAG GAGCGGCTCC ACCTCGCCCT GGAGCGCCCT CCTCCCCCCG CACGCCCCACG ACCGGGTCCG GCAAACCTGG ATGCTCCTCG ACCTCGTCCA GGGGCCCCGG
-2
```

FIG. 9h

Alpha contig sequence

```
      Leu Glu Val Glu Val Glu Ala Ser Leu Leu Asp Asp Arg Gly Val Ala His Leu Lys Ser Leu Leu Asp Glu His Ala Gly Thr Leu Pro Leu Tyr Val Arg
3501  CTCGAGGTGG AGGTGGAGGC CTCCCTCCTG GACGACCGGG GGGTGGCCCA CCTGAAAAGC CTCCTGGACG AGCACGCGGG GACCCTCCCC CTGTACGTCC
      GAGCTCCACC TCCACCTCCG GAGGGAGGAC CTGCTGGCCC CCCACCGGGT GGACTTTTCG GAGGACCTGC TCGTGCGCCC CTGGGAGGGG GACATGCAGG

Arg Val Gln Gly Ala Phe Gly Glu Ala Leu Leu Arg Glu Val Arg Gly Glu Val Gly Glu Ala Leu Ala Ala Leu Glu Ala Glu Gly Phe Arg Ala Tyr
3601  GGGTCCAGGG CGCCTTCGGC GAGGCCCTCC TCGCCCTGAG GGAGGTGCGG GTGGGGGAGG AGGCCTTGGC GGCCCTCGAG GCCGAGGGGT TCCGGGCCTA
      CCCAGGTCCC GCGGAAGCCG CTCCGGGAGG AGCGGGACTC CCTCCACGCC CACCCCCTCC TCCGGAACCG CCGGGAGCTC CGGCTCCCCA AGGCCCGGAT

Tyr Leu Pro Asp Arg Glu Val Leu Leu Gly Gln Gly Gly Gln Ala Gly Glu Ala Val Pro Phe         (SEQ ID NO: 10)
3701  CCTCCTGCCT GACCGGGAGG TCCTCCTCCA GGGCGGCCAG GCGGGAGGC CCCAGGAGGG GGTGCCCTTC TAGGGGGTGG GCCGTGAGAC AGGGTGCCAT
      GGAGGACGGA CTGGCCCTCC AGGAGGAGGT CCCGCCGGTC CCCGCCTCC GGGTCCTCCG CCACGGGAAG ATCCCCCACC CGGCACTCTG TCCCACGGTA

3801  CGTCCTCCCC GGGGGCAAGG AGGCCTGGGC CGAGCGCTTT GGGGTGGGGA GCAAGGCCCT CGTGCCCTAC CGGGCCCGGC CACTAGTGGT GGTGGTGGTC
      GCAGGAGGGG CCCCCGTTCC TCCGGACCCG GCTCGCGAAA CCCCACCCCT CGTTCCGGGA GCACGGGCCG GGCCGGCCG GTGATCACCA CCACCACCAG

3901  TGG (SEQ ID NO: 9)
      ACC (SEQ ID NO: 11)
```

FIG. 9i

Native Tth DNA Pol III Alpha Subunit
Max. Extension Rate: 240 b/sec

100 ng (5 U) Taq DNA Pol I
Max. Extension Rate: 34 b/sec

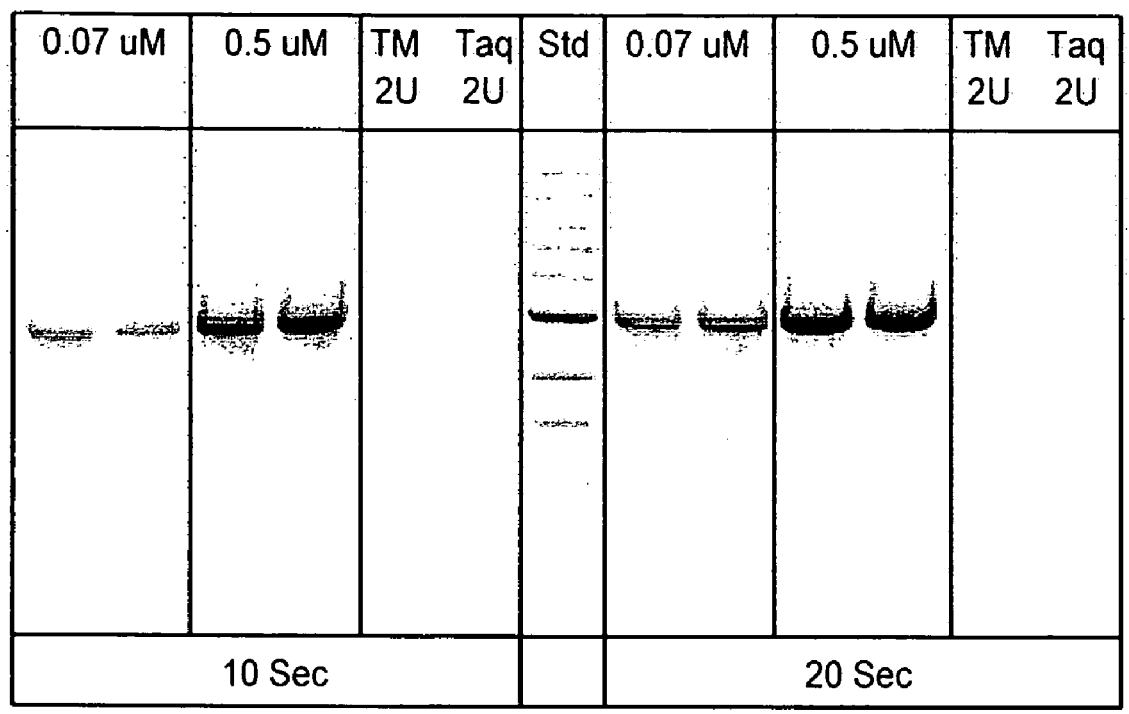
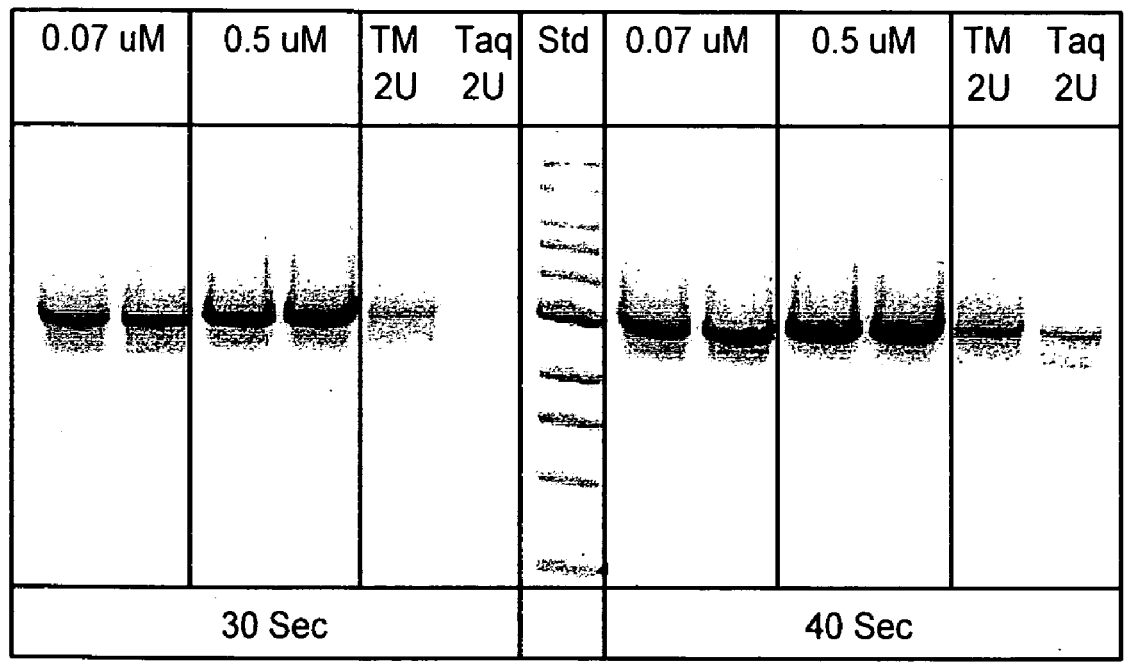
FIG. 18

Aquifex Alpha + beta PCR, pBSK Plasmid Template, + DnaB Helicase, Unmodified Primers

30 Cycles = 20 sec @ 90°C, 1 min @ 58°C, 1 min @ 70°C
Template: 3kb pBSK Plasmid

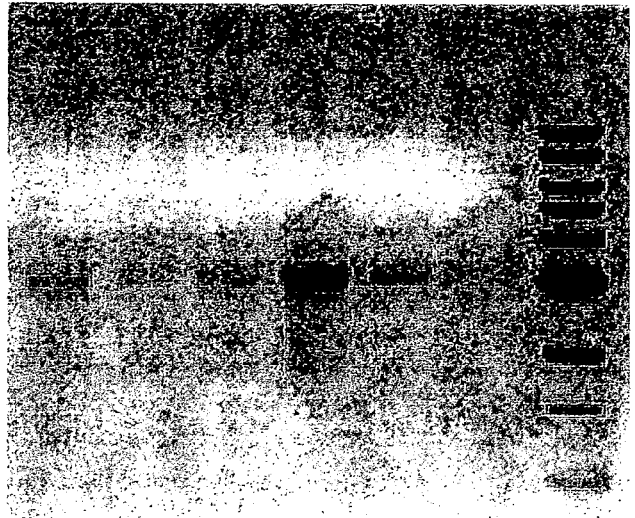

- PEG mw 20k 2% Sorbitol 15%
- PEG mw 20k 5% Sorbitol 10%
- PEG mw 20k 2% Sorbitol 10%
- PEG mw 20k 2% Sorbitol 10%, TMNO 1.1M
- PEG mw 8k 3% Sorbitol 15%
- No add Alpha + Beta

FIG. 23

Aquifex Complete Pol III Holoenzyme PCR of pBSK Plasmid + DnaB, Unmodified Primers

30 Cycles = 20 sec @ 90°C, 1 min @ 58°C, 1 min @ 70°C
Template: 3kb pBSK Plasmid

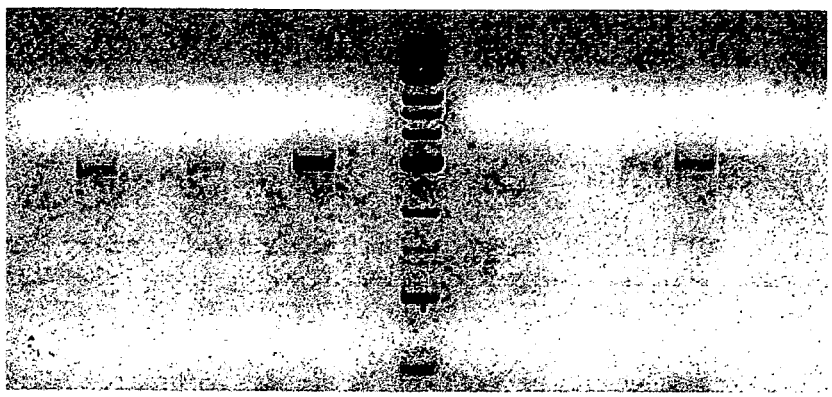

- PEG mw 20k 5% Sorbitol 15%
- PEG mw 20k 2% Sorbitol 10%
- PEG mw 8k 3%, Sorbitol 15%,
- PEG mw 20k 2%, Sorbitol 10%, TMNO 1.1M Holoenzyme Unmodified Primers    Holoenzyme + Thiol Primers

FIG. 24

SEQUENCE LISTING

```
<160> NUMBER OF SEQ ID NOS: 31

<210> SEQ ID NO 1
<211> LENGTH: 2067
<212> TYPE: PRT
<213> ORGANISM: Thermus thermophilus

<400> SEQUENCE: 1

Met Gly Arg Lys Leu Arg Phe Ala His Leu His Gln His Thr Gln Phe
1               5                   10                  15

Ser Leu Leu Asp Gly Ala Ala Lys Leu Ser Asp Leu Leu Lys Trp Val
            20                  25                  30

Lys Glu Thr Thr Pro Glu Asp Pro Ala Leu Ala Met Thr Asp His Gly
        35                  40                  45

Asn Leu Phe Gly Ala Val Glu Phe Tyr Lys Lys Ala Thr Glu Met Gly
    50                  55                  60

Ile Lys Pro Ile Leu Gly Tyr Glu Ala Tyr Val Ala Ala Glu Ser Arg
65                  70                  75                  80

Phe Asp Arg Lys Arg Gly Lys Gly Leu Asp Gly Gly Tyr Phe His Leu
                85                  90                  95

Thr Leu Leu Ala Lys Asp Phe Thr Gly Tyr Gln Asn Leu Val Arg Leu
            100                 105                 110

Ala Ser Arg Ala Tyr Leu Glu Gly Phe Tyr Glu Lys Pro Arg Ile Asp
        115                 120                 125

Arg Glu Ile Leu Arg Glu His Ala Glu Gly Leu Ile Ala Leu Ser Gly
    130                 135                 140

Cys Leu Gly Ala Glu Ile Pro Gln Phe Ile Leu Gln Asp Arg Leu Asp
145                 150                 155                 160

Leu Ala Glu Ala Arg Leu Asn Glu Tyr Leu Ser Ile Phe Lys Asp Arg
                165                 170                 175

Phe Phe Ile Glu Ile Gln Asn His Gly Leu Pro Glu Gln Lys Lys Val
            180                 185                 190

Asn Glu Val Leu Lys Glu Phe Ala Arg Lys Tyr Gly Leu Gly Met Val
        195                 200                 205

Ala Thr Asn Asp Gly His Tyr Val Arg Lys Glu Asp Ala Arg Ala His
    210                 215                 220

Glu Val Leu Leu Ala Ile Gln Ser Lys Ser Thr Leu Asp Asp Pro Gly
225                 230                 235                 240

Arg Trp Arg Phe Pro Cys Asp Glu Phe Tyr Val Lys Thr Pro Glu Glu
                245                 250                 255
```

-continued

```
Met Arg Ala Met Phe Pro Glu Glu Trp Gly Asp Glu Pro Phe Asp
            260                 265                 270

Asn Thr Val Glu Ile Ala Arg Met Cys Asn Val Glu Leu Pro Ile Gly
            275                 280                 285

Asp Lys Met Val Tyr Arg Ile Pro Arg Phe Pro Leu Pro Glu Gly Arg
            290                 295                 300

Thr Glu Ala Gln Tyr Leu Met Glu Leu Thr Phe Lys Gly Leu Leu Arg
305                 310                 315                 320

Arg Tyr Pro Asp Arg Ile Thr Glu Gly Phe Tyr Arg Glu Val Phe Arg
                325                 330                 335

Leu Leu Gly Lys Leu Pro Pro His Gly Asp Gly Glu Ala Leu Ala Glu
                340                 345                 350

Ala Leu Ala Gln Val Glu Arg Glu Ala Trp Glu Arg Leu Met Lys Ser
                355                 360                 365

Leu Pro Pro Leu Ala Gly Val Lys Glu Trp Thr Ala Glu Ala Ile Phe
            370                 375                 380

His Arg Ala Leu Tyr Glu Leu Ser Val Ile Glu Arg Met Gly Phe Pro
385                 390                 395                 400

Gly Tyr Phe Leu Ile Val Gln Asp Tyr Ile Asn Trp Ala Arg Arg Asn
                405                 410                 415

Gly Val Ser Val Gly Pro Gly Arg Gly Ser Ala Ala Gly Ser Leu Val
                420                 425                 430

Ala Tyr Ala Val Gly Ile Thr Asn Ile Asp Pro Leu Arg Phe Gly Leu
                435                 440                 445

Leu Phe Glu Arg Phe Leu Asn Pro Glu Arg Val Ser Met Pro Asp Ile
            450                 455                 460

Asp Thr Asp Phe Ser Arg Glu Arg Asp Arg Val Ile Gln Tyr Val
465                 470                 475                 480

Arg Glu Arg Tyr Gly Glu Asp Lys Val Ala Gln Ile Gly Thr Leu Gly
                485                 490                 495

Ser Leu Ala Ser Lys Ala Ala Leu Lys Asp Val Ala Arg Val Tyr Gly
                500                 505                 510

Ile Pro His Lys Lys Ala Glu Glu Leu Ala Lys Leu Ile Pro Val Gln
            515                 520                 525

Phe Gly Lys Pro Lys Pro Leu Gln Glu Ala Ile Gln Val Val Pro Glu
            530                 535                 540

Leu Arg Ala Glu Met Glu Lys Asp Pro Lys Val Arg Glu Val Leu Glu
545                 550                 555                 560

Val Ala Met Arg Leu Glu Gly Leu Asn Arg His Ala Ser Val His Ala
                565                 570                 575

Ala Gly Val Val Ile Ala Ala Glu Pro Leu Thr Asp Leu Val Pro Leu
                580                 585                 590

Met Arg Asp Gln Glu Gly Arg Pro Val Thr Gln Tyr Asp Met Gly Ala
            595                 600                 605

Val Glu Ala Leu Gly Leu Leu Lys Met Asp Phe Leu Gly Leu Arg Thr
            610                 615                 620

Leu Thr Phe Leu Asp Glu Val Lys Arg Ile Val Lys Ala Ser Gln Gly
625                 630                 635                 640

Val Glu Leu Asp Tyr Asp Ala Leu Pro Leu Asp Asp Pro Lys Thr Phe
                645                 650                 655

Ala Leu Leu Ser Arg Gly Glu Thr Lys Gly Val Phe Gln Leu Glu Ser
                660                 665                 670

Gly Gly Met Thr Ala Thr Leu Arg Gly Leu Lys Pro Arg Arg Phe Glu
```

```
                675                 680                 685
Asp Leu Ile Ala Ile Leu Ser Leu Tyr Arg Pro Gly Pro Met Glu His
690                 695                 700
Ile Pro Thr Tyr Ile Arg Arg His His Gly Leu Glu Pro Val Ser Tyr
705                 710                 715                 720
Ser Glu Phe Pro His Ala Glu Lys Tyr Leu Lys Pro Ile Leu Asp Glu
                725                 730                 735
Thr Tyr Gly Ile Pro Val Tyr Gln Glu Gln Ile Met Gln Ile Ala Ser
                740                 745                 750
Ala Val Ala Gly Tyr Ser Leu Gly Glu Ala Asp Leu Leu Arg Arg Cys
            755                 760                 765
Leu Ala Glu Gly Ser Leu Val Leu Asp Ala Ala Thr Gly Gln Arg Val
            770                 775                 780
Pro Ile Glu Lys Val Arg Pro Gly Met Glu Val Phe Ser Leu Gly Pro
785                 790                 795                 800
Asp Tyr Arg Leu Tyr Arg Val Pro Val Leu Glu Val Leu Glu Ser Gly
                805                 810                 815
Val Arg Glu Val Val Arg Leu Arg Thr Arg Ser Gly Arg Thr Leu Val
            820                 825                 830
Leu Thr Pro Asp His Pro Leu Leu Thr Pro Glu Gly Trp Lys Pro Leu
            835                 840                 845
Cys Asp Leu Pro Leu Gly Thr Pro Ile Ala Val Pro Ala Glu Leu Pro
850                 855                 860
Val Ala Gly His Leu Ala Pro Pro Glu Glu Arg Val Thr Leu Leu Ala
865                 870                 875                 880
Leu Leu Leu Gly Asp Gly Asn Thr Lys Leu Ser Gly Arg Arg Gly Thr
                885                 890                 895
Arg Pro Asn Ala Phe Phe Tyr Ser Lys Asp Pro Glu Leu Leu Ala Ala
                900                 905                 910
Tyr Arg Arg Cys Ala Glu Ala Leu Gly Ala Lys Val Lys Ala Tyr Val
            915                 920                 925
His Pro Thr Thr Gly Val Val Thr Leu Ala Thr Leu Ala Pro Arg Pro
            930                 935                 940
Gly Ala Gln Asp Pro Val Lys Arg Leu Val Val Glu Ala Gly Met Val
945                 950                 955                 960
Ala Lys Ala Glu Glu Lys Arg Val Pro Glu Val Phe Arg Tyr Arg
                965                 970                 975
Arg Glu Ala Leu Ala Leu Phe Leu Gly Arg Leu Phe Ser Thr Asp Gly
                980                 985                 990
Ser Val Glu Lys Lys Arg Ile Ser Tyr Ser Ser Ala Ser Leu Gly Leu
            995                 1000                1005
Ala Gln Asp Val Ala His Leu Leu Leu Arg Leu Gly Ile Thr Ser
        1010                1015                1020
Gln Leu Arg Ser Arg Gly Pro Arg Ala His Glu Val Leu Ile Ser
        1025                1030                1035
Gly Arg Glu Asp Ile Leu Arg Phe Ala Glu Leu Ile Gly Pro Tyr
        1040                1045                1050
Leu Leu Gly Ala Lys Arg Glu Arg Leu Ala Ala Leu Glu Ala Glu
        1055                1060                1065
Ala Arg Arg Arg Leu Pro Gly Gln Gly Trp His Leu Arg Leu Val
        1070                1075                1080
Leu Pro Ala Val Ala Tyr Arg Val Ser Glu Ala Lys Arg Arg Ser
        1085                1090                1095
```

```
Gly Phe Ser Trp Ser Glu Ala Gly Arg Arg Val Ala Val Ala Gly
1100                1105                1110

Ser Cys Leu Ser Ser Gly Leu Asn Leu Lys Leu Pro Arg Arg Tyr
1115                1120                1125

Leu Ser Arg His Arg Leu Ser Leu Leu Gly Glu Ala Phe Ala Asp
1130                1135                1140

Pro Gly Leu Glu Ala Leu Ala Glu Gly Gln Val Leu Trp Asp Pro
1145                1150                1155

Ile Val Ala Val Glu Pro Ala Gly Lys Ala Arg Thr Phe Asp Leu
1160                1165                1170

Arg Val Pro Pro Phe Ala Asn Phe Val Ser Glu Asp Leu Val Val
1175                1180                1185

His Asn Ser Met Gly Lys Lys Lys Val Glu Glu Met Lys Ser His
1190                1195                1200

Arg Glu Arg Phe Val Gln Gly Ala Lys Glu Arg Gly Val Pro Glu
1205                1210                1215

Glu Glu Ala Asn Arg Leu Phe Asp Met Leu Glu Ala Phe Ala Asn
1220                1225                1230

Tyr Gly Phe Asn Lys Cys Leu Pro Ala Arg Ala Arg Val Val Asp
1235                1240                1245

Trp Cys Thr Gly Arg Val Val Arg Val Gly Glu Ile Val Arg Gly
1250                1255                1260

Glu Ala Lys Gly Val Trp Val Val Ser Leu Asp Glu Ala Arg Leu
1265                1270                1275

Arg Leu Val Pro Arg Pro Val Val Ala Ala Phe Pro Ser Gly Lys
1280                1285                1290

Ala Gln Val Tyr Ala Leu Arg Thr Ala Thr Gly Arg Val Leu Glu
1295                1300                1305

Ala Thr Ala Asn His Pro Val Tyr Thr Pro Glu Gly Trp Arg Pro
1310                1315                1320

Leu Gly Thr Leu Ala Pro Gly Asp Tyr Val Ala Leu Pro Arg His
1325                1330                1335

Leu Ser Tyr Arg Pro Ser Leu His Leu Glu Gly His Glu Leu Asp
1340                1345                1350

Leu Leu Gly Phe Ala Leu Ala Glu Gly His Leu Arg His Pro Ser
1355                1360                1365

Gly Val Tyr Leu Tyr Thr Ser Ser Glu Glu Leu Ala Ala Met
1370                1375                1380

Glu Glu Ala Leu Arg Ala Phe Pro Asn Thr Arg Ile Arg Val Val
1385                1390                1395

Trp Arg Arg Gly Val Ala His Val Tyr Val Gly Arg Val Asp Arg
1400                1405                1410

Arg Gln Glu Ala Gly Ala Val Ala Phe Leu Arg Arg Met Gly Leu
1415                1420                1425

Leu Gly Leu Asp Ala Lys Thr Lys Arg Leu Pro Glu Ala Val Phe
1430                1435                1440

Gly Leu Pro Pro Glu Glu Val Ala Arg Phe Leu Gly Arg Leu Trp
1445                1450                1455

Thr Gly Asp Gly Gly Val Asp Pro Lys Gly Arg Leu Ile His Tyr
1460                1465                1470

Ala Thr Ala Ser Lys Glu Leu Ala Trp Gly Val Gln His Leu Leu
1475                1480                1485

Leu Arg Leu Gly Leu Gln Ser Arg Leu Val Glu Lys Arg Phe Ser
1490                1495                1500
```

```
Gly Gly Tyr Lys Gly Tyr Ala Val Tyr Leu Leu Gly Gly Leu Glu
    1505                1510                1515

Ala Ala Arg Arg Phe Ala Glu Thr Val Gly Pro Tyr Leu Val Gly
    1520                1525                1530

Lys Arg Arg Gln Asp Leu Glu Ala Leu Leu Ala Ser Trp Glu Lys
    1535                1540                1545

Ala Gly Arg Ser Thr Gly Asp Val Leu Pro Leu Ala Phe Leu Glu
    1550                1555                1560

Glu Val Arg Ala Ala Val Ala Glu Val Ala Gln Gly Gln Val Ala
    1565                1570                1575

Asp Leu Leu Arg Glu Ala Gly Leu Ala Glu Gly Leu Leu Cys Leu
    1580                1585                1590

Gly Arg Gly Arg Arg Gly Leu Ser Arg Ala Thr Val Gly Arg Leu
    1595                1600                1605

Ala Ala Leu Thr Gly Ser Leu Ala Leu Leu Arg Leu Ala Glu Ala
    1610                1615                1620

Glu Val Tyr Trp Asp Arg Val Glu Ala Val Glu Pro Leu Gly Glu
    1625                1630                1635

Glu Glu Val Phe Asp Leu Thr Val Glu Gly Thr His Thr Phe Val
    1640                1645                1650

Ala Glu Asp Val Ile Val His Asn Ser His Ala Ala Ala Tyr Ser
    1655                1660                1665

Leu Leu Ser Tyr Gln Thr Ala Tyr Val Lys Ala His Tyr Pro Val
    1670                1675                1680

Glu Phe Met Ala Ala Leu Leu Ser Val Glu Arg His Asp Ser Asp
    1685                1690                1695

Lys Val Ala Glu Tyr Ile Arg Asp Ala Arg Ala Met Gly Ile Glu
    1700                1705                1710

Val Leu Pro Pro Asp Val Asn Arg Ser Gly Phe Asp Phe Leu Val
    1715                1720                1725

Gln Gly Arg Gln Ile Leu Phe Gly Leu Ser Ala Val Lys Asn Val
    1730                1735                1740

Gly Glu Ala Ala Ala Glu Ala Ile Leu Arg Glu Arg Glu Arg Gly
    1745                1750                1755

Gly Pro Tyr Arg Ser Leu Gly Asp Phe Leu Lys Arg Leu Asp Glu
    1760                1765                1770

Lys Val Leu Asn Lys Arg Thr Leu Glu Phe Leu Ile Lys Ala Gly
    1775                1780                1785

Ala Leu Asp Gly Phe Gly Glu Arg Ala Arg Leu Leu Ala Ser Leu
    1790                1795                1800

Glu Gly Leu Leu Lys Trp Ala Ala Glu Asn Arg Glu Lys Ala Arg
    1805                1810                1815

Ser Gly Met Met Gly Leu Phe Ser Glu Val Glu Glu Pro Pro Leu
    1820                1825                1830

Ala Glu Ala Ala Pro Leu Asp Glu Ile Thr Arg Leu Arg Tyr Glu
    1835                1840                1845

Lys Glu Ala Leu Gly Ile Tyr Val Ser Gly His Pro Ile Leu Arg
    1850                1855                1860

Tyr Pro Gly Leu Arg Glu Thr Ala Thr Cys Thr Leu Glu Glu Leu
    1865                1870                1875

Pro His Leu Ala Arg Asp Leu Pro Pro Arg Ser Arg Val Leu Leu
    1880                1885                1890

Ala Gly Met Val Glu Glu Val Val Arg Lys Pro Thr Lys Ser Gly
```

```
                  1895                1900                1905

Gly Met Met Ala Arg Phe Val Leu Ser Asp Glu Thr Gly Ala Leu
        1910                1915                1920

Glu Ala Val Ala Phe Gly Arg Ala Tyr Asp Gln Val Ser Pro Arg
        1925                1930                1935

Leu Lys Glu Asp Thr Pro Val Leu Val Leu Ala Glu Val Glu Arg
        1940                1945                1950

Glu Glu Gly Gly Val Arg Val Leu Ala Gln Ala Val Trp Thr Tyr
        1955                1960                1965

Glu Glu Leu Glu Gln Val Pro Arg Ala Leu Glu Val Glu Val Glu
        1970                1975                1980

Ala Ser Leu Leu Asp Asp Arg Gly Val Ala His Leu Lys Ser Leu
        1985                1990                1995

Leu Asp Glu His Ala Gly Thr Leu Pro Leu Tyr Val Arg Val Gln
        2000                2005                2010

Gly Ala Phe Gly Glu Ala Leu Leu Ala Leu Arg Glu Val Arg Val
        2015                2020                2025

Gly Glu Glu Ala Leu Gly Ala Leu Glu Ala Ala Gly Phe Arg Ala
        2030                2035                2040

Tyr Leu Leu Pro Asp Arg Glu Val Leu Leu Gln Gly Gly Gln Ala
        2045                2050                2055

Gly Glu Ala Gln Glu Ala Val Pro Phe
        2060                2065

<210> SEQ ID NO 2
<211> LENGTH: 1161
<212> TYPE: PRT
<213> ORGANISM: Aquifex aeolicus

<400> SEQUENCE: 2

Met Ser Lys Asp Phe Val His Leu His Leu His Thr Gln Phe Ser Leu
1               5                   10                  15

Leu Asp Gly Ala Ile Lys Ile Asp Glu Leu Val Lys Lys Ala Lys Glu
            20                  25                  30

Tyr Gly Tyr Lys Ala Val Gly Met Ser Asp His Gly Asn Leu Phe Gly
        35                  40                  45

Ser Tyr Lys Phe Tyr Lys Ala Leu Lys Ala Glu Gly Ile Lys Pro Ile
    50                  55                  60

Ile Gly Met Glu Ala Tyr Phe Thr Thr Gly Ser Arg Phe Asp Arg Lys
65                  70                  75                  80

Thr Lys Thr Ser Glu Asp Asn Ile Thr Asp Lys Tyr Asn His His Leu
                85                  90                  95

Ile Leu Ile Ala Lys Asp Asp Lys Gly Leu Lys Asn Leu Met Lys Leu
            100                 105                 110

Ser Thr Leu Ala Tyr Lys Glu Gly Phe Tyr Tyr Lys Pro Arg Ile Asp
        115                 120                 125

Tyr Glu Leu Leu Glu Lys Tyr Gly Glu Gly Leu Ile Ala Leu Thr Ala
    130                 135                 140

Cys Leu Lys Gly Val Pro Thr Tyr Tyr Ala Ser Ile Asn Glu Val Lys
145                 150                 155                 160

Lys Ala Glu Glu Trp Val Lys Lys Phe Lys Asp Ile Phe Gly Asp Asp
                165                 170                 175

Leu Tyr Leu Glu Leu Gln Ala Asn Asn Ile Pro Glu Gln Glu Val Ala
            180                 185                 190

Asn Arg Asn Leu Ile Glu Ile Ala Lys Lys Tyr Asp Val Lys Leu Ile
```

```
                195                 200                 205
Ala Thr Gln Asp Ala His Tyr Leu Asn Pro Glu Asp Arg Tyr Ala His
210                 215                 220
Thr Val Leu Met Ala Leu Gln Met Lys Lys Thr Ile His Glu Leu Ser
225                 230                 235                 240
Ser Gly Asn Phe Lys Cys Ser Asn Glu Asp Leu His Phe Ala Pro Pro
                245                 250                 255
Glu Tyr Met Trp Lys Lys Phe Glu Gly Lys Phe Glu Gly Trp Glu Lys
                260                 265                 270
Ala Leu Leu Asn Thr Leu Glu Val Met Glu Lys Thr Ala Asp Ser Phe
                275                 280                 285
Glu Ile Phe Glu Asn Ser Thr Tyr Leu Leu Pro Lys Tyr Asp Val Pro
290                 295                 300
Pro Asp Lys Thr Leu Glu Glu Tyr Leu Arg Glu Leu Ala Tyr Lys Gly
305                 310                 315                 320
Leu Arg Gln Arg Ile Glu Arg Gly Gln Ala Lys Asp Thr Lys Glu Tyr
                325                 330                 335
Trp Glu Arg Leu Glu Tyr Glu Leu Glu Val Ile Asn Lys Met Gly Phe
                340                 345                 350
Ala Gly Tyr Phe Leu Ile Val Gln Asp Phe Ile Asn Trp Ala Lys Lys
                355                 360                 365
Asn Asp Ile Pro Val Gly Pro Gly Arg Gly Ser Ala Gly Gly Ser Leu
370                 375                 380
Val Ala Tyr Ala Ile Gly Ile Thr Asp Val Asp Pro Ile Lys His Gly
385                 390                 395                 400
Phe Leu Phe Glu Arg Phe Leu Asn Pro Glu Arg Val Ser Met Pro Asp
                405                 410                 415
Ile Asp Val Asp Phe Cys Gln Asp Asn Arg Glu Lys Val Ile Glu Tyr
                420                 425                 430
Val Arg Asn Lys Tyr Gly His Asp Asn Val Ala Gln Ile Ile Thr Tyr
                435                 440                 445
Asn Val Met Lys Ala Lys Gln Thr Leu Arg Asp Val Ala Arg Ala Met
450                 455                 460
Gly Leu Pro Tyr Ser Thr Ala Asp Lys Leu Ala Lys Leu Ile Pro Gln
465                 470                 475                 480
Gly Asp Val Gln Gly Thr Trp Leu Ser Leu Glu Glu Met Tyr Lys Thr
                485                 490                 495
Pro Val Glu Glu Leu Leu Gln Lys Tyr Gly Glu His Arg Thr Asp Ile
                500                 505                 510
Glu Asp Asn Val Lys Lys Phe Arg Gln Ile Cys Glu Glu Ser Pro Glu
                515                 520                 525
Ile Lys Gln Leu Val Glu Thr Ala Leu Lys Leu Glu Gly Leu Thr Arg
530                 535                 540
His Thr Ser Leu His Ala Ala Gly Val Val Ile Ala Pro Lys Pro Leu
545                 550                 555                 560
Ser Glu Leu Val Pro Leu Tyr Tyr Asp Lys Glu Gly Glu Val Ala Thr
                565                 570                 575
Gln Tyr Asp Met Val Gln Leu Glu Glu Leu Gly Leu Leu Lys Met Asp
                580                 585                 590
Phe Leu Gly Leu Lys Thr Leu Thr Glu Leu Lys Leu Met Lys Glu Leu
                595                 600                 605
Ile Lys Glu Arg His Gly Val Asp Ile Asn Phe Leu Glu Leu Pro Leu
610                 615                 620
```

-continued

```
Asp Asp Pro Lys Val Tyr Lys Leu Leu Gln Glu Gly Lys Thr Thr Gly
625                 630                 635                 640

Val Phe Gln Leu Glu Ser Arg Gly Met Lys Glu Leu Leu Lys Lys Leu
            645                 650                 655

Lys Pro Asp Ser Phe Asp Ile Val Ala Val Leu Ala Leu Tyr Arg
                660                 665                 670

Pro Gly Pro Leu Lys Ser Gly Leu Val Asp Thr Tyr Ile Lys Arg Lys
                675                 680                 685

His Gly Lys Glu Pro Val Glu Tyr Pro Phe Pro Glu Leu Glu Pro Val
            690                 695                 700

Leu Lys Glu Thr Tyr Gly Val Ile Val Tyr Gln Glu Gln Val Met Lys
705                 710                 715                 720

Met Ser Gln Ile Leu Ser Gly Phe Thr Pro Gly Glu Ala Asp Thr Leu
                725                 730                 735

Arg Lys Ala Ile Gly Lys Lys Ala Asp Leu Met Ala Gln Met Lys
                740                 745                 750

Asp Lys Phe Ile Gln Gly Ala Val Glu Arg Gly Tyr Pro Glu Glu Lys
            755                 760                 765

Ile Arg Lys Leu Trp Glu Asp Ile Glu Lys Phe Ala Ser Tyr Ser Phe
770                 775                 780

Asn Lys Ser His Ser Val Ala Tyr Gly Tyr Ile Ser Tyr Trp Thr Ala
785                 790                 795                 800

Tyr Val Lys Ala His Tyr Pro Ala Glu Phe Phe Ala Val Lys Leu Thr
                805                 810                 815

Thr Glu Lys Asn Asp Asn Lys Phe Leu Asn Leu Ile Lys Asp Ala Lys
                820                 825                 830

Leu Phe Gly Phe Glu Ile Leu Pro Pro Asp Ile Asn Lys Ser Asp Val
            835                 840                 845

Gly Phe Thr Ile Glu Gly Glu Asn Arg Ile Arg Phe Gly Leu Ala Arg
            850                 855                 860

Ile Lys Gly Val Gly Glu Thr Ala Lys Ile Ile Val Glu Ala Arg
865                 870                 875                 880

Lys Lys Tyr Lys Gln Phe Lys Gly Leu Ala Asp Phe Ile Asn Lys Thr
                885                 890                 895

Lys Asn Arg Lys Ile Asn Lys Val Val Glu Ala Leu Val Lys Ala
            900                 905                 910

Gly Ala Phe Asp Phe Thr Lys Lys Arg Lys Glu Leu Leu Ala Lys
            915                 920                 925

Val Ala Asn Ser Glu Lys Ala Leu Met Ala Thr Gln Asn Ser Leu Phe
930                 935                 940

Gly Ala Pro Lys Glu Glu Val Glu Glu Leu Asp Pro Leu Lys Leu Glu
945                 950                 955                 960

Lys Glu Val Leu Gly Phe Tyr Ile Ser Gly His Pro Leu Asp Asn Tyr
                965                 970                 975

Glu Lys Leu Leu Lys Asn Arg Tyr Thr Pro Ile Glu Asp Leu Glu Glu
            980                 985                 990

Trp Asp Lys Glu Ser Glu Ala Val Leu Thr Gly Val Ile Thr Glu Leu
            995                 1000                1005

Lys Val Lys Lys Thr Lys Asn Gly Asp Tyr Met Ala Val Phe Asn
    1010                1015                1020

Leu Val Asp Lys Thr Gly Leu Ile Glu Cys Val Val Phe Pro Gly
    1025                1030                1035

Val Tyr Glu Glu Ala Lys Glu Leu Ile Glu Glu Asp Arg Val Val
    1040                1045                1050
```

Val Val Lys Gly Phe Leu Asp Glu Asp Leu Glu Thr Glu Asn Val
1055                1060                1065

Lys Phe Val Val Lys Glu Val Phe Ser Pro Glu Glu Phe Ala Lys
1070                1075                1080

Glu Met Arg Asn Thr Leu Tyr Ile Phe Leu Lys Arg Glu Gln Ala
1085                1090                1095

Leu Asn Gly Val Ala Glu Lys Leu Lys Gly Ile Ile Glu Asn Asn
1100                1105                1110

Arg Thr Glu Asp Gly Tyr Asn Leu Val Leu Thr Val Asp Leu Gly
1115                1120                1125

Asp Tyr Phe Val Asp Leu Ala Leu Pro Gln Asp Met Lys Leu Lys
1130                1135                1140

Ala Asp Arg Lys Val Val Glu Glu Ile Glu Lys Leu Gly Val Lys
1145                1150                1155

Val Ile Ile
1160

<210> SEQ ID NO 3
<211> LENGTH: 1173
<212> TYPE: PRT
<213> ORGANISM: Pseudomonas aeruginosa

<400> SEQUENCE: 3

Met Thr Val Ser Phe Val His Leu Arg Leu His Thr Glu Phe Ser Leu
1                5                10                15

Val Asp Gly Leu Val Arg Val Lys Pro Leu Ala Lys Ala Val Ala Gly
                20                25                30

Leu Gly Met Pro Ala Val Ala Val Thr Asp Gln Ser Asn Met Cys Ser
            35                40                45

Leu Val Lys Phe Tyr Lys Thr Ala Met Gly Ala Gly Ile Lys Pro Ile
    50                55                60

Cys Gly Ala Asp Ile Trp Leu Ala Ser Arg Glu Glu Asp Gly Pro Leu
65                70                75                80

Ser Arg Leu Ser Leu Leu Ala Met Asn Ala Lys Gly Tyr Arg Asn Leu
                85                90                95

Thr Glu Leu Ile Ser Arg Gly Trp Ser Glu Gly Gln Arg Asn Gly Glu
            100                105                110

Ile Ile Ile Glu Arg Asp Trp Val Lys Glu Ala Ala Glu Gly Leu Ile
    115                120                125

Ala Leu Ser Ala Ala Lys Glu Gly Glu Ile Gly His Ala Leu Leu Asp
130                135                140

Gly Glu Glu Ala Lys Ala Glu Ala Leu Leu Arg Glu Trp Met Glu Val
145                150                155                160

Phe Pro Glu Arg Phe Tyr Val Glu Val Gln Arg Thr Ser Arg Val Asn
                165                170                175

Asp Glu Glu His Leu His Ala Val Ala Leu Ala Ser Arg Cys Asn
            180                185                190

Ala Pro Leu Val Ala Thr Asn Asp Val Arg Phe Ile Lys Gln Glu Asp
    195                200                205

Phe Glu Ala His Glu Thr Arg Val Cys Ile Gly Glu Gly Arg Thr Leu
210                215                220

Asp Asp Pro Arg Arg Pro Arg Thr Tyr Ser Asp Gln Gln Tyr Leu Lys
225                230                235                240

Ser Pro Ala Glu Met Ala Glu Leu Phe Ser Asp Leu Pro Glu Ala Leu
                245                250                255

```
Glu Asn Thr Val Glu Ile Ala Lys Arg Cys Asn Ile Glu Val Gln Leu
                260                 265                 270

Gly Lys Tyr Phe Leu Pro Asp Phe Pro Thr Pro Asn Gly Met Gly Ile
            275                 280                 285

Asp Asp Tyr Leu Arg His Ala Ser Phe Glu Gly Leu Glu Glu Arg Leu
        290                 295                 300

Glu Val Leu Leu Pro Lys Asp Thr Pro Asp Tyr Glu Ala Lys Arg Gln
305                 310                 315                 320

Val Tyr Val Asp Arg Leu Asn Phe Glu Leu Asp Ile Ile Gln Met
                325                 330                 335

Gly Phe Pro Gly Tyr Phe Leu Ile Val Met Asp Phe Ile Lys Trp Ala
                340                 345                 350

Lys Asn Asn Gly Val Pro Val Gly Pro Gly Arg Gly Ser Gly Ala Gly
                355                 360                 365

Ser Leu Val Ala Tyr Val Leu Lys Ile Thr Asp Leu Asp Pro Leu Ala
        370                 375                 380

Tyr Asp Leu Leu Phe Glu Arg Phe Leu Asn Pro Glu Arg Ile Ser Met
385                 390                 395                 400

Pro Asp Phe Asp Val Asp Phe Cys Met Glu Gly Arg Asp Arg Val Ile
                405                 410                 415

Asp Tyr Val Ala Asp Ala Tyr Gly Arg Asn Ala Val Ser Gln Ile Ile
                420                 425                 430

Thr Phe Gly Thr Met Ala Ala Lys Ala Val Val Arg Asp Val Ala Arg
            435                 440                 445

Val Gln Gly Lys Ser Tyr Gly Leu Ala Asp Arg Leu Ser Lys Met Ile
        450                 455                 460

Pro Phe Glu Val Gly Met Thr Leu Asp Lys Ala Tyr Glu Gln Glu Glu
465                 470                 475                 480

Met Leu Arg Asp Phe Leu Lys Ser Asp Glu Glu Ala Ala Glu Ile Trp
                485                 490                 495

Glu Met Ala Leu Lys Leu Glu Gly Ile Thr Arg Gly Thr Gly Lys His
            500                 505                 510

Ala Gly Gly Val Val Ile Ala Pro Thr Lys Leu Thr Asp Phe Ser Pro
        515                 520                 525

Ile Ala Cys Asp Glu Glu Gly Gly Leu Val Thr Gln Phe Asp Lys
        530                 535                 540

Asp Asp Val Glu Ala Ala Gly Leu Val Lys Phe Asp Phe Leu Gly Leu
545                 550                 555                 560

Arg Thr Leu Thr Ile Ile Lys Trp Ala Met Glu Ile Ile Asn Arg Glu
                565                 570                 575

Gln Ala Lys Lys Gly Leu Glu Pro Val Asn Ile Asp Phe Ile Pro Leu
            580                 585                 590

Asp Asp Lys Pro Thr Tyr Ser Leu Leu Gln Lys Ala Glu Thr Thr Ala
        595                 600                 605

Val Phe Gln Leu Glu Ser Arg Gly Met Lys Glu Leu Ile Lys Lys Leu
        610                 615                 620

Lys Pro Asp Cys Leu Glu Asp Leu Ile Ala Leu Val Ala Leu Phe Arg
625                 630                 635                 640

Pro Gly Pro Leu Gln Ser Gly Met Val Asp Asp Phe Ile Asn Arg Lys
                645                 650                 655

His Gly Arg Ala Glu Leu Ser Tyr Pro His Pro Asp Tyr Gln Tyr Ala
            660                 665                 670

Gly Leu Glu Pro Val Leu Lys Pro Thr Tyr Gly Ile Ile Leu Tyr Gln
```

```
                675                 680                 685
Glu Gln Val Met Gln Ile Ala Gln Val Met Ala Gly Tyr Thr Leu Gly
            690                 695                 700
Gly Ala Asp Met Leu Arg Arg Ala Met Gly Lys Lys Pro Glu Glu
705                 710                 715                 720
Met Ala Lys Gln Arg Gly Gly Phe Ile Glu Gly Cys Lys Asn Asn Gly
                725                 730                 735
Ile Asp Ala Asp Leu Ala Gly Asn Ile Phe Asp Leu Val Glu Lys Phe
            740                 745                 750
Ala Gly Tyr Gly Phe Asn Lys Ser His Ser Ala Ala Tyr Gly Leu Val
            755                 760                 765
Ser Tyr Gln Thr Ala Trp Leu Lys Thr His Phe Pro Ala Pro Phe Met
    770                 775                 780
Ala Ala Val Leu Thr Ala Asp Met Gln Asn Thr Asp Lys Val Val Thr
785                 790                 795                 800
Leu Ile Glu Glu Cys Arg His Met Lys Leu Arg Ile Val Ala Pro Asp
                805                 810                 815
Val Asn Asn Ser Glu Phe Arg Phe Thr Val Asp Asp Gly Arg Ile
            820                 825                 830
Val Tyr Gly Leu Gly Ala Ile Lys Gly Val Gly Glu Gly Pro Val Glu
            835                 840                 845
Ala Ile Thr Glu Cys Arg Ala Glu Gly Gly Pro Phe Asn Thr Leu Phe
    850                 855                 860
Asp Phe Cys Asp Arg Val Asp Leu Lys Arg Ile Asn Lys Arg Thr Leu
865                 870                 875                 880
Glu Ala Leu Ile Arg Ala Gly Ala Leu Asp Arg Leu Gly Pro His Tyr
                885                 890                 895
His Asp Glu Leu Lys Ala Tyr Gln Ala Thr Val Asp Leu Asn Arg Ala
            900                 905                 910
Val Leu Leu Ala Ala Met Glu Glu Ala Ile Gln Ala Ala Glu Gln Thr
            915                 920                 925
Ala Arg Ser His Asp Ser Gly His Met Asp Leu Phe Gly Gly Val Phe
    930                 935                 940
Ala Glu Pro Glu Ala Asp Val Tyr Ala Asn His Arg Lys Val Lys Glu
945                 950                 955                 960
Leu Thr Leu Lys Glu Arg Leu Lys Gly Glu Lys Asp Thr Leu Gly Leu
                965                 970                 975
Tyr Leu Thr Gly His Pro Ile Asp Glu Tyr Glu Gly Glu Val Arg Arg
            980                 985                 990
Phe Ala Arg Gln Arg Ile Val Glu Leu Lys Pro Ala Arg Asp Thr Gln
    995                 1000                1005
Thr Val Ala Gly Leu Ile Val Asn Leu Arg Val Met Lys Asn Lys
    1010                1015                1020
Lys Gly Asp Lys Met Gly Phe Val Thr Leu Asp Asp Arg Ser Gly
    1025                1030                1035
Arg Ile Glu Ala Ser Leu Phe Ser Glu Ala Phe Ala Ala Ala Gln
    1040                1045                1050
Ser Leu Leu Gln Thr Asp Ala Leu Val Val Val Glu Gly Glu Val
    1055                1060                1065
Ser Gln Asp Asp Phe Ser Gly Gly Leu Arg Leu Arg Ala Lys Arg
    1070                1075                1080
Val Met Ser Leu Glu Glu Ala Arg Thr Gly Leu Ala Glu Ser Leu
    1085                1090                1095
```

```
Arg  Met  Lys  Leu  His  Ala  Asp  Leu  Leu  Lys  Gly  Asp  Arg  Leu  Arg
     1100                1105                1110

Trp  Leu  Gly  Glu  Leu  Phe  Asn  Arg  His  Arg  Gly  Ser  Cys  Pro  Ile
     1115                1120                1125

Thr  Leu  Asp  Tyr  Thr  Ser  Ala  Asp  Ala  Lys  Ala  Leu  Leu  Gln  Phe
     1130                1135                1140

Gly  Glu  Ser  Trp  Arg  Val  Asp  Pro  Ala  Asp  Asp  Leu  Ile  Gln  Ala
     1145                1150                1155

Leu  Arg  Asp  Gln  Phe  Gly  Arg  Asp  Asn  Val  Phe  Leu  Asn  Tyr  Arg
     1160                1165                1170

<210> SEQ ID NO 4
<211> LENGTH: 1160
<212> TYPE: PRT
<213> ORGANISM: Escherichia coli

<400> SEQUENCE: 4

Met  Ser  Glu  Pro  Arg  Phe  Val  His  Leu  Arg  Val  His  Ser  Asp  Tyr  Ser
1                   5                   10                  15

Met  Ile  Asp  Gly  Leu  Ala  Lys  Thr  Ala  Pro  Leu  Val  Lys  Lys  Ala  Ala
                20                  25                  30

Ala  Leu  Gly  Met  Pro  Ala  Leu  Ala  Ile  Thr  Asp  Phe  Thr  Asn  Leu  Cys
                35                  40                  45

Gly  Leu  Val  Lys  Phe  Tyr  Gly  Ala  Gly  His  Gly  Ala  Gly  Ile  Lys  Pro
            50                  55                  60

Ile  Val  Gly  Ala  Asp  Phe  Asn  Val  Gln  Cys  Asp  Leu  Leu  Gly  Asp  Glu
65                  70                  75                  80

Leu  Thr  His  Leu  Thr  Val  Leu  Ala  Ala  Asn  Asn  Thr  Gly  Tyr  Gln  Asn
                85                  90                  95

Leu  Thr  Leu  Leu  Ile  Ser  Lys  Ala  Tyr  Gln  Arg  Gly  Tyr  Gly  Ala  Ala
                100                 105                 110

Gly  Pro  Ile  Ile  Asp  Arg  Asp  Trp  Leu  Ile  Glu  Leu  Asn  Glu  Gly  Leu
                115                 120                 125

Ile  Leu  Leu  Ser  Gly  Gly  Arg  Met  Gly  Asp  Val  Gly  Arg  Ser  Leu  Leu
        130                 135                 140

Arg  Gly  Asn  Ser  Ala  Leu  Val  Asp  Glu  Cys  Val  Ala  Phe  Tyr  Glu  Glu
145                 150                 155                 160

His  Phe  Pro  Asp  Arg  Tyr  Phe  Leu  Glu  Leu  Ile  Arg  Thr  Gly  Arg  Pro
                165                 170                 175

Asp  Glu  Glu  Ser  Tyr  Leu  His  Ala  Ala  Val  Glu  Leu  Ala  Glu  Ala  Arg
                180                 185                 190

Gly  Leu  Pro  Val  Val  Ala  Thr  Asn  Asp  Val  Arg  Phe  Ile  Asp  Ser  Ser
            195                 200                 205

Asp  Phe  Asp  Ala  His  Glu  Ile  Arg  Val  Ala  Ile  His  Asp  Gly  Phe  Thr
        210                 215                 220

Leu  Asp  Asp  Pro  Lys  Arg  Pro  Arg  Asn  Tyr  Ser  Pro  Gln  Gln  Tyr  Met
225                 230                 235                 240

Arg  Ser  Glu  Glu  Glu  Met  Cys  Glu  Leu  Phe  Ala  Asp  Ile  Pro  Glu  Ala
                245                 250                 255

Leu  Ala  Asn  Thr  Val  Glu  Ile  Ala  Lys  Arg  Cys  Asn  Val  Thr  Val  Arg
                260                 265                 270

Leu  Gly  Glu  Tyr  Phe  Leu  Pro  Gln  Phe  Pro  Thr  Gly  Asp  Met  Ser  Thr
                275                 280                 285

Glu  Asp  Tyr  Leu  Val  Lys  Arg  Ala  Lys  Glu  Gly  Leu  Glu  Glu  Arg  Leu
            290                 295                 300
```

-continued

```
Ala Phe Leu Phe Pro Asp Glu Glu Arg Leu Lys Arg Arg Pro Glu
305                 310                 315                 320

Tyr Asp Glu Arg Leu Glu Thr Glu Leu Gln Val Ile Asn Gln Met Gly
            325                 330                 335

Phe Pro Gly Tyr Phe Leu Ile Val Met Glu Phe Ile Gln Trp Ser Lys
        340                 345                 350

Asp Asn Gly Val Pro Val Gly Pro Gly Arg Gly Ser Gly Ala Gly Ser
    355                 360                 365

Leu Val Ala Tyr Ala Leu Lys Ile Thr Asp Leu Asp Pro Leu Glu Phe
370                 375                 380

Asp Leu Leu Phe Glu Arg Phe Leu Asn Pro Arg Val Ser Met Pro
385                 390                 395                 400

Asp Phe Asp Val Asp Phe Cys Met Glu Lys Arg Asp Gln Val Ile Glu
                405                 410                 415

His Val Ala Asp Met Tyr Gly Arg Asp Ala Val Ser Gln Ile Ile Thr
            420                 425                 430

Phe Gly Thr Met Ala Ala Lys Ala Val Ile Arg Asp Val Gly Arg Val
        435                 440                 445

Leu Gly His Pro Tyr Gly Phe Val Asp Arg Ile Ser Lys Leu Ile Pro
    450                 455                 460

Pro Asp Pro Gly Met Thr Leu Ala Lys Ala Phe Glu Ala Glu Pro Gln
465                 470                 475                 480

Leu Pro Glu Ile Tyr Glu Ala Asp Glu Glu Val Lys Ala Leu Ile Asp
                485                 490                 495

Met Ala Arg Lys Leu Glu Gly Val Thr Arg Asn Ala Gly Lys His Ala
            500                 505                 510

Gly Gly Val Val Ile Ala Pro Thr Lys Ile Thr Asp Phe Ala Pro Leu
        515                 520                 525

Tyr Cys Asp Glu Glu Gly Lys His Pro Val Thr Gln Phe Asp Lys Ser
    530                 535                 540

Asp Val Glu Tyr Ala Gly Leu Val Lys Phe Asp Phe Leu Gly Leu Arg
545                 550                 555                 560

Thr Leu Thr Ile Ile Asn Trp Ala Leu Glu Met Ile Asn Lys Arg Arg
                565                 570                 575

Ala Lys Asn Gly Glu Pro Pro Leu Asp Ile Ala Ala Ile Pro Leu Asp
            580                 585                 590

Asp Lys Lys Ser Phe Asp Met Leu Gln Arg Ser Glu Thr Thr Ala Val
        595                 600                 605

Phe Gln Leu Glu Ser Arg Gly Met Lys Asp Leu Ile Lys Arg Leu Gln
    610                 615                 620

Pro Asp Cys Phe Glu Asp Met Ile Ala Leu Val Ala Leu Phe Arg Pro
625                 630                 635                 640

Gly Pro Leu Gln Ser Gly Met Val Asp Asn Phe Ile Asp Arg Lys His
                645                 650                 655

Gly Arg Glu Glu Ile Ser Tyr Pro Asp Val Gln Trp Gln His Glu Ser
            660                 665                 670

Leu Lys Pro Val Leu Glu Pro Thr Tyr Gly Ile Ile Leu Tyr Gln Glu
        675                 680                 685

Gln Val Met Gln Ile Ala Gln Val Leu Ser Gly Tyr Thr Leu Gly Gly
    690                 695                 700

Ala Asp Met Leu Arg Arg Ala Met Gly Lys Lys Pro Glu Glu Met
705                 710                 715                 720

Ala Lys Gln Arg Ser Val Phe Ala Glu Gly Ala Glu Lys Asn Gly Ile
                725                 730                 735
```

```
Asn Ala Glu Leu Ala Met Lys Ile Phe Asp Leu Val Glu Lys Phe Ala
                740                 745                 750

Gly Tyr Gly Phe Asn Lys Ser His Ser Ala Ala Tyr Ala Leu Val Ser
            755                 760                 765

Tyr Gln Thr Leu Trp Leu Lys Ala His Tyr Pro Ala Glu Phe Met Ala
    770                 775                 780

Ala Val Met Thr Ala Asp Met Asp Asn Thr Glu Lys Val Val Gly Leu
785                 790                 795                 800

Val Asp Glu Cys Trp Arg Met Gly Leu Lys Ile Leu Pro Pro Asp Ile
                805                 810                 815

Asn Ser Gly Leu Tyr His Phe His Val Asn Asp Asp Gly Glu Ile Val
            820                 825                 830

Tyr Gly Ile Gly Ala Ile Lys Gly Val Gly Glu Gly Pro Ile Glu Ala
    835                 840                 845

Ile Ile Glu Ala Arg Asn Lys Gly Gly Tyr Phe Arg Glu Leu Phe Asp
850                 855                 860

Leu Cys Ala Arg Thr Asp Thr Lys Lys Leu Asn Arg Arg Val Leu Glu
865                 870                 875                 880

Lys Leu Ile Met Ser Gly Ala Phe Asp Arg Leu Gly Pro His Arg Ala
                885                 890                 895

Ala Leu Met Asn Ser Leu Gly Asp Ala Leu Lys Ala Ala Asp Gln His
            900                 905                 910

Ala Lys Ala Glu Ala Ile Gly Gln Ala Asp Met Phe Gly Val Leu Ala
    915                 920                 925

Glu Glu Pro Glu Gln Ile Gln Ser Tyr Ala Ser Cys Gln Pro Trp
930                 935                 940

Pro Glu Gln Val Val Leu Asp Gly Glu Arg Glu Thr Leu Gly Leu Tyr
945                 950                 955                 960

Leu Thr Gly His Pro Ile Asn Gln Tyr Leu Lys Glu Ile Glu Arg Tyr
                965                 970                 975

Val Gly Gly Val Arg Leu Lys Asp Met His Pro Thr Glu Arg Gly Lys
            980                 985                 990

Val Ile Thr Ala Ala Gly Leu Val Val Ala Ala Arg Val Met Val Thr
    995                 1000                1005

Lys Arg Gly Asn Arg Ile Gly Ile Cys Thr Leu Asp Asp Arg Ser
    1010                1015                1020

Gly Arg Leu Glu Val Met Leu Phe Thr Asp Ala Leu Asp Lys Tyr
    1025                1030                1035

Gln Gln Leu Leu Glu Lys Asp Arg Ile Leu Ile Val Ser Gly Gln
    1040                1045                1050

Val Ser Phe Asp Asp Phe Ser Gly Gly Leu Lys Met Thr Ala Arg
    1055                1060                1065

Glu Val Met Asp Ile Asp Glu Ala Arg Glu Lys Tyr Ala Arg Gly
    1070                1075                1080

Leu Ala Ile Ser Leu Thr Asp Arg Gln Ile Asp Asp Gln Leu Leu
    1085                1090                1095

Asn Arg Leu Arg Gln Ser Leu Glu Pro His Arg Ser Gly Thr Ile
    1100                1105                1110

Pro Val His Leu Tyr Tyr Gln Arg Ala Asp Ala Arg Ala Arg Leu
    1115                1120                1125

Arg Phe Gly Ala Thr Trp Arg Val Ser Pro Ser Asp Arg Leu Leu
    1130                1135                1140

Asn Asp Leu Arg Gly Leu Ile Gly Ser Glu Gln Val Glu Leu Glu
```

```
                1145                1150                1155
Phe Asp
    1160

<210> SEQ ID NO 5
<211> LENGTH: 1335
<212> TYPE: PRT
<213> ORGANISM: Deinococcus radiodurans

<400> SEQUENCE: 5

Met Thr Val Ser Asp Ala Pro Thr Pro His Ile His Leu Pro Asp Gly
1               5                   10                  15

Ser Cys Cys Gln Pro Lys Lys Phe Ala His Leu His Gln His Thr Gln
            20                  25                  30

Tyr Ser Leu Leu Asp Gly Ala Ala Lys Leu Lys Asp Leu Leu Lys Trp
        35                  40                  45

Ala Lys Glu Val Thr Pro Glu Gly Gln Thr Pro Ala Leu Ala Met Thr
    50                  55                  60

Asp His Gly Asn Met His Gly Ala Val His Phe Tyr Asn Tyr Ala Met
65              70                  75                  80

Gly Met Glu Val Lys Pro Ile Ile Gly Tyr Glu Ala Tyr Val Val Pro
                85                  90                  95

Gly Phe Gly Thr Arg Arg Asp Arg Ser Arg Ala Gln Asp Gly Glu Lys
            100                 105                 110

Gly Ile Phe His Leu Thr Leu Leu Ala Arg Asp Phe Glu Gly Tyr Gln
        115                 120                 125

Asn Leu Cys Arg Leu Ser Ser Arg Gly Tyr Thr Glu Gly Tyr Tyr Tyr
    130                 135                 140

Lys Pro Arg Ile Asp His Glu Leu Leu Gln Glu His His Lys Gly Ile
145             150                 155                 160

Ile Ala Phe Ser Gly Cys Leu Gly Ser Glu Val Gln Gln Leu Leu Met
                165                 170                 175

Gln Gly Arg Glu Asp Asp Ala Arg Ala Arg Leu Leu Trp Tyr Arg Glu
            180                 185                 190

Leu Phe Gly Asp Asn Tyr Phe Ile Glu Ile Gln Asp His Gly Leu Pro
        195                 200                 205

Glu Gln Lys Lys Asn Asn Pro Ile Leu Lys Ala Trp Ala Gln Glu Leu
    210                 215                 220

Gly Ile Gly Met Val Ala Thr Asn Asp Gly His Tyr Val Lys Lys Ser
225             230                 235                 240

Asp Ala Thr Ala His Glu Thr Leu Leu Ala Ile Gln Thr Lys Ala Thr
                245                 250                 255

Leu Ala Asp Glu Asn Arg Phe Lys Phe Pro Cys Asp Glu Phe Tyr Val
            260                 265                 270

Lys Asn Leu Glu Glu Met Gln Arg Ala Leu Pro Val Ser Glu Trp Gly
        275                 280                 285

Glu Glu Pro Phe Asp Asn Thr Ala His Ile Ala Glu Leu Cys Asn Val
    290                 295                 300

Glu Leu Pro Val Gly Lys Lys Arg Gln Tyr Gln Met Pro Gln Leu Pro
305             310                 315                 320

Ile Pro Glu Gly Arg Ser Met Ala Glu Leu Arg Val Gln Thr Tyr
                325                 330                 335

Ala Gly Ala Val Lys Arg Tyr Pro Ala His Leu Thr Glu Gly Leu Leu
            340                 345                 350

Arg Asp Tyr Ala Ala Arg Ser Leu Ala Glu Leu Gly Glu Ala Asp Ala
```

```
                355                 360                 365
Ala Arg Val Leu Lys Arg Thr Gly Gly Cys Asp Ser Ala Ser Cys Asp
    370                 375                 380
Leu Asp Thr Leu Tyr Thr Leu Leu Ala Phe Leu Gly Ser Glu Trp Glu
385                 390                 395                 400
Ala Arg Gly Lys Glu Ala Gly Glu Lys Tyr Thr Pro Tyr Pro Ala Leu
                405                 410                 415
Glu Lys Met Glu Gln Asp Gly Ser Gly Thr Leu Pro Ala Tyr Ala
                420                 425                 430
His Ala Asp Cys Arg Ala Ala Arg Gln Asp Ser Asp Thr Ser Ile
                435                 440                 445
Glu Leu Asp Pro Asp Thr Asp Asp Glu Glu Thr Thr Arg Ser His His
    450                 455                 460
Arg Tyr Ala Leu Lys Leu Leu Arg Arg Ala Glu Tyr Glu Leu Ser Val
465                 470                 475                 480
Ile Asn Asn Met Gly Phe Pro Asp Tyr Phe Leu Ile Val Ala Asp Tyr
                485                 490                 495
Ile Asn Trp Ala Lys Asp His Asp Ile Ser Val Gly Pro Gly Arg Gly
                500                 505                 510
Ser Gly Ala Gly Ser Leu Val Ala Tyr Ala Ile Arg Ile Thr Asn Leu
                515                 520                 525
Asp Pro Leu Glu Phe Glu Leu Phe Glu Arg Phe Leu Asn Pro Asp
    530                 535                 540
Arg Ile Ser Met Pro Asp Phe Asp Ile Asp Phe Asn Asp Ala Arg Arg
545                 550                 555                 560
Thr Glu Val Ile Gly Tyr Val Gln Glu Lys Tyr Gly Thr Asp Lys Val
                565                 570                 575
Ala Gln Ile Ala Thr Phe Gly Thr Met Ala Ser Lys Ala Cys Leu Lys
                580                 585                 590
Asp Val Ala Arg Val Met Gly Leu Glu Tyr Ala Lys Val Asp Lys Val
                595                 600                 605
Ser Lys Leu Ile Pro Ile Lys Phe Gly Lys Ser Tyr Ser Leu Glu Gln
    610                 615                 620
Ala Arg Glu Ala Val Pro Asp Ile Gln Gln Met Leu Ala Glu Asp Ala
625                 630                 635                 640
Gln Leu Leu Glu Ala Tyr Glu Phe Ala Gln Lys Leu Glu Gly Leu Thr
                645                 650                 655
Arg His Ala Ser Val His Ala Ala Gly Val Val Ile Gly Arg Glu Glu
                660                 665                 670
Leu Thr Asn Leu Val Pro Val Met Arg Asp Thr Ser Gly Glu Gly Gln
                675                 680                 685
Val Cys Gln Tyr Asp Met Lys Ser Val Glu Asp Ile Gly Leu Ile Lys
                690                 695                 700
Met Asp Phe Leu Gly Leu Arg Thr Leu Ser Phe Leu Asp Glu Ala Lys
705                 710                 715                 720
Arg Ile Leu Arg Glu Ser Gly Thr Asp Phe Glu Glu Lys Tyr Gly Asp
                725                 730                 735
Phe Asp His Ile Pro Phe Asp Asp Glu Lys Thr Tyr Glu Leu Met Ser
                740                 745                 750
Arg Gly Asp Thr Lys Gly Val Phe Gln Leu Glu Gly Ala Gly Ile Ala
                755                 760                 765
Asp Ala Ser Arg Arg Leu Lys Pro Arg Arg Leu Ala Asp Ile Ile Ala
    770                 775                 780
```

-continued

Leu Ser Ala Leu Tyr Arg Pro Gly Pro Met Glu Asn Ile Pro Thr Tyr
785                 790                 795                 800

Val Arg Arg His His Gly Ile Glu Glu Val Asp Tyr Asp Lys Asp Gly
            805                 810                 815

Phe Pro Asn Ser Lys Gln Trp Leu Glu Lys Ile Leu Gln Glu Thr Tyr
            820                 825                 830

Gly Ile Pro Val Tyr Gln Glu Gln Ile Met Gln Ile Ala Ser Glu Val
            835                 840                 845

Ala Gly Tyr Ser Leu Gly Gly Ala Asp Leu Leu Arg Arg Ala Met Gly
850                 855                 860

Lys Lys Asp Ala Glu Glu Met Lys Arg Gln Arg Gln Leu Phe Val Val
865                 870                 875                 880

Gly Ala Lys Glu Lys Gly Val Pro Glu Asp Glu Gly Asn Lys Leu Phe
                885                 890                 895

Asp Met Leu Asp Ala Phe Ala Asn Tyr Gly Phe Asn Lys Ser His Ser
                900                 905                 910

Ala Ala Tyr Gly Val Ile Thr Tyr Gln Thr Ala Trp Leu Lys Ala Asn
            915                 920                 925

Tyr Pro Val Gln Phe Met Ala Ala Leu Leu Thr Val Glu Arg Arg Asp
930                 935                 940

Ser Asp Lys Val Ala Glu Tyr Val Ser Asp Ala Arg Lys Met Asp Leu
945                 950                 955                 960

His Val Leu Pro Pro Asp Ile Asn Arg Ser Ser Asp Phe Ala Val
                965                 970                 975

Ala Gly Glu Glu Ile Leu Phe Gly Leu Tyr Ala Ile Lys Gly Leu Gly
                980                 985                 990

Glu Ser Ala Val Leu Arg Ile Leu Glu Glu Arg Glu Lys Ala Gly Ala
            995                 1000                1005

Phe Lys Ser Leu Ala Asp Phe Cys Ser Arg Leu Gly Asn Lys Val
    1010                1015                1020

Cys Asn Arg Lys Ala Leu Glu Ser Leu Ile Lys Ser Gly Ala Phe
    1025                1030                1035

Asp Ala Phe Gly Glu Arg His Gln Leu Ile Glu Ser Leu Glu Asp
    1040                1045                1050

Ala Leu Glu Asp Ala Ala Gly Thr Ala Glu Ile Asn Ala Arg Ala
    1055                1060                1065

Gln Ser Gly Met Ser Met Met Phe Gly Met Glu Glu Val Lys Lys
    1070                1075                1080

Glu Arg Pro Leu Arg Ser Ser Ile Ala Pro Tyr Ser Asp Leu Glu
    1085                1090                1095

Arg Leu Ala Ile Glu Lys Glu Ala Leu Gly Leu Tyr Ile Ser Gly
    1100                1105                1110

His Pro Leu Glu Gln His Glu Gly Leu Arg Glu Ala Ala Ser Cys
    1115                1120                1125

Arg Val Ser Asp Leu Asp Ala Trp Phe Ala Leu Gln Asn Val Ala
    1130                1135                1140

Pro Gly Lys Arg Gln Lys Ala Val Leu Ala Gly Met Ile Glu Gly
    1145                1150                1155

Val Val Lys Lys Pro Thr Lys Ser Gly Gly Met Met Ala Arg Phe
    1160                1165                1170

Ile Leu Ala Asp Glu Ser Gly Gln Met Glu Leu Val Ala Phe Ser
    1175                1180                1185

Arg Ala Tyr Asp Arg Ile Glu Pro Lys Leu Val Asn Asp Thr Pro
    1190                1195                1200

```
Ala Leu Val Ile Val Glu Leu Glu Ala Glu Asp Gly Gly Leu Arg
    1205                1210                1215

Ala Ile Ala Glu Glu Ile Val Ser Ile Glu Gln Leu Ser Glu Val
    1220                1225                1230

Pro Lys Val Met Tyr Val Thr Ile Asp Leu Glu Thr Ala Ser Pro
    1235                1240                1245

Asp Ala Leu Gly Asp Phe Gln Ser Val Leu Asp Glu Tyr Ala Gly
    1250                1255                1260

Ser Met Pro Thr Tyr Leu Arg Leu Glu Thr Pro Glu Gln Phe Val
    1265                1270                1275

Val Tyr Gln Leu Asp His Gly Met Gly Ser Pro Glu Ala Ile Arg
    1280                1285                1290

Ala Leu Asn Gln Thr Phe Ala Trp Ala Asp Ala His Leu Ala Tyr
    1295                1300                1305

Asp Gln Gln Thr Ile Leu Gly Arg Phe Ala Pro Lys Pro Pro Ala
    1310                1315                1320

Trp Met Asn Arg Gln Gln Gly Gly Gly Met Arg Ala
    1325                1330                1335

<210> SEQ ID NO 6
<211> LENGTH: 1220
<212> TYPE: PRT
<213> ORGANISM: Thermus aquaticus

<400> SEQUENCE: 6

Met Gly Ser Lys Leu Lys Phe Ala His Leu His Gln His Thr Gln Phe
1               5                   10                  15

Ser Leu Leu Asp Gly Ala Ala Lys Leu Gln Asp Leu Leu Lys Trp Val
            20                  25                  30

Lys Glu Thr Thr Pro Glu Asp Pro Ala Leu Ala Met Thr Asp His Gly
        35                  40                  45

Asn Leu Phe Gly Ala Val Glu Phe Tyr Lys Lys Ala Thr Ala Met Gly
    50                  55                  60

Val Lys Pro Ile Ile Gly Tyr Glu Ala Tyr Val Ala Ala Glu Ser Arg
65                  70                  75                  80

Phe Asp Arg Lys Arg Gly Lys Gly Leu Asp Gly Gly Tyr Phe His Leu
                85                  90                  95

Thr Leu Leu Ala Lys Asp Phe Thr Gly Tyr Gln Asn Leu Val Arg Leu
            100                 105                 110

Ala Ser Arg Ala Tyr Leu Glu Gly Phe Tyr Glu Lys Pro Arg Ile Asp
        115                 120                 125

Arg Glu Ile Leu Arg Glu His Ala Gln Gly Leu Ile Ala Leu Ser Gly
    130                 135                 140

Cys Leu Gly Ala Glu Ile Pro Gln Phe Ile Leu Gln Asp Arg Leu Asp
145                 150                 155                 160

Leu Ala Glu Ala Arg Leu Asn Glu Asp Leu Ser Ile Phe Gly Asp Arg
                165                 170                 175

Phe Phe Ile Glu Ile Gln Asn His Gly Leu Pro Glu Gln Lys Lys Val
            180                 185                 190

Asn Gln Val Leu Lys Glu Phe Ala Arg Lys Tyr Gly Leu Gly Met Val
        195                 200                 205

Ala Thr Asn Asp Gly His Tyr Val Arg Lys Glu Asp Ala Arg Ala His
    210                 215                 220

Glu Val Leu Leu Ala Ile Gln Ser Lys Thr Thr Leu Asp Asp Pro Glu
225                 230                 235                 240
```

```
Arg Trp Arg Phe Pro Cys Asp Glu Phe Tyr Val Lys Thr Pro Glu Glu
            245                 250                 255

Met Arg Ala Met Leu Pro Glu Ala Glu Trp Gly Asp Glu Pro Phe Asp
        260                 265                 270

Asn Thr Val Glu Ile Ala Arg Met Cys Asp Val Asp Leu Pro Ile Gly
            275                 280                 285

Asp Lys Met Val Tyr Arg Ile Pro Arg Phe Pro Leu Pro Glu Gly Arg
        290                 295                 300

Thr Glu Ala Gln Tyr Leu Arg Glu Leu Thr Phe Leu Gly Leu Leu Arg
305                 310                 315                 320

Arg Tyr Pro Asp Arg Ile Thr Glu Ala Phe Tyr Arg Glu Val Leu Arg
                325                 330                 335

Leu Leu Gly Thr Met Pro Pro His Gly Asp Glu Arg Ala Leu Ala Glu
            340                 345                 350

Ala Leu Ala Arg Val Glu Glu Lys Ala Trp Glu Glu Leu Arg Lys Arg
        355                 360                 365

Leu Pro Pro Leu Glu Gly Val Arg Glu Trp Thr Ala Glu Ala Ile Leu
    370                 375                 380

His Arg Ala Leu Tyr Glu Leu Ser Val Ile Glu Arg Met Gly Phe Pro
385                 390                 395                 400

Gly Tyr Phe Leu Ile Val Gln Asp Tyr Ile Asn Trp Ala Arg Gly His
                405                 410                 415

Gly Val Ser Val Gly Pro Gly Arg Gly Ser Ala Ala Gly Ser Leu Val
            420                 425                 430

Ala Tyr Ala Val Gly Ile Thr Asn Ile Asp Pro Leu Arg Phe Gly Leu
        435                 440                 445

Leu Phe Glu Arg Phe Leu Asn Pro Glu Arg Val Ser Met Pro Asp Ile
    450                 455                 460

Asp Thr Asp Phe Ser Asp Arg Glu Arg Asp Arg Val Ile Gln Tyr Val
465                 470                 475                 480

Arg Glu Arg Tyr Gly Glu Asp Lys Val Ala Gln Ile Gly Thr Phe Gly
                485                 490                 495

Ser Leu Ala Ser Lys Ala Ala Leu Lys Asp Val Ala Arg Val Tyr Gly
            500                 505                 510

Ile Pro His Lys Lys Ala Glu Glu Leu Ala Lys Leu Ile Pro Val Gln
        515                 520                 525

Phe Gly Lys Pro Lys Pro Leu Gln Glu Ala Ile Gln Val Val Pro Glu
    530                 535                 540

Leu Arg Ala Glu Met Glu Lys Asp Glu Arg Ile Arg Gln Val Ile Glu
545                 550                 555                 560

Val Ala Met Arg Leu Glu Gly Leu Asn Arg His Ala Ser Val His Ala
                565                 570                 575

Ala Gly Val Val Ile Ala Ala Glu Pro Leu Thr Asp Leu Val Pro Leu
            580                 585                 590

Met Arg Asp Gln Glu Gly Arg Pro Val Thr Gln Tyr Asp Met Gly Ala
        595                 600                 605

Val Glu Ala Leu Gly Leu Leu Lys Met Asp Phe Leu Gly Leu Arg Thr
    610                 615                 620

Leu Thr Phe Leu Asp Glu Ala Arg Arg Ile Val Lys Glu Ser Lys Gly
625                 630                 635                 640

Val Glu Leu Asp Tyr Asp Arg Leu Pro Leu Asp Asp Pro Lys Thr Phe
                645                 650                 655

Glu Leu Leu Ser Arg Gly Glu Thr Lys Gly Val Phe Gln Leu Glu Ser
```

-continued

```
            660                 665                 670
Gly Gly Met Thr Ala Thr Val Arg Gly Leu Lys Pro Arg Arg Leu Glu
            675                 680             685
Asp Ile Ile Ala Leu Val Ser Leu Tyr Arg Pro Gly Pro Met Glu His
            690                 695             700
Ile Pro Thr Tyr Ile Arg Arg His His Gly Gln Glu Pro Val Ser Tyr
705                 710                 715                 720
Ala Glu Phe Pro His Ala Glu Lys Tyr Leu Arg Pro Ile Leu Asp Glu
                    725                 730                 735
Thr Tyr Gly Ile Pro Val Tyr Gln Glu Gln Ile Met Gln Ile Ala Ser
                740                 745             750
Gln Val Ala Gly Tyr Ser Leu Gly Glu Ala Asp Leu Leu Arg Arg Ala
            755                 760             765
Met Gly Lys Lys Arg Val Glu Glu Met Gln Lys His Arg Glu Arg Phe
            770                 775             780
Val Arg Gly Ala Lys Glu Arg Gly Val Pro Glu Glu Ala Asn Arg
785                 790                 795                 800
Leu Phe Asp Met Leu Glu Ala Phe Ala Asn Tyr Gly Phe Asn Lys Ser
                    805                 810                 815
His Ala Ala Ala Tyr Ser Leu Leu Ser Tyr Gln Thr Ala Tyr Val Lys
                820                 825             830
Ala His Tyr Pro Val Glu Phe Met Ala Ala Leu Leu Ser Val Glu Arg
            835                 840             845
His Asp Ser Asp Lys Val Ala Glu Tyr Ile Arg Asp Ala Arg Ala Leu
            850                 855             860
Gly Ile Pro Val Leu Pro Pro Asp Val Asn Arg Ser Gly Phe Asp Phe
865                 870                 875                 880
Lys Val Val Gly Glu Glu Ile Leu Phe Gly Leu Ser Ala Val Lys Asn
                    885                 890                 895
Val Gly Glu Met Ala Ala Arg Ala Ile Leu Glu Arg Glu Arg Gly
                900                 905             910
Gly Pro Phe Lys Ser Leu Gly Asp Phe Leu Lys Arg Leu Pro Glu Gln
            915                 920             925
Val Val Asn Lys Arg Ala Leu Glu Ser Leu Val Lys Ala Gly Ala Leu
            930                 935             940
Asp Ala Phe Gly Asp Arg Ala Arg Leu Leu Ala Ser Leu Glu Pro Leu
945                 950                 955                 960
Leu Arg Trp Ala Ala Glu Thr Arg Glu Arg Gly Arg Ser Gly Leu Val
                    965                 970                 975
Gly Leu Phe Ala Glu Val Glu Glu Pro Pro Leu Val Glu Ala Ser Pro
                980                 985             990
Leu Asp Glu Ile Thr Met Leu Arg  Tyr Glu Lys Glu Ala  Leu Gly Ile
            995                 1000                1005
Tyr Val  Ser Gly His Pro Val  Leu Arg Tyr Pro Gly  Leu Arg Glu
            1010                1015                1020
Val Ala  Ser Cys Thr Ile Glu  Glu Leu Ser Glu Phe  Val Arg Glu
            1025                1030                1035
Leu Pro  Gly Lys Pro Lys Val  Leu Leu Ser Gly Met  Val Glu Glu
            1040                1045                1050
Val Val  Arg Lys Pro Thr Arg  Ser Gly Gly Met Met  Ala Arg Phe
            1055                1060                1065
Thr Leu  Ser Asp Glu Thr Gly  Ala Leu Glu Val Val  Val Phe Gly
            1070                1075                1080
```

```
Arg Ala Tyr Glu Gly Val Ser Pro Lys Leu Lys Glu Asp Ile Pro
    1085            1090                1095

Leu Leu Val Leu Ala Glu Val Glu Lys Gly Glu Glu Leu Arg Val
    1100            1105                1110

Leu Ala Gln Ala Val Trp Thr Leu Glu Glu Val Leu Glu Ala Pro
    1115            1120                1125

Lys Ala Leu Glu Val Glu Val Asp His Ala Leu Leu Asp Glu Lys
    1130            1135                1140

Gly Val Ala Arg Leu Lys Ser Leu Leu Asp Glu His Pro Gly Ser
    1145            1150                1155

Leu Pro Val Tyr Leu Arg Val Leu Gly Pro Phe Gly Glu Ala Leu
    1160            1165                1170

Phe Ala Leu Arg Glu Val Arg Val Gly Glu Glu Ala Leu Gly Leu
    1175            1180                1185

Leu Glu Ala Glu Gly Tyr Arg Ala Tyr Leu Val Pro Asp Arg Glu
    1190            1195                1200

Val Phe Leu Gln Gly Asn Gly Gly Gly Pro Lys Glu Glu Val Val
    1205            1210                1215

Pro Phe
    1220

<210> SEQ ID NO 7
<211> LENGTH: 2067
<212> TYPE: PRT
<213> ORGANISM: Thermus thermophilus

<400> SEQUENCE: 7

Met Gly Arg Lys Leu Arg Phe Ala His Leu His Gln His Thr Gln Phe
1               5                   10                  15

Ser Leu Leu Asp Gly Ala Ala Lys Leu Ser Asp Leu Leu Lys Trp Val
                20                  25                  30

Lys Glu Thr Thr Pro Glu Asp Pro Ala Leu Ala Met Thr Asp His Gly
            35                  40                  45

Asn Leu Phe Gly Ala Val Glu Phe Tyr Lys Lys Ala Thr Glu Met Gly
        50                  55                  60

Ile Lys Pro Ile Leu Gly Tyr Glu Ala Tyr Val Ala Ala Glu Ser Arg
65              70                  75                  80

Phe Asp Arg Lys Arg Gly Lys Gly Leu Asp Gly Tyr Phe His Leu
                85                  90                  95

Thr Leu Leu Ala Lys Asp Phe Thr Gly Tyr Gln Asn Leu Val Arg Leu
            100                 105                 110

Ala Ser Arg Ala Tyr Leu Glu Gly Phe Tyr Glu Lys Pro Arg Ile Asp
        115                 120                 125

Arg Glu Ile Leu Arg Glu His Ala Glu Gly Leu Ile Ala Leu Ser Gly
    130                 135                 140

Cys Leu Gly Ala Glu Ile Pro Gln Phe Ile Leu Gln Asp Arg Leu Asp
145                 150                 155                 160

Leu Ala Glu Ala Arg Leu Asn Glu Tyr Leu Ser Ile Phe Lys Asp Arg
                165                 170                 175

Phe Phe Ile Glu Ile Gln Asn His Gly Leu Pro Glu Gln Lys Lys Val
            180                 185                 190

Asn Glu Val Leu Lys Glu Phe Ala Arg Lys Tyr Gly Leu Gly Met Val
        195                 200                 205

Ala Thr Asn Asp Gly His Tyr Val Arg Lys Glu Asp Ala Arg Ala His
    210                 215                 220
```

-continued

```
Glu Val Leu Leu Ala Ile Gln Ser Lys Ser Thr Leu Asp Asp Pro Gly
225                 230                 235                 240

Arg Trp Arg Phe Pro Cys Asp Glu Phe Tyr Val Lys Thr Pro Glu Glu
            245                 250                 255

Met Arg Ala Met Phe Pro Glu Glu Glu Trp Gly Asp Glu Pro Phe Asp
        260                 265                 270

Asn Thr Val Glu Ile Ala Arg Met Cys Asn Val Glu Leu Pro Ile Gly
    275                 280                 285

Asp Lys Met Val Tyr Arg Ile Pro Arg Phe Pro Leu Pro Glu Gly Arg
290                 295                 300

Thr Glu Ala Gln Tyr Leu Met Glu Leu Thr Phe Lys Gly Leu Leu Arg
305                 310                 315                 320

Arg Tyr Pro Asp Arg Ile Thr Glu Gly Phe Tyr Arg Glu Val Phe Arg
                325                 330                 335

Leu Leu Gly Lys Leu Pro Pro His Gly Asp Gly Glu Ala Leu Ala Glu
            340                 345                 350

Ala Leu Ala Gln Val Glu Arg Glu Ala Trp Glu Arg Leu Met Lys Ser
        355                 360                 365

Leu Pro Pro Leu Ala Gly Val Lys Glu Trp Thr Ala Glu Ala Ile Phe
    370                 375                 380

His Arg Ala Leu Tyr Glu Leu Ser Val Ile Glu Arg Met Gly Phe Pro
385                 390                 395                 400

Gly Tyr Phe Leu Ile Val Gln Asp Tyr Ile Asn Trp Ala Arg Arg Asn
                405                 410                 415

Gly Val Ser Val Gly Pro Gly Arg Gly Ser Ala Ala Gly Ser Leu Val
            420                 425                 430

Ala Tyr Ala Val Gly Ile Thr Asn Ile Asp Pro Leu Arg Phe Gly Leu
        435                 440                 445

Leu Phe Glu Arg Phe Leu Asn Pro Glu Arg Val Ser Met Pro Asp Ile
    450                 455                 460

Asp Thr Asp Phe Ser Asp Arg Glu Arg Asp Arg Val Ile Gln Tyr Val
465                 470                 475                 480

Arg Glu Arg Tyr Gly Glu Asp Lys Val Ala Gln Ile Gly Thr Leu Gly
                485                 490                 495

Ser Leu Ala Ser Lys Ala Ala Leu Lys Asp Val Ala Arg Val Tyr Gly
            500                 505                 510

Ile Pro His Lys Lys Ala Glu Glu Leu Ala Lys Leu Ile Pro Val Gln
        515                 520                 525

Phe Gly Lys Pro Lys Pro Leu Gln Glu Ala Ile Gln Val Val Pro Glu
    530                 535                 540

Leu Arg Ala Glu Met Glu Lys Asp Pro Lys Val Arg Glu Val Leu Glu
545                 550                 555                 560

Val Ala Met Arg Leu Glu Gly Leu Asn Arg His Ala Ser Val His Ala
                565                 570                 575

Ala Gly Val Val Ile Ala Ala Glu Pro Leu Thr Asp Leu Val Pro Leu
            580                 585                 590

Met Arg Asp Gln Glu Gly Arg Pro Val Thr Gln Tyr Asp Met Gly Ala
        595                 600                 605

Val Glu Ala Leu Gly Leu Leu Lys Met Asp Phe Leu Gly Leu Arg Thr
    610                 615                 620

Leu Thr Phe Leu Asp Glu Val Lys Arg Ile Val Lys Ala Ser Gln Gly
625                 630                 635                 640

Val Glu Leu Asp Tyr Asp Ala Leu Pro Leu Asp Asp Pro Lys Thr Phe
                645                 650                 655
```

```
Ala Leu Leu Ser Arg Gly Glu Thr Lys Gly Val Phe Gln Leu Glu Ser
            660                 665                 670

Gly Gly Met Thr Ala Thr Leu Arg Gly Leu Lys Pro Arg Arg Phe Glu
        675                 680                 685

Asp Leu Ile Ala Ile Leu Ser Leu Tyr Arg Pro Gly Pro Met Glu His
    690                 695                 700

Ile Pro Thr Tyr Ile Arg Arg His His Gly Leu Glu Pro Val Ser Tyr
705                 710                 715                 720

Ser Glu Phe Pro His Ala Glu Lys Tyr Leu Lys Pro Ile Leu Asp Glu
                725                 730                 735

Thr Tyr Gly Ile Pro Val Tyr Gln Glu Gln Ile Met Gln Ile Ala Ser
            740                 745                 750

Ala Val Ala Gly Tyr Ser Leu Gly Glu Ala Asp Leu Leu Arg Arg Cys
        755                 760                 765

Leu Ala Glu Gly Ser Leu Val Leu Asp Ala Ala Thr Gly Gln Arg Val
    770                 775                 780

Pro Ile Glu Lys Val Arg Pro Gly Met Glu Val Phe Ser Leu Gly Pro
785                 790                 795                 800

Asp Tyr Arg Leu Tyr Arg Val Pro Val Leu Glu Val Leu Glu Ser Gly
                805                 810                 815

Val Arg Glu Val Val Arg Leu Arg Thr Arg Ser Gly Arg Thr Leu Val
            820                 825                 830

Leu Thr Pro Asp His Pro Leu Leu Thr Pro Glu Gly Trp Lys Pro Leu
        835                 840                 845

Cys Asp Leu Pro Leu Gly Thr Pro Ile Ala Val Pro Ala Glu Leu Pro
    850                 855                 860

Val Ala Gly His Leu Ala Pro Pro Glu Glu Arg Val Thr Leu Leu Ala
865                 870                 875                 880

Leu Leu Leu Gly Asp Gly Asn Thr Lys Leu Ser Gly Arg Arg Gly Thr
                885                 890                 895

Arg Pro Asn Ala Phe Phe Tyr Ser Lys Asp Pro Glu Leu Leu Ala Ala
            900                 905                 910

Tyr Arg Arg Cys Ala Glu Ala Leu Gly Ala Lys Val Lys Ala Tyr Val
        915                 920                 925

His Pro Thr Thr Gly Val Val Thr Leu Ala Thr Leu Ala Pro Arg Pro
    930                 935                 940

Gly Ala Gln Asp Pro Val Lys Arg Leu Val Val Glu Ala Gly Met Val
945                 950                 955                 960

Ala Lys Ala Glu Glu Lys Arg Val Pro Glu Glu Val Phe Arg Tyr Arg
                965                 970                 975

Arg Glu Ala Leu Ala Leu Phe Leu Gly Arg Leu Phe Ser Thr Asp Gly
            980                 985                 990

Ser Val Glu Lys Lys Arg Ile Ser Tyr Ser Ser Ala Ser Leu Gly Leu
        995                 1000                 1005

Ala Gln Asp Val Ala His Leu Leu Leu Arg Leu Gly Ile Thr Ser
    1010                 1015                 1020

Gln Leu Arg Ser Arg Gly Pro Arg Ala His Glu Val Leu Ile Ser
    1025                 1030                 1035

Gly Arg Glu Asp Ile Leu Arg Phe Ala Glu Leu Ile Gly Pro Tyr
    1040                 1045                 1050

Leu Leu Gly Ala Lys Arg Glu Arg Leu Ala Ala Leu Glu Ala Glu
    1055                 1060                 1065

Ala Arg Arg Arg Leu Pro Gly Gln Gly Trp His Leu Arg Leu Val
```

```
                1070                1075                1080
Leu Pro Ala Val Ala Tyr Arg Val Ser Glu Ala Lys Arg Arg Ser
    1085                1090                1095

Gly Phe Ser Trp Ser Glu Ala Gly Arg Arg Val Ala Val Ala Gly
    1100                1105                1110

Ser Cys Leu Ser Ser Gly Leu Asn Leu Lys Leu Pro Arg Arg Tyr
    1115                1120                1125

Leu Ser Arg His Arg Leu Ser Leu Leu Gly Glu Ala Phe Ala Asp
    1130                1135                1140

Pro Gly Leu Glu Ala Leu Ala Glu Gly Gln Val Leu Trp Asp Pro
    1145                1150                1155

Ile Val Ala Val Glu Pro Ala Gly Lys Ala Arg Thr Phe Asp Leu
    1160                1165                1170

Arg Val Pro Pro Phe Ala Asn Phe Val Ser Glu Asp Leu Val Val
    1175                1180                1185

His Asn Ser Met Gly Lys Lys Lys Val Glu Glu Met Lys Ser His
    1190                1195                1200

Arg Glu Arg Phe Val Gln Gly Ala Lys Glu Arg Gly Val Pro Glu
    1205                1210                1215

Glu Glu Ala Asn Arg Leu Phe Asp Met Leu Glu Ala Phe Ala Asn
    1220                1225                1230

Tyr Gly Phe Asn Lys Cys Leu Pro Ala Arg Ala Arg Val Val Asp
    1235                1240                1245

Trp Cys Thr Gly Arg Val Val Arg Val Gly Glu Ile Val Arg Gly
    1250                1255                1260

Glu Ala Lys Gly Val Trp Val Val Ser Leu Asp Glu Ala Arg Leu
    1265                1270                1275

Arg Leu Val Pro Arg Pro Val Val Ala Ala Phe Pro Ser Gly Lys
    1280                1285                1290

Ala Gln Val Tyr Ala Leu Arg Thr Ala Thr Gly Arg Val Leu Glu
    1295                1300                1305

Ala Thr Ala Asn His Pro Val Tyr Thr Pro Glu Gly Trp Arg Pro
    1310                1315                1320

Leu Gly Thr Leu Ala Pro Gly Asp Tyr Val Ala Leu Pro Arg His
    1325                1330                1335

Leu Ser Tyr Arg Pro Ser Leu His Leu Glu Gly His Glu Leu Asp
    1340                1345                1350

Leu Leu Gly Phe Ala Leu Ala Glu Gly His Leu Arg His Pro Ser
    1355                1360                1365

Gly Val Tyr Leu Tyr Thr Ser Ser Glu Glu Glu Leu Ala Ala Met
    1370                1375                1380

Glu Glu Ala Leu Arg Ala Phe Pro Asn Thr Arg Ile Arg Val Val
    1385                1390                1395

Trp Arg Arg Gly Val Ala His Val Tyr Val Gly Arg Val Asp Arg
    1400                1405                1410

Arg Gln Glu Ala Gly Ala Val Ala Phe Leu Arg Arg Met Gly Leu
    1415                1420                1425

Leu Gly Leu Asp Ala Lys Thr Lys Arg Leu Pro Glu Ala Val Phe
    1430                1435                1440

Gly Leu Pro Pro Glu Glu Val Ala Arg Phe Leu Gly Arg Leu Trp
    1445                1450                1455

Thr Gly Asp Gly Gly Val Asp Pro Lys Gly Arg Leu Ile His Tyr
    1460                1465                1470
```

```
Ala Thr  Ala Ser Lys Glu Leu  Ala Trp Gly Val Gln  His Leu Leu
1475             1480                  1485

Leu Arg  Leu Gly Leu Gln Ser  Arg Leu Val Glu Lys  Arg Phe Ser
1490             1495                  1500

Gly Gly  Tyr Lys Gly Tyr Ala  Val Tyr Leu Leu Gly  Gly Leu Glu
1505             1510                  1515

Ala Ala  Arg Arg Phe Ala Glu  Thr Val Gly Pro Tyr  Leu Val Gly
1520             1525                  1530

Lys Arg  Arg Gln Asp Leu Glu  Ala Leu Leu Ala Ser  Trp Glu Lys
1535             1540                  1545

Ala Gly  Arg Ser Thr Gly Asp  Val Leu Pro Leu Ala  Phe Leu Glu
1550             1555                  1560

Glu Val  Arg Ala Ala Val Ala  Glu Val Ala Gln Gly  Gln Val Ala
1565             1570                  1575

Asp Leu  Leu Arg Glu Ala Gly  Leu Ala Glu Gly Leu  Leu Cys Leu
1580             1585                  1590

Gly Arg  Gly Arg Arg Gly Leu  Ser Arg Ala Thr Val  Gly Arg Leu
1595             1600                  1605

Ala Ala  Leu Thr Gly Ser Leu  Ala Leu Leu Arg Leu  Ala Glu Ala
1610             1615                  1620

Glu Val  Tyr Trp Asp Arg Val  Glu Ala Val Glu Pro  Leu Gly Glu
1625             1630                  1635

Glu Glu  Val Phe Asp Leu Thr  Val Glu Gly Thr His  Thr Phe Val
1640             1645                  1650

Ala Glu  Asp Val Ile Val His  Asn Ser His Ala Ala  Ala Tyr Ser
1655             1660                  1665

Leu Leu  Ser Tyr Gln Thr Ala  Tyr Val Lys Ala His  Tyr Pro Val
1670             1675                  1680

Glu Phe  Met Ala Ala Leu Leu  Ser Val Glu Arg His  Asp Ser Asp
1685             1690                  1695

Lys Val  Ala Glu Tyr Ile Arg  Asp Ala Arg Ala Met  Gly Ile Glu
1700             1705                  1710

Val Leu  Pro Pro Asp Val Asn  Arg Ser Gly Phe Asp  Phe Leu Val
1715             1720                  1725

Gln Gly  Arg Gln Ile Leu Phe  Gly Leu Ser Ala Val  Lys Asn Val
1730             1735                  1740

Gly Glu  Ala Ala Ala Glu Ala  Ile Leu Arg Glu Arg  Glu Arg Gly
1745             1750                  1755

Gly Pro  Tyr Arg Ser Leu Gly  Asp Phe Leu Lys Arg  Leu Asp Glu
1760             1765                  1770

Lys Val  Leu Asn Lys Arg Thr  Leu Glu Phe Leu Ile  Lys Ala Gly
1775             1780                  1785

Ala Leu  Asp Gly Phe Gly Glu  Arg Ala Arg Leu Leu  Ala Ser Leu
1790             1795                  1800

Glu Gly  Leu Leu Lys Trp Ala  Ala Glu Asn Arg Glu  Lys Ala Arg
1805             1810                  1815

Ser Gly  Met Met Gly Leu Phe  Ser Glu Val Glu Glu  Pro Pro Leu
1820             1825                  1830

Ala Glu  Ala Ala Pro Leu Asp  Glu Ile Thr Arg Leu  Arg Tyr Glu
1835             1840                  1845

Lys Glu  Ala Leu Gly Ile Tyr  Val Ser Gly His Pro  Ile Leu Arg
1850             1855                  1860

Tyr Pro  Gly Leu Arg Glu Thr  Ala Thr Cys Thr Leu  Glu Glu Leu
1865             1870                  1875
```

Pro His Leu Ala Arg Asp Leu Pro Pro Arg Ser Arg Val Leu Leu
    1880                1885                1890

Ala Gly Met Val Glu Glu Val Arg Lys Pro Thr Lys Ser Gly
    1895                1900                1905

Gly Met Met Ala Arg Phe Val Leu Ser Asp Glu Thr Gly Ala Leu
    1910                1915                1920

Glu Ala Val Ala Phe Gly Arg Ala Tyr Asp Gln Val Ser Pro Arg
    1925                1930                1935

Leu Lys Glu Asp Thr Pro Val Leu Val Leu Ala Glu Val Glu Arg
    1940                1945                1950

Glu Glu Gly Gly Val Arg Val Leu Ala Gln Ala Val Trp Thr Tyr
    1955                1960                1965

Glu Glu Leu Glu Gln Val Pro Arg Ala Leu Glu Val Glu Val Glu
    1970                1975                1980

Ala Ser Leu Leu Asp Asp Arg Gly Val Ala His Leu Lys Ser Leu
    1985                1990                1995

Leu Asp Glu His Ala Gly Thr Leu Pro Leu Tyr Val Arg Val Gln
    2000                2005                2010

Gly Ala Phe Gly Glu Ala Leu Leu Ala Leu Arg Glu Val Arg Val
    2015                2020                2025

Gly Glu Glu Ala Leu Gly Ala Leu Glu Ala Ala Gly Phe Arg Ala
    2030                2035                2040

Tyr Leu Leu Pro Asp Arg Glu Val Leu Leu Gln Gly Gly Gln Ala
    2045                2050                2055

Gly Glu Ala Gln Glu Ala Val Pro Phe
    2060                2065

<210> SEQ ID NO 8
<211> LENGTH: 1040
<212> TYPE: PRT
<213> ORGANISM: Artificial
<220> FEATURE:
<223> OTHER INFORMATION: Synthetic

<400> SEQUENCE: 8

Leu Arg Phe Ala His Leu His Gln His Thr Gln Phe Ser Leu Leu Asp
1               5                   10                  15

Gly Ala Ala Lys Leu Asp Leu Leu Lys Trp Val Lys Glu Thr Pro Pro
                20                  25                  30

Ala Leu Ala Met Thr Asp His Gly Asn Leu Phe Gly Ala Val Phe Tyr
            35                  40                  45

Lys Ala Gly Met Gly Ile Lys Pro Ile Ile Gly Tyr Glu Ala Tyr Val
        50                  55                  60

Ala Ala Glu Ser Arg Phe Asp Arg Lys Arg Lys Gly Lys Gly Gly Phe
65                  70                  75                  80

His Leu Thr Leu Leu Ala Lys Asp Phe Thr Gly Tyr Gln Asn Leu Val
                85                  90                  95

Arg Leu Ala Ser Arg Ala Tyr Glu Gly Phe Tyr Lys Pro Arg Ile Asp
            100                 105                 110

Arg Glu Ile Leu Arg Glu His Ala Glu Gly Leu Ile Ala Leu Ser Gly
        115                 120                 125

Cys Leu Gly Ala Glu Ile Gln Phe Ile Leu Gln Arg Leu Asp Leu Ala
    130                 135                 140

Glu Ala Arg Leu Glu Tyr Leu Glu Ile Phe Asp Arg Phe Phe Ile Glu
145                 150                 155                 160

-continued

```
Ile Gln His Gly Leu Pro Glu Gln Lys Lys Asn Asn Val Leu Lys Glu
            165                 170                 175
Phe Ala Arg Lys Tyr Gly Leu Gly Met Val Ala Thr Asn Asp Gly His
        180                 185                 190
Tyr Val Arg Lys Glu Asp Ala Ala His Glu Val Leu Leu Ala Ile Gln
    195                 200                 205
Ser Lys Thr Leu Asp Asp Pro Arg Trp Arg Phe Pro Cys Asp Glu Phe
210                 215                 220
Tyr Val Lys Thr Pro Glu Glu Met Arg Met Phe Pro Glu Glu Trp Gly
225                 230                 235                 240
Asp Glu Pro Phe Asp Asn Thr Val Glu Ile Ala Arg Met Cys Asn Val
            245                 250                 255
Glu Leu Pro Ile Gly Asp Lys Tyr Ile Pro Arg Phe Pro Leu Pro Arg
        260                 265                 270
Thr Ala Asp Tyr Leu Arg Glu Leu Thr Phe Gly Leu Leu Arg Arg Tyr
    275                 280                 285
Pro Ile Thr Glu Gly Arg Glu Val Arg Gly Leu Pro His Gly Ala Glu
290                 295                 300
Ala Ile Arg Ala Tyr Glu Leu Ser Val Ile Arg Met Gly Phe Pro Gly
305                 310                 315                 320
Tyr Phe Leu Ile Val Gln Asp Tyr Ile Asn Trp Ala Lys Asn Gly Val
            325                 330                 335
Ser Val Gly Pro Gly Arg Gly Ser Ala Ala Gly Ser Leu Val Ala Tyr
        340                 345                 350
Ala Val Gly Ile Thr Asn Ile Asp Pro Leu Arg Phe Gly Leu Leu Phe
    355                 360                 365
Glu Arg Phe Leu Asn Pro Glu Arg Val Ser Met Pro Asp Ile Asp Val
370                 375                 380
Asp Phe Asp Arg Asp Arg Val Ile Tyr Val Arg Glu Arg Tyr Gly Asp
385                 390                 395                 400
Lys Val Ala Gln Ile Gly Thr Phe Gly Ser Met Ala Ser Lys Ala Leu
            405                 410                 415
Lys Asp Val Ala Arg Val Gly Ile Pro Tyr Lys Ala Asp Lys Leu Ala
        420                 425                 430
Lys Leu Ile Pro Val Phe Gly Lys Leu Glu Ala Glu Val Pro Glu Leu
    435                 440                 445
Arg Met Glu Asp Val Arg Glu Val Ile Glu Val Ala Met Lys Leu Glu
450                 455                 460
Gly Leu Thr Arg His Ala Ser Val His Ala Ala Gly Val Val Ile Ala
465                 470                 475                 480
Glu Pro Leu Thr Asp Leu Val Pro Leu Met Arg Asp Glu Gly Arg Pro
            485                 490                 495
Val Thr Gln Tyr Asp Met Ala Val Glu Ala Leu Gly Leu Leu Lys Met
        500                 505                 510
Asp Phe Leu Gly Leu Arg Thr Leu Thr Phe Leu Asp Glu Ala Lys Arg
    515                 520                 525
Ile Ile Lys Ser Gly Val Glu Leu Asp Tyr Asp Leu Pro Leu Asp Asp
530                 535                 540
Pro Lys Thr Phe Leu Leu Ser Arg Gly Glu Thr Lys Gly Val Phe Gln
545                 550                 555                 560
Leu Glu Ser Gly Gly Met Asp Leu Arg Lys Leu Lys Pro Arg Arg Phe
            565                 570                 575
Glu Asp Ile Ile Ala Leu Leu Ala Leu Tyr Arg Pro Gly Pro Met Glu
        580                 585                 590
```

```
Ile Pro Thr Tyr Ile Arg Arg His His Gly Glu Pro Val Ser Tyr Glu
            595                 600                 605

Phe Pro His Ala Tyr Leu Lys Pro Leu Asp Glu Thr Tyr Gly Ile Pro
    610                 615                 620

Val Tyr Gln Glu Gln Ile Met Gln Ile Ala Ser Val Ala Gly Tyr Ser
625                 630                 635                 640

Leu Gly Glu Ala Asp Leu Leu Arg Arg Ala Met Gly Lys Lys Lys Glu
                645                 650                 655

Glu Met Lys Arg Phe Val Gly Ala Lys Glu Arg Gly Val Pro Glu Glu
                660                 665                 670

Ala Lys Leu Phe Asp Met Leu Glu Ala Phe Ala Asn Tyr Gly Phe Asn
            675                 680                 685

Lys Ser His Ser Ala Ala Tyr Ser Leu Leu Ser Tyr Gln Thr Ala Tyr
        690                 695                 700

Val Lys Ala His Tyr Pro Val Glu Phe Met Ala Ala Leu Leu Thr Val
705                 710                 715                 720

Glu Arg Asp Ser Asp Lys Val Ala Glu Tyr Ile Arg Asp Ala Arg Met
                725                 730                 735

Gly Ile Val Leu Pro Pro Asp Val Asn Arg Ser Phe Asp Phe Val Gly
                740                 745                 750

Glu Ile Leu Phe Gly Leu Ser Ala Ile Lys Gly Val Gly Glu Ala Ala
            755                 760                 765

Ala Glu Ala Ile Leu Glu Glu Arg Glu Lys Gly Gly Pro Phe Lys Ser
    770                 775                 780

Leu Gly Asp Phe Leu Arg Leu Asp Lys Val Leu Asn Lys Arg Leu Glu
785                 790                 795                 800

Ser Leu Ile Lys Ala Gly Ala Leu Asp Ala Phe Gly Glu Arg Ala Leu
                805                 810                 815

Leu Ala Ser Leu Glu Leu Arg Ala Ala Thr Ala Glu Ala Ser Gly Met
                820                 825                 830

Gly Leu Phe Ala Glu Glu Glu Pro Ala Ala Pro Leu Asp Glu Ile Arg
            835                 840                 845

Leu Arg Glu Lys Glu Ala Leu Gly Ile Tyr Val Ser Gly His Pro Ile
        850                 855                 860

Tyr Gly Leu Arg Glu Ala Ser Cys Ile Glu Glu Leu Arg Glu Lys Val
865                 870                 875                 880

Leu Leu Ala Gly Met Val Glu Glu Val Arg Lys Pro Thr Lys Ser
                885                 890                 895

Gly Gly Met Met Ala Arg Phe Leu Ser Asp Glu Thr Gly Leu Glu Val
                900                 905                 910

Leu Phe Arg Ala Tyr Asp Val Pro Lys Leu Glu Asp Pro Val Leu Val
        915                 920                 925

Leu Ala Glu Val Glu Asp Leu Lys Val Leu Val Glu Glu
    930                 935                 940

Val Pro Arg Ala Leu Val Leu Asp Leu Leu Asp Gly Leu Ala Leu
945                 950                 955                 960

Lys Ser Leu Leu Asp Glu His Gly Ser Leu Pro Leu Tyr Leu Arg Val
                965                 970                 975

Ala Asp Gly Ala Leu Leu Glu Val Glu Ala Leu Ala Leu Leu
            980                 985                 990

Asn Ala Arg Ala Glu Val Gly Gly  Lys Ser Leu Leu Asp  Glu His Gly
            995                 1000                1005

Ser Leu  Pro Leu Tyr Leu Arg  Val Ala Asp Gly Ala  Leu Leu Leu
```

<210> SEQ ID NO 9
<211> LENGTH: 3903
<212> TYPE: DNA
<213> ORGANISM: Thermus thermophilus
<220> FEATURE:
<221> NAME/KEY: CDS
<222> LOCATION: (108)..(3770)

<400> SEQUENCE: 9

```
aacgattcgg tcccgggtct agaccatggg atacctagga ggtaataaat aatgaaaatc      60
tacctggttg gtggtgctgt tcgcgatgca ttgaggagga tcgatta atg ggc cgc       116
                                                    Met Gly Arg
                                                      1 aaa ctc cgc ttc gcc cac ctc cac cag cac acc cag ttc tcc ctc ctg       164
Lys Leu Arg Phe Ala His Leu His Gln His Thr Gln Phe Ser Leu Leu
  5                  10                  15 gac ggg gcg gcg aag ctt tcc gac ctc ctc aag tgg gtc aag gag acg       212
Asp Gly Ala Ala Lys Leu Ser Asp Leu Leu Lys Trp Val Lys Glu Thr
 20                  25                  30                  35 acc ccc gag gac ccc gcc ttg gcc atg acc gac cac ggc aac ctc ttc       260
Thr Pro Glu Asp Pro Ala Leu Ala Met Thr Asp His Gly Asn Leu Phe
                 40                  45                  50 ggg gcc gtg gag ttc tac aag aag gcc acc gaa atg ggc atc aag ccc       308
Gly Ala Val Glu Phe Tyr Lys Lys Ala Thr Glu Met Gly Ile Lys Pro
             55                  60                  65 atc ctg ggc tac gag gcc tac gtg gcg gcg gaa agc cgc ttt gac cgc       356
Ile Leu Gly Tyr Glu Ala Tyr Val Ala Ala Glu Ser Arg Phe Asp Arg
         70                  75                  80 aag cgg gga aag ggc cta gac ggg ggc tac ttt cac ctc acc ctc ctc       404
Lys Arg Gly Lys Gly Leu Asp Gly Gly Tyr Phe His Leu Thr Leu Leu
     85                  90                  95 gcc aag gac ttc acg ggg tac cag aac ctg gtg cgc ctg gcg agc cgg       452
Ala Lys Asp Phe Thr Gly Tyr Gln Asn Leu Val Arg Leu Ala Ser Arg
100                 105                 110                 115 gct tac ctg gag ggg ttt tac gaa aag ccc cgg att gac cgg gag atc       500
Ala Tyr Leu Glu Gly Phe Tyr Glu Lys Pro Arg Ile Asp Arg Glu Ile
                120                 125                 130 ctg cgc gag cac gcc gag ggc ctc atc gcc ctc tcg ggg tgc ctc ggg       548
Leu Arg Glu His Ala Glu Gly Leu Ile Ala Leu Ser Gly Cys Leu Gly
            135                 140                 145 gcg gag atc ccc cag ttc atc ctc cag gac cgt ctg gac ctg gcc gag       596
Ala Glu Ile Pro Gln Phe Ile Leu Gln Asp Arg Leu Asp Leu Ala Glu
        150                 155                 160 gcc cgg ctc aac gag tac ctc tcc atc ttc aag gac cgc ttc ttc att       644
Ala Arg Leu Asn Glu Tyr Leu Ser Ile Phe Lys Asp Arg Phe Phe Ile
    165                 170                 175 gag atc cag aac cac ggc ctc ccc gag cag aaa aag gtc aac gag gtc       692
Glu Ile Gln Asn His Gly Leu Pro Glu Gln Lys Lys Val Asn Glu Val
180                 185                 190                 195 ctc aag gag ttc gcc cga aag tac ggc ctg ggg atg gtg gcc acc aac       740
Leu Lys Glu Phe Ala Arg Lys Tyr Gly Leu Gly Met Val Ala Thr Asn
                200                 205                 210 gac ggc cat tac gtg agg aag gag gac gcc cgg gcc cac gag gtc ctc       788
Asp Gly His Tyr Val Arg Lys Glu Asp Ala Arg Ala His Glu Val Leu
            215                 220                 225
```

-continued

| | | | | | | | | | | | | | | | |
|---|---|---|---|---|---|---|---|---|---|---|---|---|---|---|---|
| ctc | gcc | atc | cag | tcc | aag | agc | acc | ctg | gac | gac | ccc | ggg | cgc | tgg | cgc | 836 |
| Leu | Ala | Ile | Gln | Ser | Lys | Ser | Thr | Leu | Asp | Asp | Pro | Gly | Arg | Trp | Arg |
| | | | 230 | | | | 235 | | | | 240 | | | | | ttc ccc tgc gac gag ttc tac gtg aag acc ccc gag gag atg cgg gcc 884
Phe Pro Cys Asp Glu Phe Tyr Val Lys Thr Pro Glu Glu Met Arg Ala
245 250 255 atg ttc ccc gag gag gag tgg ggg gac gag ccc ttt gac aac acc gtg 932
Met Phe Pro Glu Glu Glu Trp Gly Asp Glu Pro Phe Asp Asn Thr Val
260 265 270 275 gag atc gcc cgc atg tgc aac gtg gag ctg ccc atc ggg gac aag atg 980
Glu Ile Ala Arg Met Cys Asn Val Glu Leu Pro Ile Gly Asp Lys Met
280 285 290 gtc tac cgc atc ccc cgc ttc ccc ctc ccc gcc cgt cgg acc gag gcc 1028
Val Tyr Arg Ile Pro Arg Phe Pro Leu Pro Ala Arg Arg Thr Glu Ala
295 300 305 cag tac ctc atg gag ctc acc ttt aag ggg ctc ctc cgc cgc tac ccg 1076
Gln Tyr Leu Met Glu Leu Thr Phe Lys Gly Leu Leu Arg Arg Tyr Pro
310 315 320 gac cgg atc acc gag ggc ttc tac cgg gag gtc ttc cgc ctt ttg ggg 1124
Asp Arg Ile Thr Glu Gly Phe Tyr Arg Glu Val Phe Arg Leu Leu Gly
325 330 335 aag ctt ccc ccc cac ggg gac ggg gag gcc ctg gcc gag gcc ttg gcc 1172
Lys Leu Pro Pro His Gly Asp Gly Glu Ala Leu Ala Glu Ala Leu Ala
340 345 350 355 cag gtg gag cgg gag gct tgg gag agg ctc atg aag agc ctc ccc ccc 1220
Gln Val Glu Arg Glu Ala Trp Glu Arg Leu Met Lys Ser Leu Pro Pro
360 365 370 ttg gcc ggg gtc aag gag tgg acg gcg gag gcc att ttc cac cgg gcc 1268
Leu Ala Gly Val Lys Glu Trp Thr Ala Glu Ala Ile Phe His Arg Ala
375 380 385 ctt tac gag ctt tcc gtg ata gag cgc atg ggg ttt ccc ggc tac ttc 1316
Leu Tyr Glu Leu Ser Val Ile Glu Arg Met Gly Phe Pro Gly Tyr Phe
390 395 400 ctc atc gtc cag gac tac atc aac tgg gcc cgg aga aac ggc gtc tcc 1364
Leu Ile Val Gln Asp Tyr Ile Asn Trp Ala Arg Arg Asn Gly Val Ser
405 410 415 gtg ggg ccc ggc agg ggg agc gcc gcc ggg agc ctg gtg gcc tac gcc 1412
Val Gly Pro Gly Arg Gly Ser Ala Ala Gly Ser Leu Val Ala Tyr Ala
420 425 430 435 gtg ggg atc acc aac att gac ccc ctg cgc ttc ggc ctc ctc ttt gag 1460
Val Gly Ile Thr Asn Ile Asp Pro Leu Arg Phe Gly Leu Leu Phe Glu
440 445 450 cgc ttc ctg aac ccc gag agg gtc tcc atg ccc gac att gac acg gac 1508
Arg Phe Leu Asn Pro Glu Arg Val Ser Met Pro Asp Ile Asp Thr Asp
455 460 465 ttc tcc gac cgg gag cgg gac cgg gtg atc cag tac gtg cgg gaa cgc 1556
Phe Ser Asp Arg Glu Arg Asp Arg Val Ile Gln Tyr Val Arg Glu Arg
470 475 480 tac ggc gag gac aag gtg gcc cag atc ggc acc ctg gga agc ctc gcc 1604
Tyr Gly Glu Asp Lys Val Ala Gln Ile Gly Thr Leu Gly Ser Leu Ala
485 490 495 tcc aag gcc gcc ctc aag gac gtg gcc cgg gtc tac ggc atc ccc cac 1652
Ser Lys Ala Ala Leu Lys Asp Val Ala Arg Val Tyr Gly Ile Pro His
500 505 510 515 aag aag gcg gag gaa ttg gcc aag ctc atc ccg gtg cag ttc ggg aag 1700
Lys Lys Ala Glu Glu Leu Ala Lys Leu Ile Pro Val Gln Phe Gly Lys
520 525 530 ccc aag ccc ctg cag gag gcc atc cag gtg gtg ccg gag ctt agg gcg 1748
Pro Lys Pro Leu Gln Glu Ala Ile Gln Val Val Pro Glu Leu Arg Ala
535 540 545

```
gag atg gag aag gac ccc aag gtg cgg gag gtc ctc gag gtg gcc atg    1796
Glu Met Glu Lys Asp Pro Lys Val Arg Glu Val Leu Glu Val Ala Met
        550                 555                 560 cgc ctg gag ggc ctg aac cgc cac gcc tcc gtc cac gcc gcc ggg gtg    1844
Arg Leu Glu Gly Leu Asn Arg His Ala Ser Val His Ala Ala Gly Val
565                 570                 575 gtg atc gcc gcc gag ccc ctc acg gac ctc gtc ccc ctc atg cgc gac    1892
Val Ile Ala Ala Glu Pro Leu Thr Asp Leu Val Pro Leu Met Arg Asp
580                 585                 590                 595 cag gaa ggg cgg ccc gtc acc cag tac gac atg ggg gcg gtg gag gcc    1940
Gln Glu Gly Arg Pro Val Thr Gln Tyr Asp Met Gly Ala Val Glu Ala
            600                 605                 610 ttg ggc ctt ttg aag atg gac ttt ttg ggc ctc cgc acc ctc acc ttc    1988
Leu Gly Leu Leu Lys Met Asp Phe Leu Gly Leu Arg Thr Leu Thr Phe
                615                 620                 625 ctg gac gag gtc aag cgc atc gtc aag gcg tcc cag ggg gtg gag ctg    2036
Leu Asp Glu Val Lys Arg Ile Val Lys Ala Ser Gln Gly Val Glu Leu
            630                 635                 640 gac tac gat gcc ctc ccc ctg gac gac ccc aag acc ttc gcc ctc ctc    2084
Asp Tyr Asp Ala Leu Pro Leu Asp Asp Pro Lys Thr Phe Ala Leu Leu
645                 650                 655 tcc cgg ggg gag acc aag ggg gtc ttc cag ctg gag tcg ggg ggg atg    2132
Ser Arg Gly Glu Thr Lys Gly Val Phe Gln Leu Glu Ser Gly Gly Met
660                 665                 670                 675 acc gcc acg ctc cgc ggc ctc aag ccg cgg cgc ttt gag gac ctg atc    2180
Thr Ala Thr Leu Arg Gly Leu Lys Pro Arg Arg Phe Glu Asp Leu Ile
            680                 685                 690 gcc atc ctc tcc ctc tac cgc ccc ggg ccc atg gag cac atc ccc acc    2228
Ala Ile Leu Ser Leu Tyr Arg Pro Gly Pro Met Glu His Ile Pro Thr
                695                 700                 705 tac atc cgc cgc cac cac ggg ctg gag ccc gtg agc tac agc gag ttt    2276
Tyr Ile Arg Arg His His Gly Leu Glu Pro Val Ser Tyr Ser Glu Phe
            710                 715                 720 ccc cac gcc gag aag tac cta aag ccc atc ctg gac gag acc tac ggc    2324
Pro His Ala Glu Lys Tyr Leu Lys Pro Ile Leu Asp Glu Thr Tyr Gly
725                 730                 735 atc ccc gtc tac cag gag cag atc atg cag atc gcc tcg gcc gtg gcg    2372
Ile Pro Val Tyr Gln Glu Gln Ile Met Gln Ile Ala Ser Ala Val Ala
740                 745                 750                 755 ggg tac tcc ctg ggc gag gcg gac ctc ctc agg cgg gcc atg ggg aag    2420
Gly Tyr Ser Leu Gly Glu Ala Asp Leu Leu Arg Arg Ala Met Gly Lys
                760                 765                 770 aag aag ctg gag gag atg cag aag cac cgg gag cgc ttc gtc cag ggg    2468
Lys Lys Leu Glu Glu Met Gln Lys His Arg Glu Arg Phe Val Gln Gly
            775                 780                 785 gcc aag gaa agg ggc gtg ccc gag gag gag gcc aac cgc ctc ttt gac    2516
Ala Lys Glu Arg Gly Val Pro Glu Glu Glu Ala Asn Arg Leu Phe Asp
790                 795                 800 atg ctg gag gcc ttc gcc aac tac ggc ttc aac aaa tct cat gca gcg    2564
Met Leu Glu Ala Phe Ala Asn Tyr Gly Phe Asn Lys Ser His Ala Ala
805                 810                 815 gcc tac agc ctc ctc tcc tac cag acc gcc tac gtg aag gcc cac tac    2612
Ala Tyr Ser Leu Leu Ser Tyr Gln Thr Ala Tyr Val Lys Ala His Tyr
820                 825                 830                 835 ccc gtg gag ttc atg gcc gcc ctc ctc tcc gtg gag cgg cac gac tcc    2660
Pro Val Glu Phe Met Ala Ala Leu Leu Ser Val Glu Arg His Asp Ser
                840                 845                 850 gac aag gtg gcc gag tac atc cgc gac gcc cgg gcc atg ggc ata gag    2708
Asp Lys Val Ala Glu Tyr Ile Arg Asp Ala Arg Ala Met Gly Ile Glu
            855                 860                 865
```

-continued

| | |
|---|---|
| gtc ctt ccc ccg gac gtc aac cgc tcc ggg ttt gac ttt ctg gtc cag<br>Val Leu Pro Pro Asp Val Asn Arg Ser Gly Phe Asp Phe Leu Val Gln<br>870                              875                              880 | 2756 |
| ggc cgg cag atc ctc ttc ggc ctc tcc gcg gtg aaa aac gtg ggc gag<br>Gly Arg Gln Ile Leu Phe Gly Leu Ser Ala Val Lys Asn Val Gly Glu<br>885                              890                            895 | 2804 |
| gcg gcg gcg gag gcc att ctc cgg gag cgg gag cgg ggc ggc ccc tac<br>Ala Ala Ala Glu Ala Ile Leu Arg Glu Arg Glu Arg Gly Gly Pro Tyr<br>900                              905                            910                            915 | 2852 |
| cgg agc ctc ggg gac ttc ctc aag cgg ctg gac gag aag gtg ctc aac<br>Arg Ser Leu Gly Asp Phe Leu Lys Arg Leu Asp Glu Lys Val Leu Asn<br>                        920                            925                            930 | 2900 |
| aag cgg acc ctg gag tcc ctc atc aag gcg ggt gcc ctg gac ggc ttc<br>Lys Arg Thr Leu Glu Ser Leu Ile Lys Ala Gly Ala Leu Asp Gly Phe<br>                935                            940                            945 | 2948 |
| ggg gaa agg gcg cgg ctc ctc gcc tcc ctg gag ggg ctc ctc agg tgg<br>Gly Glu Arg Ala Arg Leu Leu Ala Ser Leu Glu Gly Leu Leu Arg Trp<br>              950                            955                            960 | 2996 |
| gcg gcc gag act cgg gag aag gcc cgc tcg ggc atg atg ggc ctc ttc<br>Ala Ala Glu Thr Arg Glu Lys Ala Arg Ser Gly Met Met Gly Leu Phe<br>965                              970                            975 | 3044 |
| agc gaa gtg gag gag ccg cct ttg gcc gag gcc gcc ccc ctg gac gag<br>Ser Glu Val Glu Glu Pro Pro Leu Ala Glu Ala Ala Pro Leu Asp Glu<br>980                              985                            990                            995 | 3092 |
| atc acc cgg ctc cgc tac gaa aag gag gcc ctg ggg att tat gtt<br>Ile Thr Arg Leu Arg Tyr Glu Lys Glu Ala Leu Gly Ile Tyr Val<br>                      1000                            1005                          1010 | 3137 |
| tcc ggc cat ccc atc ttg cgg tat ccc ggg ctc cgg gag acg gcc<br>Ser Gly His Pro Ile Leu Arg Tyr Pro Gly Leu Arg Glu Thr Ala<br>                      1015                            1020                          1025 | 3182 |
| acc tgc acc ctg gag gag ctt ccc cac ctg gcc cgg gac ctg ccg<br>Thr Cys Thr Leu Glu Glu Leu Pro His Leu Ala Arg Asp Leu Pro<br>                      1030                            1035                          1040 | 3227 |
| ccc cgg tct agg gtc ctc ctc gcc ggc atg gtg gag gag gtg gtg<br>Pro Arg Ser Arg Val Leu Leu Ala Gly Met Val Glu Glu Val Val<br>                      1045                            1050                          1055 | 3272 |
| cgc aag ccc acg aaa agc ggc ggg atg atg gcc cgc ttc gtc ctc<br>Arg Lys Pro Thr Lys Ser Gly Gly Met Met Ala Arg Phe Val Leu<br>                      1060                            1065                          1070 | 3317 |
| tcc gac gag acg ggg gcg ctt gag gcg gtg gcc ttc ggc cgg gcc<br>Ser Asp Glu Thr Gly Ala Leu Glu Ala Val Ala Phe Gly Arg Ala<br>                      1075                            1080                          1085 | 3362 |
| tac gac cag gtc tcc ccg agg ctc aag gag gac acc ccc gtg ctc<br>Tyr Asp Gln Val Ser Pro Arg Leu Lys Glu Asp Thr Pro Val Leu<br>                      1090                            1095                          1100 | 3407 |
| gtc ctc gcc gag gtg gag cgg gag gag ggg ggc gtg cgg gtg ctg<br>Val Leu Ala Glu Val Glu Arg Glu Glu Gly Gly Val Arg Val Leu<br>                      1105                            1110                          1115 | 3452 |
| gcc cag gcc gtt tgg acc tac gag gag ctg gag cag gtc ccc cgg<br>Ala Gln Ala Val Trp Thr Tyr Glu Glu Leu Glu Gln Val Pro Arg<br>                      1120                            1125                          1130 | 3497 |
| gcc ctc gag gtg gag gtg gag gcc tcc ctg ctg gac gac cgg ggg<br>Ala Leu Glu Val Glu Val Glu Ala Ser Leu Leu Asp Asp Arg Gly<br>                      1135                            1140                          1145 | 3542 |
| gtg gcc cac ctg aaa agc ctc ctg gac gag cac gcg ggg acc ctc<br>Val Ala His Leu Lys Ser Leu Leu Asp Glu His Ala Gly Thr Leu<br>                      1150                            1155                          1160 | 3587 |
| ccc ctg tac gtc cgg gtc cag ggc gcc ttc ggc gag gcc ctc ctc<br>Pro Leu Tyr Val Arg Val Gln Gly Ala Phe Gly Glu Ala Leu Leu<br>                      1165                            1170                          1175 | 3632 |

-continued

```
gcc ctg agg gag gtg cgg gtg ggg gag gag gcc ttg gcg gcc ctc     3677
Ala Leu Arg Glu Val Arg Val Gly Glu Glu Ala Leu Ala Ala Leu
             1180                1185                1190 gag gcc gag ggg ttc cgg gcc tac ctc ctg cct gac cgg gag gtc     3722
Glu Ala Glu Gly Phe Arg Ala Tyr Leu Leu Pro Asp Arg Glu Val
             1195                1200                1205 ctc ctc cag ggc ggc cag gcg ggg gag gcc cag gag gcg gtg ccc     3767
Leu Leu Gln Gly Gly Gln Ala Gly Glu Ala Gln Glu Ala Val Pro
             1210                1215                1220 ttc taggggtgg gccgtgagac aggtgccat cgtcctcccc gggggcaagg       3820
Phe aggcctgggc cgagcgcttt ggggtgggga gcaaggccct cgtgccctac cgcggccggc  3880
cactagtggt ggtggtggtc tgg                                       3903
```

<210> SEQ ID NO 10
<211> LENGTH: 1221
<212> TYPE: PRT
<213> ORGANISM: Thermus thermophilus

<400> SEQUENCE: 10

```
Met Gly Arg Lys Leu Arg Phe Ala His Leu His Gln His Thr Gln Phe
1               5                   10                  15

Ser Leu Leu Asp Gly Ala Ala Lys Leu Ser Asp Leu Leu Lys Trp Val
            20                  25                  30

Lys Glu Thr Thr Pro Glu Asp Pro Ala Leu Ala Met Thr Asp His Gly
        35                  40                  45

Asn Leu Phe Gly Ala Val Glu Phe Tyr Lys Lys Ala Thr Glu Met Gly
    50                  55                  60

Ile Lys Pro Ile Leu Gly Tyr Glu Ala Tyr Val Ala Ala Glu Ser Arg
65                  70                  75                  80

Phe Asp Arg Lys Arg Gly Lys Gly Leu Asp Gly Gly Tyr Phe His Leu
                85                  90                  95

Thr Leu Leu Ala Lys Asp Phe Thr Gly Tyr Gln Asn Leu Val Arg Leu
            100                 105                 110

Ala Ser Arg Ala Tyr Leu Glu Gly Phe Tyr Glu Lys Pro Arg Ile Asp
        115                 120                 125

Arg Glu Ile Leu Arg Glu His Ala Glu Gly Leu Ile Ala Leu Ser Gly
    130                 135                 140

Cys Leu Gly Ala Glu Ile Pro Gln Phe Ile Leu Gln Asp Arg Leu Asp
145                 150                 155                 160

Leu Ala Glu Ala Arg Leu Asn Glu Tyr Leu Ser Ile Phe Lys Asp Arg
                165                 170                 175

Phe Phe Ile Glu Ile Gln Asn His Gly Leu Pro Glu Gln Lys Lys Val
            180                 185                 190

Asn Glu Val Leu Lys Glu Phe Ala Arg Lys Tyr Gly Leu Gly Met Val
        195                 200                 205

Ala Thr Asn Asp Gly His Tyr Val Arg Lys Glu Asp Ala Arg Ala His
    210                 215                 220

Glu Val Leu Leu Ala Ile Gln Ser Lys Ser Thr Leu Asp Asp Pro Gly
225                 230                 235                 240

Arg Trp Arg Phe Pro Cys Asp Glu Phe Tyr Val Lys Thr Pro Glu Glu
                245                 250                 255

Met Arg Ala Met Phe Pro Glu Glu Trp Gly Asp Glu Pro Phe Asp
            260                 265                 270

Asn Thr Val Glu Ile Ala Arg Met Cys Asn Val Glu Leu Pro Ile Gly
```

```
            275                 280                 285
Asp Lys Met Val Tyr Arg Ile Pro Arg Phe Pro Leu Pro Ala Arg Arg
290                 295                 300

Thr Glu Ala Gln Tyr Leu Met Glu Leu Thr Phe Lys Gly Leu Leu Arg
305                 310                 315                 320

Arg Tyr Pro Asp Arg Ile Thr Glu Gly Phe Tyr Arg Glu Val Phe Arg
                325                 330                 335

Leu Leu Gly Lys Leu Pro Pro His Gly Asp Gly Glu Ala Leu Ala Glu
            340                 345                 350

Ala Leu Ala Gln Val Glu Arg Glu Ala Trp Glu Arg Leu Met Lys Ser
        355                 360                 365

Leu Pro Pro Leu Ala Gly Val Lys Glu Trp Thr Ala Glu Ala Ile Phe
370                 375                 380

His Arg Ala Leu Tyr Glu Leu Ser Val Ile Glu Arg Met Gly Phe Pro
385                 390                 395                 400

Gly Tyr Phe Leu Ile Val Gln Asp Tyr Ile Asn Trp Ala Arg Arg Asn
                405                 410                 415

Gly Val Ser Val Gly Pro Gly Arg Gly Ser Ala Ala Gly Ser Leu Val
            420                 425                 430

Ala Tyr Ala Val Gly Ile Thr Asn Ile Asp Pro Leu Arg Phe Gly Leu
        435                 440                 445

Leu Phe Glu Arg Phe Leu Asn Pro Glu Arg Val Ser Met Pro Asp Ile
450                 455                 460

Asp Thr Asp Phe Ser Asp Arg Glu Arg Asp Arg Val Ile Gln Tyr Val
465                 470                 475                 480

Arg Glu Arg Tyr Gly Glu Asp Lys Val Ala Gln Ile Gly Thr Leu Gly
                485                 490                 495

Ser Leu Ala Ser Lys Ala Ala Leu Lys Asp Val Ala Arg Val Tyr Gly
            500                 505                 510

Ile Pro His Lys Lys Ala Glu Glu Leu Ala Lys Leu Ile Pro Val Gln
        515                 520                 525

Phe Gly Lys Pro Lys Pro Leu Gln Glu Ala Ile Gln Val Val Pro Glu
530                 535                 540

Leu Arg Ala Glu Met Glu Lys Asp Pro Lys Val Arg Glu Val Leu Glu
545                 550                 555                 560

Val Ala Met Arg Leu Glu Gly Leu Asn Arg His Ala Ser Val His Ala
                565                 570                 575

Ala Gly Val Val Ile Ala Ala Glu Pro Leu Thr Asp Leu Val Pro Leu
            580                 585                 590

Met Arg Asp Gln Glu Gly Arg Pro Val Thr Gln Tyr Asp Met Gly Ala
        595                 600                 605

Val Glu Ala Leu Gly Leu Leu Lys Met Asp Phe Leu Gly Leu Arg Thr
610                 615                 620

Leu Thr Phe Leu Asp Glu Val Lys Arg Ile Val Lys Ala Ser Gln Gly
625                 630                 635                 640

Val Glu Leu Asp Tyr Asp Ala Leu Pro Leu Asp Asp Pro Lys Thr Phe
                645                 650                 655

Ala Leu Leu Ser Arg Gly Glu Thr Lys Gly Val Phe Gln Leu Glu Ser
            660                 665                 670

Gly Gly Met Thr Ala Thr Leu Arg Gly Leu Lys Pro Arg Arg Phe Glu
        675                 680                 685

Asp Leu Ile Ala Ile Leu Ser Leu Tyr Arg Pro Gly Pro Met Glu His
690                 695                 700
```

-continued

Ile Pro Thr Tyr Ile Arg Arg His His Gly Leu Glu Pro Val Ser Tyr
705                 710                 715                 720

Ser Glu Phe Pro His Ala Glu Lys Tyr Leu Lys Pro Ile Leu Asp Glu
            725                 730                 735

Thr Tyr Gly Ile Pro Val Tyr Gln Gln Ile Met Gln Ile Ala Ser
        740                 745                 750

Ala Val Ala Gly Tyr Ser Leu Gly Glu Ala Asp Leu Leu Arg Arg Ala
        755                 760                 765

Met Gly Lys Lys Lys Leu Glu Glu Met Gln Lys His Arg Glu Arg Phe
    770                 775                 780

Val Gln Gly Ala Lys Glu Arg Gly Val Pro Glu Glu Ala Asn Arg
785                 790                 795                 800

Leu Phe Asp Met Leu Glu Ala Phe Ala Asn Tyr Gly Phe Asn Lys Ser
            805                 810                 815

His Ala Ala Ala Tyr Ser Leu Leu Ser Tyr Gln Thr Ala Tyr Val Lys
        820                 825                 830

Ala His Tyr Pro Val Glu Phe Met Ala Ala Leu Leu Ser Val Glu Arg
    835                 840                 845

His Asp Ser Asp Lys Val Ala Glu Tyr Ile Arg Asp Ala Arg Ala Met
850                 855                 860

Gly Ile Glu Val Leu Pro Pro Asp Val Asn Arg Ser Gly Phe Asp Phe
865                 870                 875                 880

Leu Val Gln Gly Arg Gln Ile Leu Phe Gly Leu Ser Ala Val Lys Asn
            885                 890                 895

Val Gly Glu Ala Ala Ala Glu Ala Ile Leu Arg Glu Arg Glu Arg Gly
        900                 905                 910

Gly Pro Tyr Arg Ser Leu Gly Asp Phe Leu Lys Arg Leu Asp Glu Lys
    915                 920                 925

Val Leu Asn Lys Arg Thr Leu Glu Ser Leu Ile Lys Ala Gly Ala Leu
930                 935                 940

Asp Gly Phe Gly Glu Arg Ala Arg Leu Leu Ala Ser Leu Glu Gly Leu
945                 950                 955                 960

Leu Arg Trp Ala Ala Glu Thr Arg Glu Lys Ala Arg Ser Gly Met Met
            965                 970                 975

Gly Leu Phe Ser Glu Val Glu Glu Pro Pro Leu Ala Glu Ala Ala Pro
        980                 985                 990

Leu Asp Glu Ile Thr Arg Leu Arg Tyr Glu Lys Glu Ala Leu Gly Ile
    995                 1000                1005

Tyr Val Ser Gly His Pro Ile Leu Arg Tyr Pro Gly Leu Arg Glu
    1010                1015                1020

Thr Ala Thr Cys Thr Leu Glu Leu Pro His Leu Ala Arg Asp
    1025                1030                1035

Leu Pro Pro Arg Ser Arg Val Leu Leu Ala Gly Met Val Glu Glu
    1040                1045                1050

Val Val Arg Lys Pro Thr Lys Ser Gly Gly Met Met Ala Arg Phe
    1055                1060                1065

Val Leu Ser Asp Glu Thr Gly Ala Leu Glu Ala Val Ala Phe Gly
    1070                1075                1080

Arg Ala Tyr Asp Gln Val Ser Pro Arg Leu Lys Glu Asp Thr Pro
    1085                1090                1095

Val Leu Val Leu Ala Glu Val Glu Arg Glu Glu Gly Gly Val Arg
    1100                1105                1110

Val Leu Ala Gln Ala Val Trp Thr Tyr Glu Glu Leu Glu Gln Val
    1115                1120                1125

| Pro | Arg | Ala | Leu | Glu | Val | Glu | Val | Glu | Ala | Ser | Leu | Leu | Asp | Asp |
|-----|-----|-----|-----|-----|-----|-----|-----|-----|-----|-----|-----|-----|-----|-----|
| | 1130 | | | | 1135 | | | | | 1140 | | | | |

| Arg | Gly | Val | Ala | His | Leu | Lys | Ser | Leu | Leu | Asp | Glu | His | Ala | Gly |
|-----|-----|-----|-----|-----|-----|-----|-----|-----|-----|-----|-----|-----|-----|-----|
| | 1145 | | | | 1150 | | | | | 1155 | | | | |

| Thr | Leu | Pro | Leu | Tyr | Val | Arg | Val | Gln | Gly | Ala | Phe | Gly | Glu | Ala |
|-----|-----|-----|-----|-----|-----|-----|-----|-----|-----|-----|-----|-----|-----|-----|
| 1160 | | | | | 1165 | | | | | 1170 | | | | |

| Leu | Leu | Ala | Leu | Arg | Glu | Val | Arg | Val | Gly | Glu | Glu | Ala | Leu | Ala |
|-----|-----|-----|-----|-----|-----|-----|-----|-----|-----|-----|-----|-----|-----|-----|
| 1175 | | | | | 1180 | | | | | 1185 | | | | |

| Ala | Leu | Glu | Ala | Glu | Gly | Phe | Arg | Ala | Tyr | Leu | Leu | Pro | Asp | Arg |
|-----|-----|-----|-----|-----|-----|-----|-----|-----|-----|-----|-----|-----|-----|-----|
| 1190 | | | | | 1195 | | | | | 1200 | | | | |

| Glu | Val | Leu | Leu | Gln | Gly | Gly | Gln | Ala | Gly | Glu | Ala | Gln | Glu | Ala |
|-----|-----|-----|-----|-----|-----|-----|-----|-----|-----|-----|-----|-----|-----|-----|
| 1205 | | | | | 1210 | | | | | 1215 | | | | |

| Val | Pro | Phe |
|-----|-----|-----|
| 1220 | | |

<210> SEQ ID NO 11
<211> LENGTH: 3903
<212> TYPE: DNA
<213> ORGANISM: Thermus thermophilus

<400> SEQUENCE: 11

```
ccagaccacc accaccacta gtggccggcc gcggtagggc acgagggcct tgctccccac    60
cccaaagcgc tcggcccagg cctccttgcc cccggggagg acgatggcac cctgtctcac   120
ggcccacccc ctagaagggc accgcctcct gggcctcccc cgcctggccg ccctggagga   180
ggacctcccg gtcaggcagg aggtaggccc ggaacccctc ggcctcgagg ccgccaagg    240
cctcctcccc cacccgcacc tccctcaggg cgaggagggc ctcgccgaag cgccctgga   300
cccggacgta caggggagg gtcccgcgt gctcgtccag gaggcttttc aggtgggcca    360
ccccccggtc gtccaggagg gaggcctcca cctccacctc gagggcccgg ggacctgct   420
ccagctcctc gtaggtccaa acggcctggg ccagcacccg cacgccccc tcctcccgct   480
ccacctcggc gaggacgagc acggggtgt cctccttgag cctcggggag acctggtcgt   540
aggcccggcc gaaggccacc gcctcaagcg ccccccgtctc gtcggagagg acgaagcggg   600
ccatcatccc gccgcttttc gtgggcttgc gcaccacctc ctccaccatg ccggcgagga   660
ggaccctaga ccggggcggc aggtcccggg ccaggtgggg aagctcctcc agggtgcagg   720
tggccgtctc ccggagcccg ggataccgca agatgggatg ccggaaaaca taaatcccca   780
gggcctcctt ttcgtagcgg agccgggtga tctcgtccag ggggcggcc tcggccaaag   840
gcggctcctc cacttcgctg aagaggccca tcatgcccga gcgggccttc tcccgagtct   900
cggccgccca cctgaggagc ccctccaggg aggcgaggag ccgcgccctt tccccgaagc   960
cgtccagggc acccgccttg atgagggact ccagggtccg cttgttgagc accttctcgt  1020
ccagccgctt gaggaagtcc ccgaggctcc ggtaggggcc gccccgctcc cgctcccgga  1080
gaatggcctc cgccgccgcc tcgcccacgt ttttcaccgc ggagaggccg aagaggatct  1140
gccggccctg gaccagaaag tcaaacccgg agcggttgac gtccggggga aggacctcta  1200
tgcccatggc ccgggcgtcg cggatgtact cggccacctt gtcggagtcg tgccgctcca  1260
cggagaggag ggcggccatg aactccacgg ggtagtgggc cttcacgtag gcggtctggt  1320
aggagaggag gctgtaggcc gctgcatgag atttgttgaa gccgtagttg gcgaaggcct  1380
ccagcatgtc aaagaggcgg ttggcctcct cctcgggcac gcccctttcc ttggccccct  1440
ggacgaagcg ctcccggtgc ttctgcatct cctccagctt cttcttcccc atggcccgcc  1500
```

```
tgaggaggtc cgcctcgccc agggagtacc ccgccacggc cgaggcgatc tgcatgatct    1560
gctcctggta gacggggatg ccgtaggtct cgtccaggat gggctttagg tacttctcgg    1620 cgtgggaaa  ctcgctgtag ctcacgggct ccagcccgtg gtggcggcgg atgtaggtgg    1680
ggatgtgctc catgggcccg gggcggtaga gggagaggag ggcgatcagg tcctcaaagc    1740
gccgcggctt gaggccgcgg agcgtggcgg tcatccccc  cgactccagc tggaagaccc    1800
ccttggtctc cccccgggag aggagggcga aggtcttggg gtcgtccagg ggagggcat    1860 cgtagtccag ctccacccc  tgggacgcct tgacgatgcg cttgacctcg tccaggaagg    1920
tgagggtgcg gaggcccaaa aagtccatct tcaaaaggcc caaggcctcc accgccccca    1980
tgtcgtactg ggtgacgggc cgcccttcct ggtcgcgcat gaggggacg  aggtccgtga    2040 ggggctcggc ggcgatcacc accccggcgg cgtggacgga ggcgtggcgg ttcaggccct    2100
ccaggcgcat ggccacctcg aggacctccc gcaccttggg gtccttctcc atctccgccc    2160
taagctccgg caccacctgg atggcctcct gcagggcttt gggcttcccg aactgcaccg    2220
ggatgagctt ggccaattcc tccgccttct tgtgggggat gccgtagacc cgggccacgt    2280
ccttgagggc ggccttggag gcgaggcttc ccagggtgcc gatctgggcc accttgtcct    2340
cgccgtagcg ttcccgcacg tactggatca cccggtcccg ctcccggtcg gagaagtccg    2400
tgtcaatgtc gggcatggag accctctcgg ggttcaggaa gcgctcaaag aggaggccga    2460
agcgcagggg gtcaatgttg gtgatcccca cggcgtaggc caccaggctc ccggcggcgc    2520
tccccctgcc gggccccacg gagacgccgt ttctccgggc ccagttgatg tagtcctgga    2580
cgatgaggaa gtagccggga aaccccatgc gctctatcac ggaaagctcg taaagggccc    2640
ggtggaaaat ggcctccgcc gtccactcct tgacccccggc caagggggg  aggctcttca    2700 tgagcctctc ccaagcctcc cgctccacct gggccaaggc ctcggccagg gcctccccgt    2760
ccccgtgggg gggaagcttc cccaaaaggc ggaagacctc ccggtagaag ccctcggtga    2820
tccggtccgg gtagcggcgg aggagcccct taaaggtgag ctccatgagg tactgggcct    2880
cggtccgacg ggcggggagg gggaagcggg ggatgcggta gaccatcttg tccccgatgg    2940
gcagctccac gttgcacatg cgggcgatct ccacggtgtt gtcaaagggc tcgtccccc   3000 actcctcctc ggggaacatg gcccgcatct cctcgggggt cttcacgtag aactcgtcgc    3060
aggggaagcg ccagcgcccg gggtcgtcca gggtgctctt ggactggatg gcgaggagga    3120
cctcgtgggc ccgggcgtcc tccttcctca cgtaatggcc gtcgttggtg gccaccatcc    3180
ccaggccgta ctttcgggcg aactccttga ggacctcgtt gacctttttc tgctcgggga    3240
ggccgtggtt ctggatctca atgaagaagc ggtccttgaa gatggagagg tactcgttga    3300
gccgggcctc ggccaggtcc agacggtcct ggaggatgaa ctgggggatc tccgccccga    3360
ggcaccccga gagggcgatg aggccctcgg cgtgctcgcg caggatctcc cggtcaatcc    3420 ggggctttc  gtaaaacccc tccaggtaag cccggctcgc caggcgcacc aggttctggt    3480
accccgtgaa gtccttggcg aggagggtga ggtgaaagta gccccgtct  aggccctttc    3540 cccgcttgcg gtcaaagcgg ctttccgccg ccacgtaggc ctcgtagccc aggatgggct    3600
tgatgcccat ttcggtggcc ttcttgtaga actccacggc cccgaagagg ttgccgtggt    3660
cggtcatggc caaggcgggg tcctcggggg tcgtctcctt gacccacttg aggaggtcgg    3720
aaagcttcgc cgccccgtcc aggagggaga actgggtgtg ctggtggagg tgggcgaagc    3780
ggagtttgcg gcccattaat cgatcctcct caatgcatcg cgaacagcac caccaaccag    3840
gtagattttc attatttatt acctcctagg tatcccatgg tctagacccg ggaccgaatc    3900
``` gtt                                                                3903

```
<210> SEQ ID NO 12
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Xaa at position 1 can be leucine, valine,
      or methionine
<220> FEATURE:
<221> NAME/KEY: MISC_FEATURE
<222> LOCATION: (2)..(2)
<223> OTHER INFORMATION: The Xaa at position 2 can be leucine, valine,
      or isoleucine
<220> FEATURE:
<221> NAME/KEY: MISC_FEATURE
<222> LOCATION: (4)..(4)
<223> OTHER INFORMATION: The Xaa at position 4 can be any amino acid
<220> FEATURE:
<221> NAME/KEY: MISC_FEATURE
<222> LOCATION: (6)..(6)
<223> OTHER INFORMATION: The Xaa at position 6 can be phenylalanine,
      alanine, or isoleucine
<220> FEATURE:
<221> NAME/KEY: MISC_FEATURE
<222> LOCATION: (9)..(9)
<223> OTHER INFORMATION: The Xaa at position 9 can be leucine or
      histidine
<220> FEATURE:
<221> NAME/KEY: MISC_FEATURE
<222> LOCATION: (10)..(11)
<223> OTHER INFORMATION: The Xaa at positions 10 to 11 can be any amino
      acid
<220> FEATURE:
<221> NAME/KEY: MISC_FEATURE
<222> LOCATION: (12)..(12)
<223> OTHER INFORMATION: The Xaa at position 12 can be leucine or
      proline
<220> FEATURE:
<221> NAME/KEY: MISC_FEATURE
<222> LOCATION: (13)..(13)
<223> OTHER INFORMATION: The Xaa at position 13 can be threonine or
      serine

<400> SEQUENCE: 12

Xaa Xaa Lys Xaa Asp Xaa Leu Gly Xaa Xaa Xaa Xaa Xaa
1               5                   10

<210> SEQ ID NO 13
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Xaa at position 1 can be phenylalanine,
      tyrosine, or tryptophan
<220> FEATURE:
<221> NAME/KEY: MISC_FEATURE
<222> LOCATION: (2)..(6)
<223> OTHER INFORMATION: The Xaa at positions 2 to 6 can be any amino
      acid
<220> FEATURE:
<221> NAME/KEY: MISC_FEATURE
<222> LOCATION: (7)..(7)
<223> OTHER INFORMATION: The Xaa at position 7 can be phenylalanine,
      arginine, or lysine
<220> FEATURE:
<221> NAME/KEY: MISC_FEATURE
<222> LOCATION: (8)..(9)
<223> OTHER INFORMATION: The Xaa at positions 8 to 9 can be any amino
```

```
       acid
<220> FEATURE:
<221> NAME/KEY: MISC_FEATURE
<222> LOCATION: (11)..(11)
<223> OTHER INFORMATION: The Xaa at position 11 can be alanine, glycine,
      methionine, or leucine
<220> FEATURE:
<221> NAME/KEY: MISC_FEATURE
<222> LOCATION: (13)..(13)
<223> OTHER INFORMATION: The Xaa at position 13 can be asparagine or
      proline
<220> FEATURE:
<221> NAME/KEY: MISC_FEATURE
<222> LOCATION: (14)..(14)
<223> OTHER INFORMATION: The Xaa at position 14 can be arginine or
      lysine
<220> FEATURE:
<221> NAME/KEY: MISC_FEATURE
<222> LOCATION: (15)..(15)
<223> OTHER INFORMATION: The Xaa at position 15 can be any amino acid

<400> SEQUENCE: 13

Xaa Xaa Xaa Xaa Xaa Xaa Xaa Xaa Xaa Tyr Xaa Phe Xaa Xaa Xaa His
1               5                   10                  15

<210> SEQ ID NO 14
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Xaa at position 1 can be proline or serine
<220> FEATURE:
<221> NAME/KEY: MISC_FEATURE
<222> LOCATION: (2)..(2)
<223> OTHER INFORMATION: The Xaa at position 2 can be any amino acid
<220> FEATURE:
<221> NAME/KEY: MISC_FEATURE
<222> LOCATION: (3)..(3)
<223> OTHER INFORMATION: The Xaa at position 3 can be proline or
      isoleucine
<220> FEATURE:
<221> NAME/KEY: MISC_FEATURE
<222> LOCATION: (5)..(5)
<223> OTHER INFORMATION: The Xaa at position 5 can be leucine,
      isoleucine, valine, or phenylalanine
<220> FEATURE:
<221> NAME/KEY: MISC_FEATURE
<222> LOCATION: (6)..(6)
<223> OTHER INFORMATION: The Xaa at position 6 can be aspartic acid or
      asparagine
<220> FEATURE:
<221> NAME/KEY: MISC_FEATURE
<222> LOCATION: (7)..(7)
<223> OTHER INFORMATION: The Xaa at position 7 can be any amino acid
<220> FEATURE:
<221> NAME/KEY: MISC_FEATURE
<222> LOCATION: (10)..(10)
<223> OTHER INFORMATION: The Xaa at position 10 can be phenylalanine or
      isoleucine
<220> FEATURE:
<221> NAME/KEY: MISC_FEATURE
<222> LOCATION: (12)..(12)
<223> OTHER INFORMATION: The Xaa at position 12 can be any amino acid
<220> FEATURE:
<221> NAME/KEY: MISC_FEATURE
<222> LOCATION: (14)..(14)
<223> OTHER INFORMATION: The Xaa at position 14 can be phenylalanine,
      isoleucine, leucine, or valine

<400> SEQUENCE: 14

Xaa Xaa Xaa Asp Xaa Xaa Xaa Pro Asp Xaa Asp Xaa Asp Xaa
1               5                   10
```

```
<210> SEQ ID NO 15
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Xaa at position 2 can be leucine or
      methionine
<220> FEATURE:
<221> NAME/KEY: MISC_FEATURE
<222> LOCATION: (3)..(3)
<223> OTHER INFORMATION: The Xaa at position 3 can be leucine, valine,
      or isoleucine
<220> FEATURE:
<221> NAME/KEY: MISC_FEATURE
<222> LOCATION: (5)..(5)
<223> OTHER INFORMATION: The Xaa at position 5 can be any amino acid
<220> FEATURE:
<221> NAME/KEY: MISC_FEATURE
<222> LOCATION: (11)..(12)
<223> OTHER INFORMATION: The Xaa at positions 11 to 12 can be any amino
      acid

<400> SEQUENCE: 15

Gly Xaa Xaa Lys Xaa Asp Phe Leu Gly Leu Xaa Xaa Leu Thr
1               5                   10

<210> SEQ ID NO 16
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Xaa at position 1 can be phenylalanine or
      tryptophan
<220> FEATURE:
<221> NAME/KEY: MISC_FEATURE
<222> LOCATION: (2)..(6)
<223> OTHER INFORMATION: The Xaa at positions 2 to 6 can be any amino
      acid
<220> FEATURE:
<221> NAME/KEY: MISC_FEATURE
<222> LOCATION: (8)..(9)
<223> OTHER INFORMATION: The Xaa at positions 8 to 9 can be any amino
      acid
<220> FEATURE:
<221> NAME/KEY: MISC_FEATURE
<222> LOCATION: (11)..(11)
<223> OTHER INFORMATION: The Xaa at position 11 can be alanine or
      glycine

<400> SEQUENCE: 16

Xaa Xaa Xaa Xaa Xaa Xaa Phe Xaa Xaa Tyr Xaa Phe Asn Lys Ser His
1               5                   10                  15

<210> SEQ ID NO 17
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Xaa at position 2 can be any amino acid
<220> FEATURE:
<221> NAME/KEY: MISC_FEATURE
<222> LOCATION: (5)..(5)
<223> OTHER INFORMATION: The Xaa at position 5 can be phenylalanine or
```

```
                            isoleucine
<220> FEATURE:
<221> NAME/KEY: MISC_FEATURE
<222> LOCATION: (7)..(7)
<223> OTHER INFORMATION: The Xaa at position 7 can be any amino acid
<220> FEATURE:
<221> NAME/KEY: MISC_FEATURE
<222> LOCATION: (9)..(9)
<223> OTHER INFORMATION: The Xaa at position 9 can be phenylalanine or
      isoleucine

<400> SEQUENCE: 17

Ser Xaa Pro Asp Xaa Asp Xaa Asp Xaa
1               5

<210> SEQ ID NO 18
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: The Xaa at positions 2 to 3 can be leucine or
      valine
<220> FEATURE:
<221> NAME/KEY: MISC_FEATURE
<222> LOCATION: (5)..(5)
<223> OTHER INFORMATION: The Xaa at position 5 can be any amino acid
<220> FEATURE:
<221> NAME/KEY: MISC_FEATURE
<222> LOCATION: (7)..(7)
<223> OTHER INFORMATION: The Xaa at position 7 can be phenylalanine or
      isoleucine
<220> FEATURE:
<221> NAME/KEY: MISC_FEATURE
<222> LOCATION: (11)..(11)
<223> OTHER INFORMATION: The Xaa at position 11 can be arginine or
      lysine
<220> FEATURE:
<221> NAME/KEY: MISC_FEATURE
<222> LOCATION: (12)..(12)
<223> OTHER INFORMATION: The Xaa at position 12 can be any amino acid
<220> FEATURE:
<221> NAME/KEY: MISC_FEATURE
<222> LOCATION: (14)..(14)
<223> OTHER INFORMATION: The Xaa at position 14 can be threonine or
      serine

<400> SEQUENCE: 18

Gly Xaa Xaa Lys Xaa Asp Xaa Leu Gly Leu Xaa Xaa Leu Xaa
1               5                   10

<210> SEQ ID NO 19
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Xaa at position 1 can be phenylalanine,
      tyrosine, or tryptophan
<220> FEATURE:
<221> NAME/KEY: MISC_FEATURE
<222> LOCATION: (2)..(5)
<223> OTHER INFORMATION: The Xaa at positions 2 to 5 can be any amino
      acid
<220> FEATURE:
<221> NAME/KEY: MISC_FEATURE
<222> LOCATION: (6)..(6)
<223> OTHER INFORMATION: The Xaa at position 6 can be arginine or lysine
<220> FEATURE:
<221> NAME/KEY: MISC_FEATURE
```

```
<222> LOCATION: (8)..(9)
<223> OTHER INFORMATION: The Xaa at positions 8 to 9 can be any amino
      acid
<220> FEATURE:
<221> NAME/KEY: MISC_FEATURE
<222> LOCATION: (11)..(11)
<223> OTHER INFORMATION: The Xaa at position 11 can be alanine or
      glycine
<220> FEATURE:
<221> NAME/KEY: MISC_FEATURE
<222> LOCATION: (14)..(14)
<223> OTHER INFORMATION: The Xaa at position 14 can be arginine or
      lysine
<220> FEATURE:
<221> NAME/KEY: MISC_FEATURE
<222> LOCATION: (15)..(15)
<223> OTHER INFORMATION: The Xaa at position 15 can be any amino acid

<400> SEQUENCE: 19

Xaa Xaa Xaa Xaa Xaa Xaa Phe Xaa Xaa Tyr Xaa Phe Asn Xaa Xaa His
1               5                  10                  15

<210> SEQ ID NO 20
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: The Xaa at position 5 can be leucine,
      isoleucine, or valine
<220> FEATURE:
<221> NAME/KEY: MISC_FEATURE
<222> LOCATION: (7)..(7)
<223> OTHER INFORMATION: The Xaa at position 7 can be phenylalanine,
      leucine, or valine

<400> SEQUENCE: 20

Pro Asp Ile Asp Xaa Asp Xaa
1               5

<210> SEQ ID NO 21
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: The Xaa at positions 1 to 2 can be leucine or
      valine
<220> FEATURE:
<221> NAME/KEY: MISC_FEATURE
<222> LOCATION: (4)..(4)
<223> OTHER INFORMATION: The Xaa at position 4 can be any amino acid
<220> FEATURE:
<221> NAME/KEY: MISC_FEATURE
<222> LOCATION: (6)..(6)
<223> OTHER INFORMATION: The Xaa at position 6 can be alanine or
      isoleucine
<220> FEATURE:
<221> NAME/KEY: MISC_FEATURE
<222> LOCATION: (11)..(11)
<223> OTHER INFORMATION: The Xaa at position 11 can be any amino acid

<400> SEQUENCE: 21

Xaa Xaa Lys Xaa Asp Xaa Leu Gly His Asp Xaa Pro Thr
1               5                  10

<210> SEQ ID NO 22
<211> LENGTH: 16
```

```
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Xaa at position 1 can be phenylalanine or
      tyrosine
<220> FEATURE:
<221> NAME/KEY: MISC_FEATURE
<222> LOCATION: (3)..(3)
<223> OTHER INFORMATION: The Xaa at position 3 can be any amino acid
<220> FEATURE:
<221> NAME/KEY: MISC_FEATURE
<222> LOCATION: (6)..(6)
<223> OTHER INFORMATION: The Xaa at position 6 can be any amino acid
<220> FEATURE:
<221> NAME/KEY: MISC_FEATURE
<222> LOCATION: (7)..(7)
<223> OTHER INFORMATION: The Xaa at position 7 can be arginine or lysine
<220> FEATURE:
<221> NAME/KEY: MISC_FEATURE
<222> LOCATION: (11)..(11)
<223> OTHER INFORMATION: The Xaa at position 11 can be methionine or
      leucine

<400> SEQUENCE: 22

Xaa Ile Xaa Ser Cys Xaa Xaa Ile Lys Tyr Xaa Phe Pro Lys Ala His
1               5                   10                  15

<210> SEQ ID NO 23
<211> LENGTH: 8
<212> TYPE: PRT
<213> ORGANISM: Artificial
<220> FEATURE:
<223> OTHER INFORMATION: Synthetic

<400> SEQUENCE: 23

Pro Asp Ile Asp Leu Asp Phe Ser
1               5

<210> SEQ ID NO 24
<211> LENGTH: 24
<212> TYPE: DNA
<213> ORGANISM: Thermus thermophilus

<400> SEQUENCE: 24
gagcggataa caatttcaca cagg                                            24

<210> SEQ ID NO 25
<211> LENGTH: 20
<212> TYPE: DNA
<213> ORGANISM: Thermus thermophilus

<400> SEQUENCE: 25
ctcaacgagt acctctccat                                                 20

<210> SEQ ID NO 26
<211> LENGTH: 20
<212> TYPE: DNA
<213> ORGANISM: Thermus thermophilus

<400> SEQUENCE: 26
atgaagagcc tcccccccctt                                                20

<210> SEQ ID NO 27
<211> LENGTH: 20
<212> TYPE: DNA
<213> ORGANISM: Thermus thermophilus
```

```
<400> SEQUENCE: 27
gagggcctga accgccacgc                                                  20

<210> SEQ ID NO 28
<211> LENGTH: 20
<212> TYPE: DNA
<213> ORGANISM: Thermus thermophilus

<400> SEQUENCE: 28
aggcgggcca tggggaagaa                                                  20

<210> SEQ ID NO 29
<211> LENGTH: 20
<212> TYPE: DNA
<213> ORGANISM: Thermus thermophilus

<400> SEQUENCE: 29
gagactcggg agaaggcccg                                                  20

<210> SEQ ID NO 30
<211> LENGTH: 20
<212> TYPE: DNA
<213> ORGANISM: Thermus thermophilus

<400> SEQUENCE: 30
gtccagggcg ccttcggcga                                                  20

<210> SEQ ID NO 31
<211> LENGTH: 30
<212> TYPE: PRT
<213> ORGANISM: Thermus thermophilus

<400> SEQUENCE: 31

Glu Glu Met Gln Lys His Arg Glu Arg Phe Val Gln Gly Ala Lys Glu
1               5                   10                  15

Arg Gly Val Pro Glu Glu Glu Ala Asn Arg Leu Phe Asp Met
            20                  25                  30
```

ONE COMPONENT AND TWO COMPONENT DNA POL III REPLICASES AND USES THEREOF

CROSS-REFERENCE TO RELATED APPLICATIONS

This application claims the benefit under 35 U.S.C. §119(e) of U.S. Provisional Application Ser. No. 60/560,793, filed Apr. 7, 2004, and U.S. Provisional Application Ser. No. 60/641,183, filed Jan. 3, 2005, all of which are incorporated by reference in their entirety.

FIELD

The invention relates to the enzymatic replication, modification, and digestion of nucleic acid molecules.

BACKGROUND OF THE INVENTION

DNA polymerases are used for a variety of nucleic acid replication processes in molecular biology, including nucleic acid sequencing, nucleic acid quantification (Real Time PCR, NASBA), and nucleic acid amplification (PCR, RDA, SDA), as well as reverse transcription of RNA into cDNA, nucleic acid labeling, and other processes.

DNA polymerase III holoenzyme ("Pol III") was first purified and determined to be the principal replicase of the *E. coli* chromosome by Kornberg (Kornberg, A., 1982 Supplement to DNA Replication, Freeman Publications, San Francisco, pp 122-125, incorporated herein by reference). This holoenzyme is composed of 10 distinct subunits that form three separate functional components (see McHenry, et al., J. Bio Chem., 252:6478-6484 (1977); Maki, et al., J. Biol. Chem., 263:6551-6559 (1988), incorporated herein by reference).

The three components of the Pol III replicase in gram negative bacteria, such as *Escherichia coli*, are (i) the "core" (i.e. the polymerase), (ii) β (i.e., the sliding clamp), and (iii) the γ-complex (i.e., the clamp loader). In *E. coli* the τ subunit holds together two cores to form the Pol III' subassembly, and it binds one γ-complex to form Pol III*. The τ subunit and the γ subunit are both encoded by dnaX. Tau is the full length product, while γ is approximately the N-terminal ⅔ of τ and is formed by a translational frame shift (Tsuchihashi et al., "Translational Frameshifting Generates the γ Subunit of DNA Polymerase III Holoenzyme," Proc. Natl. Acad. Sci., USA., 87:2516-2520 (1990), incorporated herein by reference). In other gram negative bacteria, such as *Aquifex aeolicus*, the dnaX gene translates into a single protein (tau) only and the Pol III holoenzyme assembles into the processive replicase without a gamma subunit (Bruck I. et al., "Analysis of a multicomponent thermostable DNA polymerase III replicase from an extreme thermophile.", J Biol. Chem. 2002 May 10;277(19):17334-48. Epub 2002 Feb. 21, incorporated herein by reference).

Within the "core" are three subunits: the α subunit (encoded by dnaE) represents the catalytical subunit with the DNA polymerase activity; the ε subunit (encoded by dnaQ, mutD) is the proofreading 3'-5' exonuclease (Scheuermann, et al., Proc. Natl. Acad. Sci. USA, 81:7747-7751 (1984); and DiFrancesco, et al., J. Biol. Chem., 259:5567-5573 (1984), incorporated herein by reference), and the θ subunit (encoded by holE) stimulates ε (Studwell-Vaughan et al., "DNA Polymerase III Accessory Proteins V. theta encoded by holE*," J. Biol. Chem., 268:11785-11791 (1993), incorporated herein by reference). In *E. coli* the α subunit forms a tight 1:1 complex with ε (Maki, et al., J. Biol. Chem., 260:12987-12992 (1985) incorporated herein by reference), and θ forms a 1:1 complex with ε (Studwell-Vaughan et al., supra).

The *E. coli* Pol III replicase is highly efficient and completely replicates a uniquely primed bacteriophage single-strand DNA ("ssDNA") genome coated with the ssDNA binding protein ("SSB"), at a speed of at least 500 nucleotides per second at 30° C. without dissociating from a 5 kb circular DNA even once (Fay, et al., J. Biol. Chem., 256:976-983 (1981); O'Donnell, et al., J. Biol. Chem., 260:12884-12889 (1985); and Mok, et al., J. Biol. Chem., 262:16644-16654 (1987), incorporated herein by reference).

DNA polymerase III replicases from a number of gram negative and gram positive bacteria, including thermophilic bacteria, have since been described (for example, see Bullard et al., J. Biol. Chem., 277:13401-13408, 2002; and Bruck et al., J. Biol. Chem., 277:17334-17348, 2002; incorporated herein by reference), and the three-component organization of Pol III replicases in these bacteria appears to be similar to that of *E. coli*. In *Streptococcus pyogenes*, for example, the Pol III replicase is comprised of (i) the α subunit encoded by the polC gene (without epsilon and theta subunits, which are missing in gram-positive bacteria), (ii) β-sliding clamp, and (iii) the τ/δ/δ'-complex (i.e., the clamp loader). The assembly of the polC-derived α with β, τ, δ, and δ' is sufficient to form a functional Pol III replicase in vitro (Bruck I, O'Donnell M., "The DNA replication machine of a gram-positive organism", J Biol. Chem. 2000 Sep. 15;275(37):28971-83, incorporated herein by reference).

Gram-positive bacteria also contain a second DNA polymerase encoded by the dnaE gene with homology to the *E. coli* α subunit. Although apparently capable of interaction with β (Bruck and O'Donnell, supra), these dnaE-derived α subunits are much slower than the PolC-derived α subunits of the Pol III replicase, lack proof-reading activity and demonstrate a propensity for interlesional DNA synthesis, suggesting a potential role in induced mutagenesis and DNA repair (Fleft F. et al. "A 'gram-negative-type' DNA polymerase III is essential for replication of the linear chromosome of *Streptomyces coelicolor* A3(2)." Mol Microbiol. 1999 February;31 (3):949-58.), (Le Chatelier E. et al. "Involvement of DnaE, the second replicative DNA polymerase from *Bacillus subtilis*, in DNA mutagenesis." J Biol. Chem. 2004 Jan. 16;279 (3):1757-67. Epub 2003 Oct. 30.), (Foster K. et al. "DNA polymerase III of *Enterococcus faecalis*: expression and characterization of recombinant enzymes encoded by the polC and dnaE genes.", Protein Expr Purif. 2003 January;27 (1):90-7.), (Boshoff H I et al. "DnaE2 polymerase contributes to in vivo survival and the emergence of drug resistance in *Mycobacterium tuberculosis*.", Cell. 2003 Apr. 18;113(2): 183-93.), (Barnes M H et al. "DNA polymerases of low-GC gram-positive eubacteria: identification of the replication-specific enzyme encoded by dnaE.", J Bacteriol. 2002 July; 184(14):3834-8.). In any event, their slow speed and high frame shift frequency (based on the lesion bypass activity) render them unsuitable for use in many molecular biology applications.

The literature has consistently taught that the three principal components of a DNA polymerase III holoenzyme, the core (including the α subunit), the processivity clamp and the clamp loader, are required for a functional DNA replicase having rapid extension rates typical of genomic replication. (See, for example, U.S. Pat. Nos. 6,555,349; 6,221,642; 5,668,004; 5,583,026; 6,677,146; and 6,238,905; see also O'Donnell, Bioessays, 14:105-111, 1992; O'Donnell et al., J. Biol. Chem., 260:12875-12883, 1985; McHenry, Mol. Microbiol., 49:1157-1165, 2003; McHenry, J. Biol. Chem., 266:19127-19130, 1991; Studwell et al., J. Biol. Chem., 265:

1171-1178, 1990; Bullard et al., J. Biol. Chem., 277:13401-13408, 2002; and Bruck et al., J. Biol. Chem., 277:17334-17348, 2002. This DNA polymerase III literature has clearly established the dogma that the DNA polymerase III α subunit of gram negative bacteria and the polC-encoded α subunit of gram positive bacteria cannot function alone and that other subunits are required for polymerase stability, fidelity, and processivity.

The original reports by Kornberg et al. on the *E. coli* Pol III were the first to show that the polymerase activity of the α subunit alone or in combination with the core could only be measured at very high enzyme concentrations using a "gap-filling" assay with activated calf-thymus DNA, and produced extension rates for the polymerase core and alpha alone of only 20 b/sec and 7.7 b/sec, respectively. Many more recent reports on Pol IIIs from a variety of bacteria have supported the original finding by Kornberg et al. and further cemented the dogma that the α subunit or the core complex of a DNA polymerase III holoenzyme cannot function in a processive mode with fast extension rates. For example, Bruck et al. (J. Biol. Chem., 275: 28971-28983, 2000) report that the alpha subunit (polC) of Pol III from *Streptococcus pyogenes* does not function alone as a DNA polymerase, while Bullard et al., J. Biol. Chem., 277:13401-13408, 2002, and Bruck et al., J. Biol. Chem., 277:17334-17348, 2002, report that three components of Pol III are required for replicase activity in *Thermus thermophilus* and *Aquifex aeolicus*, respectively.

The low extension rates and high protein concentrations reported in the prior art have prevented the application of bacterial Pol III replicase α subunits alone or in combination with the β sliding clamp to molecular biology research and clinical diagnostics, including the amplification and/or sequencing of nucleic acids.

SUMMARY OF THE INVENTION

Contrary to the findings of previous reports, the present disclosure establishes that bacterial dnaE encoded and polC encoded α subunits can independently function alone and/or in combination with a processivity clamp component of a Pol III as a minimal functional Pol III replicase under appropriate conditions in vitro. Such single component and two component Pol III replicases lack a Pol III clamp loader.

In particular, disclosed herein is the surprising finding that some dnaE encoded α subunits, characterized by dnaE encoded α subunits of gram negative bacteria, and more particularly by those of non-mesophilic bacteria, possess intrinsic zinc-dependent 3'-5' exonuclease activity, and functional Pol III replicase activity in the absence of a clamp loader. Also disclosed herein is the surprising finding that polC encoded α subunits, characterized by polC encoded α subunits of gram positive bacteria, and more particularly by those of non-mesophilic bacteria, possess functional Pol III replicase activity in the absence of a clamp loader. Such α subunits are used in the one component and two component Pol III replicases of the invention. Preferred for use in the invention are α subunits derived from extremophiles. Especially preferred for use in the invention are α subunits derived from thermophiles.

Single component and two component Pol III replicases for use in the invention are referred to herein as "single component Pol III replicases" and "two component Pol III replicases", respectively, and are collectively referred to herein as "minimal functional Pol III replicases". Surprisingly, the presence and function of a clamp loader component is not required for proper functioning of the minimal functional Pol III replicases in vitro. Also surprising is the finding that the minimal functional Pol III replicases can replicate a primed ssDNA template molecule with high speed and processivity in vitro without the assistance of an initiation complex formed by the clamp loader. Despite the absence of a clamp loader, and in the case of single component Pol III replicases, the absence of a processivity clamp, the extension rates of the minimal functional Pol III replicases of the invention are at least 6 to 8 times faster than those of any type A or B repair DNA polymerase currently used for DNA sequencing, amplification, quantification, labeling and reverse transcription, such as Taq DNA polymerase I (type A), Klenow Fragment of *E. coli* DNA polymerase I (type A), T7 DNA polymerase (type A), Bst DNA polymerase I (type A), phi29 DNA polymerase (type B), Pfu DNA polymerase (type B), Tli DNA polymerase (type B) or KOD DNA polymerase (type B), as demonstrated herein.

Additionally disclosed herein is the surprising finding that minimal functional Pol III replicases derived from thermophilic organisms exhibit sufficient thermostability under appropriate conditions to sustain repetitive DNA replication reactions in a temperature-cycled mode leading to the amplification of double stranded DNA molecules in vitro.

The invention is directed to the use of minimal functional Pol III replicases in compositions and methods for nucleic acid replication, including methods of DNA amplification, such as PCR, and DNA sequencing.

Accordingly, in one aspect, the invention provides a method for replicating a nucleic acid molecule, which method comprises subjecting the nucleic acid molecule to a replication reaction in a replication reaction mixture comprising a minimal functional Pol III replicase disclosed herein. In one embodiment, the minimal functional Pol III replicase is a single component Pol III replicase. In another embodiment, the minimal functional Pol III replicase is a two component Pol III replicase. In another embodiment, a combination of minimal functional Pol III replicases is used in the replication reaction mixture.

In a preferred embodiment, the nucleic acid molecule replicated is a DNA molecule. In a further preferred embodiment, the DNA molecule is double stranded. In a further preferred embodiment, the double stranded DNA molecule is a linear DNA molecule. In other embodiments, the DNA molecule is non-linear, for example circular or supercoiled DNA.

In a preferred embodiment, the method for replicating a nucleic acid molecule is a sequencing method useful for sequencing a nucleic acid molecule, preferably DNA. In a preferred embodiment, the method involves subjecting the nucleic acid molecule to a sequencing reaction in a sequencing reaction mixture. The sequencing reaction mixture comprises a minimal functional Pol III replicase, preferably a single component Pol III replicase disclosed herein. Preferably the single component Pol III replicase possesses DNA polymerase activity and lacks 3'-5' exonuclease activity capable of removing 3' terminal dideoxy nucleotides in the sequencing reaction mixture. In a preferred embodiment, the single component Pol III replicase comprises a dnaE α subunit, preferably of the genus *Thermus* or *Aquifex*, preferably of the species *Thermus thermophilus*, *Thermus aquaticus*, or *Aquifex aeolicus*.

In another preferred embodiment, the method for replicating a nucleic acid molecule is an amplification method useful for amplifying a nucleic acid molecule, preferably DNA. In a preferred embodiment, the method involves subjecting the nucleic acid molecule to an amplification reaction in an amplification reaction mixture. The amplification reaction mixture comprises a minimal functional Pol III replicase disclosed herein. In a preferred embodiment, the minimal functional Pol III replicase possesses DNA polymerase activity and possesses 3'-5' exonuclease activity in the amplification reaction mixture.

In a preferred embodiment, the amplification method is a thermocycling amplification method useful for amplifying a nucleic acid molecule, preferably DNA, which is preferably double stranded, by a temperature-cycled mode. In a preferred embodiment, the method involves subjecting the nucleic acid molecule to a thermocycling amplification reaction in an thermocycling amplification reaction mixture. The thermocycling amplification reaction mixture comprises a thermostable minimal functional Pol III replicase, preferably a thermostable two component Pol III replicase disclosed herein. In a preferred embodiment, the thermostable two component Pol III replicase possesses DNA polymerase activity and possesses 3'-5' exonuclease activity in the thermocycling amplification reaction mixture. In a preferred embodiment, the thermostable two component Pol III replicase comprises a dnaE α subunit, preferably of the genus *Thermus* or *Aquifex*, preferably of the species *Thermus thermophilus, Thermus aquaticus*, or *Aquifex aeolicus*. In a preferred embodiment, the thermocycling amplification reaction mixture further comprises thermostabilizers, as disclosed herein. In a further preferred embodiment, the thermocycling amplification reaction mixture further comprises DNA destabilizers, as disclosed herein.

In a preferred embodiment, the thermocycling amplification method is a PCR method, useful for amplifying a nucleic acid molecule, preferably DNA, which is preferably double stranded, by PCR. In a preferred embodiment, the method involves subjecting the nucleic acid molecule to PCR in a PCR reaction mixture. In a preferred embodiment, the PCR reaction mixture comprises a thermostable minimal functional Pol III replicase, preferably a thermostable two component Pol III replicase disclosed herein. In a preferred embodiment, the thermostable two component Pol III replicase possesses DNA polymerase activity and possesses 3'-5' exonuclease activity in the PCR reaction mixture. In a preferred embodiment, the thermostable two component Pol III replicase comprises a dnaE α subunit, preferably of the genus *Thermus* or *Aquifex*, preferably of the species *Thermus thermophilus, Thermus aquaticus*, or *Aquifex aeolicus*. In a preferred embodiment, the PCR reaction mixture further comprises thermostabilizers, as disclosed herein. In a further preferred embodiment, the PCR reaction mixture further comprises DNA destabilizers, as disclosed herein.

In a preferred embodiment, the invention provides methods for fast PCR. In a preferred embodiment, the method involves subjecting the nucleic acid molecule to fast PCR in a fast PCR reaction mixture. The fast PCR reaction mixture comprises a thermostable minimal functional Pol III replicase, preferably a thermostable two component Pol III replicase disclosed herein. In a preferred embodiment, the thermostable two component Pol III replicase possesses DNA polymerase activity and possesses 3'-5' exonuclease activity in the fast PCR reaction mixture. In a preferred embodiment, the thermostable two component Pol III replicase comprises a dnaE α subunit, preferably of the genus *Thermus* or *Aquifex*, preferably of the species *Thermus thermophilus, Thermus aquaticus*, or *Aquifex aeolicus*. In a preferred embodiment, the fast PCR reaction mixture further comprises thermostabilizers, as disclosed herein. In a further preferred embodiment, the fast PCR reaction mixture further comprises DNA destabilizers, as disclosed herein. The fast PCR methods are preferably two-step PCR methods that consist of repeated two-temperature cycles, with a first temperature for denaturation, and a second temperature for both primer annealing and primer extension.

In a preferred embodiment, the invention provides methods for long range PCR. In a preferred embodiment, the method involves subjecting the nucleic acid molecule to long range PCR in a long range PCR reaction mixture. The long range PCR reaction mixture comprises a thermostable minimal functional Pol III replicase, preferably a thermostable two component Pol III replicase disclosed herein. In a preferred embodiment, the thermostable two component Pol III replicase possesses DNA polymerase activity and possesses 3'-5' exonuclease activity in the long range PCR reaction mixture. In a preferred embodiment, the thermostable two component Pol III replicase comprises a dnaE α subunit, preferably of the genus *Thermus* or *Aquifex*, preferably of the species *Thermus thermophilus, Thermus aquaticus*, or *Aquifex aeolicus*. In a preferred embodiment, the long range PCR reaction mixture further comprises thermostabilizers, as disclosed herein. In a further preferred embodiment, the long range PCR reaction mixture further comprises DNA destabilizers, as disclosed herein.

In one aspect, the invention provides a replication reaction mixture for nucleic acid replication, which mixture comprises a minimal functional Pol III replicase disclosed herein. In a preferred embodiment, the replication reaction mixture is useful for DNA replication. In one embodiment, the minimal functional Pol III replicase is a single component Pol III replicase. In another embodiment, the minimal functional Pol III replicase is a two component Pol III replicase. In another embodiment, a combination of minimal functional Pol III replicases are used in a replication reaction mixture.

In one embodiment, the invention provides a replication reaction mixture for DNA amplification or DNA sequencing, comprising a minimal functional Pol III replicase.

In a preferred embodiment, the replication reaction mixture is a sequencing reaction mixture useful for nucleic acid sequencing, preferably DNA sequencing. The sequencing reaction mixture comprises a minimal functional Pol III replicase, preferably a single component Pol III replicase disclosed herein. Preferably the single component Pol III replicase possesses DNA polymerase activity and lacks 3'-5' exonuclease activity capable of removing 3' terminal dideoxy nucleotides in the sequencing reaction mixture. In a preferred embodiment, the single component Pol III comprises a dnaE α subunit, preferably of the genus *Thermus* or *Aquifex*, preferably of the species *Thermus thermophilus, Thermus aquaticus*, or *Aquifex aeolicus*.

In another preferred embodiment, the replication reaction mixture is an amplification reaction mixture useful for nucleic acid amplification, preferably DNA amplification. The amplification reaction mixture comprises a minimal functional Pol III replicase disclosed herein. Preferably, the minimal functional Pol III replicase possesses DNA polymerase activity and possesses 3'-5' exonuclease activity in the amplification reaction mixture.

In a preferred embodiment, the amplification reaction mixture is a thermocycling amplification reaction mixture useful for amplifying nucleic acids, preferably DNA, which is preferably double stranded, by a temperature-cycled mode. Preferably, the thermocycling amplification reaction mixture comprises a thermostable minimal functional Pol III replicase, preferably a thermostable two component Pol III replicase disclosed herein. Preferably, the thermostable two component Pol III replicase possesses DNA polymerase activity and possesses 3'-5' exonuclease activity in the thermocycling amplification reaction mixture. In a preferred embodiment, the thermostable two component Pol III comprises a dnaE α subunit, preferably of the genus *Thermus* or *Aquifex*, preferably of the species *Thermus thermophilus, Thermus aquaticus*, or *Aquifex aeolicus*. Preferably, the thermocycling amplification reaction mixture further comprises thermostabilizers disclosed herein. Preferably, the thermocycling amplification reaction mixture also comprises DNA destabilizers disclosed herein.

In a preferred embodiment, the thermocycling amplification reaction mixture is a polymerase chain reaction mixture ("PCR mixture") useful for amplifying nucleic acids, preferably DNA, which is preferably double stranded, by PCR. The PCR mixture comprises a thermostable minimal functional Pol III replicase, preferably a thermostable two component Pol III replicase disclosed herein. Preferably the thermostable two component Pol III replicase possesses DNA polymerase activity and possesses 3'-5' exonuclease activity in the PCR mixture. In a preferred embodiment, the thermostable two component Pol III replicase comprises a dnaE α subunit, preferably of the genus Thermus or Aquifex, preferably of the species *Thermus thermophilus, Thermus aquaticus*, or *Aquifex aeolicus*. Preferably, the PCR mixture further comprises thermostabilizers disclosed herein. Preferably, the PCR mixture also comprises DNA destabilizers disclosed herein.

In a preferred embodiment, the invention provides PCR mixtures that are fast PCR mixtures useful in fast PCR methods.

In a preferred embodiment, the invention provides PCR mixtures that are long range PCR mixtures useful in long range PCR methods.

In a preferred embodiment, a replication reaction mixture provided herein comprises an amount of minimal functional Pol III replicase such that the reaction mixture can be combined with template DNA, and a primer capable of hybridizing thereto, and optionally appropriately diluted to produce a charged reaction mixture, wherein the minimal functional Pol III replicase is capable of replicating the DNA template by extending the hybridized primer at a rate of greater than 100, more preferably greater than 150, more preferably greater than 200, more preferably greater than 250, more preferably greater than 300, more preferably greater than 350, more preferably greater than 400, more preferably greater than 450, more preferably greater than 500, more preferably greater than 550, more preferably greater than 600, more preferably greater than 650, more preferably greater than 700 nucleotides per second. Further, the charged reaction mixture preferably has a DNA polymerase III α subunit concentration which is not less than 6 ng/μL, more preferably not less than 7 ng/μL, more preferably not less than 8 ng/μL, more preferably not less than 9 ng/μL, more preferably not less than 10 ng/μL, more preferably not less than 20 ng/μL, more preferably not less than 50 ng/μL, more preferably not less than 100 ng/μL, more preferably not less than 150 ng/μL, more preferably not less than 200 ng/μL.

In a preferred embodiment, a replication reaction mixture provided herein comprises a minimal functional Pol III replicase, wherein the DNA polymerase III α subunit is present in the reaction mixture at a concentration of not less than 6 ng/μL, more preferably not less than 7 ng/μL, more preferably not less than 8 ng/μL, more preferably not less than 9 ng/μL, more preferably not less than 10 ng/μL, more preferably not less than 20 ng/μL, more preferably not less than 50 ng/μL, more preferably not less than 100 ng/μL, more preferably not less than 150 ng/μL, more preferably not less than 200 ng/μL.

In a preferred embodiment, a replication reaction mixture provided herein comprises a zwitterionic buffer. In a preferred embodiment, the zwitterionic buffer has a pH between about pH 7.5-8.9. In a preferred embodiment, the zwitterionic buffer comprises a combination of a weak organic acid and a weak organic base.

In a preferred embodiment, a thermocycling amplification reaction mixture provided herein comprises thermostabilizers (alternatively referred to herein as "stabilizers") that increase the thermostability of a minimal functional Pol III replicase.

In a preferred embodiment, a replication reaction mixture provided herein lacks $CaCl_2$.

In a preferred embodiment, a replication reaction mixture lacks a γ subunit and/or a τ subunit.

In one aspect, the invention provides nucleic acid replication reaction tubes, which comprise nucleic acid replication reaction mixtures disclosed herein. Tubes comprising a replication reaction mixture are tubes that contain a reaction mixture. The nucleic acid replication reaction tubes comprise a minimal functional Pol III replicase disclosed herein. In one embodiment, the replication reaction tubes comprise a single component Pol III replicase. In another embodiment, the replication reaction tubes comprise a two component Pol III replicase. In another embodiment, a combination of minimal functional Pol III replicases is present in the replication reaction tubes.

In a preferred embodiment, the nucleic acid replication reaction tubes are sequencing reaction tubes, which comprise a sequencing reaction mixture disclosed herein. The sequencing reaction tubes comprise a minimal functional Pol III replicase, preferably a single component Pol III replicase disclosed herein. Preferably the single component Pol III replicase possesses DNA polymerase activity and lacks 3'-5' exonuclease activity capable of removing 3' terminal dideoxy nucleotides in the sequencing reaction mixture. In a preferred embodiment, the single component Pol III replicase comprises a dnaE α subunit, preferably of the genus *Thermus* or *Aquifex*, preferably of the species *Thermus thermophilus, Thermus aquaticus*, or *Aquifex aeolicus*.

In another preferred embodiment, the nucleic acid replication reaction tubes are amplification reaction tubes, which comprise an amplification reaction mixture disclosed herein. The amplification reaction tubes comprise a minimal Pol III disclosed herein.

In a preferred embodiment, the amplification reaction tubes are thermocycling amplification reaction tubes, which comprise a thermocycling amplification reaction mixture disclosed herein. The thermocycling amplification reaction tubes comprise a thermostable minimal functional Pol III replicase, preferably a thermostable two component Pol III replicase disclosed herein. In a preferred embodiment, the thermostable two component Pol III replicase comprises a dnaE α subunit, preferably of the genus *Thermus* or *Aquifex*, preferably of the species *Thermus thermophilus, Thermus aquaticus*, or *Aquifex aeolicus*.

In a preferred embodiment, the thermocycling amplification reaction tubes are PCR tubes, which comprise a PCR reaction mixture disclosed herein. The PCR tubes comprise a thermostable minimal functional Pol III replicase, preferably a thermostable two component Pol III replicase disclosed herein. In a preferred embodiment, the thermostable two component Pol III replicase comprises a dnaE α subunit, preferably of the genus *Thermus* or *Aquifex*, preferably of the species *Thermus thermophilus, Thermus aquaticus*, or *Aquifex aeolicus*.

In a preferred embodiment, the invention provides PCR tubes that are fast PCR tubes, which comprise a fast PCR reaction mixture disclosed herein. The fast PCR tubes comprise a thermostable minimal functional Pol III replicase, preferably a thermostable two component Pol III replicase disclosed herein. In a preferred embodiment, the thermostable two component Pol III replicase comprises a dnaE α subunit, preferably of the genus *Thermus* or *Aquifex*, preferably of the species *Thermus thermophilus, Thermus aquaticus*, or *Aquifex aeolicus*.

In a preferred embodiment, the invention provides PCR tubes that are long range PCR tubes, which comprise a long range PCR reaction mixture disclosed herein. The long range PCR tubes comprise a thermostable minimal functional Pol III replicase, preferably a thermostable two component Pol III replicase disclosed herein. In a preferred embodiment, the thermostable two component Pol III replicase comprises a dnaE α subunit, preferably of the genus *Thermus* or *Aquifex*, preferably of the species *Thermus thermophilus, Thermus aquaticus*, or *Aquifex aeolicus*.

In one aspect, the invention provides a nucleic acid replication kit useful for nucleic acid replication, which kit comprises a minimal functional Pol III replicase disclosed herein. In a preferred embodiment, the replication kit comprises a replication reaction mixture disclosed herein. The replication reaction mixture of the kit may be free of minimal functional Pol III replicase, and may require addition of minimal functional Pol III replicase prior to use. In a preferred embodiment, the replication kit is useful for DNA replication. In one embodiment, the minimal functional Pol III replicase of the kit is a single component Pol III replicase. In another embodiment, the minimal functional Pol III replicase of the kit is a two component Pol III replicase. In another embodiment, a combination of minimal functional Pol III replicases are included in a nucleic acid replication kit.

In a preferred embodiment, the nucleic acid replication kit is a sequencing kit useful for nucleic acid sequencing, preferably DNA sequencing. The sequencing kit comprises a minimal functional Pol III replicase, preferably a single component Pol III replicase disclosed herein. In a preferred embodiment, the single component Pol III replicase comprises a dnaE α subunit, preferably of the genus *Thermus* or *Aquifex*, preferably of the species *Thermus thermophilus, Thermus aquaticus*, or *Aquifex aeolicus*. Preferably, the sequencing kit comprises a sequencing reaction mixture disclosed herein.

In another preferred embodiment, the nucleic acid replication kit is an amplification kit useful for nucleic acid amplification, preferably DNA amplification. The amplification kit comprises a minimal functional Pol III replicase disclosed herein. Preferably, the amplification kit comprises a nucleic acid amplification reaction mixture disclosed herein.

In a preferred embodiment, the amplification kit is a thermocycling amplification kit useful for amplifying nucleic acids, preferably DNA, which is preferably double stranded, by a temperature-cycled mode. The thermocycling amplification kit comprises a thermostable minimal functional Pol III replicase, preferably a thermostable two component Pol III replicase disclosed herein. In a preferred embodiment, the thermostable two component Pol III comprises a dnaE α subunit, preferably of the genus *Thermus* or *Aquifex*, preferably of the species *Thermus thermophilus, Thermus aquaticus*, or *Aquifex aeolicus*. Preferably, the thermocycling amplification kit comprises a thermocycling amplification reaction mixture disclosed herein.

In a preferred embodiment, the thermocycling amplification kit is a PCR kit for amplifying nucleic acids, preferably DNA, which is preferably double stranded, by PCR. The PCR kit comprises a thermostable minimal functional Pol III replicase, preferably a thermostable two component Pol III replicase disclosed herein. In a preferred embodiment, the thermostable two component Pol III replicase comprises a dnaE α subunit, preferably of the genus *Thermus* or *Aquifex*, preferably of the species *Thermus thermophilus, Thermus aquaticus*, or *Aquifex aeolicus*. Preferably the PCR kit comprises a PCR reaction mixture disclosed herein.

In a preferred embodiment, the invention provides PCR kits that are fast PCR kits. The fast PCR kit comprises a thermostable minimal functional Pol III replicase, preferably a thermostable two component Pol III replicase disclosed herein. In a preferred embodiment, the thermostable two component Pol III replicase comprises a dnaE α subunit, preferably of the genus *Thermus* or *Aquifex*, preferably of the species *Thermus thermophilus, Thermus aquaticus*, or *Aquifex aeolicus*. Preferably the fast PCR kit comprises a fast PCR reaction mixture disclosed herein.

In a preferred embodiment, the invention provides PCR kits that are long range PCR kits. The long range PCR kit comprises a thermostable minimal functional Pol III replicase, preferably a thermostable two component Pol III replicase disclosed herein. In a preferred embodiment, the thermostable two component Pol III replicase comprises a dnaE α subunit, preferably of the genus Thermus or Aquifex, preferably of the species *Thermus thermophilus, Thermus aquaticus*, or *Aquifex aeolicus*. Preferably the long range PCR kit comprises a long range PCR reaction mixture disclosed herein.

In a preferred embodiment, a nucleic acid replication kit provided herein comprises a nucleic acid replication reaction mixture, which replication reaction mixture comprises an amount of minimal functional Pol III replicase such that the reaction mixture can be combined with template DNA, and a primer hybridizable thereto, and appropriately diluted to produce a charged reaction mixture, wherein the minimal Pol III is capable of replicating the DNA template by extending the hybridized primer at a rate of greater than 100, more preferably greater than 150, more preferably greater than 200, more preferably greater than 250, more preferably greater than 300, more preferably greater than 350, more preferably greater than 400, more preferably greater than 450, more preferably greater than 500, more preferably greater than 550, more preferably greater than 600, more preferably greater than 650, more preferably greater than 700 nucleotides per second. Further, the charged reaction mixture preferably has a DNA polymerase III α subunit concentration which is not less than 6 ng/μL, more preferably not less than 7 ng/μL, more preferably not less than 8 ng/μL, more preferably not less than 9 ng/μL, more preferably not less than 10 ng/μL, more preferably not less than 20 ng/μL, more preferably not less than 50 ng/μL, more preferably not less than 100 ng/μL, more preferably not less than 150 ng/μL, more preferably not less than 200 ng/μL.

In one aspect, the invention provides an in vitro reaction mixture, comprising a template DNA molecule, optionally a primer hybridizable thereto, a minimal functional Pol III replicase, and at least one complete copy of the template DNA molecule, wherein the complete copy of the template DNA molecule is the product of a replication reaction using the minimal functional Pol III replicase, and the solution lacks a clamp loader.

In one embodiment, the solution further lacks a processivity clamp.

In a preferred embodiment, solution has a DNA polymerase III α subunit concentration which is not less than 6 ng/μL, more preferably not less than 7 ng/μL, more preferably not less than 8 ng/μL, more preferably not less than 9 ng/μL, more preferably not less than 10 ng/μL, more preferably not less than 20 ng/µL, more preferably not less than 50 ng/µL, more preferably not less than 100 ng/µL, more preferably not less than 150 ng/µL, more preferably not less than 200 ng/µL.

Minimal Pol III replicases disclosed herein comprise at least a first component, which comprises a Pol III α subunit. In some preferred embodiments, the first component consists essentially of a Pol III α subunit. In some preferred embodiments, the first component comprises one or more additional subunits of the core polymerase complex of a Pol III. The minimal Pol III replicases disclosed herein lack a clamp loader.

The minimal Pol III replicases used herein are functional replicases, as defined herein.

Accordingly, provided for use herein are minimal functional Pol III replicases, which include single component Pol III replicases, and two component Pol III replicases.

The minimal Pol III replicases used herein are preferably derived from non-mesophilic bacteria, more preferably from extremophiles, and most preferably from thermophilic bacteria.

In a preferred embodiment, the minimal Pol III replicases used herein are single component Pol III replicases. A single component Pol III replicase consists essentially of a first component of a minimal functional Pol III replicase. The single component Pol III replicases of the invention lack a clamp loader.

In another preferred embodiment, the minimal Pol III replicases used herein further comprise a second component, which second component comprises a processivity clamp. The two component Pol III replicases thus consist essentially of a first component and a second component, wherein the first component is a single component Pol III replicase as disclosed herein, and the second component comprises a processivity clamp. In a preferred embodiment, the second component consist essentially of a processivity clamp. In preferred embodiments, the processivity clamp comprises a Pol III β subunit. In some embodiments, the processivity clamp consists essentially of a Pol III subunit. The two component Pol III replicases also lack a clamp loader component. In some embodiments, a two component Pol III replicase comprises more than one first component, which may be the same or different.

The thermostable minimal functional Pol III replicases of the invention are preferably derived from a thermophilic bacterium or thermophilic cyanobacterium. In a preferred embodiment, the thermophilic bacterium is selected from the group consisting of the genera *Thermus, Aquifex, Thermotoga, Thermocridis, Deinococcus, Methanobacterium, Hydrogenobacter, Geobacillus, Thermosynchecoccus* and *Thermoanaerobacter*. Especially preferred are single component and two component Pol IIIs derived from *Aquifex aeolicus, Aquifex pyogenes, Thermus thermophilus, Thermus aquaticus, Thermotoga neapolitana* and *Thermotoga maritima*.

The α subunit of a minimal functional Pol III replicase herein is encoded by a bacterial polC or dnaE gene, wherein the dnaE encoded α subunit possesses intrinsic zinc-dependent 3'-5' exonuclease activity, as disclosed herein.

In an especially preferred embodiment, the bacterial dnaE or polC encoded α subunits are derived from a bacterium or cyanobacterium selected from the group consisting of *Aquifex aeolicus, Thermus thermophilus, Deinococcus radiurans, Thermus aquaticus, Thermotoga maritima, Thermoanaerobacter, Geobacillus stearothermophilus, Thermus flavus, Thermus ruber, Thermus brockianus, Thermotoga neapolitana* and other species of the *Thermotoga* genus, *Methanobacterium thermoautotrophicum*, and species from the genera *Thermocridis, Hydrogenobacter, Thermosynchecoccus*, and mutants of these species.

In a preferred embodiment, the α subunit of a two component Pol III replicase used herein is encoded by a bacterial dnaE gene of a gram negative bacterium.

In another preferred embodiment, the α subunit of a two component Pol III replicase used herein is encoded by a bacterial polC gene of a gram positive bacterium.

In one embodiment, a single component Pol III replicase, or the first component of a two component Pol III replicase additionally comprises an ε subunit having 3'-5' exonuclease activity.

In one embodiment, the 3'-5' exonuclease activity of a minimal functional Pol III replicase in a reaction mixture is conferred by an ε subunit. In another embodiment, the 3'-5' exonuclease activity of a minimal functional Pol III replicase in a reaction mixture is conferred by a DNA polymerase III α subunit. The 3'-5' exonuclease activity of a DNA polymerase III α subunit can be modulated by zinc, and may differ in different reaction mixtures, as described herein.

In alternative embodiments, a minimal functional Pol III replicase does not exhibit significant 3'-5' exonuclease activity capable of removing 3' dideoxynucleotides under conditions that provide for polymerase activity of the minimal functional Pol III replicase. In a preferred embodiment, the minimal functional Pol III replicase lacking significant 3'-5' exonuclease activity is a single component Pol III replicase comprising an α subunit encoded by a dnaE gene of a gram positive bacterium.

In one embodiment, a single component Pol III replicase, or the first component of a two component Pol III replicase includes additional subunits of a Pol III DNA polymerase core, such as θ.

In some embodiments herein, single component Pol III replicases and two component Pol III replicases that are thermostable DNA polymerases are used. These thermostable DNA polymerases are referred to herein as "thermostable single component Pol III replicases" and "thermostable two component Pol III replicase", respectively, and are collectively referred to herein as "thermostable minimal functional Pol III replicase".

BRIEF DESCRIPTION OF THE DRAWINGS

FIG. 1 shows comparison between processivity of Tth versus *E. coli* alpha subunits and minimal holoenzymes. Primer extension assay with ssM13 mp18 DNA template (0.146 pmol) primed with a 30-mer oligodeoxynucleotide primer (0.375 pmol) was performed as described using either 2.03 µg (15 pmol) of the Tth α-subunit alone or 15 pmol of the corresponding minimal DNA Pol III holoenzyme. The primer extension reaction buffer for the Tth polymerases comprised 20 mM TAPS-Tris (pH 7.5), 10 mM Mg(OAc)$_2$, 15% glycerol, 40 mg/ml BSA and 1.5 mM ATP. The primer extension reaction buffer for the *E. coli* polymerases (2 µg alpha, 15 pmol or 15 pmol Pol III holoenzyme plus 800 µg *E. coli* SSB protein) comprised 20 mM Tris-Cl (pH 7.5), 8 mM Mg(OAc)$_2$, 4% glycerol, 40 mg/ml BSA, 0.5 mM ATP, 5 mM DTT.

FIG. 2 shows low primer extension rates of *Thermotoga maritima* DNA Pol III alpha subunit (dnaE). In 19.6 µl reaction mixes 350 ng (0.15 pmol) of ssM13 mp18 DNA primed with 0.375 pmol of a 30-mer oligodeoxynucleotide primer were incubated at 60° C. for 2 minutes in the presence of 100 ng (1 pmol) or 2 µg (20.8 pmol) of Tma DNA Pol III alpha (dnaE) in 20 mM TAPS-Tris (pH 7.5), 10 mM Mg(OAc)$_2$, 14% glycerol, 40 mg/ml BSA and 1.5 mM ATP. The primer extension/replication was started by adding 0.4 µl of a dNTP mix containing 10 mM dATP, 10 mM dGTP, 10 mM dTTP, and 10 mM dCTP to the final concentration of 200 mmol each. The indicated time points of the primer extension assay were taken stopping individual reactions by addition of 2 µl 0.1M EDTA and transferring them on ice. The replication products were analyzed by electrophoretic separation in a 0.7% TEAE-buffered agarose gel with subsequent ethidium bromide staining. The red arrow marks the first time point at which the full-size (7.2 kb) double-stranded replication product was detectable. At 1 pmol/ul the Tma DNA Pol III alpha (dnaE) replicated the 7.2 kb M13 template with an extension rate of 60 b/sec, whereas at 0.05 pmol/ul the primer elongation on the M13 mp18 template is barely detectable.

FIG. 3 shows PCR with a single component (alpha alone) and two component (alpha/beta; 1:2) Pol III replicase from *Aquifex aeolicus* and *Thermus thermophilus*. 50 µl inverse PCR assys were performed containing 50 ng of the pBSK plasmid template with (3 kb) and 10 pmol of the forward and reverse primer, respectively. The primers anneal tail-to-tail at ori region of the plasmid so a full-length linear amplicon of the plasmid is amplified (3 kb). The 30 cycle PCR were performed with two (alpha/beta) and single component (alpha) DNA Pol III Replicases from Aquifex and Thermus in the presence of various stabilizers. 30 cycles of the following temperature cycling protocol was applied: [Denaturation 91° C. 30"; Primer Annealing & Elongation at 62° C. 120"]. The PCR buffer used for the Aquifex replicases was 20 mM TAPS-Tris buffer, pH 8.7, 50 mMKCl; 10 mM ammonium sulfate; 0.8 mM CaCl$_2$; 15 µM ZnSO$_4$; 2% PEG 20K; 10% sorbitol; 4 mM Mg(OAc)$_2$; 10% glycerol, 1 mM DTT and 1.1 M TMAO, in the presence of 200 µM of each dNTP. The PCR buffer used for the Thermus replicases was 20 mM HEPES-Tris buffer (pH 7.5), 2% PEG 20K; 10% sorbitol; 6 mM Mg(OAc)$_2$; 10% glycerol, 1 mM DTT and 1.1 M TMAO, in the presence of 200 µM of each dNTP. The PCR amplification of a 3 kb target from plasmid DNA could successfully demonstrated for two single and two component DNA Pol III replicases.

FIG. 4 schematically compares the arrangement and spacing of motifs A, B, and C in bacterial dnaE and polC α subunits.

Figure 8B:
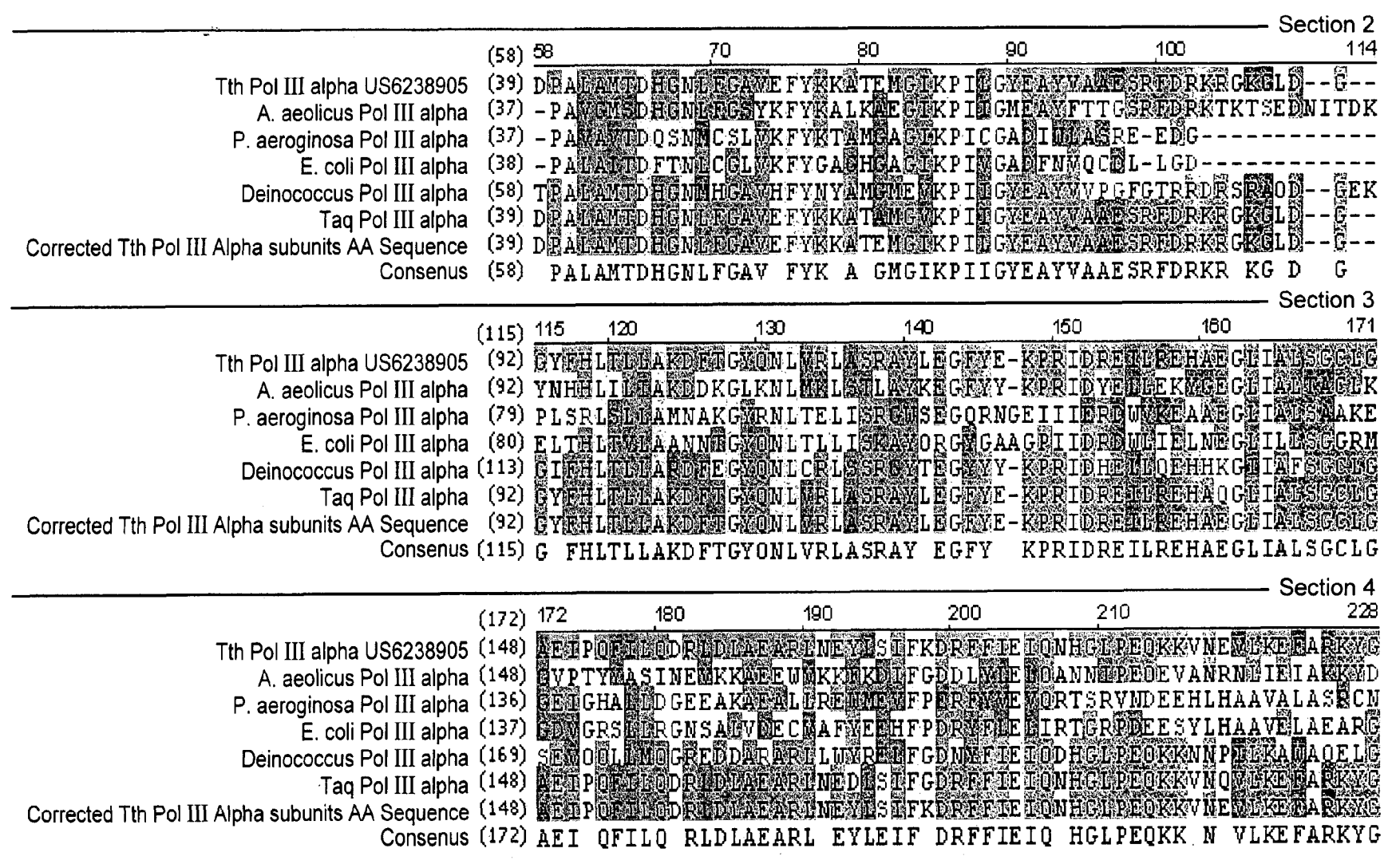
Figure 8C:
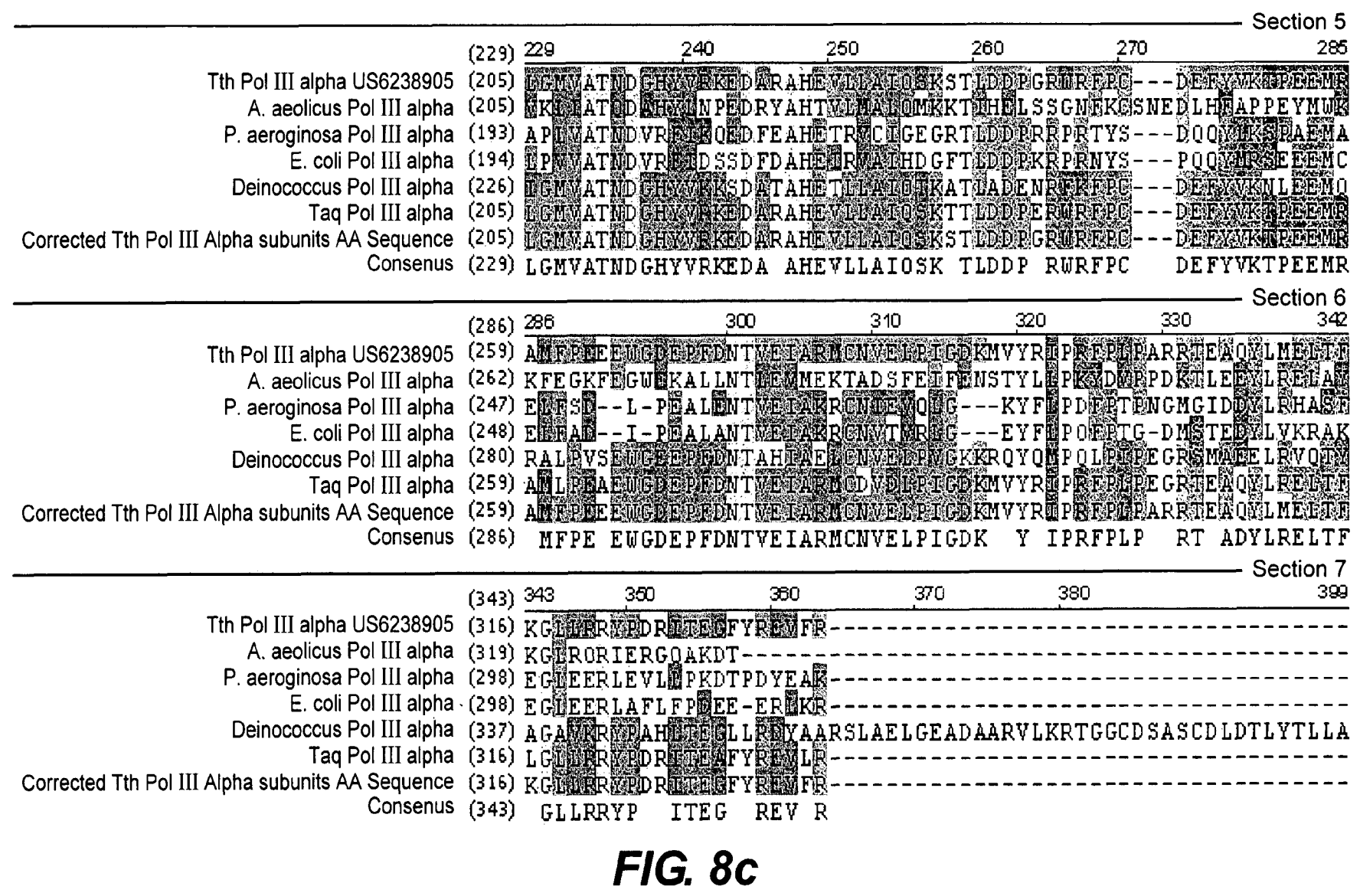
Figure 8E:
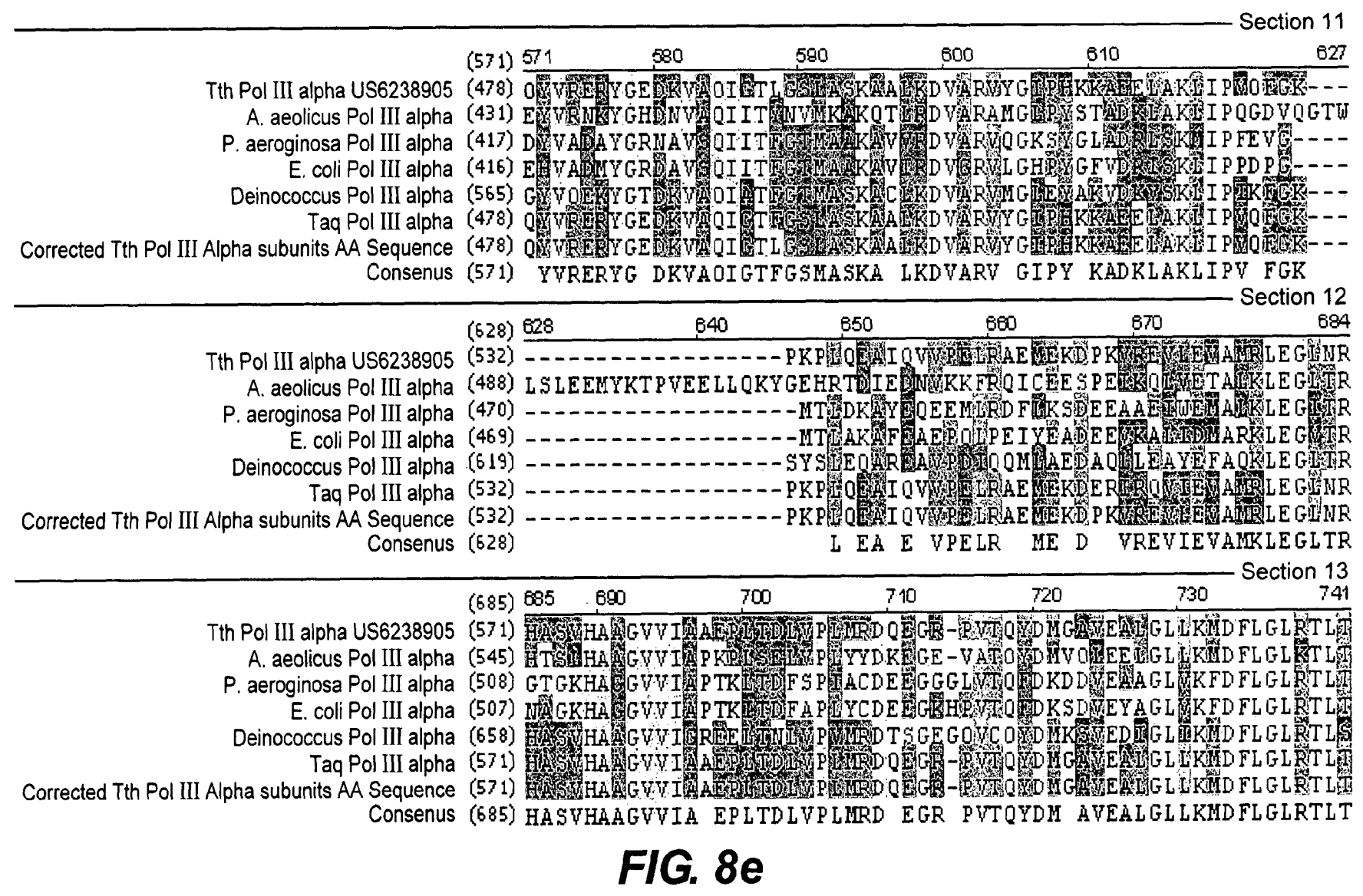
Figure 8F:
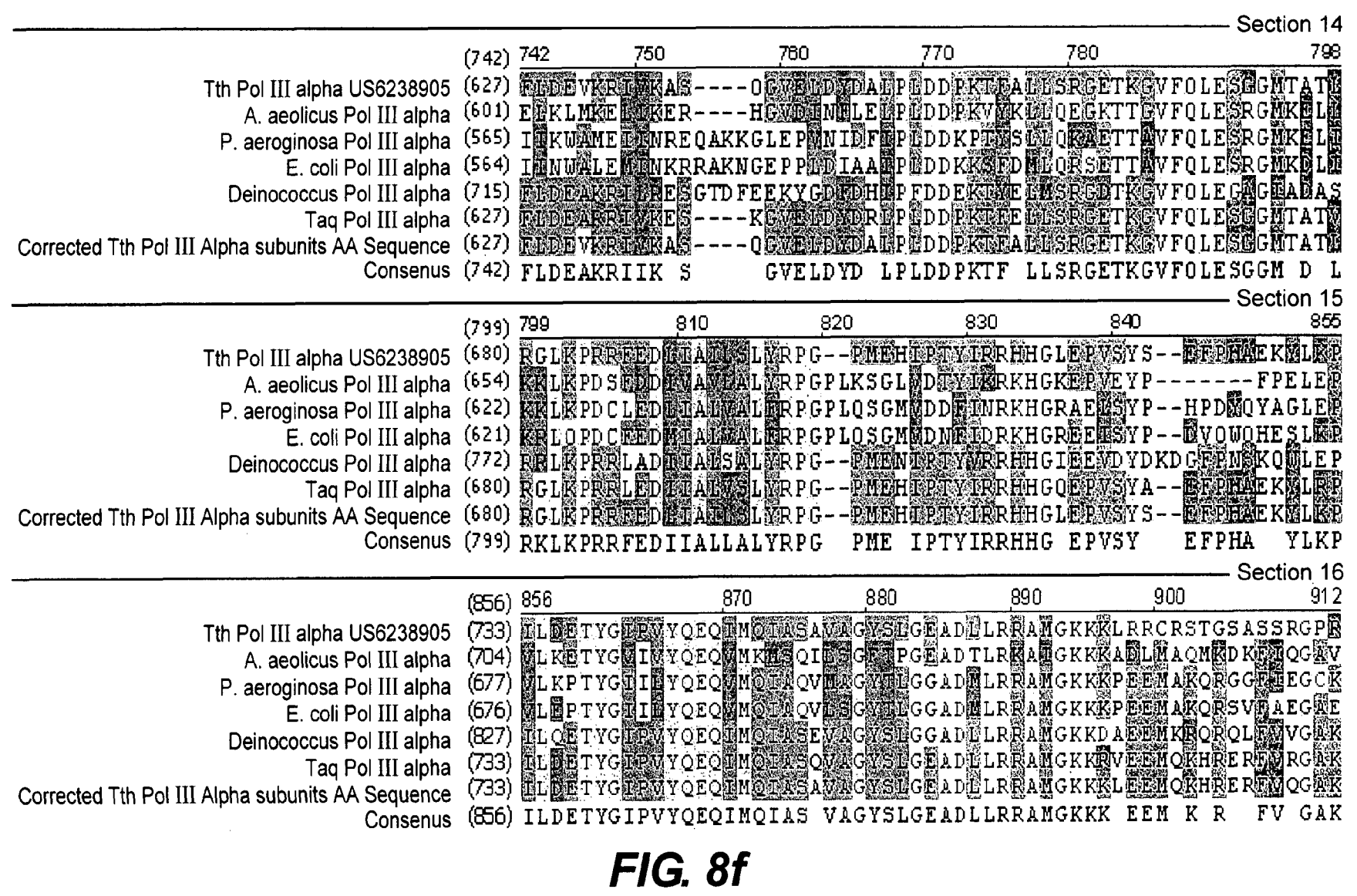
Figure 8G:
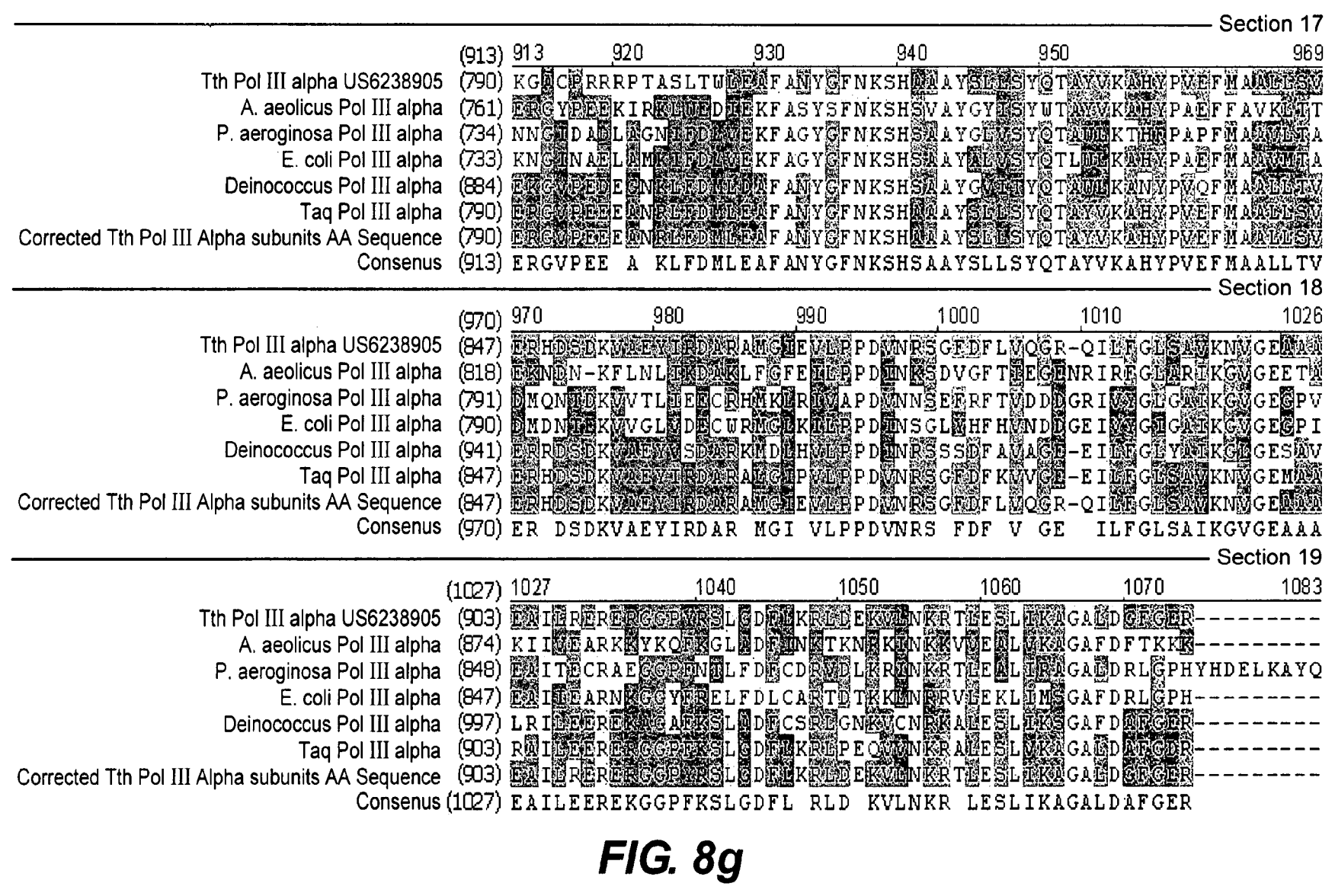
Figure 8H:
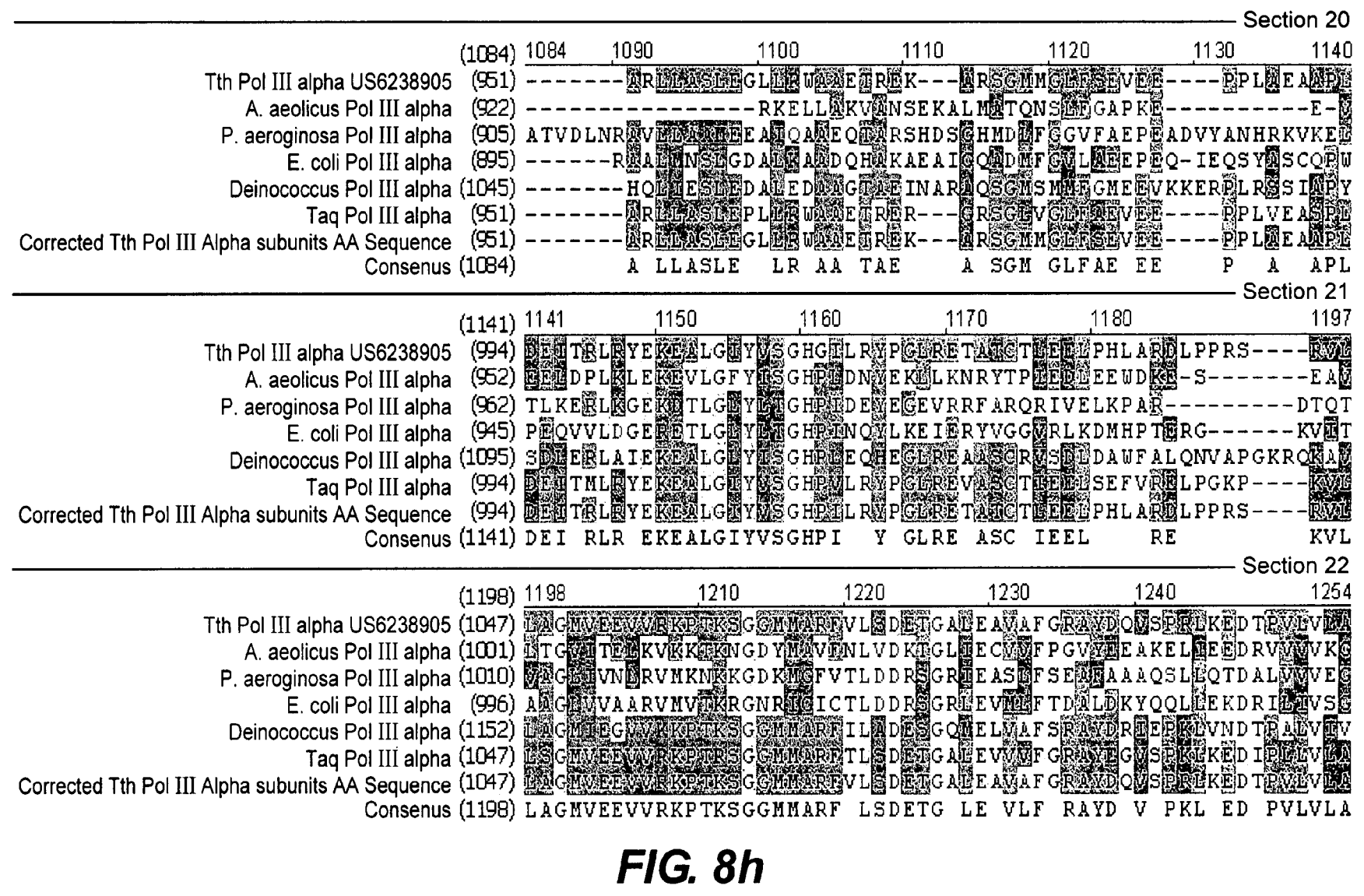
Figure 8I:
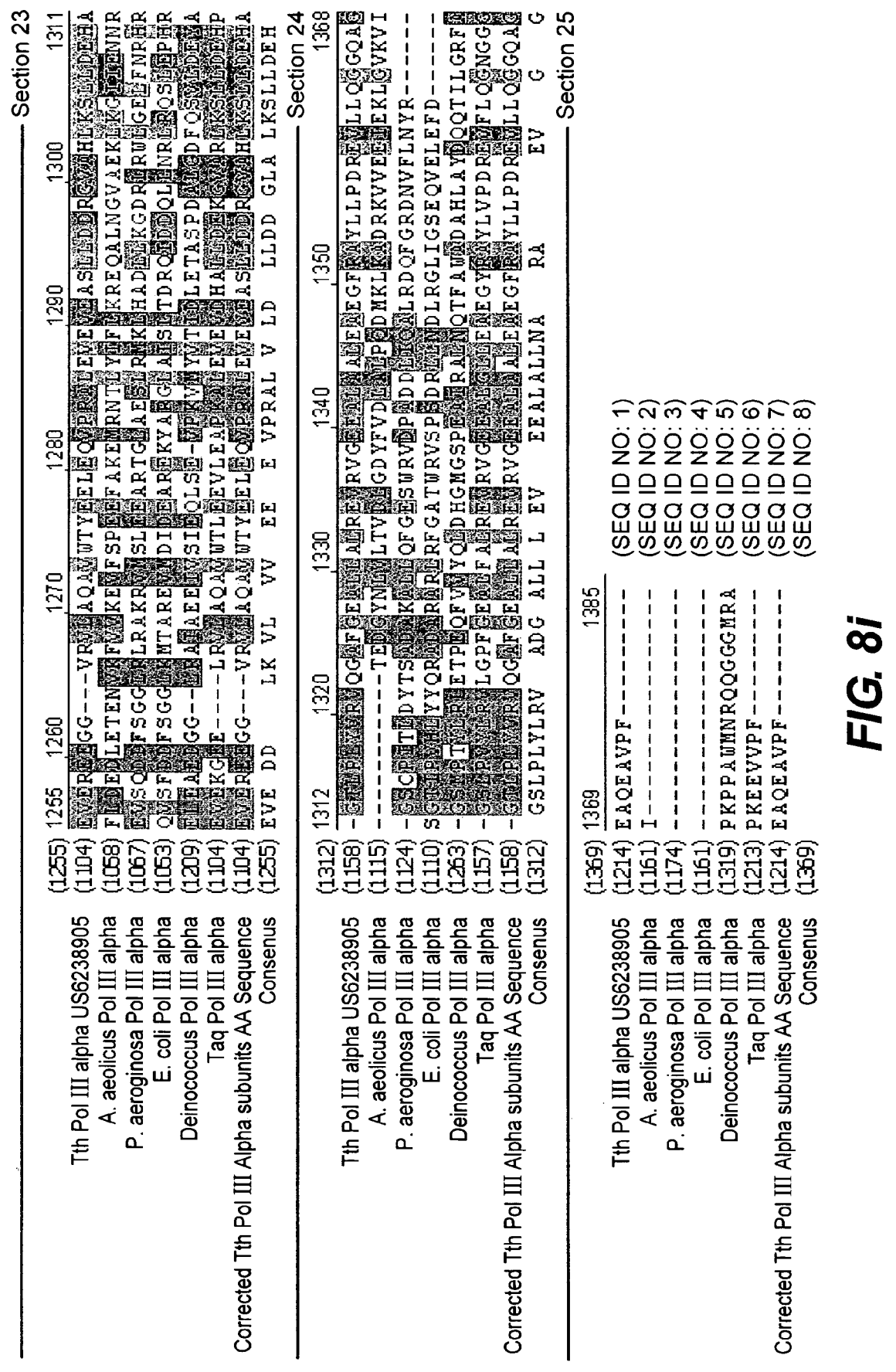

FIGS. 8a-8i illustrate the homology between the DNA Pol III alpha predicted amino acid sequence disclosed in the present invention and reported DNA Pol III alpha subunits (SEQ ID NOS:1-8).

FIGS. 9a-9i show the novel nucleic acid sequence and predicted amino acid sequence for T.th derived Pol III alpha subunit (SEQ ID NOS:9-11).

FIGS. 11 and 12 show primer extension assays using 1 µg A.ae DNA polymerase III α subunit.

FIG. 13 shows 2 µg Aquifex DNA Pol III alpha subunit in primer extension assay. Maximum extension rate 720 b/sec.

FIG. 18 shows fast PCR with the T.th alpha/beta two component Pol III replicase versus Taq DNA Polymerase I and a fast Taq/DeepVent DNA Pol B polymerase mixture (TM).

FIG. 23 shows *Aquifex aeolicus* alpha/beta PCR, pBSK plasmid, template, +dnaB helicase, unmodified primers.

FIG. 24 shows *Aquifex aeolicus* complete Pol III holoenzyme, PCR of pBSK plasmid+dnaB, unmodified primers.

DETAILED DESCRIPTION OF THE INVENTION

Figure 5:
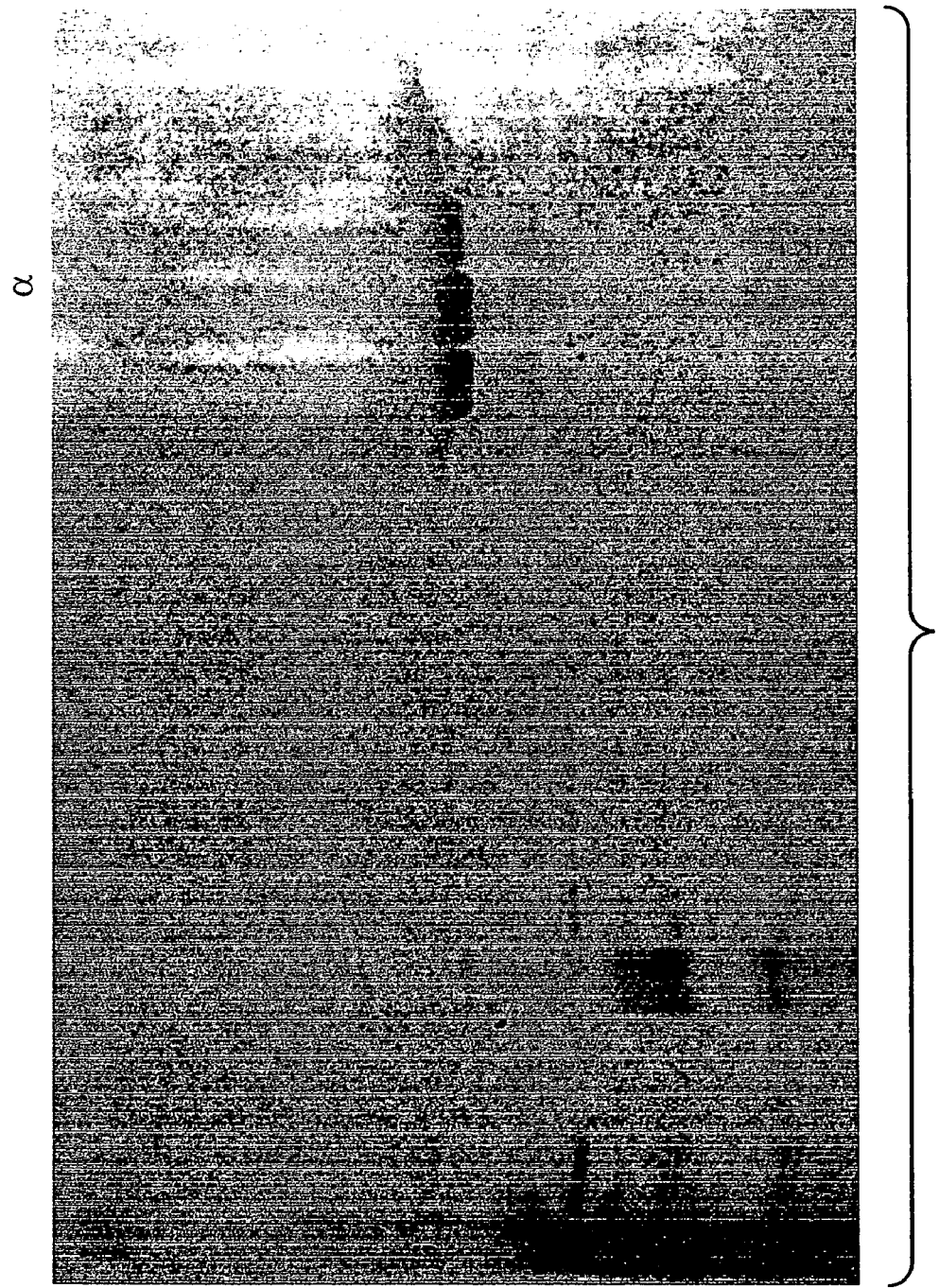
FIG. 5 shows the heated *Thermus thermophilus* alpha subunit scale-up on butyl-sepharose gel.

The minimal functional Pol III replicases used herein have several advantages over known DNA polymerases, including DNA polymerase III holoenzymes. For example, use of the single component and two component Pol III replicases has clear cost benefits over the use of DNA polymerase III holoenzymes, and provides high speed, high fidelity, optional thermostability, and processive polymerase activity that is unmatched by conventional repair-type DNA polymerases used in amplification and sequencing reactions today, or by other known single or two component DNA polymerases, such as gram positive dnaE polymerases. In particular, the minimal Pol IIIs disclosed herein can achieve a primer extension rate that is at least about 6-8 fold faster than the extension rate of conventional repair-type DNA polymerases, and an error rate that is up to 3 orders of magnitude lower ($10^{-9}$) than the error rate of the most accurate repair-type DNA polymerases.

Additionally, the ability to reconstitute a minimal functional Pol III replicase in vitro with a single subunit, single component, or two components of a DNA polymerase III holoenzymes is particularly beneficial when additional subunits present in the holoenzyme (e.g., $\gamma$ or $\delta$ subunits of a clamp loader component) have not been identified, purified, or cloned from a particular source. Moreover, as disclosed herein, an $\alpha$ subunit useful as a minimal functional Pol III replicase is identifiable by sequence analysis alone, without a requirement for prior knowledge of the polypeptide's activity or identification of a corresponding holoenzyme.

Components of a minimal functional Pol III replicase useful in the invention may be isolated from any organism that makes a corresponding DNA polymerase III.

The components of a minimal functional Pol III replicase useful in the invention may be isolated from a variety of bacteria, including thermophilic bacteria, that are available commercially (for example, from American Type Culture Collection, Rockville, Md.). It will be understood by one of ordinary skill in the art that any thermophilic microorganism might be used as a source of a thermostable single component or two component Pol IIIs. Bacterial cells may be grown according to standard microbiological techniques, using culture media and incubation conditions suitable for growing active cultures of the particular thermophilic species that are well-known to one of ordinary skill in the art (see, e.g., Brock, T. D., and Freeze, H., J. Bacteriol., 98(1):289-297 (1969); Oshima, T., and Imahori, K, Int. J. Syst. Bacteriol., 24(1):102-112 (1974), which are hereby incorporated by reference).

In a preferred embodiment, components of the DNA polymerases of the invention are produced recombinantly.

By "minimal functional Pol III replicase" is meant a functional subassembly of DNA polymerase III subunits, wherein the DNA polymerase III is a genomic replicase. Functional refers to replicase activity, which can be characterized by primer extension rate, as described below.

As used herein, a gene "of" or "derived from" a particular bacterial genus or species does not mean directly of or directly derived from a particular bacterial genus or species. Rather, the phrases refer to correspondence of the particular gene to an endogenous gene of the particular bacterial genus or species.

Nucleic Acid Replication

In one aspect, the invention provides methods for replicating a nucleic acid molecule, comprising subjecting the nucleic acid molecule to a replication reaction in a replication reaction mixture comprising a minimal functional Pol III replicase.

"Nucleic acid replication" is a process by which a template nucleic acid molecule is replicated in whole or in part. Thus, the product of a nucleic acid replication reaction can be completely or partially complementary to the template nucleic acid molecule it is replicating. Nucleic acid replication is done by extending a primer hybridized to the template nucleic acid in the 5'-3' direction, incorporating nucleotides complementary to the bases of the template nucleic acid at each position in the extension product. The primer may be, for example, a synthetic oligonucleotide that hybridizes to a region of a single stranded DNA template. The primer may also be, for example, a portion of a single stranded DNA template that is complementary to a second region of the single stranded DNA template and can self-prime. Included within the scope of nucleic acid replication reactions are isothermal replication reactions, sequencing reactions, amplification reactions, thermocycling amplification reactions, PCR, fast PCR, and long range PCR.

The nucleic acid replicated in a nucleic acid replication reaction is preferably DNA, and replication preferably involves the DNA-dependent DNA polymerase activity of a minimal functional Pol III replicase disclosed herein.

Single component and/or two component Pol III replicases may be used in a nucleic acid replication reaction. For nucleic acid sequencing reactions, a single component Pol III replicase lacking 3'-5' exonuclease activity capable of excising 3' terminal dideoxynucleotides is generally preferred. For nucleic acid amplification reactions, a two component Pol III replicase having 3'-5' exonuclease activity is generally preferred. For nucleic acid thermocycling amplification reactions, including PCR reactions, a thermostable two component Pol III replicase having 3'-5' exonuclease activity is generally preferred.

In a preferred embodiment, a replication reaction mixture comprises a zwitterionic buffer, comprising a combination of a weak organic acid, having a pK between about 7.0-8.5 (e.g., HEPES, DIPSO, TAAPS, HEPBS, HEPPSO, TRICINE, POPSO, MOBS, TAPSO, and TES) and a weak organic base, having a pK between about 6.8-8.5 (e.g., Tris, Bis-Tris-propane, imidazol, TMNO, 4-methyl imidazol, and diethanolamine), wherein the pH of the buffer is set by titration with organic base between about pH 7.5-8.9, and wherein the concentration of the organic acid is between about 10-40 mM, more preferably between about 20-30 mM.

In an especially preferred embodiment, a replication reaction mixture and minimal functional Pol III replicase combination is selected from the following combinations: (i) HEPES-Bis-Tris-Propane (20 mM, pH 7.5) with a minimal functional Pol III replicase comprising a dnaE encoded $\alpha$ subunit from the genus Thermus, preferably from the species *Thermus thermophilus*; and (ii) TAPS-Tris (20 mM, pH 8.7) with a minimal functional Pol III replicase comprising a dnaE encoded $\alpha$ subunit from the genus Aquifex, preferably from the species *Aquifex aeolicus*.

In a preferred embodiment, a nucleic acid replication reaction mixture comprises one or more ions selected from the group consisting of $Zn^{2+}$, $Mg^{2+}$, $K^+$, and $NH_4^{2+}$, which are included for optimum activity of the minimal functional Pol III replicase in the reaction mixture. The ions are preferably titrated in preliminary assays to determine the optimum concentrations for optimum activity of the minimal functional Pol III replicase in the reaction mixture. In a particularly preferred embodiment, the nucleic acid replication reaction mixture lacks $Ca^{2+}$ ion.

In some preferred embodiments, the nucleic acid replication reaction mixture includes potassium ions. Potassium ions are preferably titrated initially to determine the optimal concentration for the Pol III system being used. Generally, the $K^+$ concentration of the replication reaction mixture is preferably between 0 and about 100 mM, more preferably between about 5-25 mM. Potassium ion is preferably provided in the form of KCl, $K_2SO_4$, or potassium acetate. The particular counter anion provided with $K^+$ can impact the activity of the minimal functional Pol III replicase, and preliminary assays are preferably done in order to determine which counter anion best suits the particular minimal Pol III system for the particular replication reaction. In general, sulfate or chloride counter anion is preferably used with a minimal functional Pol III replicase derived from *Aquifex aeolicus*, with sulfate being preferred over chloride. Additionally, potassium ion is not preferred for use in a replication reaction mixture with a minimal functional Pol III replicase derived from *Thermus thermophilus*.

In some preferred embodiments, the nucleic acid replication reaction mixture includes ammonium ions. Ammonium ions are preferably titrated initially to determine the optimal concentration for the Pol III system being used. Generally, the $NH_4^{2+}$ concentration of the replication reaction mixture is preferably between 0 and about 15 mM. Ammonium ion is preferably provided in the form of ammonium sulfate. Ammonium ions are preferably included in a replication reaction mixture with a minimal functional Pol III replicase derived from *Aquifex aeolicus*. Additionally, ammonium ion is not preferred for use in a replication reaction mixture with a minimal functional Pol III replicase derived from *Thermus thermophilus*.

In some preferred embodiments, the replication reaction mixture includes zinc ions. Zinc ions are preferably titrated initially to determine the optimal concentration for the Pol III system being used. Generally, the $Zn^{2+}$ concentration in a replication reaction mixture is preferably between 0 and about 50 1M, more preferably between about 5-15 µM. Zinc ion is preferably provided in the form of a salt selected from the group consisting of $ZnSO_4$, $ZnCl_2$ and zinc acetate. The particular counter anion provided with $Zn^{2+}$ can impact the activity of the minimal functional Pol III replicase, and preliminary assays are preferably done in order to determine which counterion best suits the particular minimal Pol III system for the particular replication reaction. In general, chloride or acetate counter anions are preferably used in a replication reaction mixture with a minimal functional Pol III replicase derived from *Thermus thermophilus*, and sulfate counter anions are preferably used in a replication reaction mixture with a minimal functional Pol III replicase derived from *Aquifex aeolicus*.

In general, $Zn^{2+}$ is not preferred for use in sequencing reaction mixtures, as it can increase the 3'-5' exonuclease activity of a number of α subunits (e.g., *Thermus thermophilus* dnaE). The impact of $Zn^{2+}$ on the 3'-5' exonuclease activity of any particular minimal functional Pol III replicase, and its impact on sequencing reactions using the same, may be assessed using standard exonuclease activity assays that are well known in the art.

In some preferred embodiments, the replication reaction mixture includes magnesium ions. Magnesium ions are preferably titrated initially to determine the optimal concentration for the Pol III system being used. Generally, the $Mg^{2+}$ concentration in a replication reaction mixture is preferably between 0 and about 15 mM, more preferably between about 4-10 mM. In general, isothermal nucleic acid replication reactions, including nucleic acid sequencing reactions, are more accommodating of $Mg^{2+}$ concentrations at the higher end of the preferred concentration range. Magnesium ion is preferably provided in the form of a salt selected from the group consisting of $MgCl_2$, $MgSO_4$, and magnesium acetate. The particular counter anion provided with $Mg^{2+}$ can impact the activity of the minimal functional Pol III replicase, and preliminary assays are preferably done in order to determine which counterion best suits the particular Pol III system for the particular replication reaction. In general, acetate or chloride counter anions are preferably used with a minimal functional Pol III replicase derived from *Thermus thermophilus*, with acetate being preferred over chloride. Additionally, sulfate counter anions are preferably used with a minimal Pol III derived from *Aquifex aeolicus*.

In an especially preferred embodiment, a replication reaction mixture for use with a minimal functional Pol III replicase derived from *Aquifex aeolicus* comprises TAPS-Tris (20 mM, pH8.7), 25 mM $K_2SO_4$, 10 mM $NH_4(OAc)_2$, and 10 mM $MgSO_4$.

In another especially preferred embodiment, a replication reaction mixture for use with a minimal functional Pol III replicase derived from *Thermus thermophilus* comprises HEPES-Bis-Tris-Propane (20 mM, pH 7.5), and 10 mM $Mg(OAc)_2$.

In one embodiment, a helicase is included in a replication reaction in order to lower the denaturation temperature required to provide single stranded nucleic acid template for replication.

In one embodiment, a replication reaction mixture provided herein lacks ATP.

In one embodiment, a replication reaction mixture provided herein lacks SSB, wherein SSB, if present in the replication reaction mixture, would reduce the DNA polymerase activity of the particular minimal functional Pol III replicase used in the replication reaction mixture. In a preferred embodiment, a replication reaction mixture comprising a minimal functional Pol III replicase, which minimal functional Pol III replicase comprises an α subunit encoded by *Streptococcus pyogenes* polC lacks SSB.

In nucleic acid replication reactions herein, wherein the one component or two component Pol III replicase used is derived from a thermophilic bacterium, the reaction mixture preferably has a pH from about 7.2-8.9. In some preferred embodiments, the reaction mixture has a $Zn^{2+}$ concentration between 0 and about 50 µM, more preferably between about 5-15 µM. In some preferred embodiments, the reaction mixture has a $Mg^{2+}$ concentration between 0 and about 15 mM, more preferably between about 4-10 mM. In some preferred embodiments, the reaction mixture has a $K^+$ concentration between 0 and about 100 mM, more preferably between about 5-25 mM. In some preferred embodiments, the reaction mixture has an $NH4^{2+}$ concentration between 0 and about 12 mM, more preferably between about 5-12 mM. In some preferred embodiments, the reaction mixture has a combination of these cations in their preferred concentration ranges.

In nucleic acid replication reactions herein, the temperature at which primer extension is done is preferably between about 60-72° C., more preferably between about 62-68° C.

In a preferred embodiment, the temperature at which primer annealing and primer extension are done in a thermocycling amplification reaction is between about 60-72° C., more preferably between about 62-68° C., more preferably between about 62-65° C., though the optimum temperature will be determined by primer length, base content, degree of primer complementarity to template, and other factors, as is well known in the art.

In a preferred embodiment, the temperature at which denaturation is done in a thermocycling amplification reaction is between about 86-91° C., more preferably between 87-89° C., with temperatures at the lower end of the range being preferred for use in combination with thermocycling amplification reaction mixtures that include DNA destabilizers, as disclosed herein. Preferred thermocycling amplification methods include polymerase chain reactions involving from about 10 to about 100 cycles, more preferably from about 25 to about 50 cycles, and peak temperatures of from about 86° C. to about 91° C., more preferably 87° C.-89° C., with temperatures at the lower end of the range being preferred for use in combination with PCR reaction mixtures that include DNA destabilizers, as disclosed herein.

Stabilizers

Preferably, a combination of at least two and more preferably at least three stabilizers is included in a thermocycling amplification reaction mixture. In preferred embodiments, the stabilizers include at least one co-solvent, such as a polyol (e.g. glycerol, sorbitol, mannitol, maltitol), at least one crowding agent, such as polyethylene glycol (PEG), ficoll, polyvinyl alcohol or polypropylene glycol, and a third component selected from the group consisting of sugars, organic quaternary amines, such as betaines, and their N-oxides and detergents. In particularly preferred embodiments, the stabilizers include a co-solvent, a crowding agent, and a quaternary amine N-oxide, such as trimethylamine-N-oxide (TMNO) or morpholino-N-oxide. In further preferred embodiments, the reaction mixture further comprises a fourth stabilizer, most preferably a second polyol. Other preferred four stabilizer combinations include three different co-solvents, and a quaternary amine N-oxide.

Nucleic acid replication reactions employing high temperature denaturation steps may benefit from the inclusion of one or more stabilizers in the reaction mixture. Preferred stabilizers in accordance with the present invention include co-solvents such as polyols and crowding agents such as polyethylene glycols, typically with one or more oxides, sugars, detergents, betaines and/or salts. For holoenzyme activity in general and two component polymerase activity in particular, combinations of the foregoing components are most preferred.

As used herein, "crowding polymeric agent" or "crowding agent" refers to macromolecules that at least in part mimic protein aggregation. Illustrative crowding agents for use in the present invention include polyethylene glycol (PEG), PVP, Ficol, and propylene glycol.

As used herein, "detergent" refers to any substance that lowers the surface tension of water and includes, but is not limited to, anionic, cationic, nonionic, and zwitterionic detergents. Illustrative detergents for use in the present invention include Tween 20, NP-40 and Zwiftergent 3-10.

As used herein, "polyol" refers to a polyhydric alcohols, i.e., alcohols containing three or more hydroxyl groups. Those having three hydroxyl groups (trihydric) are glycerols; those with more than three are called sugar alcohols, with general formula $CH_2OH(CHOH)_nCH_2OH$, where n may be from 2 to 5.

TABLE 2

Preferred Stabilizer Combinations

| Preferred Embodiment 1 | Preferred Embodiment 2 | Preferred Embodiment 3 | Preferred Embodiment 4 | Preferred Embodiment 5 |
|---|---|---|---|---|
| Glycerol Sorbitol PEG (20K) TMAO | Glycerol Maltitol PEG (20K) TMAO | Glycerol PEG (20K) TMAO | PEG (20K) Maltitol TMAO | Sorbitol TMAO PEG (20K) |

| Preferred Embodiment 6 | Preferred Embodiment 7 | Preferred Embodiment 8 | Preferred Embodiment 9 | Preferred Embodiment 10 |
|---|---|---|---|---|
| Glycerol Sorbitol PEG (20K) Glycyl Betaine | Glycerol Maltitol PEG (20K) Glycyl Betaine | PEG (20K) Sorbitol Glycyl Betaine | Glycerol PEG (20K) Glycyl Betaine | Glycyl Betaine Maltitol PEG (20K) |

Embodiments of the present invention generally include combining at least two and more preferably at least three different stabilizers selected from Groups I-VII (see Table 1) together to facilitate temperature-based nucleic acid amplification. Preferred embodiments of the present invention include a combination of at least one member from Group II with a member from Group III within the amplification reaction mixture, particularly where the member from Group II is glycerol and/or sorbitol. Particularly preferred combinations include two different members of Group II combined with one member from Group III and one member from Group VII.

Nucleic Acid Amplification

In one aspect, the invention provides methods for amplifying a nucleic acid molecule, comprising subjecting the nucleic acid molecule to an amplification reaction according to an amplification method described herein, in an amplification reaction mixture comprising a minimal functional Pol III

TABLE 1

Stabilizer Agents

| Group I (Sugars) | Group II (Polyol Co-Solvents) | Group III (Crowding Agents) | Group IV (Detergents) | Group V (Betaines) | Group VI (Salts) | Group VII (Quaternary amine N-Oxides) |
|---|---|---|---|---|---|---|
| Trehalose | Glycerol | CM Cellulose | Tween 20 | Betaine Monohydrate | Potassium Glutamate | TMAO, (Trimethylamine N-oxide) |
| Sucrose | Sorbitol | PEG 4000 | NP-40 | Ectoine | KCl | 4-Methyl-Morpholin-4-Oxide |
| Lactose | Mannitol | PEG 8000 | TritonX-100 | | | |
| Ribose | Maltitol | PEG 20000 | Pluronic Acid | | | |
| Glucose | Xylitol | PVP | Zwittergent 3-10 | | | |
| D-Fructose | | Propylene glycol | Zwittergent 3-12 | | | |
| D-Mannose | | Ficoll | Zwittergent 3-14 | | | |
| D-Galactose | | | Zwittergent 3-16 | | | |
| | | | Chaps | | | |
| | | | ChapsSO | | | |
| | | | N-Octyl-Sucrose | | | |
| | | | Caprolyl Sulfo-betaine SB 3-10 | | | |
| | | | Myristyl-Sulfo-betaine SB 3-14 | | | |
| | | | N-Octyl-β-glucopyranosid | | | |
| | | | N-Octyl-β-D-thioglucopyranosid | | | | replicase disclosed herein. Preferably, the amplification reaction is done in an amplification reaction tube described herein.

Nucleic acid molecules may be amplified according to any of the literature-described manual or automated amplification methods. As used herein "amplification" refers to any in vitro method for increasing the number of copies of a desired nucleotide sequence with the use of a DNA or RNA polymerase. The nucleic acid amplified is preferably DNA, and amplification preferably involves the DNA-dependent DNA polymerase activity of a minimal functional Pol III replicase described herein.

In one embodiment, nucleic acid amplification results in the incorporation of nucleotides into a DNA molecule or primer, thereby forming a new DNA molecule complementary to a nucleic acid template. The formed DNA molecule and its template can be used as templates to synthesize additional DNA molecules. As used herein, one amplification reaction may consist of many rounds of DNA replication. DNA amplification reactions include, for example, polymerase chain reactions ("PCR"). One PCR reaction may consist of 10 to 100 "cycles" of denaturation and synthesis of a DNA molecule. Such methods include, but are not limited to, PCR (as described in U.S. Pat. Nos. 4,683,195 and 4,683,202, which are hereby incorporated by reference), Strand Displacement Amplification ("SDA") (as described in U.S. Pat. No. 5,455,166, which is hereby incorporated by reference), and Nucleic Acid Sequence-Based Amplification ("NASBA") (as described in U.S. Pat. No. 5,409,818, which is hereby incorporated by reference). For example, amplification may be achieved by a rolling circle replication system which may even use a helicase for enhanced efficiency in DNA melting with reduced heat (see Yuzhakou et al., "Replisome Assembly Reveals the Basis for Asymmetric Function in Leading and Lagging Strand Replication," Cell 86:877-886 (1996) and Mok et al., "The *Escherichia coli* Preprimosome and DnaB Helicase Can Form Replication Forks That Move at the Same Rate," J. Biol. Chem. 262:16558-16565 (1987), which are hereby incorporated by reference).

In a preferred embodiment, the temperature at which denaturation is done in a thermocycling amplification reaction is between about 86-91° C., more preferably between 87-89° C., with temperatures at the lower end of the range being preferred for use in combination with thermocycling amplification reaction mixtures that include DNA destabilizers, as disclosed herein. Preferred thermocycling amplification methods include polymerase chain reactions involving from about 10 to about 100 cycles, more preferably from about 25 to about 50 cycles, and peak temperatures of from about 86° C. to about 91° C., more preferably 87° C.-89° C., with temperatures at the lower end of the range being preferred for use in combination with PCR reaction mixtures that include DNA destabilizers, as disclosed herein. In an especially preferred embodiment, the thermostable two component Pol III replicase comprises a dnaE α subunit, preferably of the genus *Thermus* or *Aquifex*, preferably of the species *Thermus thermophilus, Thermus aquaticus*, or *Aquifex aeolicus*.

In a preferred embodiment, the amplification reaction mixture used in an amplification reaction involving one or more high temperature denaturation steps further comprises stabilizers that contribute to the thermostability of the two component polymerase, as described and exemplified more fully herein.

In a preferred embodiment, an amplification mixture provided herein lacks SSB, wherein SSB, if present in the replication reaction mixture, would inhibit the DNA polymerase activity of the particular minimal Pol III used in the replication reaction mixture.

In a preferred embodiment, a PCR reaction is done using a minimal Pol III with appropriate stabilizers to produce, in exponential quantities relative to the number of reaction steps involved, at least one target nucleic acid sequence, given (a) that the ends of the target sequence are known in sufficient detail that oligonucleotide primers can be synthesized which will hybridize to them and (b) that a small amount of the target sequence is available to initiate the chain reaction. The product of the chain reaction will be a discrete nucleic acid duplex with termini corresponding to the ends of the specific primers employed.

Any source of nucleic acid, in purified or nonpurified form, can be utilized as the starting nucleic acid, if it contains or is thought to contain the target nucleic acid sequence desired. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction using the same or different primers may be so utilized. The nucleic acid amplified is preferably DNA. The target nucleic acid sequence to be amplified may be only a fraction of a larger molecule or can be present initially as a discrete molecule, so that the target sequence constitutes the entire nucleic acid. It is not necessary that the target sequence to be amplified be present initially in a pure form; it may be a minor fraction of a complex mixture, such as a portion of the β-globin gene contained in whole human DNA or a portion of nucleic acid sequence due to a particular microorganism which organism might constitute only a very minor fraction of a particular biological sample. The starting nucleic acid may contain more than one desired target nucleic acid sequence which may be the same or different. Therefore, the method is useful not only for producing large amounts of one target nucleic acid sequence, but also for amplifying simultaneously multiple target nucleic acid sequences located on the same or different nucleic acid molecules.

The nucleic acid(s) may be obtained from any source and include plasmids and cloned DNA or RNA, as well as DNA or RNA from any source, including bacteria, yeast, viruses, and higher organisms such as plants or animals. DNA or RNA may be extracted from, for example, blood or other fluid, or tissue material such as corionic villi or amniotic cells by a variety of techniques such as that described by Maniatis et al., Molecular Cloning: A Laboratory Manual, (New York: Cold Spring Harbor Laboratory) pp 280-281 (1982).

Any specific (i.e., target) nucleic acid sequence can be produced by the present methods. It is only necessary that a sufficient number of bases at both ends of the target sequence be known in sufficient detail so that two oligonucleotide primers can be prepared which will hybridize to different strands of the desired sequence and at relative positions along the sequence such that an extension product synthesized from one primer, when it is separated from its template (complement), can serve as a template for extension of the other primer into a nucleic acid of defined length. The greater the knowledge about the bases at both ends of the sequence, the greater the specificity of the primers for the target nucleic acid sequence, and, thus, the greater the efficiency of the process. It will be understood that the word primer as used hereinafter may refer to more than one primer, particularly in the case where there is some ambiguity in the information regarding the terminal sequence(s) of the fragment to be amplified. For instance, in the case where a nucleic acid sequence is inferred from protein sequence information a collection of primers containing sequences representing all possible codon variations based on degeneracy of the genetic code can be used for each strand. One primer from this collection will be homologous with the end of the desired sequence to be amplified.

In some alternative embodiments, random primers, preferably hexamers, are used to amplify a template nucleic acid molecule. In such embodiments, the exact sequence amplified is not predetermined.

In addition, it will be appreciated by one of skill in the art that one-sided amplification using a single primer can be done.

Oligonucleotide primers may be prepared using any suitable method, such as, for example, the phosphotriester and phosphodiester methods or automated embodiments thereof. In one such automated embodiment diethylophosphoramidites are used as starting materials and may be synthesized as described by Beaucage et al., Tetrahedron Letters, 22:1859-1862 (1981), which is hereby incorporated by reference. One method for synthesizing oligonucleotides on a modified solid support is described in U.S. Pat. No. 4,458,006, which is hereby incorporated by reference. It is also possible to use a primer which has been isolated from a biological source (such as a restriction endonuclease digest).

Preferred primers have a length of from about 20-100, more preferably about 25-50, most preferably about 30-40 bases. Notably, preferred primers for use herein are longer than those preferred for Pol I polymerases.

The target nucleic acid sequence is amplified by using the nucleic acid containing that sequence as a template. If the nucleic acid contains two strands, it is necessary to separate the strands of the nucleic acid before it can be used as the template, either as a separate step or simultaneously with the synthesis of the primer extension products. This strand separation can be accomplished by any suitable denaturing method including physical, chemical, or enzymatic means. One physical method of separating the strands of the nucleic acid involves heating the nucleic acid until it is completely (>99%) denatured. Typical heat denaturation may involve temperatures ranging from about 80° C. to 105° C., preferably about 90° C. to about 98° C., still more preferably 93° C. to 94° C., for times ranging from about 1 to 10 minutes. Strand separation may also be induced by an enzyme from the class of enzymes known as helicases or the enzyme RecA, which has helicase activity and is known to denature DNA. The reaction conditions suitable for separating the strands of nucleic acids with helicases are described by Cold Spring Harbor Symposia on Quantitative Biology, Vol. XLIII "DNA: Replication and Recombination" (New York: Cold Spring Harbor Laboratory, 1978), and techniques for using RecA are reviewed in C. Radding, Ann. Rev. Genetics, 16:405-37 (1982), which is hereby incorporated by reference. Preferred helicases for use in the present invention are encoded by dnaB.

If the original nucleic acid containing the sequence to be amplified is single stranded, its complement is synthesized by adding oligonucleotide primers thereto. If an appropriate single primer is added, a primer extension product is synthesized in the presence of the primer, a two-component polymerase, and the four nucleotides described below. The product will be partially complementary to the single-stranded nucleic acid and will hybridize with the nucleic acid strand to form a duplex of unequal length strands that may then be separated into single strands, as described above, to produce two single separated complementary strands.

If the original nucleic acid constitutes the sequence to be amplified, the primer extension product(s) produced will be completely complementary to the strands of the original nucleic acid and will hybridize therewith to form a duplex of equal length strands to be separated into single-stranded molecules.

When the complementary strands of the nucleic acid or acids are separated, whether the nucleic acid was originally double or single stranded, the strands are ready to be used as a template for the synthesis of additional nucleic acid strands. This synthesis can be performed using any suitable method. Generally, it occurs in a buffered aqueous solution. In some preferred embodiments, the buffer pH is about 8.5 to 8.9, notably different from the preferred pH ranges of Pol I enzymes. Preferably, a molar excess (for cloned nucleic acid, usually about 1000:1 primer:template, and for genomic nucleic acid, usually about $10^6$:1 primer:template) of the two oligonucleotide primers is added to the buffer containing the separated template strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

Nucleoside triphosphates, preferably dATP, dCTP, dGTP, and dTTP are also added to the synthesis mixture in adequate amounts.

The newly synthesized strand and its complementary nucleic acid strand form a double-stranded molecule which is used in the succeeding steps of the process. In the next step, the strands of the double-stranded molecule are separated using any of the procedures described above to provide single-stranded molecules.

New nucleic acid is synthesized on the single-stranded molecules. Additional polymerase, nucleotides, and primers may be added if necessary for the reaction to proceed under the conditions described above. Again, the synthesis will be initiated at one end of the oligonucleotide primers and will proceed along the single strands of the template to produce additional nucleic acids.

The steps of strand separation and extension product synthesis can be repeated as often as needed to produce the desired quantity of the specific nucleic acid sequence. The amount of the specific nucleic acid sequence produced will increase in an exponential fashion.

When it is desired to produce more than one specific nucleic acid sequence from the first nucleic acid or mixture of nucleic acids, the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process. Of course in instances where terminal sequences of different template nucleic acid sequences are the same, primer sequences will be identical to each other and complementary to the template terminal sequences.

Additionally, as mentioned above, in an alternative embodiment, random primers, preferably hexamers, are used to amplify a template nucleic acid molecule.

Additionally, one-sided amplification using a single primer may be done.

The present invention can be performed in a step-wise fashion where after each step new reagents are added, or simultaneously, wherein all reagents are added at the initial step, or partially step-wise and partially simultaneously, wherein fresh reagent is added after a given number of steps. Additional materials may be added as necessary, for example, stabilizers. After the appropriate length of time has passed to produce the desired amount of the specific nucleic acid sequence, the reaction may be halted by inactivating the enzymes in any known manner or separating the components of the reaction.

Thus, in amplifying a nucleic acid molecule according to the present invention, the nucleic acid molecule is contacted with a composition comprising a thermostable two component Pol III replicase in an appropriate amplification reaction mixture, preferably with stabilizers.

In an alternative preferred embodiment, the invention provides methods of amplifying large nucleic acid molecules, by a technique commonly referred to as "long range PCR" (Barnes, W. M., Proc. Natl. Acad. Sci. USA, 91:2216-2220 (1994) ("Barnes"); Cheng, S. et. al., Proc. Natl. Acad. Sci. USA, 91:5695-5699 (1994), which are hereby incorporated by reference). In one method, useful for amplifying nucleic acid molecules larger than about 5-6 kilobases, the composition with which the target nucleic acid molecule is contacted comprises not only a minimal functional Pol III replicase, but also comprises a low concentration of a second DNA polymerase (preferably thermostable repair type polymerase, or a polC α subunit) that exhibits 3'-5' exonuclease activity ("exo+" polymerases), at concentrations of about 0.0002-200 units per milliliter, preferably about 0.002-100 units/mL, more preferably about 0.002-20 units/mL, even more preferably about 0.002-2.0 units/mL, and most preferably at concentrations of about 0.40 units/mL. Preferred exo+polymerases for use in the present methods are *Thermotoga maritima* PolC, Pfu/DEEPVENT or Tli/NENT™ (Barnes; U.S. Pat. No. 5,436,149, which are hereby incorporated by reference); thermostable polymerases from *Thermotoga* species such as Tma Pol I (U.S. Pat. No. 5,512,462, which is hereby incorporated by reference); and certain thermostable polymerases and mutants thereof isolated from *Thermotoga neapolitana* such as Tne(3'exo+). The PolC product of *Thermus thermophilus* is also preferred. By using a two component polymerase in combination with a second polymerase in the present methods, DNA sequences of at least 35-100 kilobases in length may be amplified to high concentrations with significantly improved fidelity.

For a discussion of long range PCR, see for example, Davies et al., Methods Mol Biol. 2002; 187:51-5, expressly incorporated herein by reference.

Preferably, the amplification methods of the invention include the use of stabilizers with two-component Pol III replicases. The stabilizers are preferably included in amplification reaction mixtures and increase the thermostability of the two component Pol III replicases in these reaction mixtures.

Amplification reaction mixtures of the present invention may include up to 25% co-solvent (total for all co-solvents added to a reaction mix), up to 5% crowding agent (total for all crowding agents added to a reaction mix) and up to 2M oxide (total for all oxides added to a reaction mix).

In an especially preferred embodiment, an amplification reaction mixture for use with a minimal functional Pol III replicase derived from *Aquifex aeolicus* comprises TAPS-Tris (20 mM, pH 8.7), 25 mM $K_2SO_4$, 10 mM $NH_4(OAc)_2$, 15 µmol $ZnSO_4$, and 4 mM $MgSO_4$.

In another especially preferred embodiment, an amplification reaction mixture for use with a minimal functional Pol III replicase derived from *Thermus thermophilus* comprises HEPES-Bis-Tris-Propane (20 mM, pH7.5), 0.5 µmol $ZnCl_2$ or $Zn(OAc)_2$, and 6 mM $Mg(OAc)_2$.

In one embodiment, wherein one or more high temperature denaturation steps is done at less than 89° C., a thermocycling amplification method involves the use of a helicase in the thermocycling amplification reaction mixture, and preferably a helicase encoded by a bacterial dnaB gene. Helicases are preferably not used in thermocycling amplification methods involving one or more denaturation steps at or above 89° C.

In one embodiment, a nucleic acid replication method herein involves the use of a nucleic acid replication mixture that lacks ATP.

In one embodiment, a nucleic acid replication method herein involves the use of a nucleic acid replication mixture that lacks SSB, wherein SSB, if present in the replication reaction mixture, would inhibit the DNA polymerase activity of the particular minimal functional Pol III replicase used in the replication reaction mixture.

Nucleic Acid Sequencing

In one aspect, the invention provides methods for sequencing a nucleic acid, preferably DNA, comprising subjecting the nucleic acid to a sequencing reaction in a sequencing reaction mixture comprising a minimal functional Pol III replicase.

Preferred minimal functional Pol III replicases for use in sequencing reactions are single component Pol III replicases. Preferably the single component Pol III replicases possesses DNA polymerase activity and lacks 3'-5' exonuclease activity capable of removing 3' terminal dideoxy nucleotides in the sequencing reaction mixture.

Accordingly, single component Pol III replicases comprising a polC encoded α subunit are generally not preferred for use in sequencing reactions, owing to their high level of zinc-independent 3'-5' exonuclease activity.

In a preferred embodiment, the single component Pol III replicase comprises a dnaE α subunit, preferably of the genus *Thermus* or *Aquifex*, preferably of the species *Thermus thermophilus, Thermus aquaticus*, or *Aquifex aeolicus*.

Notably, the 3'-5' exonuclease activity of dnaE α subunits used in the invention is generally capable of removing 3' terminal dideoxy nucleotides, while the 3'-5' exonuclease activity of ε subunits is generally incapable of such terminal dideoxy nucleotide removal. Accordingly, minimal functional Pol III replicases having 3'-5' exonuclease activity which is conferred by an ε subunit in a sequencing reaction mixture are generally useful in sequencing reactions herein. Moreover, undesirable dnaE α subunit 3'-5' exonuclease activity is preferably reduced or completely inhibited through chemical means (i.e., buffer conditions, more particularly, $Zn^{2+}$ concentration and pH).

Nucleic acid molecules may be sequenced according to any of the literature-described manual or automated sequencing methods. Such methods include, but are not limited to, dideoxy sequencing methods ("Sanger sequencing"; Sanger, F., et al., J. Mol. Biol., 94:444-448 (1975); Sanger, F., et al., Proc. Natl. Acad. Sci. USA, 74:5463-5467 (1977); U.S. Pat. Nos. 4,962,022 and 5,498,523, which are hereby incorporated by reference), as well as by PCR based methods and more complex PCR-based nucleic acid fingerprinting techniques such as Random Amplified Polymorphic DNA ("RAPD") analysis (Williams, J. G. K., et al., Nucl. Acids Res., 18(22):6531-6535, (1990), which is hereby incorporated by reference), Arbitrarily Primed PCR ("AP-PCR") (Welsh, J., et al., Nucl. Acids Res., 18(24):7213-7218, (1990), which is hereby incorporated by reference), DNA Amplification Fingerprinting ("DAF") (Caetano-Anolles et al., Bio/Technology, 9:553-557, (1991), which is hereby incorporated by reference), microsatellite PCR or Directed Amplification of Minisatellite-region DNA ("DAMD") (Heath, D. D., et al., Nucl. Acids Res., 21(24): 5782-5785, (1993), which is hereby incorporated by reference), and Amplification Fragment Length Polymorphism ("AFLP") analysis (Vos, P., et al., Nucl. Acids Res., 23(21):4407-4414 (1995); Lin, J. J., et al., FOCUS, 17(2):66-70, (1995), which are hereby incorporated by reference).

Once the nucleic acid molecule to be sequenced is contacted with the minimal functional Pol III replicase in a sequencing reaction mixture, the sequencing reactions may proceed according to protocols disclosed above or others known in the art.

In an especially preferred embodiment, a sequencing reaction mixture for use with a minimal functional Pol III replicase derived from *Aquifex aeolicus* comprises TAPS-Tris (20 mM, pH8.7), 25 mM $K_2SO_4$, 10 mM $NH_4(OAc)_2$, and 10 mM $MgSO_4$. Preferably, the reaction mixture lacks zinc so as to limit the 3'-5' exonuclease activity of the α subunit.

In another especially preferred embodiment, a sequencing reaction mixture for use with a minimal functional Pol III replicase derived from *Thermus thermophilus* comprises HEPES-Bis-Tris-Propane (20 mM, pH7.5), and 10 mM $Mg(OAc)_2$. Preferably, the reaction mixture lacks zinc so as to limit the 3'-5' exonuclease activity of the α subunit.

Kits

In one aspect, the invention provides kits for nucleic acid replication utilizing a minimal Pol III disclosed herein. The kits comprise a single component Pol III, a two component Pol III, or a combination of single component and two component Pol IIIs described herein.

In a preferred embodiment, a nucleic acid amplification kit includes buffers and stabilizers, or buffers with stabilizers as described herein. Stabilizers are especially preferred in kits for thermocycling reactions using a thermostable minimal Pol III.

A nucleic acid sequencing kit according to the present invention comprises minimal Pol III and dideoxynucleotide triphosphates. The sequencing kit may further comprise additional reagents and compounds necessary for carrying out standard nucleic sequencing protocols, such as pyrophosphatase, agarose or polyacrylamide media for formulating sequencing gels, and other components necessary for detection of sequenced nucleic acids (See U.S. Pat. Nos. 4,962,020 and 5,498,523, which are directed to methods of DNA sequencing).

A nucleic acid amplification kit according to the present invention comprises a minimal Pol III and dNTPs. The amplification kit may further comprise additional reagents and compounds necessary for carrying out standard nucleic acid amplification protocols (See U.S. Pat. Nos. 4,683,195 and 4,683,202, directed to methods of DNA amplification by PCR; incorporated herein by reference).

In one embodiment, a kit lacks ATP and ATP is not used in the nucleic acid replication reaction provided for by the kit.

In additional preferred embodiments, the nucleic acid replication kits of the invention may further comprise a second DNA polymerase having 3'-5' exonuclease activity. Preferred are Pfu/DEEPVENT, TliNENT™, Tma, Tne(3'exo+), and mutants and derivatives thereof. Also preferred is the polC.

Kits of the present invention may include information pamphlets.

Minimal Pol IIIs

Minimal Pol III replicases for use in the invention are minimal "functional" replicases. These minimal functional Pol III replicases are functional subassemblies of DNA polymerase III subunits, wherein the DNA polymerase III is a genomic replicase. Functional refers to replicase activity, which can be characterized by primer extension rate. A functional minimal Pol III replicase is characterized by its ability to perform in a primer extension assay at an extension rate of greater than 75 nucleotides per second. Especially preferred minimal Pol IIIs of the invention perform at an extension rate of greater than 100, more preferably greater than 150, more preferably greater than 200, more preferably greater than 250, more preferably greater than 300, more preferably greater than 350, more preferably greater than 400, more preferably greater than 450, more preferably greater than 500, more preferably greater than 550, more preferably greater than 600, more preferably greater than 650, more preferably greater than 700 nucleotides per second. Moreover, such preferred minimal functional Pol III replicases are capable of performing at a preferred extension rate at a concentration of 2 pmol/µL or less.

As such, minimal Pol IIIs comprising the *E. coli* DNA polymerase III α subunit, which are non-functional as demonstrated in the literature and confirmed herein, are not included among the minimal Pol IIIs of the invention.

By "an *E. coli* DNA polymerase III α subunit" herein is meant the native *E. coli* DNA polymerase III α subunit. For example, see Maki et al., 1985, supra.

The minimal functional Pol III replicases used in the invention comprise at least a first component, which comprises a Pol III α subunit. In some preferred embodiments, the first component consists essentially of a Pol III α subunit. In some preferred embodiments, the first component comprises one or more additional subunits of the core polymerase complex of a Pol III. The minimal Pol IIIs of the invention lack a clamp loader.

In a preferred embodiment, the invention provides minimal Pol IIIs that are single component Pol IIIs. A single component Pol III consists essentially of a first component of a minimal Pol III. The single component Pol IIIs of the invention lack a clamp loader.

In another preferred embodiment, the invention provides minimal functional Pol III replicases that further comprise a second component, which second component comprises a processivity clamp. The two component Pol IIIs of the invention thus consist essentially of a first component and a second component, wherein the first component is a single component Pol III as disclosed herein, and the second component comprises a processivity clamp. In a preferred embodiment, the second component consist essentially of a processivity clamp. In preferred embodiments, the processivity clamp comprises a Pol III β subunit. In some preferred embodiments, the processivity clamp consists essentially of a Pol III β subunit. The two component Pol IIIs of the invention also lack a clamp loader component. In some embodiments, a two component Pol III comprises more than one first component, which may be the same or different.

Single Component Pol III

The single component Pol IIIs disclosed herein may consist of a single subunit or multiple subunits. The single component Pol IIIs consist essentially of a first component of a minimal Pol III, which first component comprises an α subunit, and lack a clamp loader. In some preferred embodiments, the first component consists essentially of an α subunit. In other preferred embodiments, the first component comprises one or more additional subunits of the core polymerase complex of a Pol III. Single component Pol IIIs of the invention thus include an α subunit and lack a γ and/or τ subunit. A variety of α subunits may be used in the single component Pol IIIs of the invention.

The thermostable minimal functional Pol III replicases of the invention are preferably derived from a thermophilic bacterium or thermophilic cyanobacterium. In a preferred embodiment, the thermophilic bacterium is selected from the group consisting of the genera *Thermus, Aquifex, Thermotoga, Thermocridis, Deinococcus, Methanobacterium, Hydrogenobacter, Geobacillus, Thermosynchecoccus* and *Thermoanaerobacter*. Especially preferred are single component and two component Pol IIIs derived from *Aquifex aeolicus, Aquifex pyogenes, Thermus thermophilus, Thermus aquaticus, Thermotoga neapolitana* and *Thermotoga maritima*.

The α subunit of a minimal functional Pol III replicase herein is encoded by a bacterial polC or dnaE gene, wherein the dnaE encoded α subunit possesses intrinsic zinc-dependent 3'-5' exonuclease activity, as disclosed herein.

In an especially preferred embodiment, the bacterial dnaE or polC encoded α subunits are derived from a bacterium or cyanobacterium selected from the group consisting of *Aquifex aeolicus, Thermus thermophilus, Deinococcus radiurans, Thermus aquaticus, Thermotoga maritima, Thermoanaerobacter, Geobacillus stearothermophilus, Thermus flavus, Thermus ruber, Thermus brockianus, Thermotoga neapolitana* and other species of the *Thermotoga* genus, *Methanobacterium thermoautotrophicum*, and species from the genera *Thermocridis, Hydrogenobacter, Thermosynchecoccus*, and mutants of these species. In one embodiment, a single component Pol III includes a θ subunit and/or an ε subunit, which subunits are preferably from the same species as the α subunit of the single component Pol III.

As used herein "thermostable" refers to a DNA polymerase which is resistant to inactivation by heat. DNA polymerases, including the minimal Pol IIIs disclosed herein, synthesize the formation of a DNA molecule complementary to a single-stranded DNA template by extending a primer in the 5' to 3' direction. As used herein, a thermostable DNA polymerase is more resistant to heat inactivation than a thermolabile DNA polymerase. However, a thermostable DNA polymerase is not necessarily totally resistant to heat inactivation, and, thus, heat treatment may reduce the DNA polymerase activity to some extent. A thermostable DNA polymerase typically will also have a higher optimum temperature for synthetic function than thermolabile DNA polymerases. Thermostable DNA polymerases are typically isolated from thermophilic organisms, for example, thermophilic bacteria.

As used herein "thermolabile" refers to a DNA polymerase which is not resistant to inactivation by heat. For example, T5 DNA polymerase, the activity of which is totally inactivated by exposing the enzyme to a temperature of 90° C. for 30 seconds, is considered to be a thermolabile DNA polymerase. As used herein, a thermolabile DNA polymerase is less resistant to heat inactivation than is a thermostable DNA polymerase. A thermolabile DNA polymerase typically is also likely to have a lower optimum temperature than a thermostable DNA polymerase. Thermolabile DNA polymerases are typically isolated from mesophilic organisms, for example, mesophilic bacteria or eukaryotes, including certain animals.

Examples of α subunits are found, for example, in U.S. Pat. No. 6,238,905, issued May 29, 2001; U.S. patent application Ser. No. 09/642,218, filed Aug. 18, 2000; U.S. patent application Ser. No. 09/716,964, filed Nov. 21, 2000; U.S. patent application Ser. No. 09/151,888, filed Sep. 11, 1998; and U.S. patent application Ser. No. 09/818,780, filed Mar. 28, 2001, each of which is expressly incorporated herein by reference.

Included among the α subunits that may be used in the present single component Pol IIIs are those characterized by the presence of the following protein motifs arranged in a polypeptide as described below.

In cyanobacteria, a minimal Pol III holoenzyme has not been isolated and characterized yet. Although, sequence alignments with the corresponding subunits from gram negative bacteria allowed for the identification (allocation) of the major Pol III subunit genes (holA, holB, dnaE, dnaX, dnaQ) in the genomes of several cyanobacteria species (*Nostoc punctiforme, Thermosynechococcus elongatus, Prochlorococcus marinus, Crocosphaera watsonii, Gloeobacter violaceus, Thrichodesmium erythraeum, Anabaena variabilis*) (Nakamura Y. et al. "Complete genome structure of Gloeobacter violaceus PCC 7421, a cyanobacterium that lacks thylakoids." DNA Res. 2003 Aug. 31;10(4):137-45; Nakamura Y. et al."Complete genome structure of the thermophilic cyanobacterium Thermosynechococcus elongatus BP-1.", DNA Res. 2002 Aug. 31;9(4):123-30; Kaneko T,"Complete genomic sequence of the filamentous nitrogen-fixing cyanobacterium *Anabaena* sp. strain PCC 7120.", DNA Res. 2001 Oct. 31;8(5):205-13; 227-53; Rocap G.,"Genome divergence in two Prochlorococcus ecotypes reflects oceanic niche differentiation.", Nature. 2003 Aug. 28;424 (6952):1042-7. Epub 2003 Aug. 13; included herein by reference). One can conclude from these findings that the organization of a minimal Pol III holoenzyme in cyanobacteria is very similar or the same as in gram negative bacteria. The Pol III alpha subunit in cyanobacteria is expressed from two separate genes as protein precursors with intein sequences. In a unique process of intermolecular protein splicing the intein intervening sequences are removed and the N-terminal and C-terminal exteins of the alpha subunit precursors are spliced together (Wu H, Hu Z, Liu X Q., "Protein trans-splicing by a split intein encoded in a split DnaE gene of *Synechocystis* sp. PCC6803.", Proc Natl Acad Sci USA. 1998 Aug. 4;95(16): 9226-31, included herein by reference). The intein-free alpha subunits of cyanobacteria have the same size as the alpha subunits of gram negative bacteria and share a sequence homology 0f 30-40% with them.

In one embodiment, an α subunit for use in a single component Pol III comprises the amino acid consensus sequence motifs "A", "B", and "C", which are, respectively, [L/V/M]-[L/V/I]-K-X-D-[F/A/I]-L-G-[L/H]-X-X-[L/P]-[T/S] (SEQ ID NO:12), [F/Y/W]-X-X-X-X-X-[F/R/K/]-X-X-Y-[A/G/M/L]-F-[N/P]-[R/K]-X-H (SEQ ID NO:13), and [P/S]-X-[P/I]-D-[L/I/V/F]-[D/N]-XP-D-[F/I]-D-X-D-[F/I/L/V] (SEQ ID NO:14), wherein X is any amino acid. The motifs are arranged, from amino terminus to carboxyl terminus, in the order C-A-B. The spacing between motif C and A ranges from about 112 to about 155 amino acids. The spacing between motif A and motif B ranges from about 167 to about 201 amino acids. The spacing from motif C to motif B ranges from about 278 to about 355 amino acids.

In a preferred embodiment, an α subunit for use in a single component Pol III comprises the amino acid consensus sequence motifs "A", "B", and "C", which are, respectively, G-[L/M]-[L/V/I]-K-X-D-F-L-G-L-X-X-L-T (SEQ ID NO:15), [F/W]-X-X-X-X-X-F-X-X-Y-[A/G]-F-N-K-S-H (SEQ ID NO:16), and S-X-P-D-[F/I]-D-X-D-[F/I] (SEQ ID NO:17), wherein X is any amino acid. The motifs are arranged, from amino terminus to carboxyl terminus, in the order C-A-B. The spacing between motif C and A ranges from about 153 to about 155 amino acids. The spacing between motif A and motif B ranges from about 195 to about 201 amino acids. The spacing from motif C to motif B ranges from about 348 to about 355 amino acids.

In another preferred embodiment, an α subunit for use in a single component Pol III comprises the amino acid consensus sequence motifs "A", "B", and "C", which are, respectively, G-[L/V]-[L/V]-K-X-D-[F/I]-L-G-L-[R/K]-X-L-[T/S] (SEQ ID NO:18), [F/Y/W]-X-X-X-X-[R/K]-F-X-X-Y-[A/G]-F-N-[R/K]-X-H (SEQ ID NO:19), and P-D-I-D-[L/I/V]-D-[F/L/V] (SEQ ID NO:20), wherein X is any amino acid. The motifs are arranged, from amino terminus to carboxyl terminus, in the order C-A-B. The spacing between motif C and A ranges from about 112 to about 150 amino acids. The spacing between motif A and motif B ranges from about 167 to about 190 amino acids. The spacing from motif C to motif B ranges from about 278 to about 339 amino acids.

In another preferred embodiment, an α subunit for use in a single component Pol III comprises the amino acid consensus sequence motifs "A", "B", and "C", which are, respectively, [L/V]-[L/V]-K-X-D-[A/I]-L-G-H-D-X-P-T (SEQ ID NO:21), [F/Y]-I-X-S-C-X-[R/K]-I-K-Y-[M/L]-F-P-K-A-H (SEQ ID NO:22), and P-D-I-D-L-D-F-S (SEQ ID NO:23), wherein X is any amino acid. The motifs are arranged, from amino terminus to carboxyl terminus, in the order C-A-B. The spacing between motif C and A is about 124 amino acids. The spacing between motif A and motif B ranges from about 173 to about 179 amino acids. The spacing from motif C to motif B ranges from about 296 to about 302 amino acids.

In addition to sequence analysis and the identification of protein motifs, standard assays for thermostable DNA polymerase activity, as well as standard assays for 3'-5' exonuclease activity may be used to identify α subunits especially well suited to particular applications herein.

In a preferred embodiment, the α subunit of a minimal functional Pol III replicase is a dnaE or polC α subunit, preferably of an extremophile bacterium taxonomically positioned at the base of the phylogentic tree eubacteria, such as the genera, but not limited to, *Aquifex, Hydrogenobacter, Thermus, Thermocrinis, Deinococcus* and *Thermotoga*.

Extremophile bacteria are bacteria that grow and propagate under extreme environmental conditions that out of the range of normal physiological conditions such as high radiation, extremely low humidity, high (above 60° C.) or low (below 10° C.) temperature and high osmotic pressure (salt concentration above 0.5 M).

Among the dnaE and polC α subunits of extremophile bacteria, dnaE and polC α subunits derived from thermophilic bacteria are especially preferred.

In a preferred embodiment, an α subunit for use in a single component Pol III is derived from *Thermus thermophilus*.

In a preferred embodiment, an α subunit for use in a single component Pol III comprises an amino acid sequence having at least about 85%, more preferably about 90%, more preferably about 95%, more preferably 99% sequence identity to the amino acid sequence shown in FIG. 9 (SEQ ID NOS:9-11), and further comprises an amino acid sequence having at least about 85%, more preferably about 90%, more preferably about 95%, more preferably 99% sequence identity to amino acids 775-805.

In another preferred embodiment, an α subunit for use in a single component Pol III consists essentially of an amino acid sequence having at least about 85%, more preferably about 90%, more preferably about 95%, more preferably 99% sequence identity to the amino acid sequence shown in FIG. 9 (SEQ ID NOS:9-11) and further comprises an amino acid sequence having at least about 85%, more preferably about 90%, more preferably about 95%, more preferably 99% sequence identity to amino acids 775-805.

In another preferred embodiment, an α subunit for use in a single component Pol III comprises the amino acid sequence shown in FIG. 9 (SEQ ID NOS:9-11), or a fragment thereof exhibiting DNA polymerase activity, which fragment includes amino acids 775-805.

In another preferred embodiment, an α subunit for use in a single component Pol III consists essentially of the amino acid sequence shown in FIG. 9 (SEQ ID NOS:9-11), or a fragment thereof exhibiting DNA polymerase activity, which fragment includes amino acids 775-805.

In another preferred embodiment, an α subunit for use in a single component Pol III comprises an amino acid sequence encoded by the nucleic acid sequence shown in FIG. 9 (SEQ ID NOS:9-11).

In another preferred embodiment, an α subunit for use in a single component Pol III consists essentially of an amino acid sequence encoded by the nucleic acid sequence shown in FIG. 9 (SEQ ID NOS:9-11).

In one embodiment, a single component Pol III of the invention includes an ε subunit encoded by a bacterial dnaQ gene, preferably of a thermophilic bacterium. Examples of preferred ε subunits are found, for example, in U.S. patent application Ser. No. 09/642,218, filed Aug. 18, 2000; U.S. patent application Ser. No. 09/716,964, filed Nov. 21, 2000; U.S. patent application Ser. No. 09/151,888, filed Sep. 11, 1998; and U.S. patent application Ser. No. 09/818,780, filed Mar. 28, 2001.

In one embodiment, an α subunit for use in a single component Pol III is obtained by the biochemical isolation method disclosed in Example 1.

Purification of T.th α

An α subunit may be genetically engineered to be expressed within a target host cell, for example within *E. coli* cells. Initially, transformed cells are grown, harvested and lysed. In some embodiments the cells are lysed using a lysozyme/spermidine solution, preferably having from about 1 to about 4 mg/ml lysozyme and from about 1.5 to about 3.0 mM final spermidine concentration. Alternatively, the cells can be ruptured using a Microfluidizer processor (Moedel M-110L).

As an initial step, the protein fraction precipitating at approximately 30 to 45% saturation of ammonium sulfate is isolated from the extract. This fraction contains the majority of the expressed α subunit. Briefly, the precipitate is formed by adjusting the cell extracts to 30 to 45% ammonium sulfate saturation, preferably to about 30% saturation with ammonium sulfate. Precipitated protein is removed, typically via centrifugation, although other conventional means can be used. The pelleted protein is re-suspended in a re-suspension buffer having a pH of from about 7.0 to about 8.0, preferably about 7.5. In preferred embodiments the re-suspension buffer includes approximately 10 to 30% glycerol, preferably about 25% glycerol. In some embodiments, the re-suspension buffer is Tris based and includes a chelator like EDTA. Approximately 25 to 30% ammonium sulfate is included in the buffer to maximize the α subunit's hydrophobic characteristics on butyl-sepharose. Other separation materials can be used.

Resuspended protein is passed over the butyl-sepharose column, the flow-through being discarded. Elution of the column contents is performed using a 30 to 0% ammonium sulfate gradient. The α subunit elutes at higher levels of ammonium sulfate, along with other hydrophobic proteins. Fractions are tested for α subunit via either size based assays (gel electrophoresis and the like) or functional activity (extension assays). In some assays, the α subunit is precipitated with 50% ammonium sulfate. The precipitated α containing material is resuspended as above and fractions having α subunit run through a sephacrile 300 sizing column. In preferred embodiments, from 0.15 M to 1M KCl is added to the sephacrile separating buffer. In some embodiments, a dialysis or adjustment is made on the α-containing fractions to optimize the conductivity of the buffer for a blue-sepharose column.

Preferably, isolated α subunit is further purified by loading the α subunit on a blue-sepharose or other like material affinity column. Elution of the column contents is performed using a KCL or NaCl gradient. Alpha subunit generally elutes at about 0.25-0.6 M KCl, which is determined through either sized or functional based assays.

Purified α subunit is typically stored in a high glycerol containing buffer, for example in a 5 to 20 mM Tris, 0.5 to 1.5 mM DTT, 0.3 to 0.6 mM EDTA and 40 to 50% glycerol buffer. In some cases, the high salt buffer that the α is eluted in is replaced with the storage buffer using dialysis or other like method. Alpha subunit can be concentrated or diluted as needed, and stored at −20° C.

In an alternative method, the re-suspended 30-45% ammonium sulfate fraction is heated to 70° C. for approximately 30 minutes prior to addition to the butyl-sepharose column. The heating step provides for an improvement on α subunit purity over the previously described embodiment. Activity data from this heat induced protein suggest that two fractions of α are isolated, a first less hydrophobic fraction having excellent gap filling activity (DNA polymerase activity) and a second more hydrophobic fraction having activity similar in nature to the non-heated purified α subunit. As such, the heat treatment may facilitate the purification of a higher activity α subunit.

Note that τ subunit can be purified using a combination of 35% ammonium sulfate precipitation, heating to 65° C. for thirty minutes and separation on Sp-sepharose.

For those single component Pol IIIs consisting of more than one subunit, the subunits may be coincubated and allowed to form a single component Pol III in solution. The coincubation solution may be a reaction mixture, or, preferably, the components may be associated prior to addition to reaction mixture.

Two Component Pol III DNA Polymerases

The two component Pol III replicases disclosed herein consist essentially of a first component and a second component, wherein the first component is a single component Pol III replicase as disclosed herein, and the second component comprises a processivity clamp. In a preferred embodiment, the second component consists essentially of a processivity clamp. In preferred embodiments, the processivity clamp comprises a Pol III β subunit. In some preferred embodiments, the processivity clamp consists essentially of a Pol III β subunit. The two component Pol III replicases of the invention also lack a clamp loader component. In some embodiments, a two component Pol III comprises more than one first component, which may be the same or different.

Two component Pol III replicases used herein are characterized by their ability to perform in a primer extension assay (i.e., replication assay) at a rate of greater than 100, more preferably greater than 150, more preferably greater than 200, more preferably greater than 250, more preferably greater than 300, more preferably greater than 350, more preferably greater than 400, more preferably greater than 450, more preferably greater than 500, more preferably greater than 550, more preferably greater than 600, more preferably greater than 650, more preferably greater than 700 nucleotides per second.

Further, the two component Pol III replicases are used in reaction mixtures such that the DNA polymerase III α subunit concentration is preferably not less than 6 ng/μL, more preferably not less than 7 ng/μL, more preferably not less than 8 ng/μL, more preferably not less than 9 ng/μL, more preferably not less than 10 ng/μL, more preferably not less than 20 ng/μL, more preferably not less than 50 ng/μL, more preferably not less than 100 ng/μL, more preferably not less than 150 ng/μL, more preferably not less than 200 ng/μL.

In a preferred embodiment, the α subunit of the first component of a two component Pol III replicase and the processivity clamp of the two component Pol III replicase are derived from the same species.

In addition to motifs "A", "B", and "C", described above, which may be used to identify an α subunit useful herein, a motif that is typically located toward the middle of Pol III α subunits and which is involved in β subunit binding by the α subunit may be used to identify α subunits that are especially preferred for use in a two component Pol III replicase of the present invention. Further, this region of a Pol III α subunit may be modified to create a motif in a Pol III α that renders it very well suited for use in a two component Pol III replicase herein. The modification preferably increases the strength of the interaction between a first component and a second component of a two component Pol III replicase herein.

In a preferred embodiment, the two component Pol III replicase is derived from thermophilic bacteria, and consists of a first core component that comprises an α subunit and optionally an ε subunit, and a second component that comprises a β subunit, wherein the two component polymerase lacks a γ subunit and/or a β subunit.

Examples of β subunits are found, for example, in U.S. patent application Ser. No. 09/642,218, filed Aug. 18, 2000; U.S. patent application Ser. No. 09/716,964, filed Nov. 21, 2000; U.S. patent application Ser. No. 09/151,888, filed Sep. 11, 1998; and U.S. patent application Ser. No. 09/818,780, filed Mar. 28, 2001, each expressly incorporated herein in its entirety by reference.

In one embodiment, an α subunit for use in a two component Pol III is obtained by the biochemical isolation method described above for a single component Pol III.

The first and second components of the two component Pol IIIs of the invention may be coincubated and allowed to form a two component Pol III in solution. The coincubation solution may be a reaction mixture, or, preferably, the components may be associated prior to addition to reaction mixture. In one embodiment, more than one first component is coincubated with a second component to provide a two component Pol III, wherein only two different components are present in the Pol III, and the Pol III lacks a clamp loader (i.e., third component).

Novel α Subunits, Fragments Thereof, and Polynucleotides

In one aspect, the invention provides novel T. th derived DNA polymerase III α subunits and novel fragments thereof. The α subunits of the invention include polypeptides having at least about 85%, more preferably about 90%, more preferably about 95%, more preferably 99% sequence identity to the amino acid sequence shown in FIG. 9 (SEQ ID NOS:9-11) and further comprises an amino acid sequence having at least about 85%, more preferably about 90%, more preferably about 95%, more preferably 99% sequence identity to amino acids 775-805. Also included among the α subunits of the invention are polypeptides comprising the amino acid sequence shown in FIG. 9 (SEQ ID NOS:9-11), or a fragment thereof exhibiting DNA polymerase activity, which fragment includes amino acids 775-805. Also included among the α subunits of the invention are polypeptides consisting essentially of the amino acid sequence shown in FIG. 9 (SEQ ID NOS:9-11), or a fragment thereof exhibiting DNA polymerase activity, which fragment includes amino acids 775-

805. Also included among the α subunits of the invention are polypeptides comprising an amino acid sequence encoded by the nucleic acid sequence shown in FIG. 9 (SEQ ID NOS:9-11), or a fragment thereof including amino acids 775-805 which encodes a polypeptide having DNA polymerase activity. Also included among the α subunits of the invention are polypeptides comprising an amino acid sequence encoded by a α encoding polynucleotide of the invention.

The invention also provides polynucleotide molecules encoding the α subunits of the subject invention. Polynucleotide molecules of the invention include those molecules comprising a nucleic acid sequence as shown in FIG. 9 (SEQ ID NOS:9-11); those that hybridize to the nucleic acid sequence of FIG. 9 under high stringency hybridization conditions and comprise nucleotides 2430-2519; those having at least about 85%, more preferably about 90%, more preferably about 95%, more preferably 99% sequence identity to the nucleic acid sequence shown in FIG. 9 (SEQ ID NOS:9-11) and further comprising nucleotides 2430-2519; and those that encode the amino acid sequences of the novel Pol III α subunits of the invention.

In one embodiment, the invention provides novel nucleic acid probes useful for detecting the presence of T.th in a host through hybridization to nucleic acid derived from the host, wherein the probe comprises or consists essentially of nucleotides 2430-2519 in FIG. 9 (SEQ ID NOS:9-11). It will be appreciated that because nucleotides 2430-2519 encode a portion of the catalytic domain of T.th α subunit, the probes provided herein are particularly desirable as they are capable of detecting the presence of a functioning bacterial Pol III.

The invention includes certain variants and derivatives of the a polypeptide, including soluble forms and fusion proteins. For example, the fusion proteins of the invention include a polypeptide fused to a heterologous protein or peptide that confers a desired function. The heterologous protein or peptide can facilitate, for example, purification, stability, or secretion of the α subunit. The invention also provides vectors, plasmids, expression systems, host cells, and the like, comprising the a polynucleotide molecules of the invention. Genetic engineering methods for the production of a polypeptides of the invention include expression of polynucleotide molecules in cell free expression systems, in cellular hosts, and in tissues.

As demonstrated herein, a novel fragment of thirty (30) contiguous amino acids has been located within the reported polypeptide sequence, located between amino acid positions 775 and 805 of the T. th derived molecule (see FIG. 9) (SEQ ID NOS:9-11).

The α subunit polynucleotide molecule of the invention can be cDNA, chemically synthesized DNA, DNA amplified by PCR, RNA, or combinations thereof. Due to the degeneracy of the genetic code, two DNA sequences may differ and yet encode identical amino acid sequences.

In addition, the polypeptide sequences of the present invention include a polypeptide fragment having the 30 contiguous amino acid residues shown in FIG. 9, from amino acid residue 775 to residue 804 (SEQ ID NOS:9-11).

The percentage identity, also termed homology, can be readily determined, for example by comparing the two polypeptide sequences using any of the computer programs commonly employed for this purpose, such as the Vector NCI, version 9.0 program (Invitrogen, Carlsbad, Calif.).

Modifications of the α subunit can be accomplished by any of a number of known techniques. For example, mutations may be introduced at particular locations by oligonucleotide-directed mutagenesis (Walder et al., 1986, Gene, 42:133; Bauer et al., 1985, Gene, 37:73).

The α subunits of the present invention are preferably provided in an isolated form, and preferably are substantially purified. The polypeptides are recovered and purified from recombinant cell cultures, preferably as described herein.

The novel 30 amino acid fragment described above, residue number 775 to 805 (see FIG. 9) (SEQ ID NOS:9-11), can be used for example, to generate specific anti-α antibodies.

Vectors and Host Cells

The present invention provides vectors containing the polynucleotide molecules of the invention, as well as host cells transformed with such vectors. Any of the polynucleotide molecules of the invention can be contained in a vector, which generally includes a selectable marker and an origin of replication. The vectors further include suitable transcriptional or translational regulatory sequences, such as those derived from microbial or viral molecules. Examples of such regulatory sequences include transcriptional promoters, operators, or enhancers, mRNA ribosomal binding sites, and appropriate sequences. A promoter nucleotide sequence is operably linked to a DNA pol III a DNA sequence if the promoter nucleotide sequence directs the transcription of the α subunit.

Selection of suitable vectors for the cloning of α subunit molecules encoding the target a polypeptides of the invention will depend upon the host cell in which the vector will be transformed, and, where applicable, the host cell from which the target polypeptide is to be expressed. Suitable host cells have been discussed above, but include prokaryotes, yeast, and other like organisms. Specific examples include bacteria of the genera *Escherichia, Bacillus* and *Salmonella*, as well as members of the genera *Pseudomonas, Streptomyces*, and *Staphylococcus*; yeast from the genera Sacchoromyces, *Pichia*, and *Kluveromyces*.

The DNA pol III alpha subunit polypeptides of the present invention to be expressed in such host cells may also be fusion proteins that include regions from heterologous proteins. As discussed throughout, such regions may be included to allow for example, enhanced purification, increased secretion, and increased stability. For example, a nucleic acid sequence encoding a signal peptide (secretory leader) may be fused in-frame to the α subunit sequence so that a is translated as a fusion protein comprising the signal peptide.

As noted above, the novel polynucleotide molecules of the invention may be contained in a vector, which generally includes a selectable marker and an origin of replication, for propagation in a host. The vectors further include suitable transcriptional or translational regulatory sequences, such as those derived from a mammalian, microbial, viral or insect gene, operably linked to the DNA pol III a polynucleotide molecule. Nucleotide sequences are operably linked when the regulatory sequence functionally relates to the DNA encoding the target protein. Thus, a promoter nucleotide sequence is operably linked to a DNA sequence if the promoter nucleotide sequence.

Modification of a DNA pol III alpha polynucleotide molecule of the invention to facilitate insertion into a particular vector, ease of use in a particular expression system or host (for example, by modifying restriction sites), and the like, are known and are contemplated for use in the invention. Genetic engineering methods for the production of a polypeptides include the expression of the polynucleotide molecules in cell free expression systems, in cellular systems, in host cells, in tissues, and in animal models, according to known methods.

Antibodies

The novel polypeptides of the present invention, in whole or in part, may be used to raise polyclonal and monoclonal antibodies that are useful in diagnostic assays for detecting DNA pol III alpha polypeptide expression as well as a reagent tool for characterizing the molecular actions of the alpha subunit. Preferably, a peptide containing the unique epitope of the alpha subunit (30 aa sequence discussed above, see FIG. 9) is used in preparation of anti-alpha antibodies. Methods for the design and production of antibodies are known in the art, see for example, Antibodies: A Laboratory Manual, Harlow and Land (eds.), 1988 Cold Spring Harbor Laboratory Press, Cold Spring Harbor, N.Y.; Monoclonal Antibodies, Hybridomas: A New Dimension in Biological Analysis, Kennet et al (eds), 1980 Plenum Press, New York.

Provisional application Ser. No. 60/560,793, titled "DNA Polymerase III α Subunit", and filed 7 Apr. 2004, is expressly incorporated herein in its entirety by reference. Provisional application Ser. No. 60/641,183, titled "Two-Component DNA Polymerases and Uses Thereof", and filed 3 Jan. 2005, is expressly incorporated herein in its entirety by reference.

Citations herein are expressly incorporated herein in their entirety by reference.

EXPERIMENTAL

EXAMPLE 1

Figure 6:
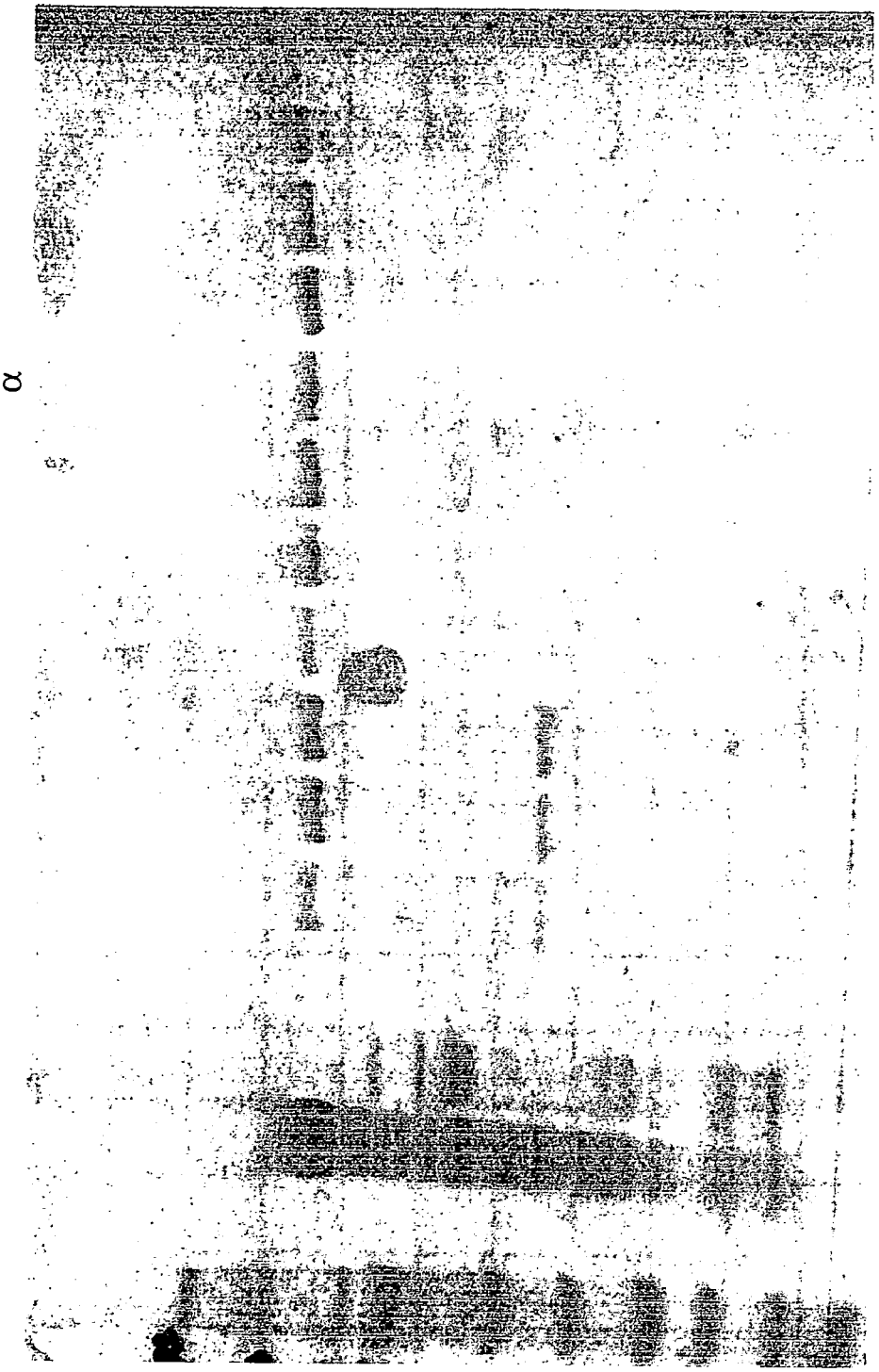
FIG. 6 shows the *Thermus thermophilus* alpha subunit after butyl-sepharose on blue-HP.
Figure 7:
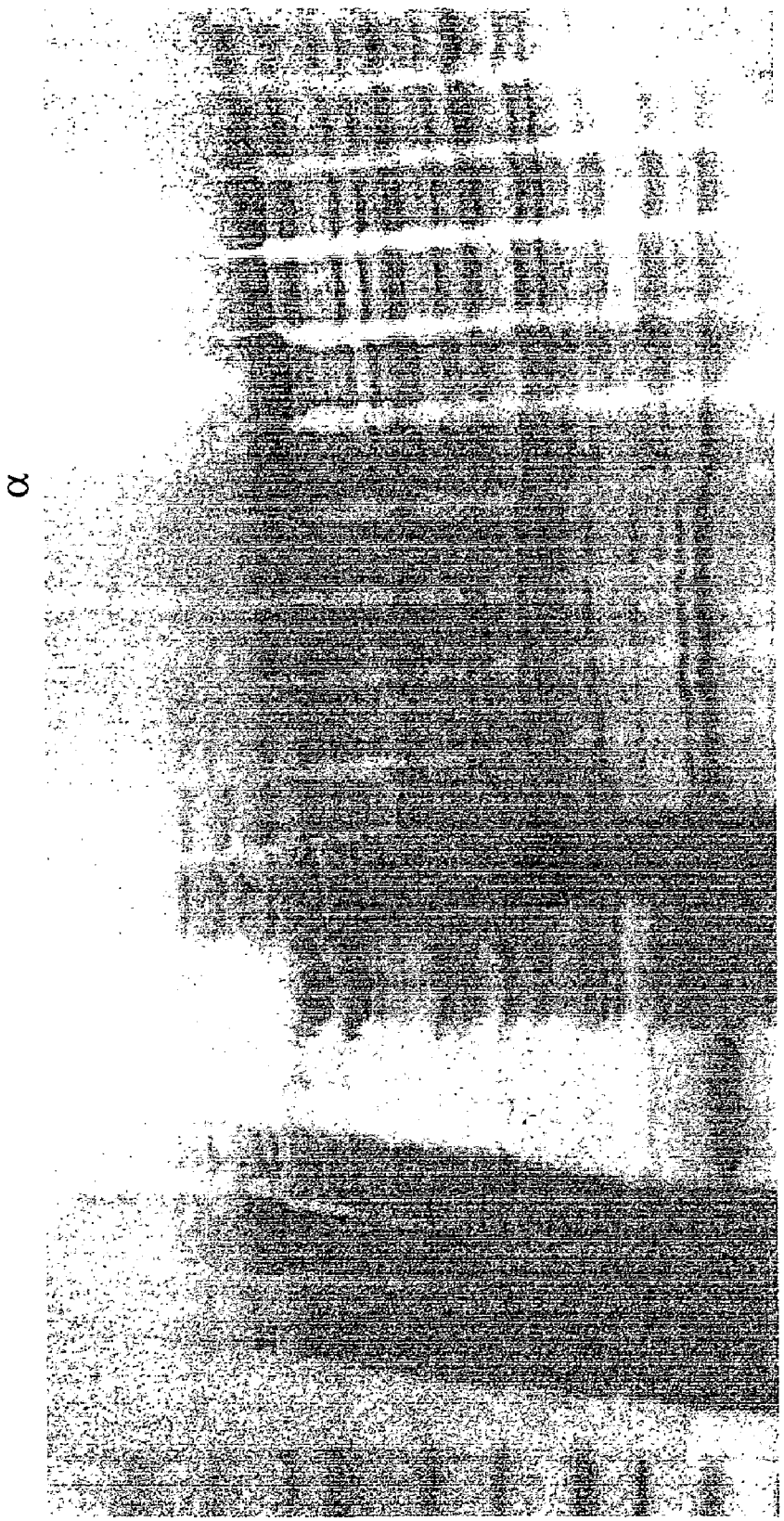
FIG. 7 shows the *Thermus thermophilus* alpha subunit on butyl-sepharose.

DNA Pol III Alpha & Beta Subunit Purification (FIGS. 5, 6, and 7): Fermentation, expression and purification of the DNA Pol III subunits were performed according to standard procedures familiar to anyone skilled in the fart of DNA polymerase expression and purification.

All DNA pol III subunits in the present invention were cloned into conventional pET-series expression vector plasmids (Novagen) and expressed in different complementary E. coli host strains (BL21, BL21 pLysS, Rosetta, RosettaGami, Origami) from Novagen. The expression from a T7 RNA polymerase promoter on the vector was induced with IPTG at 37° C. Only in the case of Aae DnaE the expression induction was carried out 15° C.

After expression induction for 2 to 8 hours the cells were harvested by centrifugation at 5000 g. The total protein fraction was extracted from the cell biomass in an appropriate Lysis buffer using a Microfluidizer.

All chromatographic purification steps were performed at room temperature (22-27° C.). Lysis and extraction, nucleic acid precipitation and dialysis were carried out at 4° C. or on ice.

Depending on the heat stability of different Pol III subunits, the crude cell extracts were heated between 55 to 80° C. for 20-30 min to precipitate the majority of heat-labile host proteins. The precipitated host proteins were separated from the heat-stable soluble protein fraction by centrifugation at 20,000 g (30 minutes) at 4° C.

The total nucleic acid fraction was removed from the heat-treated protein fraction by precipitation with polyethyleneimine (PEI) at various concentrations (0.025-0.1%). The precipitated total nucleic acids were separated from the protein fraction by centrifugation at 20,000 g (30 minutes) at 4° C.

The order of the heat-treatment and PEI precipitation steps were switched from case to case as indicated below.

The concentration of ammonium sulfate in the post-PEI supernatant was adjusted to the concentration below the point of precipitation of the corresponding subunit in order to load it onto the hydrophobic resin column.

All alpha-subunits were purified using hydrophobic columns (Butyl-Sepharose) and two consecutive affinity columns (Blue-Sepharose and Heparin-Sepharose, respectively). An additional gel filtration chromatography step was used as needed (see below). Between subsequent chromatographic steps the pooled fractions containing the subunit were dialyzed into storage buffer.

All beta-subunits were purified using a hydrophobic column (Butyl-Sepharose) in the first step followed by an anion-exchange column (Q-Sepharose). A dialysis step was used in between the columns to transfer the pooled fraction into the beta subunit storage buffer into storage buffer.

For the anion exchange chromatography on Q-Sepharose a 20 mM Tris-HCl, (pH 8.5) was used, containing 1 mM DTT, 0.5 mM EDTA to load proteins onto the column. The elution of the protein was carried out in the same basic buffer with a KCl concentration gradient from 0.025 (buffer A) to 1 M (buffer B). The Beta subunits eluted at 40-50% saturation of buffer B.

As a storage buffer for Pol III beta subunits was used: 25 mM Tris-HCl (pH 8.0) containing 0.1 mM EDTA, 1 mM DTT, 25-50 mM KCl and 50% Glycerol.

For the HIC chromatography on Butyl-Sepharose a 50 mM Tris-HCl buffer (pH 7.5) was used containing 1 mM EDTA, 1 mM DTT (or 0.1 mM TCEP instead) with 10-25% glycerol and various concentrations of ammonium sulfate to promote tight binding of the Pol III subunits onto the resin. The same buffer without ammonium sulfate was used to elute the proteins from the column.

For the affinity chromatography on Blue- or Heparin-Sepharose a 20 mM Tris-HCl (pH 7.5) buffer was used, containing 25 mM KCl, 1 mM DTT, 0.5 mM EDTA (buffer A) to load proteins onto the affinity resin. The proteins were eluted from the affinity columns using a KCl concentration gradient ranging from 0.025M (buffer A) to 1M (buffer B).

The final pooled subunit fractions were concentrated by dialysis from an aqueous storage buffer without glycerol into a storage buffer containing 50% glycerol. All purified Pol III subunits were stored at −20° C.

*Thermotoga maritima* PoIC
1. The crude cell extract was heated for 20 min at 60° C.
2. The total nucleic acid fraction was precipitated from the post heat-treatment supernatant with PEI at the final concentration of 0.025%.
3. The ammonium sulfate concentration in the post-PEI supernatant was adjusted to 20% saturation prior to loading onto the butyl-Sepharose column.
4. Two chromatographic steps were used for purification, the butyl- and heparin-Sepharose chromatography.
5. The alpha-containing fraction after elution from butyl-Sepharose were pooled and then dialyzed against the heparin buffer A (50 mM Tris-HCl, pH 8.0, 1 mM DTT, 0.1 mM EDTA and 50 mM KCl). Tma PoIC eluted at 78.7% saturation of buffer B with 1M KCl.
6. The storage buffer is: 10 mM Tris-HCl, pH 8.0, 0.25 mM EDTA, 0.5 mM DTT, 25 mM KCl, 50% Glycerol

| Biomass | DnaE Yield | Expression Yield |
|---|---|---|
| 24.4 g | 2.5 mg | 0.1 mg/g cells |

*Thermotoga maritima* DnaN
1. Nucleic acids in the crude extract were precipitated at a PEI concentration of 0.05%.
2. The post-PEI supernatant was heated for 20 min at 60° C.
3. All buffers contained 10% glycerol
4. The ammonium sulfate concentration in the supernatant after heat-precipitation of the host proteins was adjusted to 20% saturation prior to loading onto the Butyl-Sepharose column.

5. The beta-subunit eluted from Butyl-Sepharose at 52% buffer B.
6. The beta-subunit eluted from Q-Sepharose at 54% of elution buffer B.

The beta subunit storage buffer for Tma DnaN was adjusted to 25 mM KCl.

| Biomass | DnaE Yield | Expression Yield |
|---------|------------|------------------|
| 37 g    | 77.8 mg    | 2.1 mg/g cells   |

*Thermus thermophilus* DnaE
1. The cell extract was heated for 20 min at 55° C. and PEI was added to the final concentration of 0.075%.
2. An ammonium sulfate cut from 30% to 45% saturation was carried out with the post-PEI supernatant to eliminate contaminants prior to subsequent purification steps.
3. The 45% ammonium sulfate pellet was dissolved in the butyl-Sepharose loading buffer and the ammonium sulfate concentration was adjusted to 30% prior to loading the supernatant onto the butyl-Sepharose column.
4. After the elution from butyl Sepharose the alpha-containing fractions were precipitated at 50% ammonium sulfate. The resulting pellet was dissolved in 20 mM Tris-HCl buffer, pH 7.4, 0.5 mM EDTA, 0.1 mM TCEP and 0.15 M KCl and loaded onto a Sephacryl-300 gel filtration column.
5. The alpha-containing fractions the gel filtration column were pooled and then applied onto a blue-Sepharose column in 20 mM Tris-HCl buffer, pH 7.4, containing 0.5 mM EDTA, 0.1 mM TCEP and 10% glycerol. Tth DnaE eluted at 55% saturation of buffer B with 1M KCl.
6. Storage buffer is: 10 mM Tris-HCl, pH 7.4, 0.25 mM EDTA, 0.05 mM TCEP and 50% glycerol

| Biomass | DnaE Yield | Expression Yield |
|---------|------------|------------------|
| 65.8 g  | 8.4 mg     | 0.13 mg/g cells  |

*Thermus thermophilus* DnaN
1. Nucleic acids in the crude extract were precipitated at a PEI concentration of 0.2% PEI.
2. The post-PEI precipitation supernatant was heated for 20 min at 75° C. to precipitate heat-labile host proteins.
3. The ammonium sulfate concentration in the supernatant after heat-precipitation of host proteins was adjusted to 30% saturation prior to loading onto the Butyl-Sepharose column.
4. The beta subunit eluted from Butyl-Sepharose at 97.6% of buffer B.
5. The beta subunit eluted from Q-Sepharose at 28.5% of the Q-Sepharose elution buffer B.

The beta subunit storage buffer for Tth DnaN was adjusted to 50 mM KCl.

| Biomass | DnaE Yield | Expression Yield |
|---------|------------|------------------|
| 18.5 g  | 371.2 mg   | 20.1 mg/g cells  |

*Aquifex aeolicus* DnaE
1. The total nucleic acid fraction in the crude extract was removed from the crude extract prior to heat treatment by PEI precipitation at a final concentration of 0.05%.
2. The post-PEI supernatant was heated for 20 min at 60° C. to eliminate the *E. coli* host proteins.
3. The ammonium sulfate concentration in the supernatant after precipitating the heat-denatured host proteins was adjusted to 20% saturation prior to loading it onto the butyl-Sepharose column in 50 mM Tris-HCl buffer, pH 7.5 with 1 mM DTT, 1 mM EDTA, 10% Glycerol and 10 µM $ZnSO_4$. DnaE was eluted in the same buffer without ammonium sulfate.
4. The alpha-containing fractions were pooled and dialyzed against Blue-Sepharose buffer A (50 mM Tris-HCl buffer, pH 7.5 containing 0.5 mM EDTA, 1 mM DTT, 50 mM KCl), then applied onto the column. The Aae DnaE eluted at 41.6% saturation with buffer B containing 1M KCl.
5. Storage buffer is: 25 mM Tris-HCl, pH 7.5, containing 0.25 mM EDTA, 0.5 mM DTT, 25 mM KCl, 10 µM $ZnSO_4$ and 50% Glycerol

| Biomass | DnaE Yield | Expression Yield |
|---------|------------|------------------|
| 9 g     | 27.8 mg    | 3.08 mg/g cells  |

*Aquifex aeolicus* DnaN
1. The crude cell extract was heated for 20 min at 80° C.
2. The total nucleic acid fraction was removed from the heat treatment supernatant by precipitation with 0.05% PEI.
3. The ammonium sulfate concentration in the post-PEI supernatant was adjusted to 25% to load onto the Butyl-Sepharose-column
4. The beta-subunit was eluted from Butyl-Sepharose at 75% buffer B
5. The beta-subunit was eluted from Q-Sepharose at 64% buffer B.

The storage buffer contains 25 mM KCl.

| Biomass | DnaE Yield | Expression Yield |
|---------|------------|------------------|
| 6.15 g  | 20.5 mg    | 3.33 mg/g cells  |

EXAMPLE 2

Combinations of Stabilizing Agents Facilitate Enzyme Stability For Pol III Based Cycling Reactions Cycling reactions were performed to determine the effect different combinations of stabilizing agents have on the thermostability of holoenzyme for nucleic acid extension. Base PCR buffer was combined with one or more stabilizing agent(s) and tested for its protective effect on holoenzyme thermal stability. Extension rates were compared to positive control holoenzyme conditions at 60° C. and normalized against each of the tested temperatures (87° C.-95° C.). Percent of activity is shown for each combination (see Table 3). Each cycle (five total) included 85° C. for twenty seconds, 60° C. for two minutes and 70° C. for two minutes. At the end of the five cycles, template was added to the reaction and an extension assay performed. New synthesis was detected by cpm incorporation, which in turn provided an indication of the polymerases activity and the effect that the heat cycling had on the polymerase.

Data shown in Table 3 indicates that combinations of two or more stabilizing agents provide a significant stabilizing effect on pol III driven extension when the enzyme is heated to higher temperatures. Note that not all tested combinations provide support for enzyme stability at these higher temperatures, for example, glycerol combined with sorbitol clearly facilitated subsequent extension assays whereas a combination of glycerol and pyrrolidinone did not.

TABLE 3

Cycling Assays to Determine Stabilizing Agent Activity

|  | 87° C. | 88° C. | 89° C. | 90° C. | 91° C. | 92° C. | 93° C. | 94° C. | 95° C. |
|---|---|---|---|---|---|---|---|---|---|
| Co-Solvents |  |  |  |  |  |  |  |  |  |
| 15% Glycerol/1 mM ATP/5 mM MgOAc | 25% |  |  |  |  |  |  |  |  |
| 15% Glycerol/1.5 mM ATP/10 mM MgOAc | 100% | 70% | 70% | 40% | 20% |  |  |  |  |
| 15% Glycerol/15% Sorbitol |  |  |  | 35% | 55% | 45% | 50% | 19% | 13% |
| 15% Glycerol/25% Sorbitol |  |  |  |  |  |  |  | 26% |  |
| 15% Glycerol/7.5% Mannitol |  |  |  |  | 55% | 60% | 25% | 12% |  |
| 15% Glycerol/15% Maltitol |  |  |  |  | 90% | 65% | 30% | 14% |  |
| 15% Glycerol/1-methyl-pyrrolidinone |  |  |  |  | >2% |  |  |  |  |
| 15% Glycerol/1-methylindole |  |  |  |  | >4% |  |  |  |  |
| 15% Glycerol/2-pyrrolidinone |  |  |  |  | >2% |  |  |  |  |
| 15% Glycerol/0.25 M Acetamide |  |  |  |  | 19% |  |  |  |  |
| 1 M Trimethylamine N-Oxide |  |  | 90% | 100% | 96% | 83% | 49% | 37% | 13% |
| 1 M Tertiary Butane |  |  | <5% |  |  |  |  |  |  |
| 1 M Trimethyl ammonium chloride |  |  | <5% |  |  |  |  |  |  |
| 15% Sorbitol |  |  |  |  | 54% |  |  |  |  |
| 25% Sorbitol |  |  |  |  | 36% |  |  |  |  |
| 15% Maltitol |  |  |  |  | 61% |  |  |  |  |
| 25% Maltitol |  |  |  |  | 64% |  |  |  |  |
| Betaines |  |  |  |  |  |  |  |  |  |
| NDSB 195 |  |  |  | 15% |  |  |  |  |  |
| NDSB 201 |  |  |  | 5% |  |  |  |  |  |
| NDSB 256 |  |  |  | 5% |  |  |  |  |  |
| 3-1-Pyridino-1-Propan-Sulfonate |  |  |  |  |  |  |  |  |  |
| 4-Methyl-morpholin-4-oxid |  |  |  |  |  |  |  |  |  |
| Betaine monohydrate |  |  |  |  | 30% |  |  |  |  |
| Betaine hydrochloride |  |  |  |  | 5% |  |  |  |  |
| New Betaine (1 M) |  |  |  |  | 43% |  |  |  |  |
| Crowding Agents |  |  |  |  |  |  |  |  |  |
| CM Cellulose (0.16%) |  |  |  |  | 19% |  |  |  |  |
| PEG 4000 |  |  |  |  | 50% |  |  |  |  |
| PEG 8000 |  |  |  |  | 57% |  |  |  |  |
| PEG 20000 |  |  |  |  | 62% |  |  |  |  |
| PVP |  |  |  | >5% |  |  |  |  |  |
| Sugars |  |  |  |  |  |  |  |  |  |
| 720 mM Trehalose/15% Glycerol |  |  |  |  | 50% |  |  |  |  |
| 680 mM Sucrose/15% Glycerol |  |  |  |  | 60% | 40% | 25% |  |  |
| 680 mM Sucrose |  |  |  | 100% |  |  |  |  |  |
| 7.2 mM β-Cyclodextrin/15% Glycerol |  |  |  |  | 10% |  |  |  |  |
| 8.4 mM α-Cyclodextrin/15% Glycerol |  |  |  |  | 10% |  |  |  |  |
| 8% Glucose/15% Glycerol |  |  |  |  | 40% | 20% | 13% |  |  |
| 8% D-Mannose/15% Glycerol |  |  |  |  | 22% |  |  |  |  |
| 8% D-Fructose/15% Glycerol |  |  |  |  | 34% |  |  |  |  |
| 8% D-Galactose/15% Glycerol |  |  |  |  | 24% |  |  |  |  |

EXAMPLE 3

Combinations of Stabilizing Agents Facilitate Enzyme Stability For Aae Pol III Based PCR (FIGS. 26, 27, 28, and 29): Temperature dependent amplification reactions were performed to determine the effect different combinations of stabilizing agents had on pol III directed nucleic acid synthesis. In all cases, the pol III was derived from *Aquifex aeolicus* (A. ae). Reaction assays included approximately 0.2 μg β subunit and 0.352 μg α subunit. Surprisingly, A ae directed PCR did not require additional subunits, and proceeded in the presence of just the alpha and beta subunits. Buffer conditions supported a pH of about 8.8.

Figure 22:
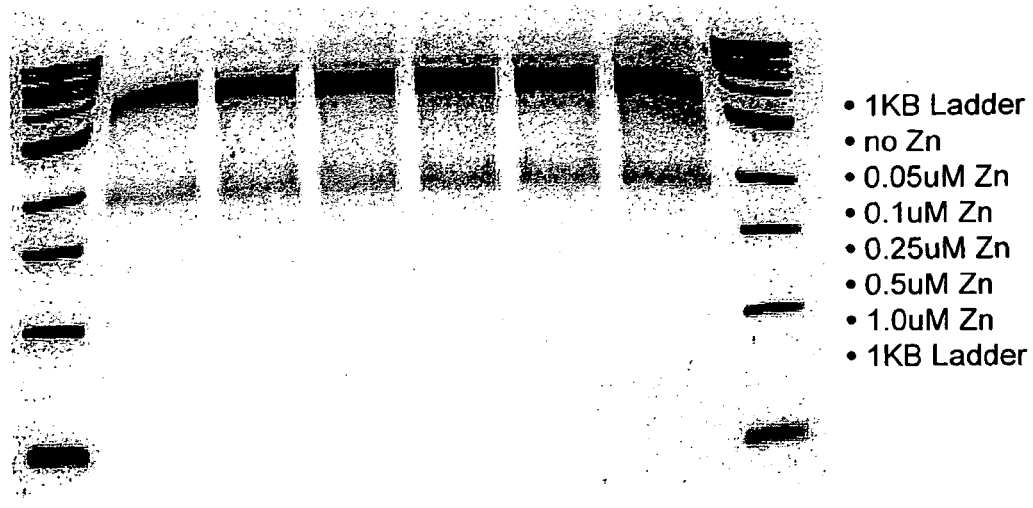
FIG. 22 shows *aquifex aeolicus* Pol III holoenzyme PCR, zinc titration, pBSK plasmid, +DNA.

Data in FIG. 22 was performed in a reaction mix that contained 0.2 mM dNTPs, 0.3 μM plasmid primer (sense and anti-sense), 1 ng/μl template plasmid, 40 mM TAPS-Tris, 0.04 mg/ml BSA, 50 mM KCl, 4 mM Mg(OAc)$_2$, and 9 μM ZnSO$_4$. Stabilizing agents were then added to each reaction and PCR performed over a course of 30 cycles at 93° C. As can be seen from the data in FIG. 26, combinations of 10% glycerol, 1.1M TMNO and 10% Sorbitol provided a vast improvement in PCR results as compared to reactions conducted in the absence of additives. Note also that combinations of 10% glycerol, 1.1M TMNO and 15% Maltitol also provided improved results, although 10% Sorbitol appears to have worked better. In addition, a pH of 8.7-8.9 supported the reactions in a superior fashion, as compared to the same reactions conducted at a pH of 8.5.

Figure 26A:
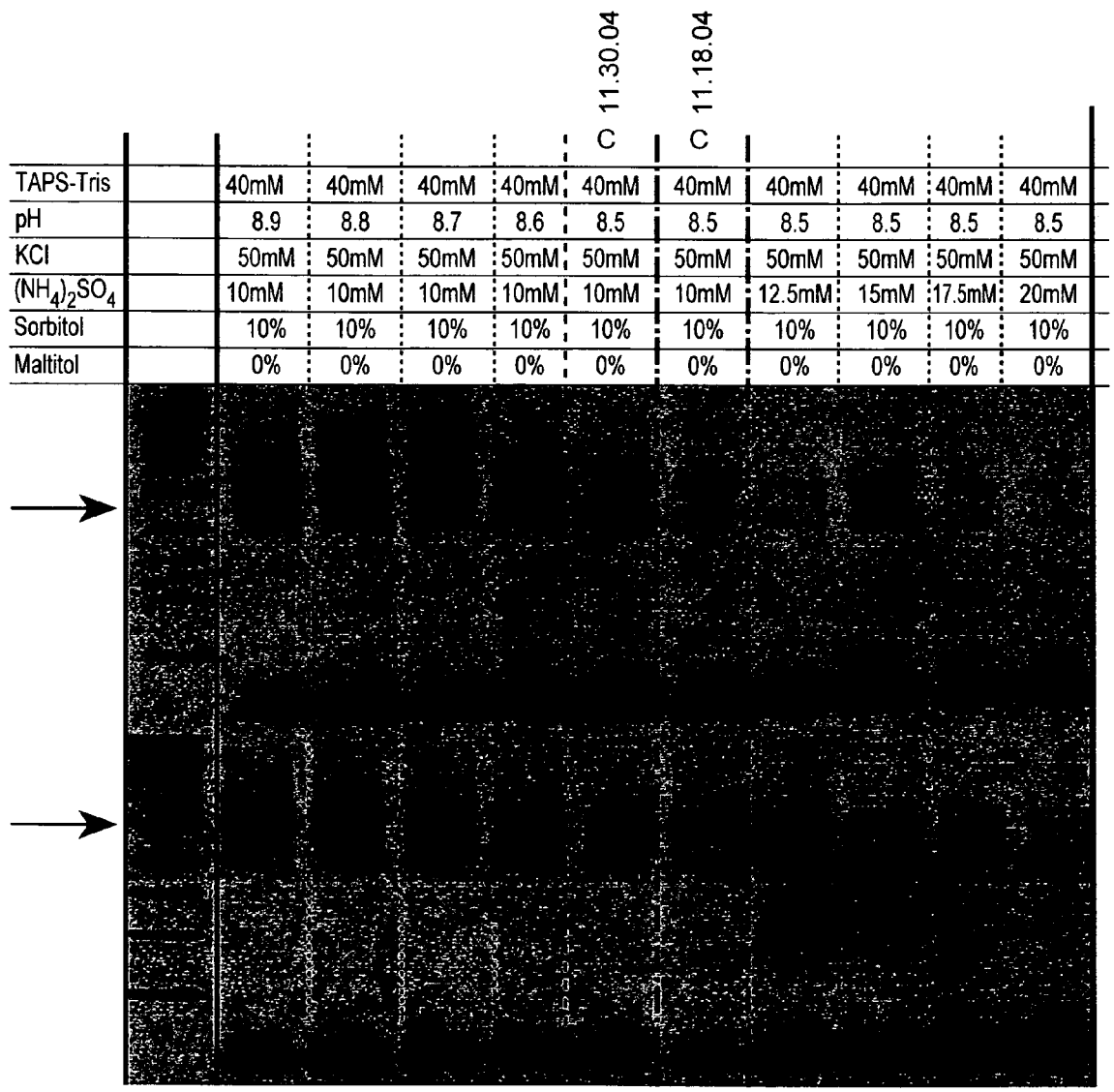
FIG. 26 shows *Aquifex aeolicus* alpha/beta PCR (no dnaB) at 93° C. Optimal pH 8.8; optimal (NH$_4$)$_2$SO$_4$ 10 mM; KCL is necessary and cannot be replaced by (NH$_4$)$_2$SO$_4$; 15% maltitol is not as effective as 10% sorbitol.
Figure 26B:
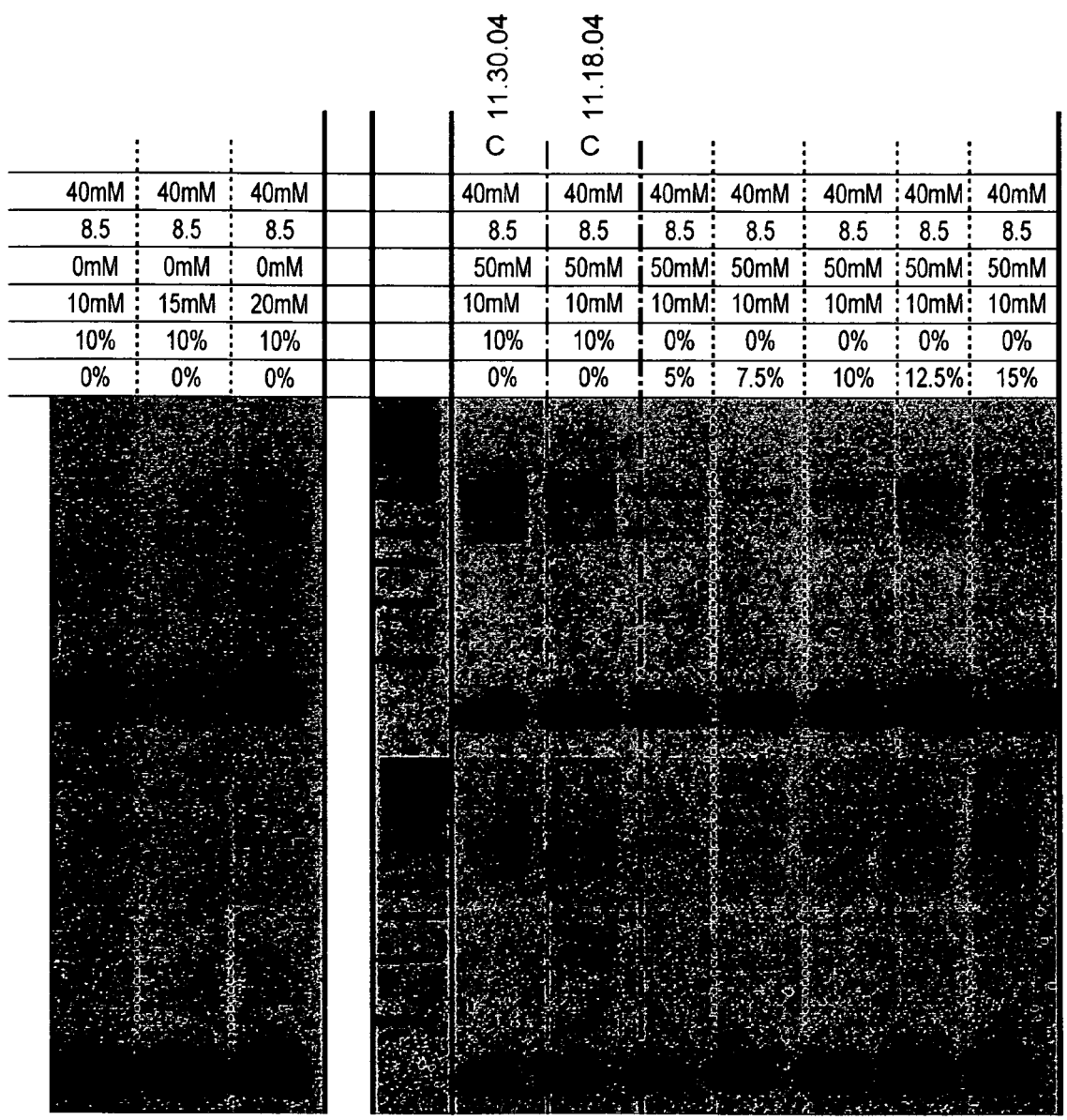

Data from this Figure shows that combinations of three stabilizing agents in temperature dependent amplification reactions provided significant improvement over reactions without additives. In addition, results showed that inclusion of 10 mM (NH$_4$)$_2$SO$_4$ also facilitated A ae driven reactions. In addition, data in FIG. 26, showed that KCl was necessary for A ae driven activity.

Figure 25:
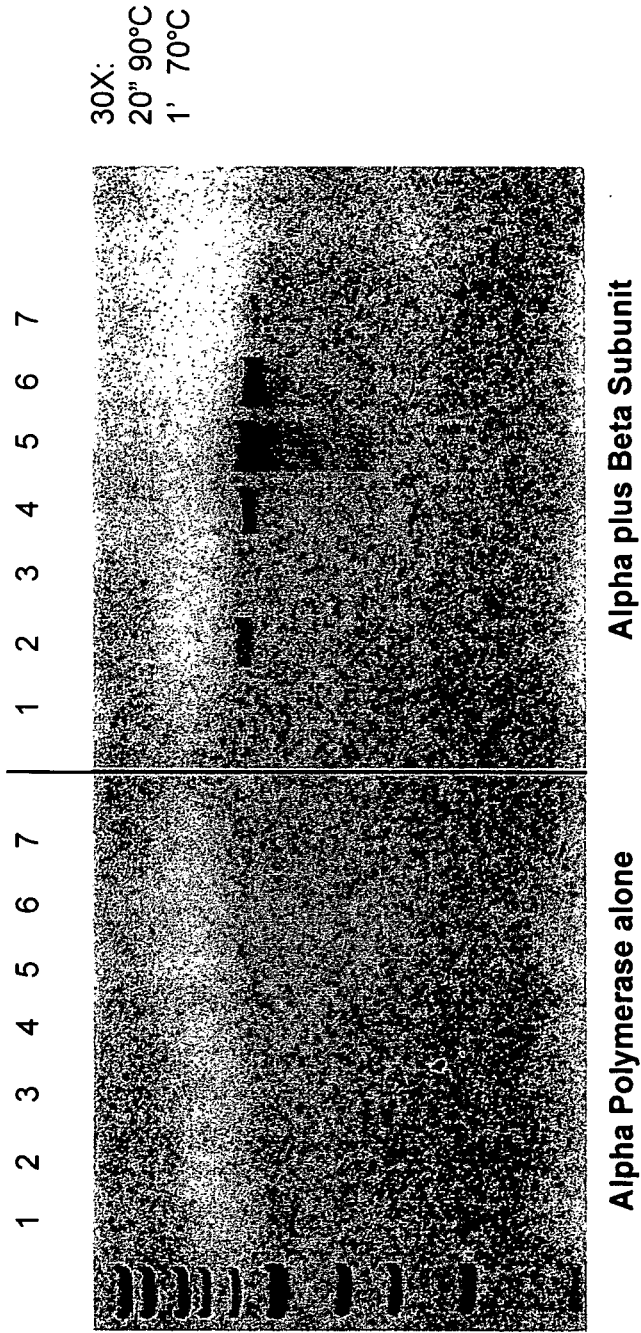
FIG. 25 shows PCR amplification of pSBK (3 kb) plasmid with *Aquifex aeolicus* Pol III alpha and alpha/beta.
Figure 29:
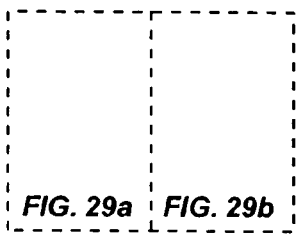
FIG. 29 shows *Aquifex aeolicus* alpha/beta PCR (no dnaB) at 93° C.
Figure 29A:
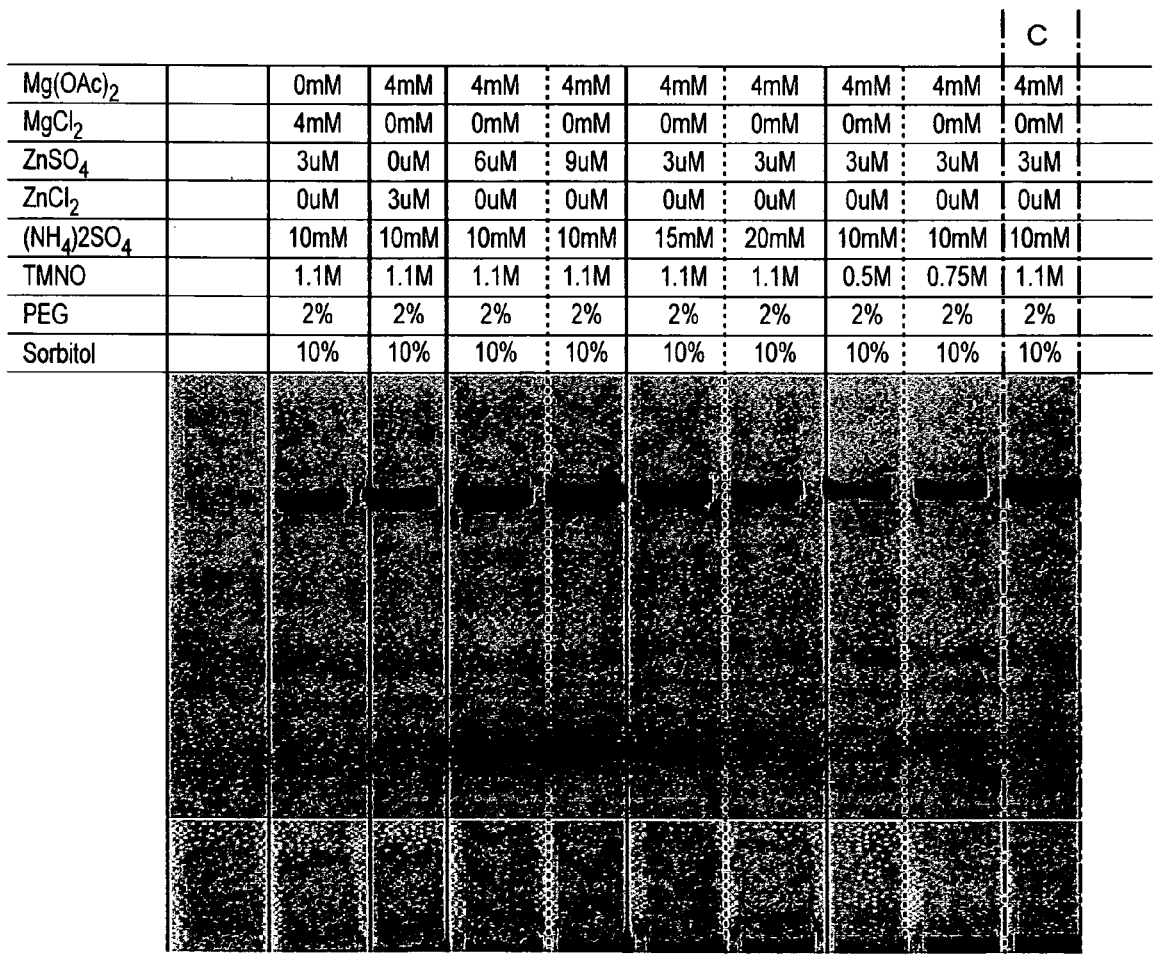
Figure 29B:
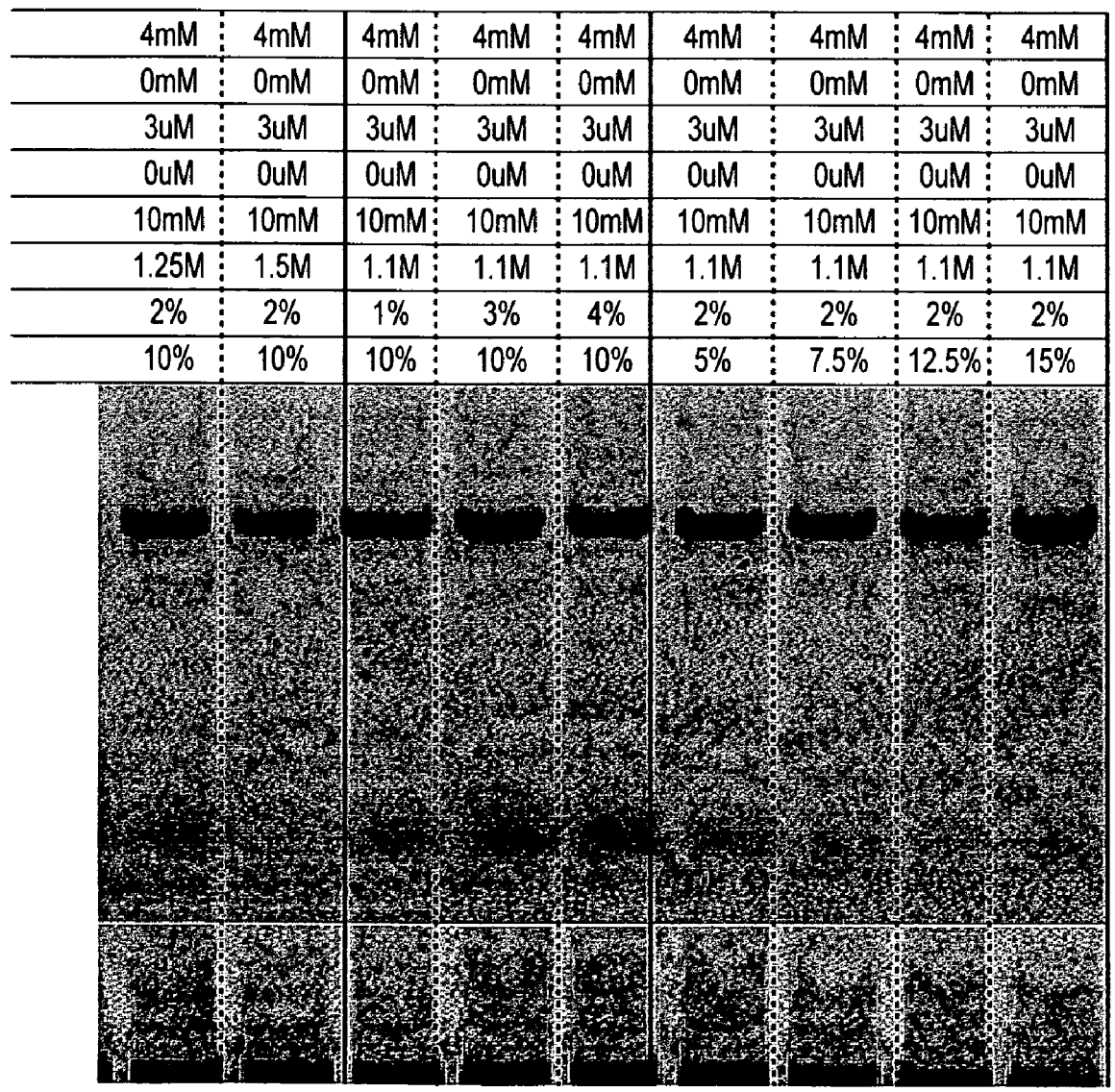

FIG. 29 shows data for amplification reactions that include 15% glycerol in relation to including from 0.5-1.25M TMNO, 1-4% PEG and 5-15% Sorbitol. Maximum effects were obtained when 15% glycerol, 2% PEG, 10% sorbitol and 1.1M TMNO were combined. Other buffer conditions were as described for FIG. 26. Data in FIG. 25 illustrates that a combination of 4 stabilizing agents provided significant support for PCR performed at 93° C. over 30 cycles. As in FIG. 26, data in FIG. 29 shows that A ae based PCR can be performed under conditions that allow for excellent amplicon production.

Figure 27:
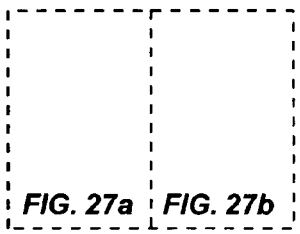
FIG. 27 shows *Aquifex aeolicus* alpha/beta PCR (no dnaB) at 93° C.
Figure 27A:
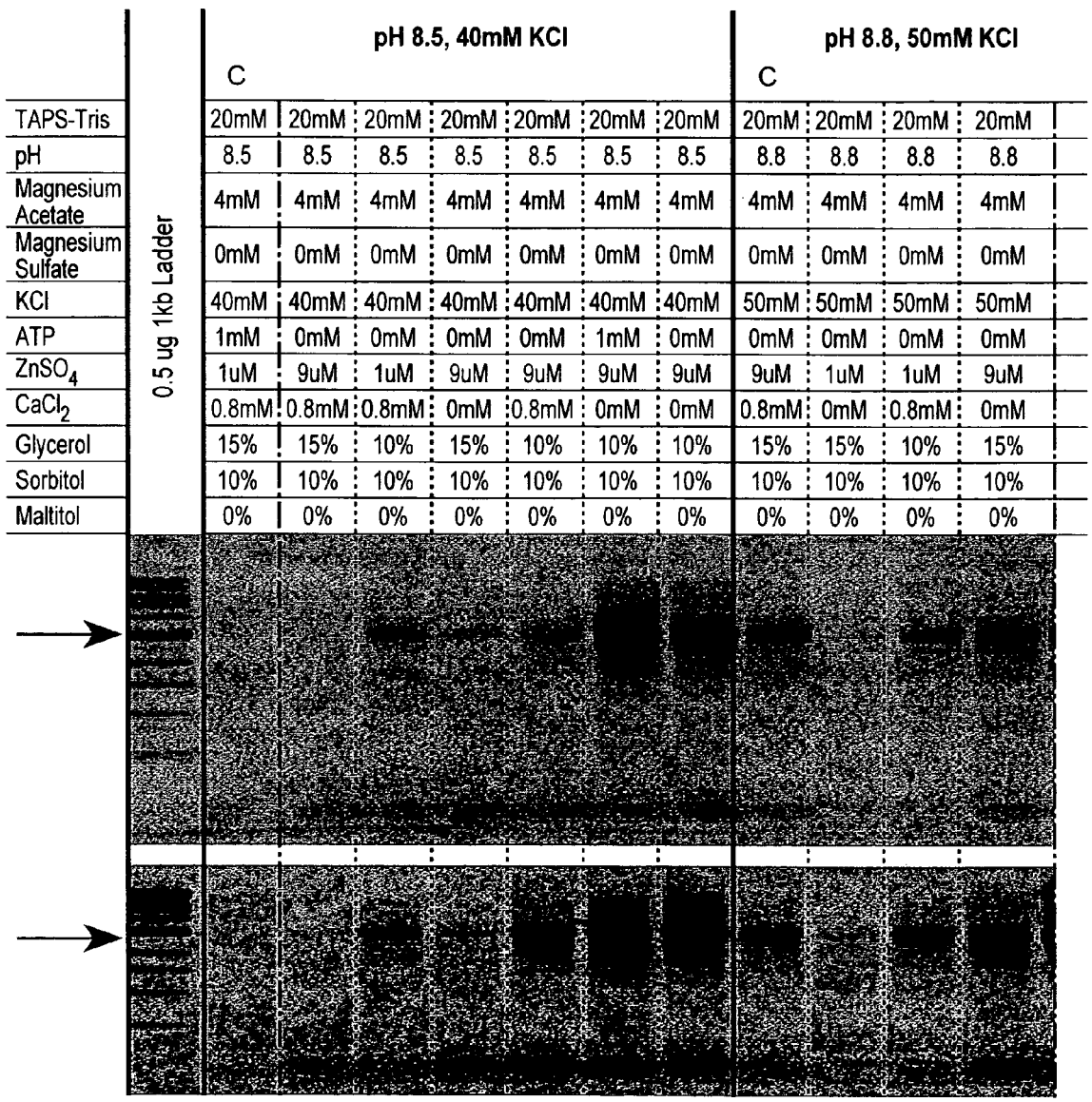
Figure 27B:
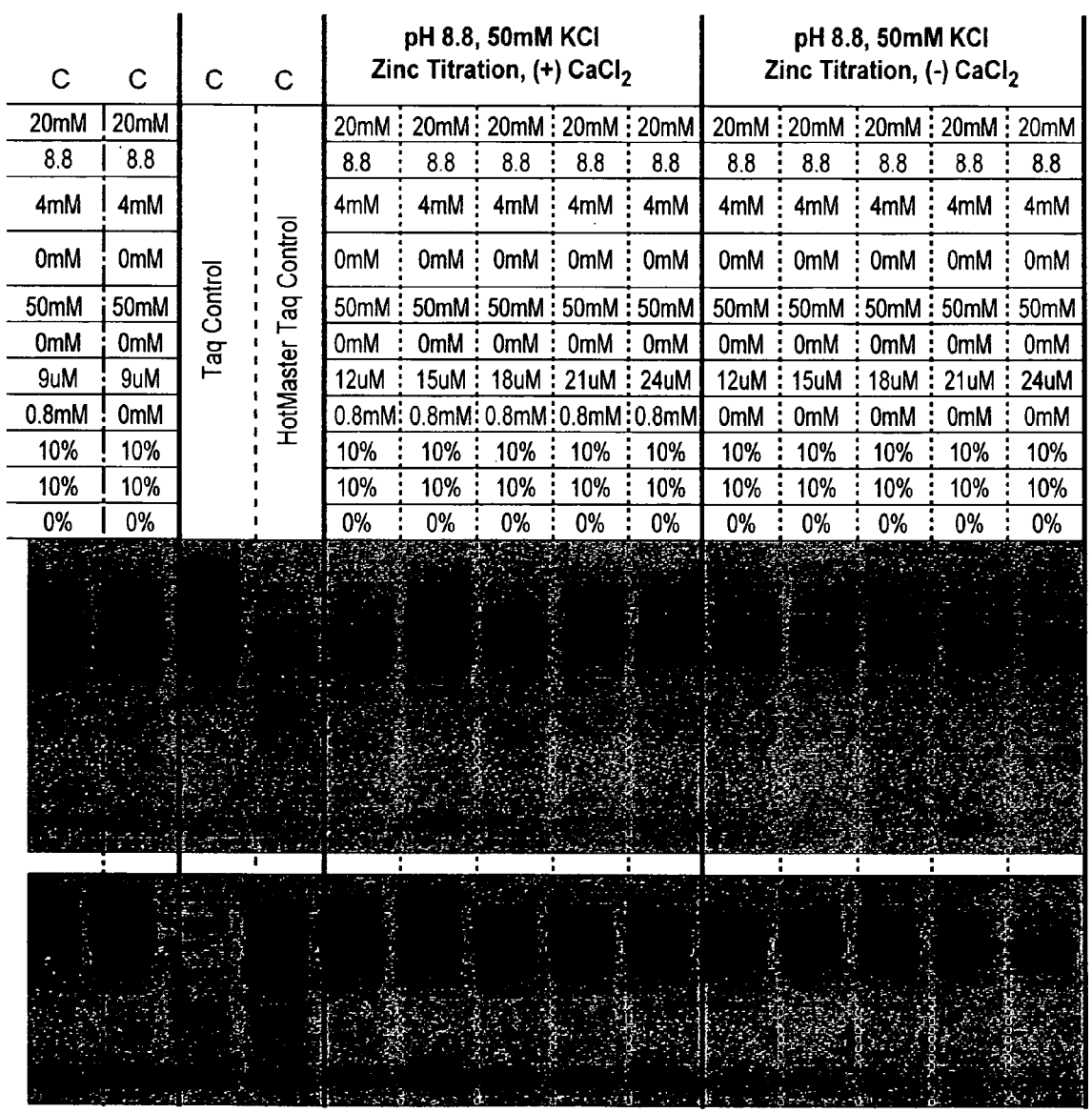
Figure 28:
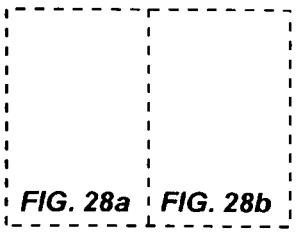
FIG. 28 shows *Aquifex aeolicus* alpha/beta PCR (no dnaB) at 93° C.
Figure 28A:
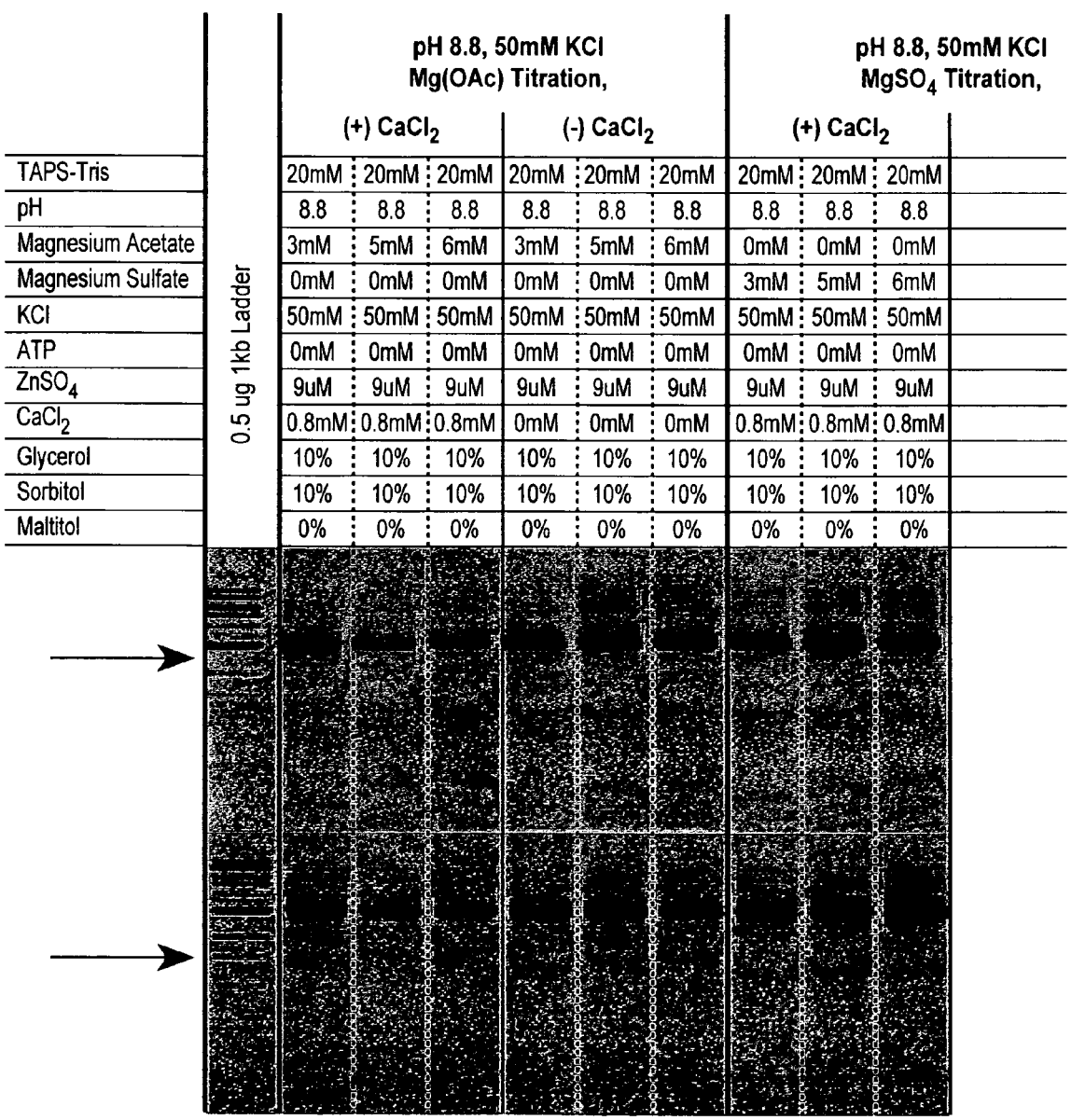
Figure 28B:
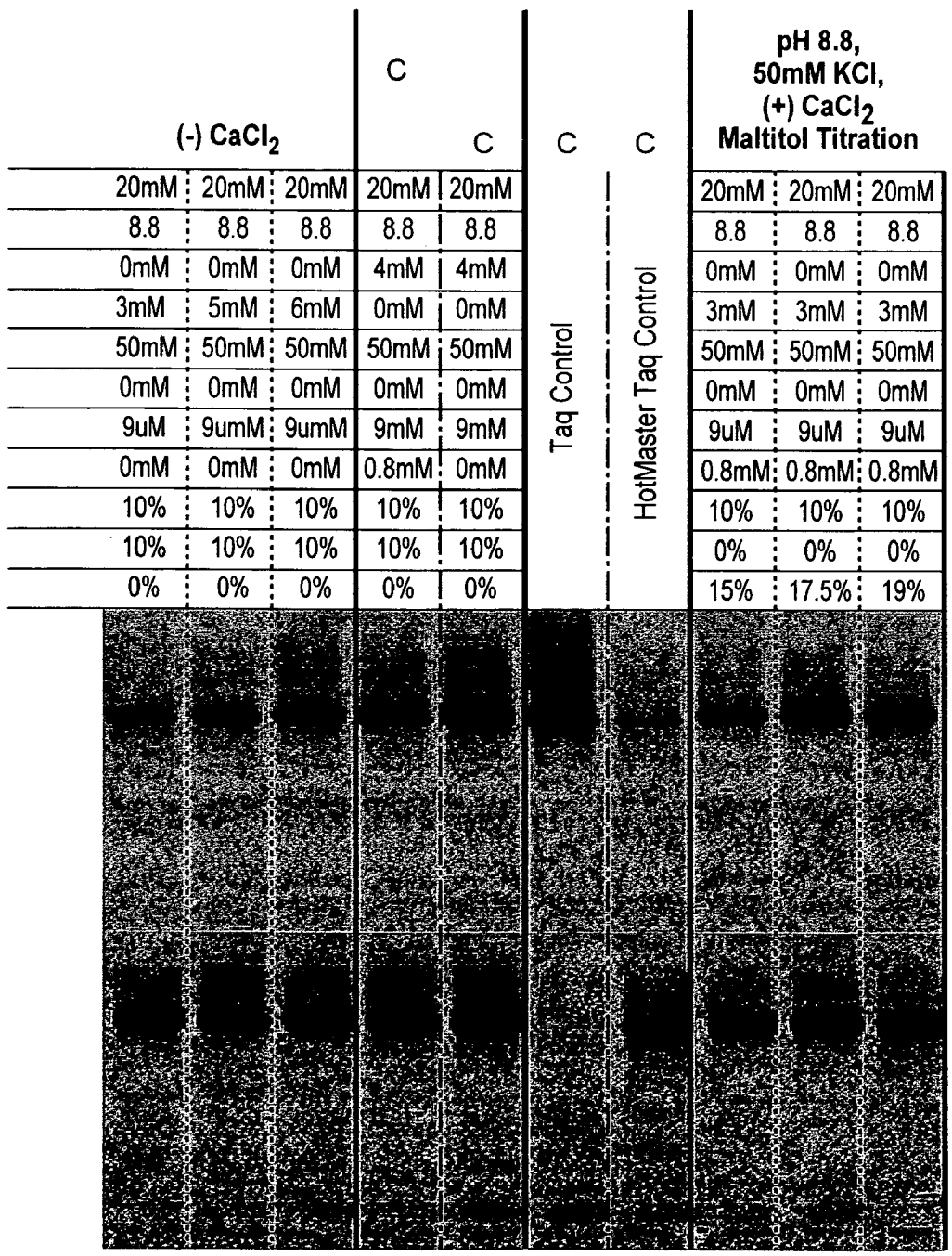

FIGS. 28 and 27 show data from PCR conditions using A ae subunits (as above) in the presence of various combinations of one or more polyols. All reactions contained 1.1M TMNO and 2% PEG (20K). Excellent results were obtained when PCR was performed with 10% glycerol and 10% sorbitol. Note also that adverse effects were seen when the level of glycerol approached 15%.

The data in FIGS. 26-29 show that combinations of one or more polyols in combination with other stabilizing agents facilitate PCR under conditions of 93° C. using A ae based pol III. In addition, the data shows that different combinations support PCR to different levels, and that different concentrations of stabilizing agent have different effects on facilitating pol III based PCR.

EXAMPLE 3

α Subunit DNA Polymerase Activity and Exonuclease Activity

The minimal DNA Polymerase III holoenzyme from *Thermus Thermophilus* (Tth) utilizes six essential subunits. We have shown that in addition to its ability to function within the holoenzyme, the Tth Pol III α-subunit is a powerful polymerase by itself, which distinguishes it from Pol III α-subunits of *E. coli* and other gram negative bacteria. Its intrinsic extension rate is fast enough to replicate a primed 7.2 kb M13 ssDNA template in 30 seconds. In addition, the Tth α-subunit possesses its own 3'→5' exonuclease activity. We have demonstrated that the α subunit interacts with a putative Pol III E-subunit at 60° C. This interaction stimulates the 3'→5' exonuclease activity 5 fold and also enhances the thermal stability of both subunits. As demonstrated by ICP-MS data, the Tth α-subunit contains 1 atom of zinc per molecule of α, although the α-subunit lacks a zinc finger domain (data not shown).

EXAMPLE 5

Sequencing of Isolated Tth α

The present Example illustrates nucleotide sequencing of α subunit, as purified using the methodology described herein. A series of 6 primers were prepared for use in sequencing:

Ptac Forward Sequencing Primer (24 MER)

5'-d(GAGCGGATAACAATTTCACACAGG)-3' (SEQ ID NO: 24)

601-621 pTAC-CCA-TE

5'-ctcaacgagtacctctccat-3' (SEQ ID NO: 25)

1201-1221 pTAC-CCA-TE

5'-atgaagagcctcccccctt-3' (SEQ ID NO: 26)

1801-1821 pTAC-CCA-TE

5'-gagggcctgaaccgccacgc-3' (SEQ ID NO: 27)

2401-2421 pTAC-CCA-TE

5'-aggcgggccatggggaagaa-3' (SEQ ID NO: 28)

3001-3021 pTAC-CCA-TE

5'-gagactcgggagaaggcccg-3' (SEQ ID NO: 29)

3601-3621 pTAC-CCA-TE

5'-gtccagggcgccttcggcga-3' (SEQ ID NO: 30)

Reactions were set-up for sequencing using 0.25 reactions (2 μl Big-Dye) including 2 μl Big-Dye v3.1 (ABI), 1 to 2 μl (400 to 600 ng) plasmid DNA (purified using Perfect Prep Plasmid Mini), 2 μl 1 pmol/μl primer, 1 μl 5× Sequencing Buffer (ABI), bringing to a final reaction volume of 10 μl. Cycling and preparation was performed using an ABI25Cyc on MJ Thermalcycler, cleaned by isopropanol precipitation (15 μl 1900×g for 30 minutes) and resuspended in 10 μl 1/10 TE. Cycle was repeated 25 times. Samples were sequenced using the ABI 3700. Samples were scored using Phred, and compared to the sequences of the clone in the Vector NTI database. Note that 12 replicates of each primer on 96 well plate were utilized.

Sequencing data was extracted using ABI software inherent on the sequencer (ABI data collection) and data evaluated by PHRED score using CodonCode InterPhace software. In addition, electropherograms were evaluated by ABI Sequencing Analysis 3.6 software (data not shown).

Informax Vector NTI version 9 ContigExpress software was used to generate contig data. Data was evaluated and trimmed to remove ambiguous data points. Resultant sequence was saved and evaluated against the previously reported sequence data within the database. Nucleotide and amino acid residue numbering are used in correspondence to the NTI software parameters. (FIGS. 8 and 9) (SEQ ID NOS: 1-11).

Sequence comparison and corresponding electropherogram of nucleotide sequence between 2407 and 2459 from T th α sequence as reported in U.S. Pat. No. 6,238,905 and from T th α of the present invention which sequence was obtained using the methods as described in the present Example shows the location of a G nucleotide at 2431 not reported in any published or reported sequencing data for T th α subunit (data not shown).

Sequence comparison and corresponding electropherogram of nucleotide sequence between 2497 and 2525 from T th α sequence as reported in U.S. Pat. No. 6,238,905 and from T th α sequence as obtained using the methods as described in the present Example.—shows the location of a G nucleotide at 2520 reported in the published sequencing data for T th α subunit, but not found in the sequence as determined using the methods of the present invention (data not shown).

The predicted amino acid sequence of a as determined from the sequenced plasmid of the invention is shown in FIG. 9. A thirty amino acid difference exists between amino acid number 776 and 806 as compared to previously reported alpha subunit polypeptide sequence. The stretch of 30 amino acids corresponding to an inserted G nucleotide at nucleotide number 2431 not reported in U.S. Pat. No. 6,238,905 and a missing nucleotide or blank where a G nucleotide is present at position 2521 in U.S. Pat. No. 6,238,905. The a amino acid sequence for the present invention includes the following amino acid sequence starting at amino acid number 775-EEMQKHRERFVQGAKERGVPEEEANRLFDM-805 (SEQ ID NO:31).

EXAMPLE 6

Figure 10:
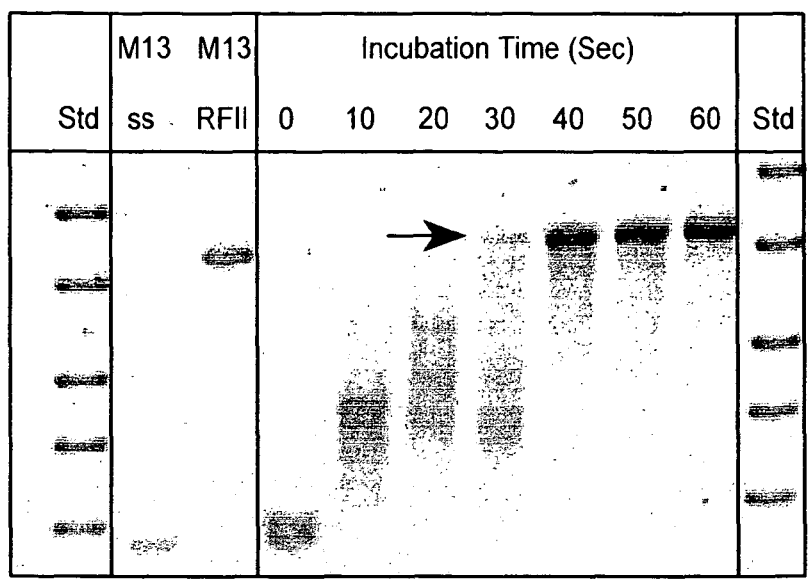
FIG. 10 shows the native T.th DNA Pol III alpha subunit. Maximum extension rate 240 b/sec.

Primer Extension by T.th α Subunit and Tth DNA Pol III Holoenzyme (FIG. 10) *Thermus thermophilus* ("T.th") α subunit was used in a time course primer extension assay to compare its extension rate as a stand alone polymerase to that of the minimal T.th DNA Pol III holoenzyme. In 19.6 μl reaction mixes 350 ng (0.15 pmol) of ssM13 mp18 DNA primed with 0.375 pmol of a 30-mer oligodeoxynucleotide primer were incubated at 60° C. for 2 minutes in the presence of 2 μg (15 pmol) of T.th α subunit in 20 mM TAPS-Tris (pH 7.5), 8 mM Mg(OAc)$_2$, 14% glycerol, 40 μg/ml BSA and 40 mM Sorbitol. The primer extension/replication was started by adding 0.4 μl of a dNTP mix containing 10 mM dATP, 10 mM dGTP, 10 mM dTTP, and 10 mM dCTP to the final concentration of 200 μmol each. The indicated time points of the primer extension assay were taken stopping individual reactions by addition of 2 μl 0.1M EDTA and transferring them on ice. The replication products were analyzed by electrophoretic separation in a 0.7% TEAE-buffered agarose gel with subsequent ethidium bromide staining. The arrow marks the first time point at which the full-size (7.2 kb) double-stranded replication product was detectable. The α-subunit alone is capable of replicating a DNA-primed 7.2 kb M13 template with a maximum extension rate of 240 b/sec. That is about 6-8× faster then the extension rate of Taq DNA polymerase I (30-40-b/sec) under equivalent conditions. The extension rate of the minimal holoenzyme with clamp loader and processivity clamp is about 3× faster (725 b/sec) than the replication speed of a alone.

EXAMPLE 7

Primer Extension by A.ae α Subunit

*Aquifex aeolicus* ("A.ae") α subunit was used in a time course primer extension assay to examine its extension rate as a stand alone polymerase. In 19.6 III reaction mixes 350 ng (0.15 pmol) of ssM13 mp18 DNA primed with 0.375 pmol of a 30-mer oligodeoxynucleotide primer were incubated at 60° C. for 2 minutes in the presence of 350 ng (2.5 pmol) of A.ae DNA Pol III alpha subunit in 20 mM TAPS-Tris (pH 8.7), 25 mM KCl, 10 mM (NH4)2SO4, 8 mM Mg(OAc)2, 10 uM ZnSO4, 14% glycerol, 40 mg/ml BSA and 40 mM Sorbitol (data not shown). The primer extension/replication was started by adding 0.4 μl of a dNTP mix containing 10 mM dATP, 10 mM dGTP, 10 mM dTTP, and 10 mM dCTP to the final concentration of 200 μmol each. The time points of the primer extension assay were taken stopping individual reactions by addition of 2 μl 0.1M EDTA and transferring them on ice. The replication products were analyzed by electrophoretic separation in a 0.7% TEAE-buffered agarose gel with subsequent ethidium bromide staining. The A.ae α subunit replicated the 7.2 kb M13 template with an extension rate of 120 b/sec.

Figure 11:
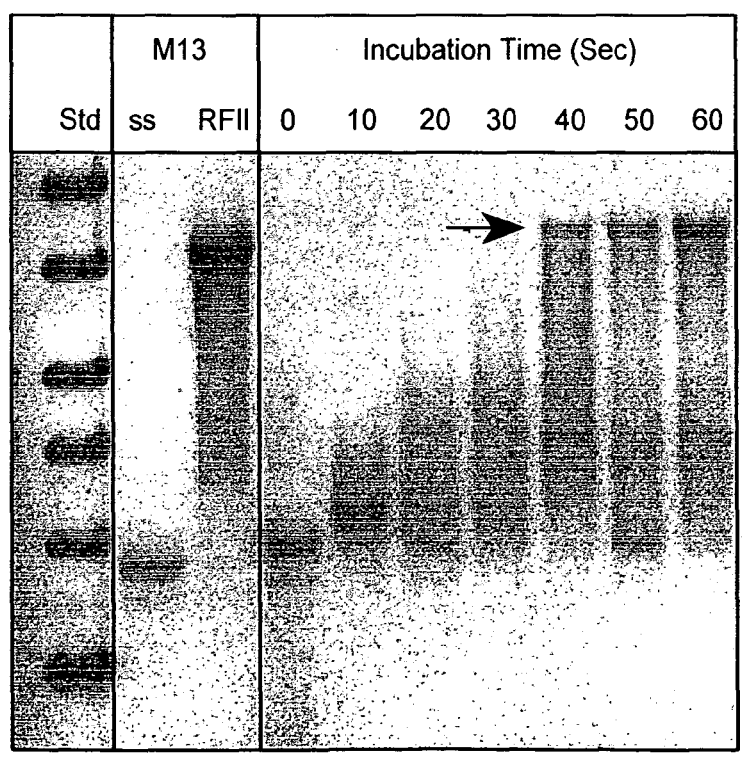
Figures 12, 13:
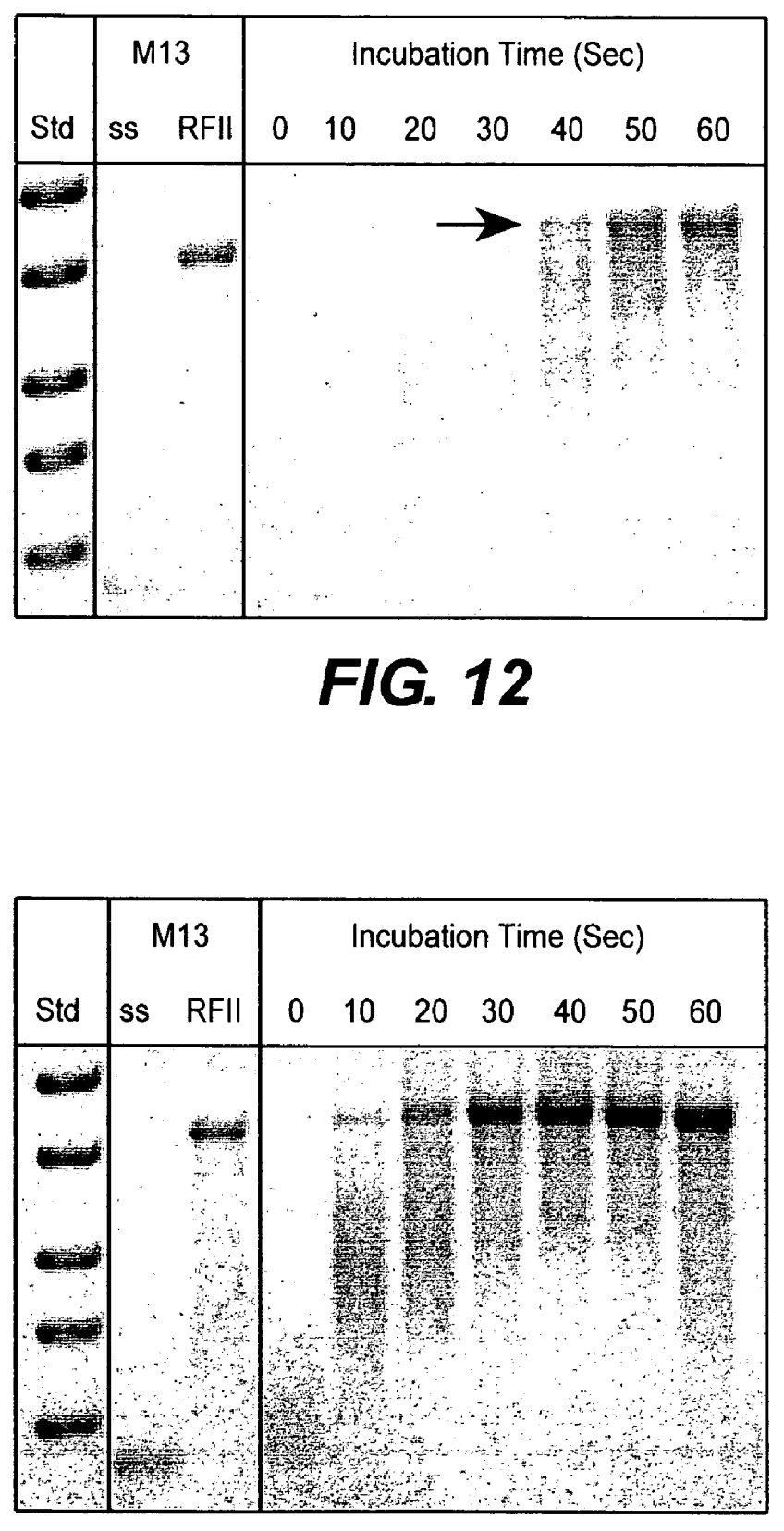

(FIGS. 11 and 12) In another 19.6 μl reaction, 1 μg (7.5 pmol) of A.ae α subunit was incubated with 350 ng (0.15 pmol) of ssM13 mp18 DNA primed with 0.375 pmol of a 30-mer oligodeoxynucleotide primer at 60° C. for 2 minutes in the presence of in 20 mM TAPS-Tris (pH 8.7), 25 mM KCl, 10 mM (NH$_4$)$_2$SO$_4$, 8 mM Mg(OAc)$_2$, 10 uM ZnSO$_4$, 14% glycerol, 40 mg/ml BSA and 40 mM Sorbitol. The primer extension/replication was started by adding 0.4 μl of a dNTP mix containing 10 mM dATP, 10 mM dGTP, 10 mM dTTP, and 10 mM dCTP to the final concentration of 200 μmol each. The indicated time points of the primer extension assay were taken stopping individual reactions by addition of 2 μl 0.1M EDTA and transferring them on ice. The replication products were analyzed by electrophoretic separation in a 0.7% TEAE-buffered agarose gel with subsequent ethidium bromide staining. The arrow marks the first time point at which the full-size (7.2 kb) double-stranded replication product was detectable. The A.ae DNA Pol III a-subunit replicated the 7.2 kb M13 template with an extension rate of 160 b/sec.

EXAMPLE 8

Primer Extension by T.ma α Subunit (polC)

Figure 14:
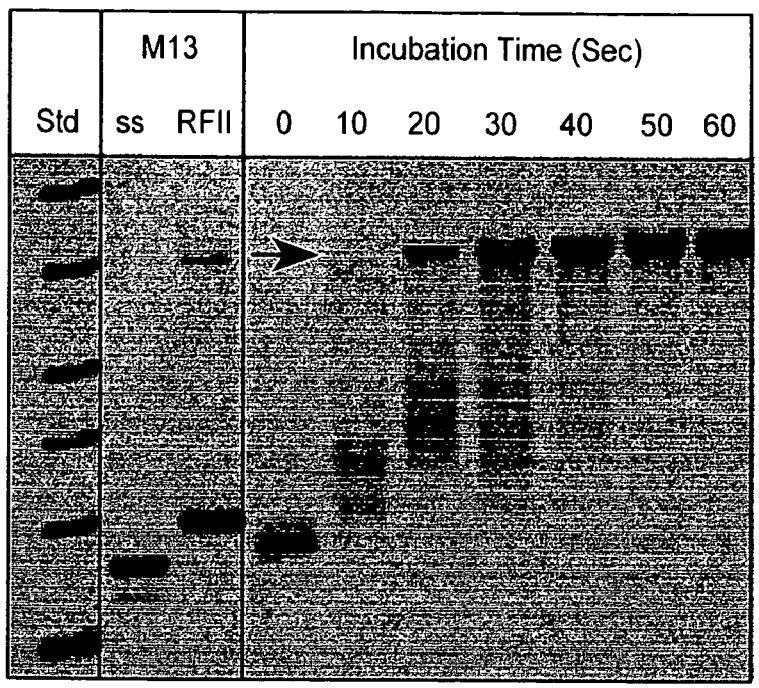
FIG. 14 shows primer extension assays using T.ma DNA polymerase III α subunit (polC).

(FIG. 14) *Thermotoga maritima* ("T.ma") α subunit was used in a time course primer extension assay to examine its extension rate as a stand alone polymerase. In 19.6 μl reaction mixes 350 ng (0.15 pmol) of ssM13 mp18 DNA primed with 0.375 pmol of a 30-mer oligodeoxynucleotide primer were incubated at 60° C. for 2 minutes in the presence of 100 ng (0.64 pmol) of Tma DNA Pol III alpha subunit (polC) in 20 mM TAPS-Tris (pH 7.5), 25 mM KCl, 10 mM (NH$_4$)$_2$SO$_4$, 8 mM Mg(OAc)$_2$, 14% glycerol, 40 mg/ml BSA and 40 mM Sorbitol. The primer extension/replication was started by adding 0.4 μl of a dNTP mix containing 10 mM dATP, 10 mM dGTP, 10 mM dTTP, and 10 mM dCTP to the final concentration of 200 μmol each. The indicated time points of the primer extension assay were taken stopping individual reactions by addition of 2 μl 0.1M EDTA and transferring them on ice. The replication products were analyzed by electrophoretic separation in a 0.7% TEAE-buffered agarose gel with subsequent ethidium bromide staining. The arrow marks the first time point at which the full-size (7.2 kb) double-stranded replication product was detectable. The T.ma α subunit (polC) replicated the 7.2 kb M13 template with an extension rate of 720 b/sec.

EXAMPLE 9

Figure 15:
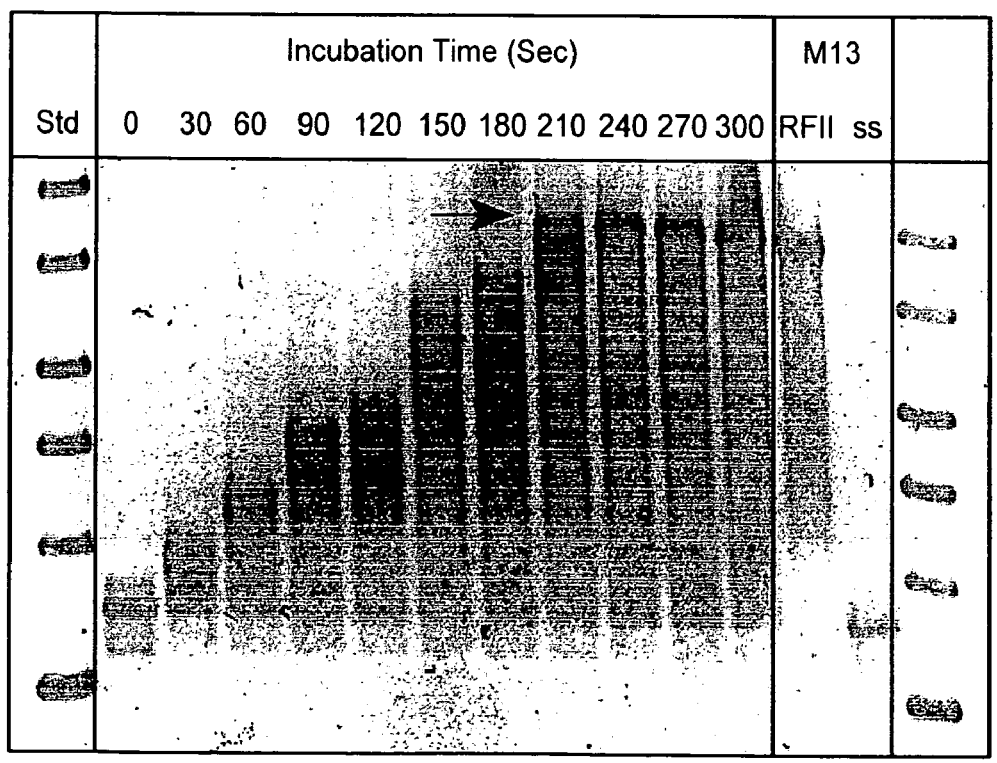
FIG. 15 shows primer extension assays using T.aq DNA polymerase 1.

Primer Extension by T.aq Pol I (FIG. 15) In 19.6 ml reaction mixes 350 ng (0.15 pmol) of ssM13 mp18 DNA primed with 0.375 pmol of a 30-mer oligodeoxynucleotide primer were incubated at 60° C. for 2 minutes in the presence of 100 ng (1.1 pmol) of Taq DNA Pol I in 20 mM Bicine-Tris (pH 8.7), 50 mM KCl, 2.5 mM Mg(OAc)$_2$. The primer extension/replication was started by adding 0.4 μl of a dNTP mix containing 10 mM dATP, 10 mM dGTP, 10 mM dTTP, and 10 mM dCTP to the final concentration of 200 μmol each. The indicated time points of the primer extension assay were taken stopping individual reactions by addition of 2 μl 0.1M EDTA and transferring them on ice. The replication products were analyzed by electrophoretic separation in a 0.7% TEAE-buffered agarose gel with subsequent ethidium bromide staining. The arrow marks the first time point at which the full-size (7.2 kb) double-stranded replication product was detectable. The Taq DNA Pol I replicated the 7.2 kb M13 template with an extension rate of 34 b/sec.

EXAMPLE 10

T.th versus *E. coli* α Subunits and Minimal Holoenzymes (FIG. 1) Primer extension assays were done with ssM13 mp18 DNA template (0.146 pmol) primed with a 30-mer oligodeoxynucleotide primer (0.375 pmol) using either 2.5 μg (15 pmol) of the α-subunit alone or 15 pmol of the corresponding minimal DNA Pol III holoenzyme. The primer extension reaction buffer for the T.th enzymes comprised 20 mM HEPES-Tris (pH 7.5), 8 mM Mg(OAc)$_2$, 14% glycerol, 40 mg/ml BSA and 40 mM Sorbitol. The primer extension reaction buffer for the *E. coli* enzymes comprised 50 mM Tris-Cl (pH 7.5), 8 mM Mg(OAc)$_2$, 14% glycerol, 40 mg/ml BSA and 40 mM Sorbitol, 1 mM DTT.

EXAMPLE 11

Figure 16:
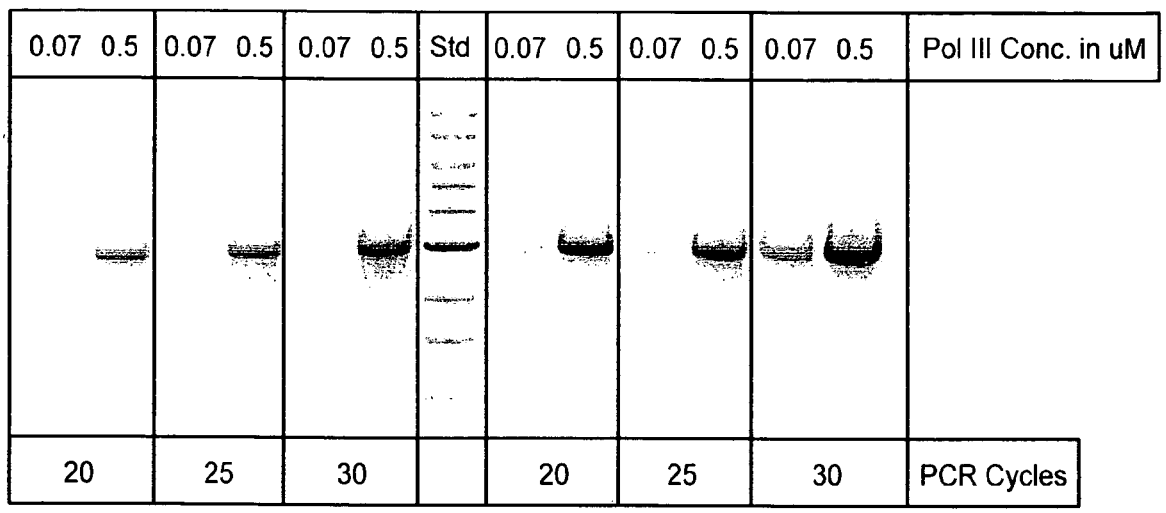
FIG. 16 shows fast and sensitive PCR with the T.th alpha/beta two component Pol III replicase.

Fast and Sensitive PCR with T.th α/β Two Component Pol III Replicase (FIG. 16) 50 ul inverse PCR assays were performed containing 50 ng of a pBSK plasmid template and 10 pmol of the forward and reverse primer, respectively. The primers anneal tail-to-tail at origin of the plasmid so a full-lengths linear amplicon of the plasmid is amplified (3 kb). The PCR were performed with two different concentrations of the Two Component Tth Pol III Replicase and stopped after various cycle numbers. The time intervals at each PCR cycle in the temperature protocol applied are extremely fast for a 3 kb target [Denaturation 90° C. 30"; Primer Annealing & Elongation 62° C. 10"]. The PCR was performed in 40 mM HEPES-Bis-Tris-Propane (pH 7.5), 1M TMAO (trimethylamine N-oxide), 5% Glycerol, 2% 20K PEG, 6 mM, Mg(OAc)$_2$; 10% sorbitol with 200 mmol of each dNTP. With the higher enzyme concentration the 3 kb target can already be detected after 20 cycles with total time span of only 20 minutes for the PCR. The average extension of the two component replicase to support the fast amplification is 300 bases/sec. Note, that the high enzyme and magnesium concentration (4 mM magnesium) in the reaction does not compromise PCR specificity, which would be possible using equivalent amounts of Taq DNA polymerase.

EXAMPLE 12

Figure 17:
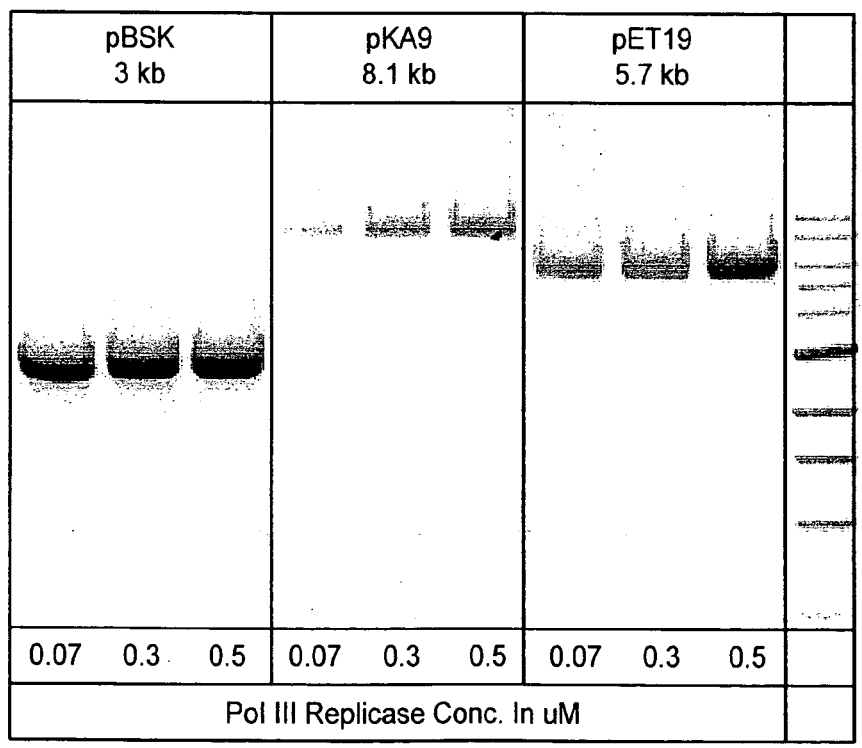
FIG. 17 shows fast and long range PCR with the T.th alpha/beta two component Pol III replicase.

Fast and Long Range PCR with the T.th α/β Two Component Pol III Replicase (FIG. 17) 50 ul inverse PCR assys were performed containing 50 ng of various plasmid templates with increasing sizes (3 kb, 5.7 kb and 8.1 kb) and 10 pmol of the forward and reverse primer, respectively. The primers anneal tail-to-tail at ori region of the plasmid so a full-length linear amplicon of the plasmid is amplified (3 to 8.1 kb). The 30 cycle PCR were performed with three different concentrations of the Two Component Tth Pol III Replicase. The time intervals at each PCR cycle in the temperature protocol applied are fast: for the 3 kb, 5.7 kb and 8.1 kb targets [Denaturation 90° C. 30"; Primer Annealing & Elongation 62° C. 60"]. The PCR was performed in 40 mM HEPES-Bis-Tris-Propane (pH 7.5), 1M TMAO (trimethylamine N-oxide), 5% Glycerol, 2% 20K PEG, 6 mM, Mg(OAc)$_2$; 10% sorbitol with 200 mmol of each dNTP. All targets could be amplified in the same short time frame. The highest enzyme concentration (0.5 uM) was the most efficient on the longest 8.1 kb target. The average extension of the two component replicase to support the fast amplification is 300 bases/sec. Note, that the high enzyme and magnesium concentration (4 mM magnesium) in the reaction does not compromise PCR specificity, which would be possible using equivalent amounts of Taq DNA polymerase.

EXAMPLE 13

Fast PCR with the T.th α/β Two Component Pol II Replicase versus T.aq DNA Polymerase I and a fast Taq/DeepVent DNA Pol B Polymerase Mixture (TM)

(FIG. 18) 50 ul inverse PCR assays were performed containing 50 ng of the pBSK plasmid template with (3 kb) and 10 pmol of the forward and reverse primer, respectively. The primers anneal tail-to-tail at ori region of the plasmid so a full-length linear amplicon of the plasmid is amplified (3 kb). The 30 cycle PCR were performed with two different concentrations of the Two Component Tth Pol III Replicase in comparison to Taq DNA polymerase (2 U) and 2 U of a fast Taq/DeepVent Pol B polymerase mixture for long range PCR (TM—TripleMaster, Eppendorf). The various time intervals in each PCR cycle temperature protocol are indicated on the picture [Denaturation 90° C. 30"; Primer Annealing & Elongation at 62° C. 10 to 40"]. The PCR was performed in 40 mM HEPES-Bis-Tris-Propane (pH 7.5), 1M TMAO (trimethylamine N-oxide), 5% Glycerol, 2% 20K PEG, 6 mM, Mg(OAc)$_2$; 10% sorbitol with 200 mmol of each dNTP. The Taq DNA Pol I drops out at 30 seconds extension time barely amplifying a small amount of the right product at 40 sec. The TripleMaster (TM) long range PCR polymerase mix drops out at 30 sec. Even the at the lower concentration the Tth two component replicase amplifies the 3 kb target at 10 sec extension/cycle corresponding to an extension rate in PCR of 300 b/sec.

EXAMPLE 14

Figure 19:
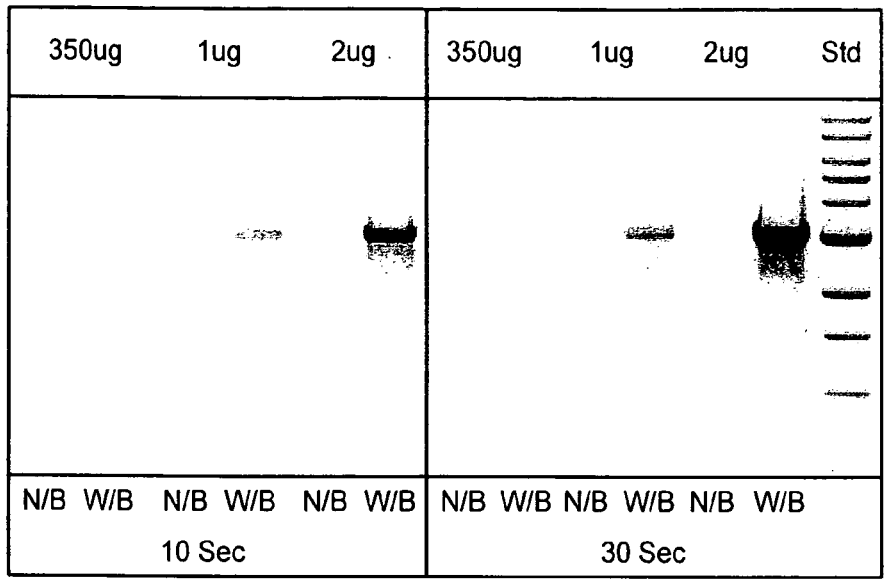
FIG. 19 shows fast PCR with the A.ae alpha/beta two component Pol III replicase.
Figure 20:
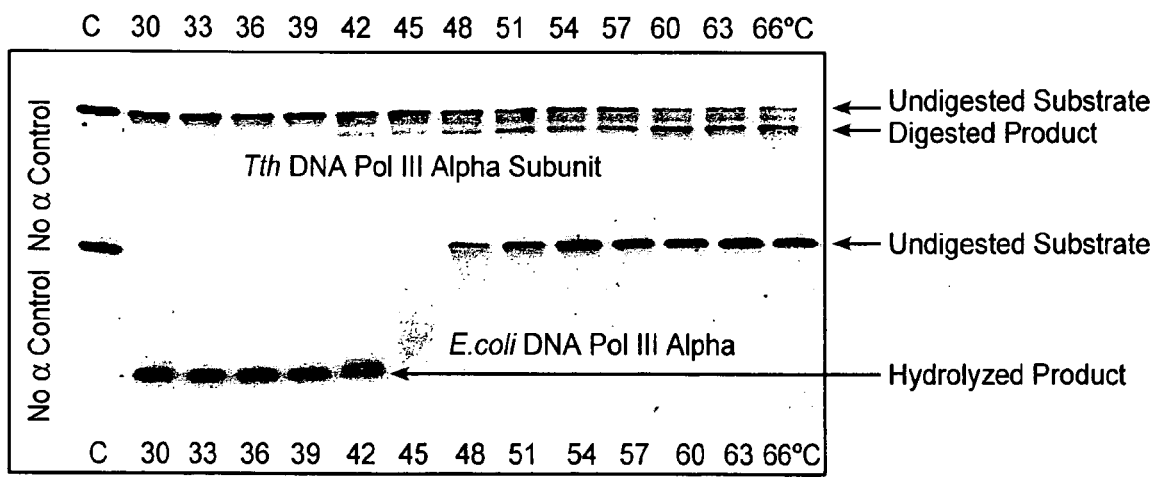
FIG. 20 shows temperature dependency of the 3'-5' exonuclease activity of *Thermus thermophilus* and *E. coli* DNA Pol III alpha subunits. An exonuclease activity assay was performed varying the incubation temperature from 30° C. to 66° C. In 20 µl reaction volumes 0.7 µmol of a 5'-FAM-labelled oligodeoxynucleotide substrate was incubated with 15 pmol (2 µg) of the corresponding α subunit for 10 minutes at the indicated temperatures. The reactions were stopped by adding 10 mM EDTA on ice and the resulting product were separated on a denaturing 15% TBE-polyacrylamide gel (Criterion™ Precast Gels; BioRad). The FAM-fluorescence gel image was recorded wit a Lumi-Imager F1™ (Roche) using the 520 nm filter with top illumination and 1 second integration time. The Tth DNA Pol III alpha subunit shows exonuclease activity which gradually increases from 42° C. to 66° C. with an optimum >60° C. The *E. coli* DNA Pol III alpha subunit, instead, possesses full exonuclease activity up to 42° C. and has no activity >54° C. This data strongly indicates that the 3'-5' exonucleolytic activity of the Tth DNA Pol III alpha subunit is not related to a contaminant derived from the *E. coli* host expression strain. The 3'-5' exonuclease represents a truly intrinsic catalytical activity of the Tth DNA Pol III alpha subunit.
Figure 21:
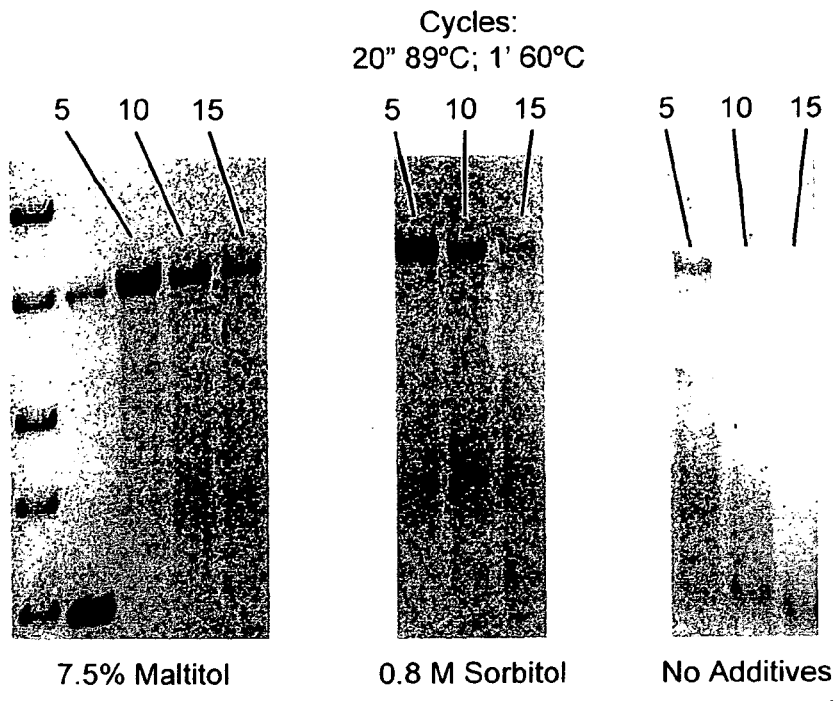
FIG. 21 shows increased temperature stability of the *Thermus thermophilus* DNA Pol III with stabilizing additives.

Fast PCR with the A.ae α/β Two Component Pol III Replicase (FIG. 19) 50 ul inverse PCR assys were performed containing 50 ng of the pBSK plasmid template with (3 kb) and 10 pmol of the forward and reverse primer, respectively. The primers anneal tail-to-tail at ori region of the plasmid so a full-length linear amplicon of the plasmid is amplified (3 kb). The 30 cycle PCR were performed with three different concentrations of the Two Component Aae DNA Pol III Replicase in the presence and absence of the stabilizer glycyl betain. 30 cycles of the following temperature cycling protocol was applied: Denaturation 90° C. 30"; Primer Annealing & Elongation at 62° C. 10 & 30". The PCR was performed in the buffer 20 mM TAPS-Tris buffer, pH 8.7, 50 mMKCl; 10 mM ammonium sulfate; 0.8 mM $CaCl_2$; 15 uM $ZnSO_4$; 2% PEG 20K; 10% sorbitol; 4 mM $Mg(Oac)_2$; 10% Glycerol and optional 1M Betaine, in the presence of 200 uM of each dNTP. The two component Dna Pol III relicase from Aquifex can also amplify 3 kb in the fast PCR mode where Taq fails. Efficient amplification requires the presence of betaine, when high protein concentrations are used. TMAO can not be used as a substitute stabilizer for glycyl betaine at higher enzyme concentrations (data not shown).

We claim:

1. A method for replicating a DNA molecule, comprising subjecting a DNA molecule to a replication reaction in a replication reaction mixture, which replication reaction mixture comprises a minimal functional Pol III replicase, wherein said minimal functional Pol III replicase comprises a first component, which first component comprises an α subunit from a gram negative bacteria, wherein said α subunit comprises amino acid consensus sequence motifs A, B, and C arranged in the order C-A-B from amino terminus to carboxyl terminus, wherein said minimal functional Pol III replicase and said replication reaction mixture lack each subunit (τ/γ, δ and δ') of the clamp loader, and wherein said DNA molecule is replicated in said replication reaction in said replication reaction mixture by said minimal functional Pol III at a rate of at least 100 nucleotides per second.

2. The method according to claim 1, wherein said minimal functional Pol III replicase is a thermostable minimal Pol III.

3. The method according to claim 1, wherein said gram negative bacteria is selected from the group consisting of the genera *Thermus, Aquifex,* and *Thermatoga*.

4. The method according to claim 1, wherein said DNA is double stranded DNA.

5. The method according to claim 1, wherein said first component further comprises an ε subunit.

6. The method according to claim 1, wherein said minimal functional Pol III replicase is a single component Pol III replicase.

7. The method according to claim 1, wherein said minimal functional Pol III replicase is a two component Pol III replicase further comprising a second component, which second component comprises a processivity clamp.

8. The method according to claim 1, wherein said method is an amplification method, wherein said replication reaction is an amplification reaction, and said replication reaction mixture is an amplification reaction mixture.

9. The method according to claim 8, wherein said amplification method is a PCR method, wherein said amplification reaction is a polymerase chain reaction, and wherein said amplification reaction mixture is a PCR mixture.

10. The method according to claim 1, wherein said method is a sequencing method, wherein said replication reaction is a sequencing reaction, wherein said replication reaction mixture is a sequencing reaction mixture.

11. The method according to claim 1, wherein said replication reaction mixture lacks CaCl2.

12. The method according to claim 1, wherein said replication reaction mixture is a zwitterionic buffer comprising a weak organic acid and a weak organic base.

13. The method according to claim 1, wherein said replication reaction mixture has a pH of between about pH7.5-8.9.

14. The method according to claim 1, wherein said a subunit is present in said replication reaction mixture at a concentration of not less than 6 ng/μL.

15. The method according to claim 1, wherein said a subunit is a DnaE a subunit from a gram negative bacteria and the spacing between said motif C and said motif A ranges from about 153 to about 155 amino acids, and wherein the spacing between said motif A and said motif B ranges from about 195 to about 201 amino acids.

16. The method according to claim 15, wherein said motif A comprises the sequence set forth in SEQ ID NO:15.

17. The method according to claim 15, wherein said motif B comprises the sequence set forth in SEQ ID NO:16.

18. The method according to claim 15, wherein said motif C comprises the sequence set forth in SEQ ID NO:17.

19. The method according to claim 15, wherein said motif A comprises the sequence set forth in SEQ ID NO:21.

20. The method according to claim 15, wherein said motif B comprises the sequence set forth in SEQ ID NO:22.

21. The method according to claim 15, wherein said motif C comprises the sequence set forth in SEQ ID NO:23.

* * * * *